(12) United States Patent
Loosmore et al.

(10) Patent No.: US 7,740,863 B2
(45) Date of Patent: Jun. 22, 2010

(54) RECOMBINANT VACCINE AGAINST WEST NILE VIRUS

(75) Inventors: Sheena May Loosmore, Aurora (CA); Jean-Christophe Francis Audonnet, Lyons (FR); Jules Maarten Minke, Corbas (FR)

(73) Assignee: Merial, Duluth, GA (US)

( * ) Notice: Subject to any disclaimer, the term of this patent is extended or adjusted under 35 U.S.C. 154(b) by 574 days.

(21) Appl. No.: 10/714,781

(22) Filed: Nov. 17, 2003

(65) Prior Publication Data

US 2005/0255127 A1    Nov. 17, 2005

Related U.S. Application Data

(63) Continuation-in-part of application No. 10/679,520, filed on Oct. 6, 2003, now abandoned, which is a continuation-in-part of application No. 10/676,502, filed on Sep. 30, 2003, now abandoned, which is a continuation-in-part of application No. 10/374,953, filed on Feb. 26, 2003, now abandoned, which is a continuation-in-part of application No. 10/116,298, filed on Apr. 4, 2002, now abandoned.

(60) Provisional application No. 60/281,923, filed on Apr. 6, 2001.

(51) Int. Cl.
  *A61K 39/12* (2006.01)
  *A61K 39/275* (2006.01)

(52) U.S. Cl. ............... 424/199.1; 424/218.1; 424/232.1

(58) Field of Classification Search .............. 424/199.1, 424/186.1, 204.1, 184.1, 202.1, 218.1; 514/44; 435/5, 320.1, 436; 536/23.72
See application file for complete search history.

(56) References Cited

U.S. PATENT DOCUMENTS

| 5,338,683 | A | * | 8/1994 | Paoletti | ................... 435/235.1 |
| 5,505,941 | A | * | 4/1996 | Paoletti | ...................... 424/93.2 |
| 5,744,141 | A | * | 4/1998 | Paoletti et al. | ........... 424/199.1 |
| 5,756,103 | A | * | 5/1998 | Paoletti et al. | ........... 424/199.1 |
| 6,713,068 | B1 | * | 3/2004 | Audonnet et al. | ........ 424/206.1 |
| 7,227,011 | B2 | * | 6/2007 | Chang | ..................... 536/23.72 |
| 2003/0022849 | A1 | * | 1/2003 | Chang | ......................... 514/44 |

FOREIGN PATENT DOCUMENTS

| WO | WO 99/44633 | * | 9/1999 |
| WO | WO 01/60847 | * | 8/2001 |

OTHER PUBLICATIONS

Yamshikov et al (Gene 149:193-201).*
Ramshaw et al (Immunology Today 21:163-165, 2000).*
Paoletti (Proc Natl Acad Sci USA, 1996, 93:11349-11353).*
Goverdhan et al. (Acta Virol, 1992, 36: 277-283).*
Ostlund et al. (Vet Clin North Am Equine Pract, 2000, 16: 427-41, Abstract).*
Stocks et al. (J Virol, 1998, 72: 2141-2149).*
Chang et al. (J Virol, 2000, 74: 4244-4252).*
Mumford et al. (Epidemiol Infect, 1994, 112: 421-437, Abstract).*
Varga et al. (Veterinary Microbiol, 1997, 56: 205-212).*
Ruitengerg et al. (Vaccine, 2000, 18:1367-1373).*
Siger et al (Veterinary Therapy 7:249-256, 2006).*

* cited by examiner

*Primary Examiner*—Mary E Mosher
(74) *Attorney, Agent, or Firm*—Judy Jarecki-Black; Merial Limited; Thomas Kowalski, Esq.

(57) ABSTRACT

An immunogenic or vaccine composition to induce an immune response or protective immune response against West Nile virus (WNV) in an animal susceptible to WNV. The composition includes a pharmaceutically or veterinarily acceptable vehicle or excipient, and a vector. The vector contains heterologous nucleic acid molecule(s), expresses in vivo in the animal WNV antigen, immunogen or epitope thereof, e.g., WNV E; WNV prM and E; WNV M and E; WNV prM, WNV M and E, WNV polyprotein prM-E, WNV polyprotein M-E, or WNV polyprotein prM-M-E. The composition can contain an adjuvant, such as carbomer. Methods for making and using such a composition, including prime-boost regimes and including as to differential diagnosis, are also contemplated.

16 Claims, 66 Drawing Sheets

Figure 1. Construction of a pC5 H6p WNV *prM-M-E* donor plasmid, pDS-2946-1-1

Figure 2. Sequence of C5 H6p WNV *prM-M-E* C5 in pDS-2646-1-1

```
          ==>C5R
    1   TGAATGTTAA ATGTTATACT TTGGATGAAG CTATAAATAT GCATTGGAAA AATAATCCAT
   61   TTAAAGAAAG GATTCAAATA CTACAAAACC TAAGCGATAA TATGTTAACT AAGCTTATTC
  121   TTAACGACGC TTTAAATATA CACAAATAAA CATAATTTTT GTATAACCTA ACAAATAACT
  181   AAAACATAAA AATAATAAAA GGAAATGTAA TATCGTAATT ATTTTACTCA GGAATGGGGT
  241   TAAATATTTA TATCACGTGT ATATCTATAC TGTTATCGTA TACTCTTTAC AATTACTATT
  301   ACGAATATGC AAGAGATAAT AAGATTACGT ATTTAAGAGA ATCTTGTCAT GATAATTGGG
  361   TACGACATAG TGATAAATGC TATTTCGCAT CGTTACATAA AGTCAGTTGG AAAGATGGAT
  421   TTGACAGATG TAACTTAATA GGTGCAAAAA TGTTAAATAA CAGCATTCTA TCGGAAGATA
  481   GGATACCAGT TATATTATAC AAAAATCACT GGTTGGATAA AACAGATTCT GCAATATTCG
  541   TAAAGATGA AGATTACTGC GAATTTGTAA ACTATGACAA TAAAAAGCCA TTTATCTCAA
  601   CGACATCGTG TAATTCTTCC ATGTTTTATG TATGTGTTTC AGATATTATG AGATTACTAT
  661   AAACTTTTTG TATACTTATA TTCCGTAAAC TATATTAATC ATGAAGAAAA TGAAAAAGTA
  721   TAGAAGCTGT TCACGAGCGG TTGTTGAAAA CAACAAAATT ATACATTCAA GATGGCTTAC
  781   ATATACGTCT GTGAGGCTAT CATGGATAAT GACAATGCAT CTCTAAATAG GTTTTTGGAC
  841   AATGGATTCG ACCCTAACAC GGAATATGGT ACTCTACAAT CTCCTCTTGA AATGGCTGTA
  901   ATGTTCAAGA ATACCGAGGC TATAAAAATC TTGATGAGGT ATGGAGCTAA ACCTGTAGTT
  961   ACTGAATGCA CAACTTCTTG TCTGCATGAT GCGGTGTTGA GAGACGACTA CAAAATAGTG
 1021   AAAGATCTGT TGAAGAATAA CTATGTAAAC AATGTTCTTT ACAGCGGAGG CTTTACTCCT
 1081   TTGTGTTTGG CAGCTTACCT TAACAAAGTT AATTTGGTTA AACTTCTATT GGCTCATTCG
 1141   GCGGATGTAG ATATTTCAAA CACGGATCGG TTAACTCCTC TACATATAGC CGTATCAAAT
 1201   AAAAATTTAA CAATGGTTAA ACTTCTATTG AACAAAGGTG CTGATACTGA CTTGCTGGAT
 1261   AACATGGGAC GTACTCCTTT AATGATCGCT GTACAATCTG GAAATATTCA AATATGTAGC
 1321   ACACTACTTA AAAAAAATAA AATGTCCAGA CTGGGAAAA ATTGATCTTG CCAGCTGTAA
 1381   TTCATGCTAG AAAAGAAGTG CTCAGGCTAC TTTTCAACAA AGGAGCAGAT GTAAACTACA
 1441   TCTTTGAAAG AAATGGAAAA TCATATACTG TTTTGGAATT GATTAAAGAA AGTTACTCTG
 1501   AGACACAAAA GAGGTAGCTG AAGTGGTACT CTCAAAAAGG TACGTGACTA ATTAGCTATA
 1561   AAAAGGATCC GGGTTAATTA ATTAGTCATC AGGCAGGGCG AGAACGAGAC TATCTGCTCG
```

Figure 2 continued

```
                    ⇒H6p
1621    TTAATTAATT AGAGCTTCTT TATTCTATAC TTAAAAAGTG AAAATAAATA CAAAGGTTCT

1681    TGAGGGTTGT GTTAAATTGA AAGCGAGAAA TAATCATAAA TTATTTCATT ATCGCGATAT

⇒ WNV capsid leader
                        M  T  G  I  A  V  M  I  G  L  I  A  S  V ·
1741    CCGTTAAGTT TGTATCGTAA TGACCGGAAT TGCAGTCATG ATTGGCCTGA TCGCCAGCGT ⇒ WNV prM
        · G  A  V  T  L  S  N  F  Q  G  K  V  M  M  T  V  N  A  T  D ·
1801    AGGAGCAGTT ACCCTCTCTA ACTTCCAAGG GAAGGTGATG ATGACGGTAA ATGCTACTGA · V  T  D  V  I  T  I  P  T  A  G  K  N  L  C  I  V  R  A ·
1861    CGTCACAGAT GTCATCACGA TTCCAACAGC TGCTGGAAAG AACCTATGCA TTGTCAGAGC · M  D  V  G  Y  M  C  D  D  T  I  T  Y  E  C  P  V  L  S  A ·
1921    AATGGATGTG GGATACATGT GCGATGATAC TATCACTTAT GAATGCCCAG TGCTGTCGGC · G  N  D  P  E  D  I  D  C  W  C  T  K  S  A  V  Y  V  R  Y ·
1981    TGGTAATGAT CCAGAAGACA TCGACTGTTG GTGCACAAAG TCAGCAGTCT ACGTCAGGTA ⇒ WNV M
        · G  R  C  T  K  T  R  H  S  R  R  S  R  R  S  L  T  V  Q  T ·
2041    TGGAAGATGC ACCAAGACAC GCCACTCAAG ACGCAGTCGG AGGTCACTGA CAGTGCAGAC · H  G  E  S  T  L  A  N  K  K  G  A  W  M  D  S  T  K  A  T ·
2101    ACACGGAGAA AGCACTCTAG CGAACAAGAA GGGGGCTTGG ATGGACAGCA CCAAGGCCAC · R  Y  L  V  K  T  E  S  W  I  L  R  N  P  G  Y  A  L  V  A ·
2161    AAGGTATTTG GTAAAAACAG AATCATGGAT CTTGAGGAAC CCTGGATATG CCCTGGTGGC · A  V  I  G  W  M  L  G  S  N  T  M  Q  R  V  V  F  V  V  L ·
2221    AGCCGTCATT GGTTGGATGC TTGGGAGCAA CACCATGCAG AGAGTTGTGT TTGTCGTGCT ⇒ WNV E
        · L  L  L  V  A  P  A  Y  S  F  N  C  L  G  M  S  N  R  D  F ·
2281    ATTGCTTTTG GTGGCCCCAG CTTACAGCTT CAACTGCCTT GGAATGAGCA ACAGAGACTT · L  E  G  V  S  G  A  T  W  V  D  L  V  L  E  G  D  S  C  V ·
2341    CTTGGAAGGA GTGTCTGGAG CAACATGGGT GGATTTGGTT CTCGAAGGCG ACAGCTGCGT · T  I  M  S  K  D  K  P  T  I  D  V  K  M  M  N  M  E  A  A ·
2401    GACTATCATG TCTAAGGACA AGCCTACCAT CGATGTGAAG ATGATGAATA TGGAGGCGGC · N  L  A  E  V  R  S  Y  C  Y  L  A  T  V  S  D  L  S  T  K ·
2461    CAACCTGGCA GAGGTCCGCA GTTATTGCTA TTTGGCTACC GTCAGCGATC TCTCCACCAA · A  A  C  P  T  M  G  E  A  H  N  D  K  R  A  D  P  A  F  V ·
2521    AGCTGCGTGC CCGACCATGG GAGAAGCTCA CAATGACAAA CGTGCTGACC CAGCTTTTGT · C  R  Q  G  V  V  D  R  G  W  G  N  G  C  G  L  F  G  K  G ·
2581    GTGCAGACAA GGAGTGGTGG ACAGGGGCTG GGGCAACGGC TGCGGACTAT TTGGCAAAGG
```

Figure 2 continued

```
             .  S   I   D      T   C   A   K      F   A   C      S   T   K      A   I   G   R      T   I   L  .
     2641    AAGCATTGAC  ACATGCGCCA  AATTTGCCTG  CTCTACCAAG  GCAATAGGAA  GAACCATCTT
                                              mutated T5NT
             .  K   E   N      I   K   Y   E      V   A   I      F   V   H      G   P   T   T      V   E   S  .
     2701    GAAAGAGAAT  ATCAAGTACG  AAGTGGCCAT  CTTCGTGCAC  GGACCAACTA  CTGTGGAGTC .  H   G   N      Y   S   T   Q      V   G   A      T   Q   A      G   R   F   S      I   T   P  .
     2761    GCACGGAAAC  TACTCCACAC  AGGTTGGAGC  CACTCAGGCA  GGGAGATTCA  GCATCACTCC .  A   A   P      S   Y   T   L      K   L   G      E   Y   G      E   V   T   V      D   C   E  .
     2821    TGCGGCGCCT  TCATACACAC  TAAAGCTTGG  AGAATATGGA  GAGGTGACAG  TGGACTGTGA .  P   R   S      G   I   D   T      N   A   Y      Y   V   M      T   V   G   T      K   T   F  .
     2881    ACCACGGTCA  GGGATTGACA  CCAATGCATA  CTACGTGATG  ACTGTTGGAA  CAAAGACTTT .  L   V   H      R   E   W   F      M   D   L      N   L   P      W   S   S   A      G   S   T  .
     2941    CTTGGTCCAT  CGTGAGTGGT  TCATGGACCT  CAACCTCCCT  TGGAGCAGTG  CTGGAAGTAC .  V   W   R      N   R   E   T      L   M   E      F   E   E      P   H   A   T      K   Q   S  .
     3001    TGTGTGGAGG  AACAGAGAGA  CGTTAATGGA  GTTTGAGGAA  CCACACGCCA  CGAAGCAGTC .  V   I   A      L   G   S   Q      E   G   A      L   H   Q      A   L   A   G      A   I   P  .
     3061    TGTGATAGCA  TTGGGCTCAC  AAGAGGGAGC  TCTGCATCAA  GCTTTGGCTG  GAGCCATTCC .  V   E   F      S   S   N   T      V   K   L      T   S   G      H   L   K   C      R   V   K  .
     3121    TGTGGAATTT  TCAAGCAACA  CTGTCAAGTT  GACGTCGGGT  CATTTGAAGT  GTAGAGTGAA .  M   E   K      L   Q   L   K      G   T   T      Y   G   V      C   S   K   A      F   K   F  .
     3181    GATGGAAAAA  TTGCAGTTGA  AGGGAACAAC  CTATGGCGTC  TGTTCAAAGG  CTTTCAAGTT .  L   G   T      P   A   D   T      G   H   G      T   V   V      L   E   L   Q      Y   T   G  .
     3241    TCTTGGGACT  CCCGCAGACA  CAGGTCACGG  CACTGTGGTG  TTGGAATTGC  AGTACACTGG .  T   D   G      P   C   K   V      P   I   S      S   A   A      S   L   N   D      L   T   P  .
     3301    CACGGATGGA  CCTTGCAAAG  TTCCTATCTC  GTCAGCGGCT  TCATTGAACG  ACCTAACGCC .  V   G   R      L   V   T   V      N   P   F      V   S   V      A   T   N   A      K   V  .
     3361    AGTGGGCAGA  TTGGTCACTG  TCAACCCTTT  TGTTTCAGTG  GCCACGGCCA  ACGCTAAGGT .  L   I   E      L   P   P      F   G   D      S   Y   I      V   V   G   R      G   E   Q  .
     3421    CCTGATTGAA  TTGGAACCAC  CCTTTGGAGA  CTCATACATA  GTGGTGGGCA  GAGGAGAACA .  Q   I   N      H   H   W   H      K   S   G      S   S   I      G   K   A   F      T   T   T  .
     3481    ACAGATCAAT  CACCATTGGC  ACAAGTCTGG  AAGCAGCATT  GGCAAAGCCT  TTACAACCAC .  L   K   G      A   Q   R   L      A   A   L      G   D   T      A   W   D   F      G   S   V  .
     3541    CCTCAAAGGA  GCGCAGAGAC  TAGCCGCTCT  AGGAGACACA  GCTTGGGACT  TTGGATCAGT .  G   G   V      F   T   S   V      G   K   A      V   H   Q      V   F   G   G      A   F   R  .
     3601    TGGAGGGGTG  TTCACCTCAG  TTGGGAAGGC  TGTCCATCAA  GTGTTCGGAG  GAGCATTCCG .  S   L   F      G   G   M   S      W   I   T      Q   G   L      L   G   A   L      L   L   W  .
     3661    CTCACTGTTC  GGAGGCATGT  CCTGGATAAC  GCAAGGATTG  CTGGGGGCTC  TCCTGTTGTG
```

Figure 2 continued

```
            . M   G   I   N   A   R   D   R   S   I   A   L   T   F   L   A   V   G   G   V ·
    3721    GATGGGCATC AATGCTCGTG ATAGGTCCAT AGCTCTCACG TTTCTCGCAG TTGGAGGAGT

. L   L   F   L   S   V   N   V   H   A
    3781    TCTGCTCTTC CTCTCCGTGA ACGTGCACGC TTAATTTTTA TCTAGAATCG ATCCCGGGTT
                                              ⇒ C5L
    3841    TTTATGACTA GTTAATCACG GCCGCCTTAT AAAGATCTAA AATGCATAAT TTCTAAATAA

3901    TGAAAAAAAG TACATCATGA CCAACGCGTT AGTATATTTT ACAATGGAGA TTAACGCTCT

3961    ATACCGTTCT ATGTTTATTG ATTCAGATGA TGTTTTAGAA AAGAAAGTTA TTGAATATGA

4021    AAACTTTAAT GAAGATGAAG ATGACGACGA TGATTATTGT TGTAAATCTG TTTAGATGA

4081    AGAAGATGAC GCGCTAAAGT ATACTATGGT TACAAAGTAT AAGTCTATAC TACTAATGGC

4141    GACTTGTGCA AGAAGGTATA GTATAGTGAA AATGTTGTTA GATTATGATT ATGAAAAACC

4201    AAATAAATCA GATCCATATC TAAAGGTATC TCCTTTGCAC ATAATTTCAT CTATTCCTAG

4261    TTTAGAATAC
```

Figure 3. Construction of a pF8 H6p WNV *prM-M-E* donor plasmid, pSL-5513-1-1-1.

Figure 4. Sequence of F8 H6p WNV prM-M-E F8 in pSL-5513-1-1-1.

```
          => F8R
    1  GACCCTTTAC AAGAATAAAA GAAGAAACAA CTGTGAAATA GTTTATAAAT GTAATTCGTA
   61  TGCAGAAAAC GATAATATAT TTTGGTATGA GAAATCTAAA GGAGACATAG TTTGTATAGA
  121  CATGCGCTCT TCCGATGAGA TATTCGATGC TTTTCTAATG TATCATATAG CTACAAGATA
  181  TGCCTATCAT GATGATGATA TATATCTACA AATAGTGTTA TATTATTCTA ATAATCAAAA
  241  TGTTATATCT TATATTACGA AAAATAAATA CGTTAACTAT ATAAGAAATA AAACTAGACA
  301  CGATATTCAT AAAGTAAAAA TATTAGCTCT AGAAGACTTT ACAACGGAAG AAATATATTG
  361  TTGGATTAGT AATATATAAC AGCGTAGCTG CACGGTTTTG ATCATTTTCC AACAATATAA
  421  ACCAATGAAG GAGGACGACT CATCAAACAT AAATAACATT CACGGAAAAT ATTCAGTATC
  481  AGATTTATCA CAAGATGATT ATGTTATTGA ATGTATAGAC GGATCTTTTG ATTCGATCAA
  541  GTATAGAGAT ATAAAGGTTA TAATAATGAA GAATAACGGT TACGTTAATT GTAGTAAATT
  601  ATGTAAAATG CGGAATAAAT ACTTTTCTAG ATGGTTGCGT CTTTCTACTT CTAAAGCATT
  661  ATTAGACATT TACAATAATA AGTCAGTAGA TAATGCTATT GTTAAAGTCT ATGGTAAAGG
  721  TAAGAAACTT ATTATAACAG GATTTTATCT CAAACAAAAT ATGATACGTT ATGTTATTGA
  781  GTGGATAGGG GATGATTTTA CAAACGATAT ATACAAAATG ATTAATTTCT ATAATGCGTT
  841  ATTCGGTAAC GATGAATTAA AAATAGTATC CTGTGAAAAC ACTCTATGCC CGTTTATAGA
  901  ACTTGGTAGA TGCTATTATG GTAAAAAATG TAAGTATATA CACGGAGATC AATGTGATAT
  961  CTGTGGTCTA TATATACTAC ACCCTACCGA TATTAACCAA CGAGTTTCTC ACAAGAAAAC
 1021  TTGTTTAGTA GATAGAGATT CTTTGATTGT GTTTAAAAGA AGTACCAGTA AAAAGTGTGG
 1081  CATATGCATA GAAGAAATAA ACAAAAAACA TATTTCCGAA CAGTATTTTG GAATTCTCCC
 1141  AAGTTGTAAA CATATTTTTT GCCTATCATG TATAAGACGT TGGGCAGATA CTACCAGAAA
 1201  TACAGATACT GAAAATACGT GTCCTGAATG TAGAATAGTT TTTCCTTTCA TAATACCCAG
 1261  TAGGTATTGG ATAGATAATA AATATGATAA AAAAATATTA TATAATAGAT ATAAGAAAAT
 1321  GATTTTTACA AAAATACCTA TAAGAACAAT AAAAATATAA TTACATTTAC GGAAAATAGC
 1381  TGGTTTTAGT TTACCAACTT AGAGTAATTA TCATATTGAA TCTATATTGC TAATTAGCTA
 1441  ATAAAACCC GGGTTAATTA ATTAGTCATC AGGCAGGGCG AGAACGAGAC TATCTGCTCG
          => H6p
 1501  TTAATTAATT AGAGCTTCTT TATTCTATAC TTAAAAAGTG AAAATAAATA CAAAGGTTCT
```

Figure 4 continued

```
1561  TGAGGGTTGT GTTAAATTGA AAGCGAGAAA TAATCATAAA TTATTTCATT ATCGCGATAT

⇒ WNV capsid leader
                      M   T  G  I  A  V  M  I  G  L  I  A  S  V  ·
1621  CCGTTAAGTT TGTATCGTAA TGACCGGAAT TGCAGTCATG ATTGGCTGA TCGCCAGCGT ⇒ WNV prM
      · G  A  V   T  L  S  N   F  Q  G   K  V  M   M  T  V  N   A  T  D  ·
1681  AGGAGCGGTT ACCCTCTCTA ACTTCCAAGG GAAGGTGATG ATGACGGTAA ATGCTACTGA · V  T  D   V  I  T  I   P  T  A   A  G  K   N  L  C  I   V  R  A  ·
1741  CGTCACAGAT GTCATCACGA TTCCAACAGC TGCTGGAAAG AACCTATGCA TTGTCAGAGC · M  D  V   G  Y  M  C   D  D  T   I  T  Y   E  C  P  V   L  S  A  ·
1801  AATGGATGTG GGATACATGT GCGATGATAC TATCACTTAT GAATGCCCAG TGCTGTCGGC · G  N  D   P  E  D  I   D  C  W   C  T  K   S  A  V  Y   V  R  Y  ·
1861  TGGTAATGAT CCAGAAGACA TCGACTGTTG GTGCACAAAG TCAGCAGTCT ACGTCAGGTA ⇒ WNV M
      · G  R  C   T  K  T  R   H  S  R   R  S  R   R  S  L  T   V  Q  T  ·
1921  TGGAAGATGC ACCAAGACAC GCCACTCAAG ACGCAGTCGG AGGTCACTGA CAGTGCAGAC · H  G  E   S  T  L  A   N  K  K   G  A  W   M  D  S  T   K  A  T  ·
1981  ACACGGAGAA AGCACTCTAG CGAACAAGAA GGGGGCTTGG ATGGACAGCA CCAAGGCCAC · R  Y  L   V  K  T  E   S  W  I   L  R  N   P  G  Y  A   L  V  A  ·
2041  AAGGTATTTG GTAAAAACAG AATCATGGAT CTTGAGGAAC CCTGGATATG CCCTGGTGGC · A  V  I   G  W  M  L   G  S  N   T  M  Q   R  V  V  F   V  V  L  ·
2101  AGCCGTCATT GGTTGGATGC TTGGGAGCAA CACCATGCAG ACAGTTGTGT TTGTCGTGCT ⇒ WNV E
      · L  L  L   V  A  P  A   Y  S  F   N  C  L   G  M  S  N   R  D  F  ·
2161  ATTGCTTTTG GTGGCCCCAG CTTACAGCTT CAACTGCCTT GGAATGAGCA ACAGAGACTT · L  E  G   V  S  G  A   T  W  V   D  L  V   L  E  G  D   S  C  V  ·
2221  CTTGGAAGGA GTGTCTGGAG CAACATGGGT GGATTTGGTT CTCGAAGGCG ACAGCTGCGT · T  I  M   S  K  D  K   P  T  I   D  V  K   M  M  N  M   E  A  A  ·
2281  GACTATCATG TCTAAGGACA AGCCTACCAT CGATGTGAAG ATGATGAATA TGGAGGCGGC · N  L  A   E  V  R  S   Y  C  Y   L  A  T   V  S  D  L   S  T  K  ·
2341  CAACCTGGCA GAGGTCCGCA GTTATTGCTA TTTGGCTACC GTCAGCGATC TCTCCACCAA · A  A  C   P  T  M  G   E  A  H   N  D  K   R  A  D  P   A  F  V  ·
2401  AGCTGCGTGC CCGACCATGG GAGAAGCTCA CAATGACAAA CGTGCTGACC CAGCTTTTGT · C  R  Q   G  V  V  D   R  G  W   G  N  G   C  G  L  F   G  K  G  ·
2461  GTGCAGACAA GGAGTGGTGG ACAGGGGCTG GGGCAACGGC TGCGGACTAT TTGGCAAAGG · S  I  D   T  C  A  K   F  A  C   S  T  K   A  I  G  R   T  I  L  ·
2521  AAGCATTGAC ACATGCGCCA AATTTGCCTG CTCTACCAAG GCAATAGGAA GAACCATCTT
```

Figure 4 continued

```
          . K   E   N     I   K   Y   E     V   A   I     F   V   H     G   P   T   T   V   E   S .
   2581   GAAAGAGAAT ATCAAGTACG AAGTGGCCAT CTTCGTGCAC GGACCAACTA CTGTGGAGTC

. H   G   N     Y   S   T   Q     V   G   A     T   Q   A     G   R   F   S   I   T   P .
   2641   GCACGGAAAC TACTCCACAC AGGTTGGAGC CACTCAGGCA GGGAGATTCA GCATCACTCC

. A   A   P     S   Y   T   L     K   L   G     E   Y   G     E   V   T   V   D   C   E .
   2701   TGCGGCGCCT TCATACACAC TAAAGCTTGG AGAATATGGA GAGGTGACAG TGGACTGTGA

. P   R   S     G   I   D   T     N   A   Y     Y   V   M     T   V   G   T   K   T   F .
   2761   ACCACGGTCA GGGATTGACA CCAATGCATA CTACGTGATG ACTGTTGGAA CAAAGACGTT

. L   V   H     R   E   W   F     M   D   L     N   L   P     W   S   S   A   G   S   T .
   2821   CTTGGTCCAT CGTGAGTGGT TCATGGACCT CAACCTCCCT TGGAGCAGTG CTGGAAGTAC

. V   W   R     N   R   E   T     L   M   E     F   E   E     P   H   A   T   K   Q   S .
   2881   TGTGTGGAGG AACAGAGAGA CGTTAATGGA GTTTGAGGAA CCACACGCCA CGAAGCAGTC

. V   I   A     L   G   S   Q     E   G   A     L   H   Q     A   L   A   G   A   I   P .
   2941   TGTGATAGCA TTGGGCTCAC AAGAGGGAGC TCTGCATCAA GCTTTGGCTG GAGCCATTCC

. V   E   F     S   S   N   T     V   K   L     T   S   G     H   L   K   C   R   V   K .
   3001   TGTGGAATTT TCAAGCAACA CTGTCAAGTT GACGTCGGGT CATTTGAAGT GTAGAGTGAA

. M   E   K     L   Q   L   K     G   T   T     Y   G   V     C   S   K   A   F   K   F .
   3061   GATGGAAAAA TTGCAGTTGA AGGGAACAAC CTATGGCGTC TGTTCAAAGG CTTTCAAGTT

. L   G   T     P   A   D   T     G   H   G     T   V   V     L   E   L   Q   Y   T   G .
   3121   TCTTGGGACT CCCGCAGACA CAGGTCACGG CACTGTGGTG TTGGAATTGC AGTACACTGG

. T   D   G     P   C   K   V     P   I   S     S   A   A     S   L   N   D   L   T   P .
   3181   CACGGATGGA CCTGCAAAG TTCCTATCTC GTCAGCGGCT TCATTGAACG ACCTAACGCC

. V   G   R     L   V   T   V     N   P   F     V   S   V     A   T   A   N   A   K   V .
   3241   AGTGGGCAGA TTGGTCACTG TCAACCCTTT TGTTTCAGTG GCCACGGCCA ACGCTAAGGT

. L   I   E     L   P   P   F     G   D   S     Y   I     V   V   G   R   G   E   Q .
   3301   CCTGATTGAA TTGGAACCAC CCTTTGGAGA CTCATACATA GTGGTGGGCA GAGGAGAACA

. Q   I   N     H   H   W   H     K   S   G     S   S   I     G   K   A   F   T   T   T .
   3361   ACAGATCAAT CACCATTGGC ACAAGTCTGG AAGCAGCATT GGCAAAGCCT TTACAACCAC

. L   K   G     A   Q   R   L     A   A   L     G   D   T     A   W   D   F   G   S   V .
   3421   CCTCAAAGGA GCGCAGAGAC TAGCCGCTCT AGGAGACACA GCTTGGGACT TTGGATCAGT

. G   G   V     F   T   S   V     G   K   A     V   H   Q     V   F   G   G   A   F   R .
   3481   TGGAGGGGTG TTCACCTCAG TTGGAAGGC TGTCCATCAA GTGTTCGGAG GAGCATTCCG

. S   L   F     G   G   M   S     W   I   T     Q   G   L     L   G   A   L   L   L   W .
   3541   CTCACTGTTC GGAGGCATGT CCTGGATAAC GCAAGGATTG CTGGGGGCTC TCCTGTTGTG

. M   G   I     N   A   R   D     R   S   I     A   L   T     F   L   A   V   G   G   V .
   3601   GATGGGCATC AATGCTCGTG ATAGGTCCAT AGCTCTCACG TTTCTCGCAG TTGGAGGAGT
```

Figure 4 continued

```
            . L   L   F     L   S   V   N     V   H   A
     3661   TCTGCTCTTC  CTCTCCGTGA  ACGTGCACGC  TTAATTTTTA  TCTAGAGTCG  AGTTTTTATT

==> FSL
     3721   GACTAGTTAA  TCATAAGATA  AATAATATAC  AGCATTGTAA  CCATCGTCAT  CCGTTATACG

3781   GGGAATAATA  TTACCATACA  GTATTATTAA  ATTTTCTTAC  GAAGAATATA  GATCGGTATT

3841   TATCGTTAGT  TTATTTTACA  TTTATTAATT  AAACATGTCT  ACTATTACCT  GTTATGAAA

3901   TGACAAATTT  AGTTATATAA  TTTATGATAA  AATTAAGATA  ATAATAATGA  AATCAAATAA

3961   TTATGTAAAT  GCTACTAGAT  TATGTGAATT  ACGAGGAAGA  AAGTTTACGA  ACTGGAAAAA

4021   ATTAAGTGAA  TCTAAAATAT  TAGTCGATAA  TGTAAAAAAA  ATAAATGATA  AAACTAACCA

4081   GTTAAAAACG  GATATGATTA  TATACGTTAA  GGATATTGAT  CATAAAGGAA  GAGATACTTG

4141   CGGTTACTAT  GTACACCAAG  ATCTGGTATC  TTCTATATCA  AATTGGATAT  CTCCGTTATT

4201   CGCCGTTAAG  GTAAATAAAA  TTATTAACTA  TTATATATGT  AATGAATATG  ATATACGACT

4261   TAGCGAAATG  GAATCTGATA  TGACAGAAGT  AATAGATGTA  GTTGATAAAT  TAGTAGGAGG

4321   ATACAATGAT  GAAATAGCAG  AAATAATATA  TTTGTTTAAT  AAATTTATAG  AAAATATAT

4381   TGCTAACATA  TCGTTATCAA  CTGAATTATC  TAGTATATTA  AATAATTTTA  TAAATTTTAA

4441   TAAAAAATAC  AATAACGACA  TAAAAGATAT  TAAATCTTTA  ATTCTTGATC  TGAAAAACAC

4501   ATCTATAAAA  CTAGATAAAA  AGTTATTCGA  TAAAGATAAT  AATGAATCGA  ACGATGAAAA

4561   ATTGGAAACA  GAAGTTGATA  AGCTAATTTT  TTTCATCTAA  ATAGTATTAT  TTTATTGAAG

4621   TACGAAGTTT  TACGTTAGAT  AAATAATAAA  GGTCGATTTT  TACTTTGTTA  AATATCAAAT

4681   ATGTCATTAT  CTGATAAAGA  TACAAAAACA  CACGGTGATT  ATCAACCATC  TAACGAACAG

4741   ATATTACAAA  AAATACGTCG  GACTATGGAA  AACGAAGCTG  ATAGCCTCAA  TAGAAGAAGC

4801   ATTAAAGAAA  TTGTTGTAGA  TGTTATGAAG  AATTGGGATC  ATCCTCTCAA  CGAAGAAATA

4861   GATAAAGTTC  TAAACTGGAA  AAATGATACA  TTAAACGATT  TAGATCATCT  AAATACAGAT

4921   GATAATATTA  AGGAAATCAT  ACAATGTCTG  ATTAGAGAAT  TTGCGTTTAA  AAAGATCAAT

4981   TCTATTATGT  ATAGTTATGC  TATGCTAAAA  CTCAATTCAG  ATAACGAAAC  ATTGAAAGAT

5041   AAAATTAAGG  ATTATTTTAT  AGAAACTATT  CTTAAAGACA  AACGTGGTTA  TAAACAAAAG

5101   CCATTACCC
```

Figure 5. Immunoblot analysis of the expression of WNV proteins from pox recombinants in CEFs Lane 1: ALVAC
Lane 2: Fowlpox
Lane 3: vCP2017 24h harvest
Lane 4: vCP2017 48h harvest
Lane 5: vCP2018 24h harvest
Lane 6: vCP2018 48h harvest
Lane 7: vFP2000 24h harvest
Lane 8: vFP2000 48h harvest vCP2017 = ALVAC WNV *prM-M-E*
vCP2018 = ALVAC-2 WNV *prM-M-E*
vFP2000 = Fowlpox WNV *prM-M-E*

Figure 6. Immunoblot analysis of the expression of WNV proteins from pox recombinants in BHK cells Lane 1: vFP2000.3.2.1.2.1 pellet
Lane 2: vCP2017.3.3 pellet
Lane 3: vCP2018.6.3.3.2 pellet
Lane 4: mock infected BHK pellet
Lane 5: pTriEx-WNV transfection pellet
Lane 6: mock transfected BHK pellet
Lane 7: vFP2000.3.2.1.2.1 supt
Lane 8: vCP2017.3.3 supt
Lane 9: vCP2018.6.3.3.2 supt
Lane 10: mock infected BHK supt
Lane 11: pTriEx-WNV transfection supt
Lane 12: mock transfection supt vCP2017 = ALVAC WNV
vCP2018 = ALVAC-2 WNV
vFP2000 = Fowlpox WNV Figure 7. Construction of pVR1012 WNV prM-M-E, pSL-5448-1-1.

Figure 8. Nucleotide sequence and translation of the WNV *prM-M-E* region in pSL-5448-1-1, pVR1012 WNV *prM-M-E*.

```
        PstI       Kozak          ⇒ WNV capsid leader
                              M   G   S   T   G   I   A   V   M   I   G   L   I   A   S   V ·
  1     CTGCAGCCGC CACCATGGGA TCAACCGGAA TTGCAGTCAT GATTGGCCTG ATCGCCAGCG ⇒ WNV prM
        .. G   A   V   T   L   S   N   F   Q   G   K   V   M   M   T   V   N   A   T   D ·
 61     TAGGCAGCAGT TACCCTCTCT AACTTCCAAG GGAAGGTGAT GATGACGGTA AATGCTACTG .. V   T   D   V   I   T   I   P   T   A   G   K   N   L   C   I   V   R   A ·
121     ACGTCACAGA TGTCATCACG ATTCCAACAG CTGCTGGAAA GAACCTATGC ATTGTCAGAG .. M   D   V   G   Y   M   C   D   D   T   I   T   Y   E   C   P   V   L   S   A ·
181     CAATGGATGT GGGATACATG TGCGATGATA CTATCACTTA TGAATGCCCA GTGCTGTCGG .. G   N   D   P   E   D   I   D   C   W   C   T   K   S   A   V   Y   V   R   Y ·
241     CTGGTAATGA TCCAGAAGAC ATCGACTGTT GGTGCACAAA GTCAGCAGTC TACGTCAGGT ⇒ WNV M
        .. G   R   C   T   K   T   R   H   S   R   R   S   R   R   S   L   T   V   Q   T ·
301     ATGGAAGATG CACCAAGACA CGCCACTCAA GACGCAGTCG GAGGTCACTG ACAGTGCAGA .. H   G   E   S   T   L   A   N   K   K   G   A   W   M   D   S   T   K   A   T ·
361     CACACGGAGA AAGCACTCTA GCGAACAAGA AGGGGGCTTG GATGGACAGC ACCAAGGCCA .. R   Y   L   V   K   T   E   S   W   I   L   R   N   P   G   Y   A   L   V   A ·
421     CAAGGTATTT GGTAAAAACA GAATCATGGA TCTTGAGGAA CCCTGGATAT GCCCTGGTGG .. A   V   I   G   W   M   L   G   S   N   T   M   Q   R   V   V   F   V   V   L ·
481     CAGCCGTCAT TGGTTGGATG CTTGGGAGCA ACACCATGCA GAGAGTTGTG TTTGTCGTGC ⇒ WNV E
        .. L   L   L   V   A   P   A   Y   S   F   N   C   L   G   M   S   N   R   D   F ·
541     TATTGCTTTT GGTGGCCCCA GCTTACAGCT TCAACTGCCT TGGAATGAGC AACAGAGACT .. L   E   G   V   S   G   A   T   W   V   D   L   V   L   E   G   D   S   C   V ·
601     TCTTGGAAGG AGTGTCTGGA GCAACATGGG TGGATTTGGT TCTCGAAGGC GACAGCTGCG ClaI
        .. T   I   M   S   K   D   K   P   T   I   D   V   K   M   M   N   M   E   A   A ·
661     TGACTATCAT GTCTAAGGAC AAGCCTACCA TCGATGTGAA GATGATGAAT ATGGAGGCGG .. N   L   A   E   V   R   S   Y   C   Y   L   A   T   V   S   D   L   S   T   K ·
721     CCAACCTGGC AGAGGTCCGC AGTTATTGCT ATTTGGCTAC CGTCAGCGAT CTCTCCACCA .. A   A   C   P   T   M   G   E   A   H   N   D   K   R   A   D   P   A   F   V ·
781     AAGCTGCGTG CCCGACCATG GGAGAAGCTC ACAATGACAA ACGTGCTGAC CCAGCTTTTG .. C   R   Q   G   V   V   D   R   G   W   G   N   G   C   G   L   F   G   K   G ·
841     TGTGCAGACA AGGAGTGGTG GACAGGGGCT GGGGCAACGG CTGCGGACTA TTTGGCAAAG .. S   I   D   T   C   A   K   F   A   C   S   T   K   A   I   G   R   T   I   L ·
901     GAAGCATTGA CACATGCGCC AAATTTGCCT GCTCTACCAA GGCAATAGGA AGAACCATCT .. K   E   N   I   K   Y   E   V   A   I   F   V   H   G   P   T   T   V   E   S ·
961     TGAAAGAGAA TATCAAGTAC GAAGTGGCCA TTTTTGTCCA TGGACCAACT ACTGTGGAGT
```

Figure 8 continued

```
             .. H  G  N    Y  S  T    Q  V  G    A  T  Q    A    G  R  F    S  I  T  P  ·
     1021    CGCACGGAAA CTACTCCACA CAGGTTGGAG CCACTCAGGC AGGGAGATTC AGCATCACTC

.. A  A  P    S  Y  T    L  K  L    G  E  Y    G    E  V  T    V  D  C  E  ·
     1081    CTGCGGCGCC TTCATACACA CTAAAGCTTG GAGAATATGG AGAGGTGACA GTGGACTGTG

.. P  R  S    G  I  D    T  N  A    Y  V  M    T    V  G  T    K  T  F  ·
     1141    AACCACGGTC AGGGATTGAC ACCAATGCAT ACTACGTGAT GACTGTTGGA ACAAAGACGT

.. L  V  H    R  E  W    F  M  D    L  N  L    P    W  S  S    A  G  S  T  ·
     1201    TCTTGGTCCA TCGTGAGTGG TTCATGGACC TCAACCTCCC TTGGAGCAGT GCTGGAAGTA

.. V  W  R    N  R  E    T  L  M    E  F  E    E    F  H  A    T  K  Q  S  ·
     1261    CTGTGTGGAG GAACAGAGAG ACGTTAATGG AGTTTGAGGA ACCACACGCC ACGAAGCAGT

.. V  I  A    L  G  S    Q  E  G    A  L  H    Q    A  L  A    G  A  I  P  ·
     1321    CTGTGATAGC ATTGGGCTCA CAAGAGGGAG CTCTGCATCA AGCTTGGCT  GGAGCCATTC

.. V  E  F    S  S  N    T  V  K    L  T  S    G    H  L  K    C  R  V  K  ·
     1381    CTGTGGAATT TTCAAGCAAC ACTGTCAAGT TGACGTCGGG TCATTTGAAG TGTAGAGTGA

.. M  E  K    L  Q  L    K  G  T    T  Y  G    V    C  S  K    A  F  K  F  ·
     1441    AGATGGAAAA ATTGCAGTTG AAGGGAACAA CCTATGGCGT CTGTTCAAAG GCTTTCAAGT

.. L  G  T    P  A  D    T  G  H    G  T  V    V    L  E  L    Q  Y  T  G  ·
     1501    TCTTGGGAC  TCCCGCAGAC ACAGGTCACG GCACTGTGGT GTTGGAATTG CAGTACACTG

.. T  D  G    P  C  K    V  P  I    S  A  A    S    L  N  D    L  T  F  ·
     1561    GCACGGATGG ACCTTGCAAA GTTCCTATCT CGTCAGCGGC TTCATTGAAC GACCTAACGC

.. V  G  R    L  V  T    V  N  P    F  V  S    V    A  T  A    N  A  K  V  ·
     1621    CAGTGGGCAG ATTGGTCACT GTCAACCCTT TTGTTTCAGT GGCCACGGCC AACGCTAAGG

.. L  I  E    L  E  P    P  F  G    D  S  Y    I    V  V  G    R  G  E  Q  ·
     1681    TCCTGATTGA ATTGGAACCA CCCTTTGGAG ACTCATACAT AGTGGTGGGC AGAGGAGAAC

.. Q  I  N    H  H  W    H  K  S    G  S  S    I    G  K  A    F  T  T  T  ·
     1741    AACAGATCAA TCACCATTGG CACAAGTCTG GAAGCAGCAT TGGCAAAGCC TTTACAACCA

.. L  K  G    A  Q  R    L  A  A  L    G  D    T    A  W  D    F  G  S  V  ·
     1801    CCCTCAAAGG AGCGCAGAGA CTAGCCGCTC TAGGAGACAC AGCTTGGGAC TTTGGATCAG

.. G  G  V    F  T  S    V  G  K    A  V  H    Q    V  F  G    G  A  F  R  ·
     1861    TTGGAGGGGT GTTCACCTCA GTTGGGAAGG CTGTCCATCA AGTGTTCGGA GGAGCATTCC

.. S  L  F    G  G  M    S  W  I    T  Q  G    L    L  G  A    L  L  L  W  ·
     1921    GCTCACTGTT CGGAGGCATG TCCTGGATAA CGCAAGGATT GCTGGGGGCT CTCCTGTTGT

.. M  G  I    N  A  R    D  R  S    I  A  L    T    F  L  A    V  G  G  V  ·
     1981    GGATGGGCAT CAATGCTCGT GATAGGTCCA TAGCTCTCAC GTTTCTCGCA GTTGGAGGAG
                                                                       XbaI
             .. L  L  F    L  S  V    N  V  H    A
     2041    TTCTGCTCTT CCTCTCCGTG AACGTGCACG CTTAATTTTT A TCTAGA
```

FIGURE 9
Sequence of pDS-2946-1-1, pC5 H6p WNV *prM-M-E*.

```
   1    GCGCCCAATACGCAAACCGCCTCTCCCCGCGCGTTGGCCGATTCATTAATGCAGCTGGCA
  61    CGACAGGTTTCCCGACTGGAAAGCGGGCAGTGAGCGCAACGCAATTAATGTGAGTTAGCT
 121    CACTCATTAGGCACCCCAGGCTTTACACTTTATGCTTCCGGCTCGTATGTTGTGTGGAAT
                                                              ⇒ C5R
 181    TGTGAGCGGATAACAATTTCACACAGGAAACAGCTATGACCATGATTACGAATTGCGGCC
 241    GCAATTCTGAATGTTAAATGTTATACTTTGGATGAAGCTATAAATATGCATTGGAAAAAT
 301    AATCCATTTAAAGAAAGGATTCAAATACTACAAAACCTAAGCGATAATATGTTAACTAAG
 361    CTTATTCTTAACGACGCTTTAAATATACACAAATAAACATAATTTTGTATAACCTAACA
 421    AATAACTAAAACATAAAAATAATAAAAGGAAATGTAATATCGTAATTATTTACTCAGGA
 481    ATGGGGTTAAATATTTATATCACGTGTATATCTATACTGTTATCGTATACTCTTTACAAT
 541    TACTATTACGAATATGCAAGAGATAATAAGATTACGTATTTAAGAGAATCTTGTCATGAT
 601    AATTGGGTACGACATAGTGATAAATGCTATTTCGCATCGTTACATAAAGTCAGTTGGAAA
 661    GATGGATTTGACAGATGTAACTTAATAGGTGCAAAAATGTTAAATAACAGCATTCTATCG
 721    GAAGATAGGATACCAGTTATATTATACAAAAATCACTGGTTGGATAAAACAGATTCTGCA
 781    ATATTCGTAAAAGATGAAGATTACTGCGAATTTGTAAACTATGACAATAAAAAGCCATTT
 841    ATCTCAACGACATCGTGTAATTCTTCCATGTTTTATGTATGTGTTTCAGATATTATGAGA
 901    TTACTATAAACTTTTTGTATACTTATATTCCGTAAACTATATTAATCATGAAGAAAATGA
 961    AAAAGTATAGAAGCTGTTCACGAGCGGTTGTTGAAAACAACAAAATTATACATTCAAGAT
1021    GGCTTACATATACGTCTGTGAGGCTATCATGGATAATGACAATGCATCTCTAAATAGGTT
1081    TTTGGACAATGGATTCGACCCTAACACGGAATATGGTACTCTACAATCTCCTCTTGAAAT
1141    GGCTGTAATGTTCAAGAATACCGAGGCTATAAAAATCTTGATGAGGTATGGAGCTAAACC
1201    TGTAGTTACTGAATGCACAACTTCTTGTCTGCATGATGCGGTGTTGAGAGACGACTACAA
1261    AATAGTGAAAGATCTGTTGAAGAATAACTATGTAAACAATGTTCTTTACAGCGGAGGCTT
1321    TACTCCTTTGTGTTTGGCAGCTTACCTTAACAAAGTTAATTTGGTTAAACTTCTATTGGC
1381    TCATTCGGCGGATGTAGATATTTCAAACACGGATCGGTTAACTCCTCTACATATAGCCGT
1441    ATCAAATAAAAATTTAACAATGGTTAAACTTCTATTGAACAAAGGTGCTGATACTGACTT
1501    GCTGGATAACATGGATGTACTCCTTTAATGATCGCTGTACAATCTGGAAATATTGAAAT
```

Figure 9 continued

```
1561  ATGTAGCACACTACTTAAAAAAAATAAAATGTCCAGAACTGGGAAAAATTGATCTTGCCA

1621  GCTGTAATTCATGGTAGAAAAGAAGTGCTCAGGCTACTTTTCAACAAAGGAGCAGATGTA

1681  AACTACATCTTTGAAAGAAATGGAAAATCATATACTGTTTTGGAATTGATTAAAGAAAGT

1741  TACTCTGAGACACAAAGAGGTAGCTGAAGTGGTACTCTCAAAGGTACGTGACTAATTAG

1801  CTATAAAAAGGATCCGGGTTAATTAATTAGTCATCAGGCAGGGCGAGAACGAGACTATCT

⇒ H6p
1861  GCTCGTTAATTAATTAGAGCTTCTTTATTCTATACTTAAAAAGTGAAAATAAATACAAAG

1921  GTTCTTGAGGGTTGTGTTAAATTGAAAGCGAGAAATAATCATAAATTATTTCATTATCGC

⇒ WNV capsid leader
                            M  T  G  I  A  V  M  I  G  L  I  A
1981  GATATCCGTTAAGTTTGTATCGTAATGACCGGAATTGCAGTCATGATTGGCCTGATCGCC ⇒ WNV prM start
      S  V  G  A  V  T  L  S  N  F  Q  G  K  V  M  M  T  V  N  A
2041  AGCGTAGGAGCGGTTACCCTCTCTAACTTCCAAGGGAAGGTGATGATGACGGTAAATGCT T  D  V  T  D  V  I  T  I  P  T  A  A  G  K  N  L  C  I  V
2101  ACTGACGTCACAGATGTCATCACGATTCCAACAGCTGCTGGAAAGAACCTATGCATTGTC R  A  M  D  V  G  Y  M  C  D  D  T  I  T  Y  E  C  P  V  L
2161  AGAGCAATGGATGTGGGATACATGTGCGATGATACTATCACTTATGAATGCCCAGTGCTG S  A  G  N  D  P  E  D  I  D  C  W  C  T  K  S  A  V  Y  V
2221  TCGGCTGGTAATGATCCAGAAGACATCGACTGTTGGTGCACAAAGTCAGCAGTCTACGTC ⇒ WNV M start
      R  Y  G  R  C  T  K  T  R  H  S  R  R  S  R  R  S  L  T  V
2281  AGGTATGGAAGATGCACCAAGACACGCCACTCAAGACGCAGTCGGAGGTCACTGACAGTG Q  T  H  G  E  S  T  L  A  N  K  K  G  A  W  M  D  S  T  K
2341  CAGACACACGGAGAAAGCACTCTAGCGAACAAGAAGGGGGCTTGGATGGACAGCACCAAG A  T  R  Y  L  V  K  T  E  S  W  I  L  R  N  P  G  Y  A  L
2401  GCCACAAGGTATTTGGTAAAAACAGAATCATGGATCTTGAGGAACCCTGGATATGCCCTG V  A  A  V  I  G  W  M  L  G  S  N  T  M  Q  R  V  V  F  V
2461  GTGGCAGCCGTCATTGGTTGGATGCTTGGGAGCAACACCATGCAGAGAGTTGTGTTTGTC ⇒ WNV E start
      V  L  L  L  V  A  P  A  Y  S  F  N  C  L  G  M  S  N  R
2521  GTGCTATTGCTTTTGGTGGCCCCAGCTTACAGCTTCAACTGCCTTGGAATGAGCAACAGA D  F  L  E  G  V  S  G  A  T  W  V  D  L  V  L  E  G  D  S
2581  GACTTCTTGGAAGGAGTGTCTGGAGCAACATGGGTGGATTTGGTTCTCGAAGGCGACAGC
```

Figure 9 continued

```
            C  V  T  I  M  S  K  D  K  P  T  I  D  V  K  M  M  N  M  E
2641    TGCGTGACTATCATGTCTAAGGACAAGCCTACCATCGATGTGAAGATGATGAATATGGAG

A  A  N  L  A  E  V  R  S  Y  C  Y  L  A  T  V  S  D  L  S
2701    GCGGCCAACCTGGCAGAGGTCCGCAGTTATTGCTATTTGGCTACCGTCAGCGATCTCTCC

T  K  A  A  C  P  T  M  G  E  A  H  N  D  K  R  A  D  P  A
2761    ACCAAAGCTGCGTGCCCGACCATGGGAGAAGCTCACAATGACAAACGTGCTGACCCAGCT

F  V  C  R  Q  G  V  V  D  R  G  W  G  N  G  C  G  L  F  G
2821    TTTGTGTGCAGACAAGGAGTGGTGGACAGGGGCTGGGGCAACGGCTGCGGACTATTTGGC

K  G  S  I  D  T  C  A  K  F  A  C  S  T  K  A  I  G  R  T
2881    AAAGGAAGCATTGACACATGCGCCAAATTTGCCTGCTCTACCAAGGCAATAGGAAGAACC mutated T5NT
            I  L  K  E  N  I  K  Y  E  V  A  I  F  V  H  G  P  T  T  V
2941    ATCTTGAAAGAGAATATCAAGTACGAAGTGGCCATCTTCGTGCACGGACCAACTACTGTG E  S  H  G  N  Y  S  T  Q  V  G  A  T  Q  A  G  R  F  S  I
3001    GAGTCGCACGGAAACTACTCCACACAGGTTGGAGCCACTCAGGCAGGGAGATTCAGCATC T  P  A  A  P  S  Y  T  L  K  L  G  E  Y  G  E  V  T  V  D
3061    ACTCCTGCGGCGCCTTCATACACACTAAAGCTTGGAGAATATGGAGAGGTGACAGTGGAC C  E  P  R  S  G  I  D  T  N  A  Y  Y  V  M  T  V  G  T  K
3121    TGTGAACCACGGTCAGGGATTGACACCAATGCATACTACGTGATGACTGTTGGAACAAAG T  F  L  V  H  R  E  W  F  M  D  L  N  L  P  W  S  S  A  G
3181    ACGTTCTTGGTCCATCGTGAGTGGTTCATGGACCTCAACCTCCCTTGGAGCAGTGCTGGA S  T  V  W  R  N  R  E  T  L  M  E  F  E  E  P  H  A  T  K
3241    AGTACTGTGTGGAGGAACAGAGAGACGTTAATGGAGTTTGAGGAACCACACGCCACGAAG Q  S  V  I  A  L  G  S  Q  E  G  A  L  H  Q  A  L  A  G  A
3301    CAGTCTGTGATAGCATTGGGCTCACAAGAGGGAGCTCTGCATCAAGCTTTGGCTGGAGCC I  P  V  E  F  S  S  N  T  V  K  L  T  S  G  H  L  K  C  R
3361    ATTCCTGTGGAATTTTCAAGCAACACTGTCAAGTTGACGTCGGGTCATTTGAAGTGTAGA V  K  M  E  K  L  Q  L  K  G  T  T  Y  G  V  C  S  K  A  F
3421    GTGAAGATGGAAAAATTGCAGTTGAAGGGAACAACCTATGGCGTCTGTTCAAAGGCTTTC K  F  L  G  T  P  A  D  T  G  H  G  T  V  V  L  E  L  Q  Y
3481    AAGTTTCTTGGGACTCCCGCAGACACAGGTCACGGCACTGTGGTGTTGGAATTGCAGTAC T  G  T  D  G  P  C  K  V  P  I  S  S  A  A  S  L  N  D  L
3541    ACTGGCACGGATGGACCTTGCAAAGTTCCTATCTCGTCAGCGGCTTCATTGAACGACCTA T  P  V  G  R  L  V  T  V  N  P  F  V  S  V  A  T  A  N  A
3601    ACGCCAGTGGGCAGATTGGTCACTGTCAACCCTTTTGTTTCAGTGGCCACGGCCAACGCT K  V  L  I  E  L  P  P  F  G  D  S  Y  I  V  V  G  R  G
3661    AAGGTCCTGATTGAATTGGAACCACCCTTTGGAGACTCATACATAGTGGTGGGCAGAGGA
```

Figure 9 continued

```
            E  Q  Q  I  N  H  H  W  H  K  S  G  S  S  I  G  K  A  F  T
   3721     GAACAACAGATCAATCACCATTGGCACAAGTCTGGAAGCAGCATTGGCAAAGCCTTTACA

T  T  L  K  G  A  Q  R  L  A  A  L  G  D  T  A  W  D  F  G
   3781     ACCACCCTCAAAGGAGCGCAGAGACTAGCCGCTCTAGGAGACACAGCTTGGGACTTTGGA

S  V  G  G  V  F  T  S  V  G  K  A  V  H  Q  V  F  G  G  A
   3841     TCAGTTGGAGGGGTGTTCACCTCAGTTGGGAAGGCTGTCCATCAAGTGTTCGGAGGAGCA

F  R  S  L  F  G  G  M  S  W  I  T  Q  G  L  L  G  A  L  L
   3901     TTCCGCTCACTGTTCGGAGGCATGTCCTGGATAACGCAAGGATTGCTGGGGCTCTCCTG

L  W  M  G  I  N  A  R  D  R  S  I  A  L  T  F  L  A  V  G
   3961     TTGTGGATGGGCATCAATGCTCGTGATAGGTCCATAGCTCTCACGTTTCTCGCAGTTGGA

⇒ C5L
            G  V  L  L  F  L  S  V  N  V  H  A  *
   4021     GGAGTTCTGCTCTTCCTCTCCGTGAACGTGCACGCTTAATTTTTATCTAGAATCGATCCC

4081     GGGTTTTTATGACTAGTTAATCACGGCCGCTTATAAAGATCTAAAATGCATAATTTCTAA

4141     ATAATGAAAAAAAGTACATCATGAGCAACGCGTTAGTATATTTTACAATGGAGATTAACG

4201     CTCTATACCGTTCTATGTTTATTGATTCAGATGATGTTTTAGAAAAGAAAGTTATTGAAT

4261     ATGAAAACTTTAATGAAGATGAAGATGACGACGATGATTATTGTTGTAAATCTGTTTTAG

4321     ATGAAGAAGATGACGCGCTAAAGTATACTATGGTTACAAAGTATAAGTCTATACTACTAA

4381     TGGCCACTTGTGCAACAAGGTATAGTATACTGAAAATGTTGTTAGATTATGATTATGAAA

4441     AACCAAATAAATCAGATCCATATCTAAAGGTATCTCCTTTGCACATAATTTCATCTATTC

4501     CTAGTTTAGAATACCTGCAGCCAAGCTTGGCACTGGCCGTCGTTTTACAACGTCGTGACT

4561     GGGAAAACCCTGGCGTTACCCAACTTAATCGCCTTGCAGCACATCCCCCTTTCGCCAGCT

4621     GGCGTAATAGCGAAGAGGCCCGCACCGATCGCCCTTCCCAACAGTTGCGCAGCCTGAATG

4681     GCGAATGGCGCCTGATGCGGTATTTTCTCCTTACGCATCTGTGCGGTATTTCACACCGCA

4741     TATGGTGCACTCTCAGTACAATCTGCTCTGATGCCGCATAGTTAAGCCAGCCCCGACACC

4801     CGCCAACACCCGCTGACGCGCCCTGACGGGCTTGTCTGCTCCCGGCATCCGCTTACAGAC

4861     AAGCTGTGACCGTCTCCGGGAGCTGCATGTGTCAGAGGTTTTCACCGTCATCACCGAAAC

4921     GCGCGAGACGAAAGGGCCTCGTGATACGCCTATTTTTATAGGTTAATGTCATGATAATAA

4981     TGGTTTCTTAGACGTCAGGTGGCACTTTTCGGGGAAATGTGCGCGGAACCCCTATTTGTT

5041     TATTTTTCTAAATACATTCAAATATGTATCCGCTCATGAGACAATAACCCTGATAAATGC

5101     TTCAATAATATTGAAAAGGAAGAGTATGAGTATTCAACATTTCCGTGTCGCCCTTATTC
```

Figure 9 continued

```
5161  CCTTTTTTGCGGCATTTTGCCTTCCTGTTTTTGCTCACCCAGAAACGCTGGTGAAAGTAA
5221  AAGATGCTGAAGATCAGTTGGGTGCACGAGTGGGTTACATCGAACTGGATCTCAACAGCG
5281  GTAAGATCCTTGAGAGTTTTCGCCCCGAAGAACGTTTTCCAATGATGAGCACTTTTAAAG
5341  TTCTGCTATGTGGCGCGGTATTATCCCGTATTGACGCCGGGCAAGAGCAACTCGGTCGCC
5401  GCATACACTATTCTCAGAATGACTTGGTTGAGTACTCACCAGTCACAGAAAAGCATCTTA
5461  CGGATGGCATGACAGTAAGAGAATTATGCAGTGCTGCCATAACCATGAGTGATAACACTG
5521  CGGCCAACTTACTTCTGACAACGATCGGAGGACCGAAGGAGCTAACCGCTTTTTTGCACA
5581  ACATGGGGGATCATGTAACTCGCCTTGATCGTTGGGAACCGGAGCTGAATGAAGCCATAC
5641  CAAACGACGAGCGTGACACCACGATGCCTGTAGCAATGGCAACAACGTTGCGCAAACTAT
5701  TAACTGGCGAACTACTTACTCTAGCTTCCCGGCAACAATTAATAGACTGGATGGAGGCGG
5761  ATAAAGTTGCAGGACCACTTCTGCGCTCGGCCCTTCCGGCTGGCTGGTTTATTGCTGATA
5821  AATCTGGAGCCGGTGAGCGTGGGTCTCGCGGTATCATTGCAGCACTGGGGCCAGATGGTA
5881  AGCCCTCCCGTATCGTAGTTATCTACACGACGGGGAGTCAGGCAACTATGGATGAACGAA
5941  ATAGACAGATCGCTGAGATAGGTGCCTCACTGATTAAGCATTGGTAACTGTCAGACCAAG
6001  TTTACTCATATATACTTTAGATTGATTTAAAACTTCATTTTTAATTTAAAAGGATCTAGG
6061  TGAAGATCCTTTTTGATAATCTCATGACCAAAATCCCTTAACGTGAGTTTTCGTTCCACT
6121  GAGCGTCAGACCCCGTAGAAAAGATCAAAGGATCTTCTTGAGATCCTTTTTTTCTGCGCG
6181  TAATCTGCTGCTTGCAAACAAAAAAACCACCGCTACCAGCGGTGGTTTGTTTGCCGGATC
6241  AAGAGCTACCAACTCTTTTTCCGAAGGTAACTGGCTTCAGCAGAGCGCAGATACCAAATA
6301  CTGTCCTTCTAGTGTAGCCGTAGTTAGGCCACCACTTCAAGAACTCTGTAGCACCGCCTA
6361  CATACCTCGCTCTGCTAATCCTGTTACCAGTGGCTGCTGCCAGTGGCGATAAGTCGTGTC
6421  TTACCGGGTTGGACTCAAGACGATAGTTACCGGATAAGGCGCAGCGGTCGGGCTGAACGG
6481  GGGGTTCGTGCACACAGCCCAGCTTGGAGCGAACGACCTACACCGAACTGAGATACCTAC
6541  AGCGTGAGCTATGAGAAAGCGCCACGCTTCCCGAAGGGAGAAAGGCGGACAGGTATCCGG
6601  TAAGCGGCAGGGTCGGAACAGGAGAGCGCACGAGGGAGCTTCCAGGGGGAAACGCCTGGT
6661  ATCTTTATAGTCCTGTCGGGTTTCGCCACCTCTGACTTGAGCGTCGATTTTTGTGATGCT
6721  CGTCAGGGGGCGGAGCCTATGGAAAAACGCCAGCAACGCGGCCTTTTTACGGTTCCTGG
6781  CCTTTTGCTGGCCTTTTGCTCACATGTTCTTTCCTGCGTTATCCCCTGATTCTGTGGATA
```

Figure 9 continued

6841    ACCGTATTACCGCCTTTGAGTGAGCTGATACCGCTCGCCGCAGCCGAACGACCGAGCGCA

6901    GCGAGTCAGTGAGCGAGGAAGCGGAAGA

FIGURE 10
Construction of pC5 H6p WNV *prM-M-E* donor plasmids with a truncated H6p +/- truncated WNV capsid leader sequence.

FIGURE 11
ALVAC WNV constructs with truncated H6p +/- truncated leader sequence

Explanation of terms:

H6p (t) is the truncated H6p promoter deleted between Nru I and the 3'-end

WNV-L (t) refers to the truncated WNV capsid leader, which is missing the initiating Met, so results in a shorter leader sequence

H6p 5'-WNV sequence in actual vCP2017:

```
                           ⇒ H6p
1861    GCTCGTTAATTAATTAGAGCTTCTTTATTCTATACTTAAAAAGTGAAAATAAATACAAAG

Nru I
1921    GTTCTTGAGGGTTGTGTTAAATTGAAAGCGAGAAATAATCATAAATTATTTCATTA TCGC

⇒ WNV capsid leader
                          M  T  G  I  A  V  M  I  G  L  I  A
1981    GA TATCCGTTAAGTTTGTATCGTAATGACCGGAATTGCAGTCATGATTGGCCTGATCGCC ⇒ WNV prM start
         S  V  G  A  V  T  L  S  N  F  Q  G  K  V  M  M  T  V  N  A
2041    AGCGTAGGAGCGGTTACCCTCTCTAACTTCCAAGGGAAGGTGATGATGACGGTAAATGCT T  D  V  T  D  V  I  T  I  P  T  A  A  G  K  N  L  C  I  V
2101    ACTGACGTCACAGATGTCATCACGATTCCAACAGCTGCTGGAAAGAACCTATGCATTGTC
```

**PCR primers for H6p (t) WNV *prM-M-E* WNV-L (t):**

```
                         ⇒ WNV capsid
               NruI    T  G  I  A  V  M  I  G  L
11344.SL   5'  ATTATCGCGAACCGGAATTGCAGTCATGATTGGCCTG
```

```
               K  P  T  I  D  V  K  M
               AAGCCTACCATCGATGTGAAGATG
7616.SL    3'  TTCGGATGGTAGCTACACTTCTAC
                         Cla I
```

**PCR primers for H6p (t) WNV *prM-M-E*:**

```
                         ⇒ WNV capsid
               NruI  M  T  G  I  A  V  M  I  G  L
11345.SL   5'  ATTATCGCGAATGACCGGAATTGCAGTCATGATTGGCCTG
```

FIGURE 12

```
agtagttcgc ctgtgtgagc tgacaaactt agtagtgttt gtgaggatta acaacaatta
60 acacagtgcg agctgtttct tagcacgaag atctcg atg tct aag aaa cca gga
114
                                        Met Ser Lys Lys Pro Gly
                                        1             5 ggg ccc ggc aag agc cgg gct gtc aat atg cta aaa cgc gga atg ccc
162
Gly Pro Gly Lys Ser Arg Ala Val Asn Met Leu Lys Arg Gly Met Pro
            10              15              20 cgc gtg ttg tcc ttg att gga ctg aag agg gct atg ttg agc ctg atc
210
Arg Val Leu Ser Leu Ile Gly Leu Lys Arg Ala Met Leu Ser Leu Ile
        25              30              35 gac ggc aag ggg cca ata cga ttt gtg ttg gct ctc ttg gcg ttc ttc
258
Asp Gly Lys Gly Pro Ile Arg Phe Val Leu Ala Leu Leu Ala Phe Phe
    40              45              50 agg ttc aca gca att gct ccg acc cga gca gtg ctg gat cga tgg aga
306
Arg Phe Thr Ala Ile Ala Pro Thr Arg Ala Val Leu Asp Arg Trp Arg
55          60              65                  70 ggt gtg aac aaa caa aca gcg atg aaa cac ctt ctg agt ttt aag aag
354
Gly Val Asn Lys Gln Thr Ala Met Lys His Leu Leu Ser Phe Lys Lys
                75              80              85 gaa cta ggg acc ttg acc agt gct atc aat cgg cgg agc tca aaa caa
402
Glu Leu Gly Thr Leu Thr Ser Ala Ile Asn Arg Arg Ser Ser Lys Gln
            90              95              100 aag aaa aga gga gga aag acc gga att gca gtc atg att ggc ctg atc
450
Lys Lys Arg Gly Gly Lys Thr Gly Ile Ala Val Met Ile Gly Leu Ile
        105             110             115 gcc agc gta gga gca gtt acc ctc tct aac ttc caa ggg aag gtg atg
498
Ala Ser Val Gly Ala Val Thr Leu Ser Asn Phe Gln Gly Lys Val Met
    120             125             130
```

Figure 12 continued

```
atg acg gta aat gct act gac gtc aca gat gtc atc acg att cca aca
546
Met Thr Val Asn Ala Thr Asp Val Thr Asp Val Ile Thr Ile Pro Thr
135                 140                 145                 150 gct gct gga aag aac cta tgc att gtc aga gca atg gat gtg gga tac
594
Ala Ala Gly Lys Asn Leu Cys Ile Val Arg Ala Met Asp Val Gly Tyr
                155                 160                 165 atg tgc gat gat act atc act tat gaa tgc cca gtg ctg tcg gct ggt
642
Met Cys Asp Asp Thr Ile Thr Tyr Glu Cys Pro Val Leu Ser Ala Gly
                170                 175                 180 aat gat cca gaa gac atc gac tgt tgg tgc aca aag tca gca gtc tac
690
Asn Asp Pro Glu Asp Ile Asp Cys Trp Cys Thr Lys Ser Ala Val Tyr
            185                 190                 195 gtc agg tat gga aga tgc acc aag aca cgc cac tca aga cgc agt cgg
738
Val Arg Tyr Gly Arg Cys Thr Lys Thr Arg His Ser Arg Arg Ser Arg
        200                 205                 210 agg tca ctg aca gtg cag aca cac gga gaa agc act cta gcg aac aag
786
Arg Ser Leu Thr Val Gln Thr His Gly Glu Ser Thr Leu Ala Asn Lys
215                 220                 225                 230 aag ggg gct tgg atg gac agc acc aag gcc aca agg tat ttg gta aaa
834
Lys Gly Ala Trp Met Asp Ser Thr Lys Ala Thr Arg Tyr Leu Val Lys
                235                 240                 245 aca gaa tca tgg atc ttg agg aac cct gga tat gcc ctg gtg gca gcc
882
Thr Glu Ser Trp Ile Leu Arg Asn Pro Gly Tyr Ala Leu Val Ala Ala
            250                 255                 260 gtc att ggt tgg atg ctt ggg agc aac acc atg cag aga gtt gtg ttt
930
Val Ile Gly Trp Met Leu Gly Ser Asn Thr Met Gln Arg Val Val Phe
            265                 270                 275 gtc gtg cta ttg ctt ttg gtg gcc cca gct tac agc ttc aac tgc ctt
978
Val Val Leu Leu Leu Leu Val Ala Pro Ala Tyr Ser Phe Asn Cys Leu
        280                 285                 290
```

Figure 12 continued

```
gga atg agc aac aga gac ttc ttg gaa gga gtg tct gga gca aca tgg
1026
Gly Met Ser Asn Arg Asp Phe Leu Glu Gly Val Ser Gly Ala Thr Trp
295                 300             305                 310 gtg gat ttg gtt ctc gaa ggc gac agc tgc gtg act atc atg tct aag
1074
Val Asp Leu Val Leu Glu Gly Asp Ser Cys Val Thr Ile Met Ser Lys
            315             320                 325 gac aag cct acc atc gat gtg aag atg atg aat atg gag gcg gcc aac
1122
Asp Lys Pro Thr Ile Asp Val Lys Met Met Asn Met Glu Ala Ala Asn
            330             335             340 ctg gca gag gtc cgc agt tat tgc tat ttg gct acc gtc agc gat ctc
1170
Leu Ala Glu Val Arg Ser Tyr Cys Tyr Leu Ala Thr Val Ser Asp Leu
        345             350             355 tcc acc aaa gct gcg tgc ccg acc atg gga gaa gct cac aat gac aaa
1218
Ser Thr Lys Ala Ala Cys Pro Thr Met Gly Glu Ala His Asn Asp Lys
    360             365             370 cgt gct gac cca gct ttt gtg tgc aga caa gga gtg gtg gac agg ggc
1266
Arg Ala Asp Pro Ala Phe Val Cys Arg Gln Gly Val Val Asp Arg Gly
375             380             385                 390 tgg ggc aac ggc tgc gga cta ttt ggc aaa gga agc att gac aca tgc
1314
Trp Gly Asn Gly Cys Gly Leu Phe Gly Lys Gly Ser Ile Asp Thr Cys
            395             400                 405 gcc aaa ttt gcc tgc tct acc aag gca ata gga aga acc atc ttg aaa
1362
Ala Lys Phe Ala Cys Ser Thr Lys Ala Ile Gly Arg Thr Ile Leu Lys
            410             415                 420 gag aat atc aag tac gaa gtg gcc att ttt gtc cat gga cca act act
1410
Glu Asn Ile Lys Tyr Glu Val Ala Ile Phe Val His Gly Pro Thr Thr
            425             430             435 gtg gag tcg cac gga aac tac tcc aca cag gtt gga gcc act cag gca
1458
Val Glu Ser His Gly Asn Tyr Ser Thr Gln Val Gly Ala Thr Gln Ala
    440             445             450
```

Figure 12 continued

```
ggg aga ttc agc atc act cct gcg gcg cct tca tac aca cta aag ctt
1506
Gly Arg Phe Ser Ile Thr Pro Ala Ala Pro Ser Tyr Thr Leu Lys Leu
455             460             465                 470 gga gaa tat gga gag gtg aca gtg gac tgt gaa cca cgg tca ggg att
1554
Gly Glu Tyr Gly Glu Val Thr Val Asp Cys Glu Pro Arg Ser Gly Ile
                475             480              485 gac acc aat gca tac tac gtg atg act gtt gga aca aag acg ttc ttg
1602
Asp Thr Asn Ala Tyr Tyr Val Met Thr Val Gly Thr Lys Thr Phe Leu
            490             495             500 gtc cat cgt gag tgg ttc atg gac ctc aac ctc cct tgg agc agt gct
1650
Val His Arg Glu Trp Phe Met Asp Leu Asn Leu Pro Trp Ser Ser Ala
        505             510             515 gga agt act gtg tgg agg aac aga gag acg tta atg gag ttt gag gaa
1698
Gly Ser Thr Val Trp Arg Asn Arg Glu Thr Leu Met Glu Phe Glu Glu
    520             525             530 cca cac gcc acg aag cag tct gtg ata gca ttg ggc tca caa gag gga
1746
Pro His Ala Thr Lys Gln Ser Val Ile Ala Leu Gly Ser Gln Glu Gly
535             540             545                 550 gct ctg cat caa gct ttg gct gga gcc att cct gtg gaa ttt tca agc
1794
Ala Leu His Gln Ala Leu Ala Gly Ala Ile Pro Val Glu Phe Ser Ser
                555             560             565 aac act gtc aag ttg acg tcg ggt cat ttg aag tgt aga gtg aag atg
1842
Asn Thr Val Lys Leu Thr Ser Gly His Leu Lys Cys Arg Val Lys Met
            570             575             580 gaa aaa ttg cag ttg aag gga aca acc tat ggc gtc tgt tca aag gct
1890
Glu Lys Leu Gln Leu Lys Gly Thr Thr Tyr Gly Val Cys Ser Lys Ala
        585             590             595 ttc aag ttt ctt ggg act ccc gca gac aca ggt cac ggc act gtg gtg
1938
Phe Lys Phe Leu Gly Thr Pro Ala Asp Thr Gly His Gly Thr Val Val
    600             605             610
```

Figure 12 continued

```
ttg gaa ttg cag tac act ggc acg gat gga cct tgc aaa gtt cct atc
1986
Leu Glu Leu Gln Tyr Thr Gly Thr Asp Gly Pro Cys Lys Val Pro Ile
615             620             625             630 tcg tca gtg gct tca ttg aac gac cta acg cca gtg ggc aga ttg gtc
2034
Ser Ser Val Ala Ser Leu Asn Asp Leu Thr Pro Val Gly Arg Leu Val
                635             640             645 act gtc aac cct ttt gtt tca gtg gcc acg gcc aac gct aag gtc ctg
2082
Thr Val Asn Pro Phe Val Ser Val Ala Thr Ala Asn Ala Lys Val Leu
            650             655             660 att gaa ttg gaa cca ccc ttt gga gac tca tac ata gtg gtg ggc aga
2130
Ile Glu Leu Glu Pro Pro Phe Gly Asp Ser Tyr Ile Val Val Gly Arg
        665             670             675 gga gaa caa cag atc aat cac cat tgg cac aag tct gga agc agc att
2178
Gly Glu Gln Gln Ile Asn His His Trp His Lys Ser Gly Ser Ser Ile
    680             685             690 ggc aaa gcc ttt aca acc acc ctc aaa gga gcg cag aga cta gcc gct
2226
Gly Lys Ala Phe Thr Thr Thr Leu Lys Gly Ala Gln Arg Leu Ala Ala
695             700             705             710 cta gga gac aca gct tgg gac ttt gga tca gtt gga ggg gtg ttc acc
2274
Leu Gly Asp Thr Ala Trp Asp Phe Gly Ser Val Gly Gly Val Phe Thr
            715             720             725 tca gtt ggg aag gct gtc cat caa gtg ttc gga gga gca ttc cgc tca
2322
Ser Val Gly Lys Ala Val His Gln Val Phe Gly Gly Ala Phe Arg Ser
        730             735             740 ctg ttc gga ggc atg tcc tgg ata acg caa gga ttg ctg ggg gct ctc
2370
Leu Phe Gly Gly Met Ser Trp Ile Thr Gln Gly Leu Leu Gly Ala Leu
    745             750             755 ctg ttg tgg atg ggc atc aat gct cgt gat agg tcc ata gct ctc acg
2418
Leu Leu Trp Met Gly Ile Asn Ala Arg Asp Arg Ser Ile Ala Leu Thr
    760             765             770
```

Figure 12 continued

```
ttt ctc gca gtt gga gga gtt ctg ctc ttc ctc tcc gtg aac gtg cac
2466
Phe Leu Ala Val Gly Gly Val Leu Leu Phe Leu Ser Val Asn Val His
775             780             785                 790 gct gac act ggg tgt gcc ata gac atc agc cgg caa gag ctg aga tgt
2514
Ala Asp Thr Gly Cys Ala Ile Asp Ile Ser Arg Gln Glu Leu Arg Cys
                795             800                 805 gga agt gga gtg ttc ata cac aat gat gtg gag gct tgg atg gac cgg
2562
Gly Ser Gly Val Phe Ile His Asn Asp Val Glu Ala Trp Met Asp Arg
            810             815                 820 tac aag tat tac cct gaa acg cca caa ggc cta gcc aag atc att cag
2610
Tyr Lys Tyr Tyr Pro Glu Thr Pro Gln Gly Leu Ala Lys Ile Ile Gln
        825             830             835 aaa gct cat aag gaa gga gtg tgc ggt cta cga tca gtt tcc aga ctg
2658
Lys Ala His Lys Glu Gly Val Cys Gly Leu Arg Ser Val Ser Arg Leu
    840             845             850 gag cat caa atg tgg gaa gca gtg aag gac gag ctg aac act ctt ttg
2706
Glu His Gln Met Trp Glu Ala Val Lys Asp Glu Leu Asn Thr Leu Leu
855             860             865                 870 aag gag aat ggt gtg gac ctt agt gtc gtg gtt gag aaa cag gag gga
2754
Lys Glu Asn Gly Val Asp Leu Ser Val Val Val Glu Lys Gln Glu Gly
            875             880                 885 atg tac aag tca gca cct aaa cgc ctc acc gcc acc acg gaa aaa ttg
2802
Met Tyr Lys Ser Ala Pro Lys Arg Leu Thr Ala Thr Thr Glu Lys Leu
        890             895             900 gaa att ggc tgg aag gcc tgg gga aag agt att tta ttt gca cca gaa
2850
Glu Ile Gly Trp Lys Ala Trp Gly Lys Ser Ile Leu Phe Ala Pro Glu
        905             910             915 ctc gcc aac aac acc ttt gtg gtt gat ggt ccg gag acc aag gaa tgt
2898
Leu Ala Asn Asn Thr Phe Val Val Asp Gly Pro Glu Thr Lys Glu Cys
    920             925             930
```

Figure 12 continued

```
ccg act cag aat cgc gct tgg aat agc tta gaa gtg gag gat ttt gga
                                                                    2946
Pro Thr Gln Asn Arg Ala Trp Asn Ser Leu Glu Val Glu Asp Phe Gly
935                 940             945                 950 ttt ggt ctc acc agc act cgg atg ttc ctg aag gtc aga gag agc aac
                                                                    2994
Phe Gly Leu Thr Ser Thr Arg Met Phe Leu Lys Val Arg Glu Ser Asn
            955                 960                 965 aca act gaa tgt gac tcg aag atc att gga acg gct gtc aag aac aac
                                                                    3042
Thr Thr Glu Cys Asp Ser Lys Ile Ile Gly Thr Ala Val Lys Asn Asn
            970                 975                 980 ttg gcg atc cac agt gac ctg tcc tat tgg att gaa agc agg ctc aat
                                                                    3090
Leu Ala Ile His Ser Asp Leu Ser Tyr Trp Ile Glu Ser Arg Leu Asn
        985                 990                 995 gat acg  tgg aag ctt gaa agg  gca gtt ctg ggt gaa  gtc aaa tca
                                                                    3135
Asp Thr  Trp Lys Leu Glu Arg  Ala Val Leu Gly Glu  Val Lys Ser
    1000                 1005                 1010 tgt acg  tgg cct gag acg cat  acc ttg tgg ggc gat  gga atc ctt
                                                                    3180
Cys Thr  Trp Pro Glu Thr His  Thr Leu Trp Gly Asp  Gly Ile Leu
    1015                 1020                 1025 gag agt  gac ttg ata ata cca  gtc aca ctg gcg gga  cca cga agc
                                                                    3225
Glu Ser  Asp Leu Ile Ile Pro  Val Thr Leu Ala Gly  Pro Arg Ser
    1030                 1035                 1040 aat cac  aat cgg aga cct ggg  tac aag aca caa aac  cag ggc cca
                                                                    3270
Asn His  Asn Arg Arg Pro Gly  Tyr Lys Thr Gln Asn  Gln Gly Pro
    1045                 1050                 1055 tgg gac  gaa ggc cgg gta gag  att gac ttc gat tac  tgc cca gga
                                                                    3315
Trp Asp  Glu Gly Arg Val Glu  Ile Asp Phe Asp Tyr  Cys Pro Gly
    1060                 1065                 1070 act acg  gtc acc ctg agt gag  agc tgc gga cac cgt  gga cct gcc
                                                                    3360
Thr Thr  Val Thr Leu Ser Glu  Ser Cys Gly His Arg  Gly Pro Ala
    1075                 1080                 1085
```

Figure 12 continued

```
act cgc  acc acc aca gag agc  gga aag ttg ata aca  gat tgg tgc
3405
Thr Arg  Thr Thr Thr Glu Ser  Gly Lys Leu Ile Thr  Asp Trp Cys
    1090             1095              1100 tgc agg  agc tgc acc tta cca  cca ctg cgc tac caa  act gac agc
3450
Cys Arg  Ser Cys Thr Leu Pro  Pro Leu Arg Tyr Gln  Thr Asp Ser
    1105             1110              1115 ggc tgt  tgg tat ggt atg gag  atc aga cca cag aga  cat gat gaa
3495
Gly Cys  Trp Tyr Gly Met Glu  Ile Arg Pro Gln Arg  His Asp Glu
    1120             1125              1130 aag acc  ctc gtg cag tca caa  gtg aat gct tat aat  gct gat atg
3540
Lys Thr  Leu Val Gln Ser Gln  Val Asn Ala Tyr Asn  Ala Asp Met
    1135             1140              1145 att gac  cct ttt cag ttg ggc  ctt ctg gtc gtg ttc  ttg gcc acc
3585
Ile Asp  Pro Phe Gln Leu Gly  Leu Leu Val Val Phe  Leu Ala Thr
    1150             1155              1160 cag gag  gtc ctt cgc aag agg  tgg aca gcc aag atc  agc atg cca
3630
Gln Glu  Val Leu Arg Lys Arg  Trp Thr Ala Lys Ile  Ser Met Pro
    1165             1170              1175 gct ata  ctg att gct ctg cta  gtc ctg gtg ttt ggg  ggc att act
3675
Ala Ile  Leu Ile Ala Leu Leu  Val Leu Val Phe Gly  Gly Ile Thr
    1180             1185              1190 tac act  gat gtg tta cgc tat  gtc atc ttg gtg ggg  gca gct ttc
3720
Tyr Thr  Asp Val Leu Arg Tyr  Val Ile Leu Val Gly  Ala Ala Phe
    1195             1200              1205 gca gaa  tct aat tcg gga gga  gac gtg gta cac ttg  gcg ctc atg
3765
Ala Glu  Ser Asn Ser Gly Gly  Asp Val Val His Leu  Ala Leu Met
    1210             1215              1220 gcg acc  ttc aag ata caa cca  gtg ttt atg gtg gca  tcg ttt ctc
3810
Ala Thr  Phe Lys Ile Gln Pro  Val Phe Met Val Ala  Ser Phe Leu
    1225             1230              1235
```

Figure 12 continued

```
aaa  gcg  aga  tgg  acc  aac  cag  gag  aac  att  ttg  ttg  atg  ttg  gcg
3855
Lys  Ala  Arg  Trp  Thr  Asn  Gln  Glu  Asn  Ile  Leu  Leu  Met  Leu  Ala
     1240                667   1245                         1250 gct  gtt  ttc  ttt  caa  atg  gct  tat  cac  gat  gcc  cgc  caa  att  ctg
3900
Ala  Val  Phe  Phe  Gln  Met  Ala  Tyr  His  Asp  Ala  Arg  Gln  Ile  Leu
     1255                     1260                    1265 ctc  tgg  gag  atc  cct  gat  gtg  ttg  aat  tca  ctg  gcg  gta  gct  tgg
3945
Leu  Trp  Glu  Ile  Pro  Asp  Val  Leu  Asn  Ser  Leu  Ala  Val  Ala  Trp
     1270                     1275                    1280 atg  ata  ctg  aga  gcc  ata  aca  ttc  aca  acg  aca  tca  aac  gtg  gtt
3990
Met  Ile  Leu  Arg  Ala  Ile  Thr  Phe  Thr  Thr  Thr  Ser  Asn  Val  Val
     1285                     1290                    1295 gtt  ccg  ctg  cta  gcc  ctg  cta  aca  ccc  ggg  ctg  aga  tgc  ttg  aat
4035
Val  Pro  Leu  Leu  Ala  Leu  Leu  Thr  Pro  Gly  Leu  Arg  Cys  Leu  Asn
     1300                     1305                    1310 ctg  gat  gtg  tac  agg  ata  ctg  ctg  ttg  atg  gtc  gga  ata  ggc  agc
4080
Leu  Asp  Val  Tyr  Arg  Ile  Leu  Leu  Leu  Met  Val  Gly  Ile  Gly  Ser
     1315                     1320                    1325 ttg  atc  agg  gag  aag  agg  agt  gca  gct  gca  aaa  aag  aaa  gga  gca
4125
Leu  Ile  Arg  Glu  Lys  Arg  Ser  Ala  Ala  Ala  Lys  Lys  Lys  Gly  Ala
     1330                     1335                    1340 agt  ctg  cta  tgc  ttg  gct  cta  gcc  tca  aca  gga  ctt  ttc  aac  ccc
4170
Ser  Leu  Leu  Cys  Leu  Ala  Leu  Ala  Ser  Thr  Gly  Leu  Phe  Asn  Pro
     1345                     1350                    1355 atg  atc  ctt  gct  gct  gga  ctg  att  gca  tgt  gat  ccc  aac  cgt  aaa
4215
Met  Ile  Leu  Ala  Ala  Gly  Leu  Ile  Ala  Cys  Asp  Pro  Asn  Arg  Lys
     1360                     1365                    1370 cgc  gga  tgg  ccc  gca  act  gaa  gtg  atg  aca  gct  gtc  ggc  cta  atg
4260
Arg  Gly  Trp  Pro  Ala  Thr  Glu  Val  Met  Thr  Ala  Val  Gly  Leu  Met
     1375                     1380                    1385
```

Figure 12 continued

```
ttt gcc atc gtc gga ggg ctg gca gag ctt gac att gac tcc atg
                                                              4305
Phe Ala Ile Val Gly Gly Leu Ala Glu Leu Asp Ile Asp Ser Met
        1390            1395            1400 gcc att cca atg act atc gcg ggg ctc atg ttt gct gct ttc gtg
                                                              4350
Ala Ile Pro Met Thr Ile Ala Gly Leu Met Phe Ala Ala Phe Val
        1405            1410            1415 att tct ggg aaa tca aca gat atg tgg att gag aga acg gcg gac
                                                              4395
Ile Ser Gly Lys Ser Thr Asp Met Trp Ile Glu Arg Thr Ala Asp
        1420            1425            1430 att tcc tgg gaa agt gat gca gaa att aca ggc tcg agc gaa aga
                                                              4440
Ile Ser Trp Glu Ser Asp Ala Glu Ile Thr Gly Ser Ser Glu Arg
        1435            1440            1445 gtt gat gtg cgg ctt gat gat gat gga aac ttc cag ctc atg aat
                                                              4485
Val Asp Val Arg Leu Asp Asp Asp Gly Asn Phe Gln Leu Met Asn
        1450            1455            1460 gat cca gga gca cct tgg aag ata tgg atg ctc aga atg gtc tgt
                                                              4530
Asp Pro Gly Ala Pro Trp Lys Ile Trp Met Leu Arg Met Val Cys
        1465            1470            1475 ctc gcg att agt gcg tac acc ccc tgg gca atc ttg ccc tca gta
                                                              4575
Leu Ala Ile Ser Ala Tyr Thr Pro Trp Ala Ile Leu Pro Ser Val
        1480            1485            1490 gtt gga ttt tgg ata act ctc caa tac aca aag aga gga ggc gtg
                                                              4620
Val Gly Phe Trp Ile Thr Leu Gln Tyr Thr Lys Arg Gly Gly Val
        1495            1500            1505 ttg tgg gac act ccc tca cca aag gag tac aaa aag ggg gac acg
                                                              4665
Leu Trp Asp Thr Pro Ser Pro Lys Glu Tyr Lys Lys Gly Asp Thr
        1510            1515            1520 acc acc ggc gtc tac agg atc atg act cgt ggg ctg ctc ggc agt
                                                              4710
Thr Thr Gly Val Tyr Arg Ile Met Thr Arg Gly Leu Leu Gly Ser
        1525            1530            1535
```

Figure 12 continued

```
tat caa gca gga gcg ggc gtg atg gtt gaa ggt gtt ttc cac acc
4755
Tyr Gln Ala Gly Ala Gly Val Met Val Glu Gly Val Phe His Thr
    1540              1545              1550 ctt tgg cat aca aca aaa gga gcc gct ttg atg agc gga gag ggc
4800
Leu Trp His Thr Thr Lys Gly Ala Ala Leu Met Ser Gly Glu Gly
    1555              1560              1565 cgc ctg gac cca tac tgg ggc agt gtc aag gag gat cga ctt tgt
4845
Arg Leu Asp Pro Tyr Trp Gly Ser Val Lys Glu Asp Arg Leu Cys
    1570              1575              1580 tac gga gga ccc tgg aaa ttg cag cac aag tgg aac ggg cag gat
4890
Tyr Gly Gly Pro Trp Lys Leu Gln His Lys Trp Asn Gly Gln Asp
    1585              1590              1595 gag gtg cag atg att gtg gtg gaa cct ggc aag aac gtt aag aac
4935
Glu Val Gln Met Ile Val Val Glu Pro Gly Lys Asn Val Lys Asn
    1600              1605              1610 gtc cag acg aaa cca ggg gtg ttc aaa aca cct gaa gga gaa atc
4980
Val Gln Thr Lys Pro Gly Val Phe Lys Thr Pro Glu Gly Glu Ile
    1615              1620              1625 ggg gcc gtg act ttg gac ttc ccc act gga aca tca ggc tca cca
5025
Gly Ala Val Thr Leu Asp Phe Pro Thr Gly Thr Ser Gly Ser Pro
    1630              1635              1640 ata gtg gac aaa aac ggt gat gtg att ggg ctt tat ggc aat gga
5070
Ile Val Asp Lys Asn Gly Asp Val Ile Gly Leu Tyr Gly Asn Gly
    1645              1650              1655 gtc ata atg ccc aac ggc tca tac ata agc gcg ata gtg cag ggt
5115
Val Ile Met Pro Asn Gly Ser Tyr Ile Ser Ala Ile Val Gln Gly
    1660              1665              1670 gaa agg atg gat gag cca atc cca gcc gga ttc gaa cct gag atg
5160
Glu Arg Met Asp Glu Pro Ile Pro Ala Gly Phe Glu Pro Glu Met
    1675              1680              1685
```

Figure 12 continued

```
ctg agg  aaa aaa cag atc act  gta ctg gat ctc cat  ccc ggc gcc
5205
Leu Arg  Lys Lys Gln Ile Thr  Val Leu Asp Leu His  Pro Gly Ala
    1690             1695             1700 ggt aaa  aca agg agg att ctg  cca cag atc atc aaa  gag gcc ata
5250
Gly Lys  Thr Arg Arg Ile Leu  Pro Gln Ile Ile Lys  Glu Ala Ile
    1705             1710             1715 aac aga  aga ctg aga aca gcc  gtg cta gca cca acc  agg gtt gtg
5295
Asn Arg  Arg Leu Arg Thr Ala  Val Leu Ala Pro Thr  Arg Val Val
    1720             1725             1730 gct gct  gag atg gct gaa gca  ctg aga gga ctg ccc  atc cgg tac
5340
Ala Ala  Glu Met Ala Glu Ala  Leu Arg Gly Leu Pro  Ile Arg Tyr
    1735             1740             1745 cag aca  tcc gca gtg ccc aga  gaa cat aat gga aat  gag att gtt
5385
Gln Thr  Ser Ala Val Pro Arg  Glu His Asn Gly Asn  Glu Ile Val
    1750             1755             1760 gat gtc  atg tgt cat gct acc  ctc acc cac agg ctg  atg tct cct
5430
Asp Val  Met Cys His Ala Thr  Leu Thr His Arg Leu  Met Ser Pro
    1765             1770             1775 cac agg  gtg ccg aac tac aac  ctg ttc gtg atg gat  gag gct cat
5475
His Arg  Val Pro Asn Tyr Asn  Leu Phe Val Met Asp  Glu Ala His
    1780             1785             1790 ttc acc  gac cca gct agc att  gca gca aga ggt tac  att tcc aca
5520
Phe Thr  Asp Pro Ala Ser Ile  Ala Ala Arg Gly Tyr  Ile Ser Thr
    1795             1800             1805 aag gtc  gag cta ggg gag gcg  gcg gca ata ttc atg  aca gcc acc
5565
Lys Val  Glu Leu Gly Glu Ala  Ala Ala Ile Phe Met  Thr Ala Thr
    1810             1815             1820 cca cca  ggc act tca gat cca  ttc cca gag tcc aat  tca cca att
5610
Pro Pro  Gly Thr Ser Asp Pro  Phe Pro Glu Ser Asn  Ser Pro Ile
    1825             1830             1835
```

Figure 12 continued

```
tcc gac tta cag act gag atc ccg gat cga gct tgg aac tct gga
5655
Ser Asp Leu Gln Thr Glu Ile Pro Asp Arg Ala Trp Asn Ser Gly
     1840             1845             1850 tac gaa tgg atc aca gaa tac acc ggg aag acg gtt tgg ttt gtg
5700
Tyr Glu Trp Ile Thr Glu Tyr Thr Gly Lys Thr Val Trp Phe Val
     1855             1860             1865 cct agt gtc aag atg ggg aat gag att gcc ctt tgc cta caa cgt
5745
Pro Ser Val Lys Met Gly Asn Glu Ile Ala Leu Cys Leu Gln Arg
     1870             1875             1880 gct gga aag aaa gta gtc caa ttg aac aga aag tcg tac gag acg
5790
Ala Gly Lys Lys Val Val Gln Leu Asn Arg Lys Ser Tyr Glu Thr
     1885             1890             1895 gag tac cca aaa tgt aag aac gat gat tgg gac ttt gtt atc aca
5835
Glu Tyr Pro Lys Cys Lys Asn Asp Asp Trp Asp Phe Val Ile Thr
     1900             1905             1910 aca gac ata tct gaa atg ggg gct aac ttc aag gcg agc agg gtg
5880
Thr Asp Ile Ser Glu Met Gly Ala Asn Phe Lys Ala Ser Arg Val
     1915             1920             1925 att gac agc cgg aag agt gtg aaa cca acc atc ata aca gaa gga
5925
Ile Asp Ser Arg Lys Ser Val Lys Pro Thr Ile Ile Thr Glu Gly
     1930             1935             1940 gaa ggg aga gtg atc ctg gga gaa cca tct gca gtg aca gca gct
5970
Glu Gly Arg Val Ile Leu Gly Glu Pro Ser Ala Val Thr Ala Ala
     1945             1950             1955 agt gcc gcc cag aga cgt gga cgt atc ggt aga aat ccg tcg caa
6015
Ser Ala Ala Gln Arg Arg Gly Arg Ile Gly Arg Asn Pro Ser Gln
     1960             1965             1970 gtt ggt gat gag tac tgt tat ggg ggg cac acg aat gaa gac gac
6060
Val Gly Asp Glu Tyr Cys Tyr Gly Gly His Thr Asn Glu Asp Asp
     1975             1980             1985
```

Figure 12 continued

```
tcg aac  ttc gcc  cat tgg  act gag  gca cga  atc atg  ctg gac aac
6105
Ser Asn  Phe Ala  His Trp  Thr Glu  Ala Arg  Ile Met  Leu Asp Asn
    1990              1995              2000 atc aac  atg cca  aac gga  ctg atc  gct caa  ttc tac  caa cca gag
6150
Ile Asn  Met Pro  Asn Gly  Leu Ile  Ala Gln  Phe Tyr  Gln Pro Glu
    2005              2010              2015 cgt gag  aag gta  tat acc  atg gat  ggg gaa  tac cgg  ctc aga gga
6195
Arg Glu  Lys Val  Tyr Thr  Met Asp  Gly Glu  Tyr Arg  Leu Arg Gly
    2020              2025              2030 gaa gag  aga aaa  aac ttt  ctg gaa  ctg ttg  agg act  gca gat ctg
6240
Glu Glu  Arg Lys  Asn Phe  Leu Glu  Leu Leu  Arg Thr  Ala Asp Leu
    2035              2040              2045 cca gtt  tgg ctg  gct tac  aag gtt  gca gcg  gct gga  gtg tca tac
6285
Pro Val  Trp Leu  Ala Tyr  Lys Val  Ala Ala  Ala Gly  Val Ser Tyr
    2050              2055              2060 cac gac  cgg agg  tgg tgc  ttt gat  ggt cct  agg aca  aac aca att
6330
His Asp  Arg Arg  Trp Cys  Phe Asp  Gly Pro  Arg Thr  Asn Thr Ile
    2065              2070              2075 tta gaa  gac aac  aac gaa  gtg gaa  gtc atc  acg aag  ctt ggt gaa
6375
Leu Glu  Asp Asn  Asn Glu  Val Glu  Val Ile  Thr Lys  Leu Gly Glu
    2080              2085              2090 agg aag  att ctg  agg ccg  cgc tgg  att gac  gcc agg  gtg tac tcg
6420
Arg Lys  Ile Leu  Arg Pro  Arg Trp  Ile Asp  Ala Arg  Val Tyr Ser
    2095              2100              2105 gat cac  cag gca  cta aag  gcg ttc  aag gac  ttc gcc  tcg gga aaa
6465
Asp His  Gln Ala  Leu Lys  Ala Phe  Lys Asp  Phe Ala  Ser Gly Lys
    2110              2115              2120 cgt tct  cag ata  ggg ctc  att gag  gtt ctg  gga aag  atg cct gag
6510
Arg Ser  Gln Ile  Gly Leu  Ile Glu  Val Leu  Gly Lys  Met Pro Glu
    2125              2130              2135
```

Figure 12 continued

```
cac ttc  atg ggg aag aca tgg  gaa gca ctt gac  acc atg tac gtt
6555
His Phe  Met Gly Lys Thr Trp  Glu Ala Leu Asp  Thr Met Tyr Val
    2140                 2145                  2150 gtg gcc  act gca gag aaa gga  gga aga gct cac  aga atg gcc ctg
6600
Val Ala  Thr Ala Glu Lys Gly  Gly Arg Ala His  Arg Met Ala Leu
    2155                 2160                  2165 gag gaa  ctg cca gat gct ctt  cag aca att gcc  ttg att gcc tta
6645
Glu Glu  Leu Pro Asp Ala Leu  Gln Thr Ile Ala  Leu Ile Ala Leu
    2170                 2175                  2180 ttg agt  gtg atg acc atg gga  gta ttc ttc ctc  ctc atg cag cgg
6690
Leu Ser  Val Met Thr Met Gly  Val Phe Phe Leu  Leu Met Gln Arg
    2185                 2190                  2195 aag ggc  att gga aag ata ggt  ttg gga ggc gct  gtc ttg gga gtc
6735
Lys Gly  Ile Gly Lys Ile Gly  Leu Gly Gly Ala  Val Leu Gly Val
    2200                 2205                  2210 gcg acc  ttt ttc tgt tgg atg  gct gaa gtt cca  gga acg aag atc
6780
Ala Thr  Phe Phe Cys Trp Met  Ala Glu Val Pro  Gly Thr Lys Ile
    2215                 2220                  2225 gcc gga  atg ttg ctg ctc tcc  ctt ctc ttg atg  att gtg cta att
6825
Ala Gly  Met Leu Leu Leu Ser  Leu Leu Leu Met  Ile Val Leu Ile
    2230                 2235                  2240 cct gag  cca gag aag caa cgt  tcg cag aca gac  aac cag cta gcc
6870
Pro Glu  Pro Glu Lys Gln Arg  Ser Gln Thr Asp  Asn Gln Leu Ala
    2245                 2250                  2255 gtg ttc  ctg att tgt gtc atg  acc ctt gtg agc  gca gtg gca gcc
6915
Val Phe  Leu Ile Cys Val Met  Thr Leu Val Ser  Ala Val Ala Ala
    2260                 2265                  2270 aac gag  atg ggt tgg cta gat  aag acc aag agt  gac ata agc agt
6960
Asn Glu  Met Gly Trp Leu Asp  Lys Thr Lys Ser  Asp Ile Ser Ser
    2275                 2280                  2285
```

Figure 12 continued

```
ttg ttt  ggg caa aga att gag  gtc aag gag aat ttc  agc atg gga
7005
Leu Phe  Gly Gln Arg Ile Glu  Val Lys Glu Asn Phe  Ser Met Gly
    2290              2295                 2300 gag ttt  ctt ttg gac ttg agg  ccg gca aca gcc tgg  tca ctg tac
7050
Glu Phe  Leu Leu Asp Leu Arg  Pro Ala Thr Ala Trp  Ser Leu Tyr
    2305              2310                 2315 gct gtg  aca aca gcg gtc ctc  act cca ctg cta aag  cat ttg atc
7095
Ala Val  Thr Thr Ala Val Leu  Thr Pro Leu Leu Lys  His Leu Ile
    2320              2325                 2330 acg tca  gat tac atc aac acc  tca ttg acc tca ata  aac gtt cag
7140
Thr Ser  Asp Tyr Ile Asn Thr  Ser Leu Thr Ser Ile  Asn Val Gln
    2335              2340                 2345 gca agt  gca cta ttc aca ctc  gcg cga ggc ttc ccc  ttc gtc gat
7185
Ala Ser  Ala Leu Phe Thr Leu  Ala Arg Gly Phe Pro  Phe Val Asp
    2350              2355                 2360 gtt gga  gtg tcg gct ctc ctg  cta gca gcc gga tgc  tgg gga caa
7230
Val Gly  Val Ser Ala Leu Leu  Leu Ala Ala Gly Cys  Trp Gly Gln
    2365              2370                 2375 gtc acc  ctc acc gtt acg gta  aca gcg gca aca ctc  ctt ttt tgc
7275
Val Thr  Leu Thr Val Thr Val  Thr Ala Ala Thr Leu  Leu Phe Cys
    2380              2385                 2390 cac tat  gcc tac atg gtt ccc  ggt tgg caa gct gag  gca atg cgc
7320
His Tyr  Ala Tyr Met Val Pro  Gly Trp Gln Ala Glu  Ala Met Arg
    2395              2400                 2405 tca gcc  cag cgg cgg aca gcg  gcc gga atc atg aag  aac gct gta
7365
Ser Ala  Gln Arg Arg Thr Ala  Ala Gly Ile Met Lys  Asn Ala Val
    2410              2415                 2420 gtg gat  ggc atc gtg gcc acg  gac gtc cca gaa tta  gag cgc acc
7410
Val Asp  Gly Ile Val Ala Thr  Asp Val Pro Glu Leu  Glu Arg Thr
    2425              2430                 2435
```

Figure 12 continued

```
aca ccc atc atg cag aag aaa gtt gga cag atc atg ctg atc ttg
                                                                7455
Thr Pro Ile Met Gln Lys Lys Val Gly Gln Ile Met Leu Ile Leu
    2440            2445            2450 gtg tct cta gct gca gta gta gtg aac ccg tct gtg aag aca gta
                                                                7500
Val Ser Leu Ala Ala Val Val Val Asn Pro Ser Val Lys Thr Val
    2455            2460            2465 cga gaa gcc gga att ttg atc acg gcc gca gcg gtg acg ctt tgg
                                                                7545
Arg Glu Ala Gly Ile Leu Ile Thr Ala Ala Ala Val Thr Leu Trp
    2470            2475            2480 gag aat gga gca agc tct gtt tgg aac gca aca act gcc atc gga
                                                                7590
Glu Asn Gly Ala Ser Ser Val Trp Asn Ala Thr Thr Ala Ile Gly
    2485            2490            2495 ctc tgc cac atc atg cgt ggg ggt tgg ttg tca tgt cta tcc ata
                                                                7635
Leu Cys His Ile Met Arg Gly Gly Trp Leu Ser Cys Leu Ser Ile
    2500            2505            2510 aca tgg aca ctc ata aag aac atg gaa aaa cca gga cta aaa aga
                                                                7680
Thr Trp Thr Leu Ile Lys Asn Met Glu Lys Pro Gly Leu Lys Arg
    2515            2520            2525 ggt ggg gca aaa gga cgc acc ttg gga gag gtt tgg aaa gaa aga
                                                                7725
Gly Gly Ala Lys Gly Arg Thr Leu Gly Glu Val Trp Lys Glu Arg
    2530            2535            2540 ctc aac cag atg aca aaa gaa gag ttc act agg tac cgc aaa gag
                                                                7770
Leu Asn Gln Met Thr Lys Glu Glu Phe Thr Arg Tyr Arg Lys Glu
    2545            2550            2555 gcc atc atc gaa gtc gat cgc tca gcg gca aaa cac gcc agg aaa
                                                                7815
Ala Ile Ile Glu Val Asp Arg Ser Ala Ala Lys His Ala Arg Lys
    2560            2565            2570 gaa ggc aat gtc act gga ggg cat cca gtc tct agg ggc aca gca
                                                                7860
Glu Gly Asn Val Thr Gly Gly His Pro Val Ser Arg Gly Thr Ala
    2575            2580            2585
```

Figure 12 continued

```
aaa ctg  aga tgg ctg gtc gaa  cgg agg ttt ctc gaa  ccg gtc gga
7905
Lys Leu  Arg Trp Leu Val Glu  Arg Arg Phe Leu Glu  Pro Val Gly
    2590                 2595                 2600 aaa gtg  att gac ctt gga tgt  gga aga ggc ggt tgg  tgt tac tat
7950
Lys Val  Ile Asp Leu Gly Cys  Gly Arg Gly Gly Trp  Cys Tyr Tyr
    2605                 2610                 2615 atg gca  acc caa aaa aga gtc  caa gaa gtc aga ggg  tac aca aag
7995
Met Ala  Thr Gln Lys Arg Val  Gln Glu Val Arg Gly  Tyr Thr Lys
    2620                 2625                 2630 ggc ggt  ccc gga cat gaa gag  ccc caa cta gtg caa  agt tat gga
8040
Gly Gly  Pro Gly His Glu Glu  Pro Gln Leu Val Gln  Ser Tyr Gly
    2635                 2640                 2645 tgg aac  att gtc acc atg aag  agt gga gtg gat gtg  ttc tac aga
8085
Trp Asn  Ile Val Thr Met Lys  Ser Gly Val Asp Val  Phe Tyr Arg
    2650                 2655                 2660 cct tct  gag tgt tgt gac acc  ctc ctt tgt gac atc  gga gag tcc
8130
Pro Ser  Glu Cys Cys Asp Thr  Leu Leu Cys Asp Ile  Gly Glu Ser
    2665                 2670                 2675 tcg tca  agt gct gag gtt gaa  gag cat agg acg att  cgg gtc ctt
8175
Ser Ser  Ser Ala Glu Val Glu  Glu His Arg Thr Ile  Arg Val Leu
    2680                 2685                 2690 gaa atg  gtt gag gac tgg ctg  cac cga ggg cca agg  gaa ttt tgc
8220
Glu Met  Val Glu Asp Trp Leu  His Arg Gly Pro Arg  Glu Phe Cys
    2695                 2700                 2705 gtg aag  gtg ctc tgc ccc tac  atg ccg aaa gtc ata  gag aag atg
8265
Val Lys  Val Leu Cys Pro Tyr  Met Pro Lys Val Ile  Glu Lys Met
    2710                 2715                 2720 gag ctg  ctc caa cgc cgg tat  ggg ggg gga ctg gtc  aga aac cca
8310
Glu Leu  Leu Gln Arg Arg Tyr  Gly Gly Gly Leu Val  Arg Asn Pro
    2725                 2730                 2735
```

Figure 12 continued

```
ctc tca cgg aat tcc acg cac  gag atg tat tgg gtg  agt cga gct
8355
Leu Ser Arg Asn Ser Thr His  Glu Met Tyr Trp Val  Ser Arg Ala
        2740              2745              2750 tca ggc aat gtg gta cat tca  gtg aat atg acc agc  cag gtg ctc
8400
Ser Gly Asn Val Val His Ser  Val Asn Met Thr Ser  Gln Val Leu
        2755              2760              2765 cta gga aga atg gaa aaa agg  acc tgg aag gga ccc  caa tac gag
8445
Leu Gly Arg Met Glu Lys Arg  Thr Trp Lys Gly Pro  Gln Tyr Glu
        2770              2775              2780 gaa gat gta aac ttg gga agt  gga acc agg gcg gtg  gga aaa ccc
8490
Glu Asp Val Asn Leu Gly Ser  Gly Thr Arg Ala Val  Gly Lys Pro
        2785              2790              2795 ctg ctc aac tca gac acc agt  aaa atc aag aac agg  att gaa cga
8535
Leu Leu Asn Ser Asp Thr Ser  Lys Ile Lys Asn Arg  Ile Glu Arg
        2800              2805              2810 ctc agg cgt gag tac agt tcg  acg tgg cac cac gat  gag aac cac
8580
Leu Arg Arg Glu Tyr Ser Ser  Thr Trp His His Asp  Glu Asn His
        2815              2820              2825 cca tat aga acc tgg aac tat  cac ggc agt tat gat  gtg aag ccc
8625
Pro Tyr Arg Thr Trp Asn Tyr  His Gly Ser Tyr Asp  Val Lys Pro
        2830              2835              2840 aca ggc tcc gcc agt tcg ctg  gtc aat gga gtg gtc  agg ctc ctc
8670
Thr Gly Ser Ala Ser Ser Leu  Val Asn Gly Val Val  Arg Leu Leu
        2845              2850              2855 tca aaa cca tgg gac acc atc  acg aat gtt acc acc  atg gcc atg
8715
Ser Lys Pro Trp Asp Thr Ile  Thr Asn Val Thr Thr  Met Ala Met
        2860              2865              2870 act gac act act ccc ttc ggg  cag cag cga gtg ttc  aaa gag aag
8760
Thr Asp Thr Thr Pro Phe Gly  Gln Gln Arg Val Phe  Lys Glu Lys
        2875              2880              2885
```

Figure 12 continued

```
gtg gac  acg aaa gct cct  gaa  ccg cca gaa  gga gtg aag tac gtg
8805
Val Asp  Thr Lys Ala Pro  Glu  Pro Pro Glu  Gly Val Lys Tyr Val
    2890             2895               2900 ctc aat  gag acc acc aac  tgg  ttg tgg gcg  ttt ttg gcc aga gaa
8850
Leu Asn  Glu Thr Thr Asn  Trp  Leu Trp Ala  Phe Leu Ala Arg Glu
    2905             2910               2915 aaa cgt  ccc aga atg tgc  tct  cga gag gaa  ttc ata aga aag gtc
8895
Lys Arg  Pro Arg Met Cys  Ser  Arg Glu Glu  Phe Ile Arg Lys Val
    2920             2925               2930 aac agc  aat gca gct ttg  ggt  gcc atg ttt  gaa gag cag aat caa
8940
Asn Ser  Asn Ala Ala Leu  Gly  Ala Met Phe  Glu Glu Gln Asn Gln
    2935             2940               2945 tgg agg  agc gcc aga gaa  gca  gtt gaa gat  cca aaa ttt tgg gag
8985
Trp Arg  Ser Ala Arg Glu  Ala  Val Glu Asp  Pro Lys Phe Trp Glu
    2950             2955               2960 atg gtg  gat gag gag cgc  gag  gca cat ctg  cgg ggg gaa tgt cac
9030
Met Val  Asp Glu Glu Arg  Glu  Ala His Leu  Arg Gly Glu Cys His
    2965             2970               2975 act tgc  att tac aac atg  atg  gga aag aga  gag aaa aaa ccc gga
9075
Thr Cys  Ile Tyr Asn Met  Met  Gly Lys Arg  Glu Lys Lys Pro Gly
    2980             2985               2990 gag ttc  gga aag gcc aag  gga  agc aga gcc  att tgg ttc atg tgg
9120
Glu Phe  Gly Lys Ala Lys  Gly  Ser Arg Ala  Ile Trp Phe Met Trp
    2995             3000               3005 ctc gga  gct cgc ttt ctg  gag  ttc gag gct  ctg ggt ttt ctc aat
9165
Leu Gly  Ala Arg Phe Leu  Glu  Phe Glu Ala  Leu Gly Phe Leu Asn
    3010             3015               3020 gaa gac  cac tgg ctt gga  aga  aag aac tca  gga gga ggt gtc gag
9210
Glu Asp  His Trp Leu Gly  Arg  Lys Asn Ser  Gly Gly Gly Val Glu
    3025             3030               3035
```

Figure 12 continued

```
ggc ttg  ggc ctc  caa aaa  ctg  ggt tac  atc ctg  cgt   gaa gtt  ggc
9255
Gly Leu  Gly Leu  Gln Lys  Leu  Gly Tyr  Ile Leu  Arg   Glu Val  Gly
         3040              3045           3050 acc cgg  cct ggg  ggc aag  atc  tat gct  gat gac  aca   gct ggc  tgg
9300
Thr Arg  Pro Gly  Gly Lys  Ile  Tyr Ala  Asp Asp  Thr   Ala Gly  Trp
         3055              3060           3065 gac acc  cgc atc  acg aga  gct  gac ttg  gaa aat  gaa   gct aag  gtg
9345
Asp Thr  Arg Ile  Thr Arg  Ala  Asp Leu  Glu Asn  Glu   Ala Lys  Val
         3070              3075           3080 ctt gag  ctg ctt  gat ggg  gaa  cat cgg  cgt ctt  gcc   agg gcc  atc
9390
Leu Glu  Leu Leu  Asp Gly  Glu  His Arg  Arg Leu  Ala   Arg Ala  Ile
         3085              3090           3095 att gag  ctc acc  tat cgt  cac  aaa gtt  gtg aaa  gtg   atg cgc  ccg
9435
Ile Glu  Leu Thr  Tyr Arg  His  Lys Val  Val Lys  Val   Met Arg  Pro
         3100              3105           3110 gct gct  gat gga  aga acc  gtc  atg gat  gtt atc  tcc   aga gaa  gat
9480
Ala Ala  Asp Gly  Arg Thr  Val  Met Asp  Val Ile  Ser   Arg Glu  Asp
         3115              3120           3125 cag agg  ggg agt  gga caa  gtt  gtc acc  tac gcc  cta   aac act  ttc
9525
Gln Arg  Gly Ser  Gly Gln  Val  Val Thr  Tyr Ala  Leu   Asn Thr  Phe
         3130              3135           3140 acc aac  ctg gcc  gtc cag  ctg  gtg agg  atg atg  gaa   ggg gaa  gga
9570
Thr Asn  Leu Ala  Val Gln  Leu  Val Arg  Met Met  Glu   Gly Glu  Gly
         3145              3150           3155 gtg att  ggc cca  gat gat  gtg  gag aaa  ctc aca  aaa   ggg aaa  gga
9615
Val Ile  Gly Pro  Asp Asp  Val  Glu Lys  Leu Thr  Lys   Gly Lys  Gly
         3160              3165           3170 ccc aaa  gtc agg  acc tgg  ctg  ttt gag  aat ggg  gaa   gaa aga  ctc
9660
Pro Lys  Val Arg  Thr Trp  Leu  Phe Glu  Asn Gly  Glu   Glu Arg  Leu
         3175              3180           3185
```

Figure 12 continued

```
agc cgc  atg gct  gtc agt  gga  gat gac  tgt gtg  gta  aag ccc  ctg
9705
Ser Arg  Met Ala  Val Ser  Gly  Asp Asp  Cys Val  Val  Lys Pro  Leu
    3190              3195              3200 gac gat  cgc ttt  gcc acc  tcg  ctc cac  ttc ctc  aat  gct atg  tca
9750
Asp Asp  Arg Phe  Ala Thr  Ser  Leu His  Phe Leu  Asn  Ala Met  Ser
    3205              3210              3215 aag gtt  cgc aaa  gac atc  caa  gag tgg  aaa ccg  tca  act gga  tgg
9795
Lys Val  Arg Lys  Asp Ile  Gln  Glu Trp  Lys Pro  Ser  Thr Gly  Trp
    3220              3225              3230 tat gat  tgg cag  cag gtt  cca  ttt tgc  tca aac  cat  ttc act  gaa
9840
Tyr Asp  Trp Gln  Gln Val  Pro  Phe Cys  Ser Asn  His  Phe Thr  Glu
    3235              3240              3245 ttg atc  atg aaa  gat gga  aga  aca ctg  gtg gtt  cca  tgc cga  gga
9885
Leu Ile  Met Lys  Asp Gly  Arg  Thr Leu  Val Val  Pro  Cys Arg  Gly
    3250              3255              3260 cag gat  gaa ttg  gta ggc  aga  gct cgc  ata tct  cca  ggg gcc  gga
9930
Gln Asp  Glu Leu  Val Gly  Arg  Ala Arg  Ile Ser  Pro  Gly Ala  Gly
    3265              3270              3275 tgg aac  gtc cgc  gac act  gct  tgt ctg  gct aag  tct  tat gcc  cag
9975
Trp Asn  Val Arg  Asp Thr  Ala  Cys Leu  Ala Lys  Ser  Tyr Ala  Gln
    3280              3285              3290 atg tgg  ctg ctt  ctg tac  ttc  cac aga  aga gac  ctg  cgg ctc  atg
10020
Met Trp  Leu Leu  Leu Tyr  Phe  His Arg  Arg Asp  Leu  Arg Leu  Met
    3295              3300              3305 gcc aac  gcc att  tgc tcc  gct  gtc cct  gtg aat  tgg  gtc cct  acc
10065
Ala Asn  Ala Ile  Cys Ser  Ala  Val Pro  Val Asn  Trp  Val Pro  Thr
    3310              3315              3320 gga aga  acc acg  tgg tcc  atc  cat gca  gga gga  gag  tgg atg  aca
10110
Gly Arg  Thr Thr  Trp Ser  Ile  His Ala  Gly Gly  Glu  Trp Met  Thr
    3325              3330              3335
```

Figure 12 continued

```
aca gag  gac atg ttg gag gtc  tgg aac cgt gtt tgg  ata gag gag
10155
Thr Glu  Asp Met Leu Glu Val  Trp Asn Arg Val Trp  Ile Glu Glu
    3340                3345                3350 aat gaa  tgg atg gaa gac aaa  acc cca gtg gag aaa  tgg agt gac
10200
Asn Glu  Trp Met Glu Asp Lys  Thr Pro Val Glu Lys  Trp Ser Asp
    3355                3360                3365 gtc cca  tat tca gga aaa cga  gag gac atc tgg tgt  ggc agc ctg
10245
Val Pro  Tyr Ser Gly Lys Arg  Glu Asp Ile Trp Cys  Gly Ser Leu
    3370                3375                3380 att ggc  aca aga gcc cga gcc  acg tgg gca gaa aac  atc cag gtg
10290
Ile Gly  Thr Arg Ala Arg Ala  Thr Trp Ala Glu Asn  Ile Gln Val
    3385                3390                3395 gct atc  aac caa gtc aga gca  atc atc gga gat gag  aag tat gtg
10335
Ala Ile  Asn Gln Val Arg Ala  Ile Ile Gly Asp Glu  Lys Tyr Val
    3400                3405                3410 gat tac  atg agt tca cta aag  aga tat gaa gac aca  act ttg gtt
10380
Asp Tyr  Met Ser Ser Leu Lys  Arg Tyr Glu Asp Thr  Thr Leu Val
    3415                3420                3425 gag gac  aca gta ctg tag atatttaatc aattgtaaat agacaatata
10428
Glu Asp  Thr Val Leu
    3430 agtatgcata aaagtgtagt tttatagtag tatttagtgg tgttagtgta aatagttaag
10488 aaaattttga ggagaaagtc aggccgggaa gttcccgcca ccggaagttg agtagacggt
10548 gctgcctgcg actcaacccc aggaggactg ggtgaacaaa gccgcgaagt gatccatgta
10608 agccctcaga accgtctcgg aaggaggacc ccacatgttg taacttcaaa gcccaatgtc
10668 agaccacgct acggcgtgct actctgcgga gagtgcagtc tgcgatagtg ccccaggagg
10728
```

Figure 12 continued

```
actgggttaa caaaggcaaa ccaacgcccc acgcggccct agccccggta atggtgttaa
10788 ccagggcgaa aggactagag gttagaggag accccgcggt ttaaagtgca cggcccagcc
10848 tgactgaagc tgtaggtcag gggaaggact agaggttagt ggagacccg tgccacaaaa
10908 caccacaaca aaacagcata ttgacacctg ggatagacta ggagatcttc tgctctgcac
10968 aaccagccac acggcacagt gcgccgacaa tggtggctgg tggtgcgaga acacaggatc
11028 t
11029
```

Figure 13  5kb C5 locus and PCR primers to amplify C5 arms (SEQ ID NO: 77)

```
CTGAAATGTAATTTCTACATGTAGAGAAGGTTTTGATATTGATGGTTTTAACAGAAACG
GACTTTAACATTAAAGATGTACATCTCTTCCAAAACTATAACTACCAAAATTGTCTTTGC
         10        20        30        40        50        60

TAGAAACTATATCAAGGGATAACATTTATATGATATAGTTTTAAAGTGTAAGATGGAAT
ATCTTTAATATAGTTCCCTATGTAAAATATACTATATCAAAATTTCACATTCTACCTTA
         70        80        90       100       110       120

TAAATTTCATGTGCACAAGAGGCATAGGAGATAAAAGCATTTTCAGACTTTGTATAATGA
ATTTAAAGTACACGTGTTCTCCGTATCCTCTATTTTCGTAAAAGTCTGAAACATATTACT
        130       140       150       160       170       180

AGGAATATGATCAAATAAACAAGAATCTGTTAGTTAGTTACTTGGATAAATTAATCGAGA
TCCTTATACTAGTTTATTTGTTCTTAGACAATCAATCAATCAACCTATTTAATTAGCTCT
        190       200       210       220       230       240

CGCCTGATAAAATGACTATGTACCCTTATTCCATGAACGATATTATAAATATAGGTTCTC
GCGGACTATTTTACTGATACATGGCAATAACGTACTTGCTATAATATTTATATCCAAGAG
        250       260       270       280       290       300

(C5A1)      GGCCGAATTC
GTAGGAGAGAACTATCGACTATGGCAA TGAATGTTAAATGTTATACTTTGCATCAACCTA
CATCCTCTCTTGATAACTGATACCGTTACTTACAATTTACAATATGAAACCTACTTCGAT
        310       320       330       340       350       360

TAAATATGCATTGGAAAAATAATCCATTTAAAGAAGGATTCAAATACTACAAAACCTAA
ATTTATACGTAACCTTTTCATTAGGTAAATTTCTTTCCTAAGTTTATGATGTTTTGGATT
        370       380       390       400       410       420

GCGATAATATGTTAACTAAGCTTATTCTTAACGACGCTTTAAATATACACAAATAAACAT
CGCTATTATACAATTGATTCGAATAAGAATTGCTGCGAAATTTATATGTGTTTATTTGTA
        430       440       450       460       470       480

AATTTTTGTATAACCTAACAAATAACTAAAACATAAAAATAATAAAAGGAAATGTAATAT
TTAAAAACATATTGGATTGTTTATTGATTTTGTATTTTATTATTTTCCTTTACATTATA
        490       500       510       520       530       540
```

Figure 13 continued

```
CGTAATTATTTTACTCAGGAATGCGGTTAAATATTTATATCACGTCTATATCTATACTGT
GCATTAATAAAATGAGTCCTTACCCCAATTTATAAATATAGTGCACATATAGATATGACA
         550       560       570       580       590       600

TATCGTATACTCCTTACAATTACTATTACGAATATGCAAGAGATAATAAGATTACGTATT
ATAGCATATGAGAAATGTTAATGATAATGCTTATACGTTCTCTATTATTCTAATGCATAA
         610       620       630       640       650       660

TAAGAGAATCTTGTCATGATAATTGGGTACGACATAGTGATAAATGCTATTTCGCATCGT
ATTCTCTTACAACACTACTATTAACCCATGCTGTATCACTATTTACGATAAAGCGTACCA
         670       680       690       700       710       720

TACATAAAGTCAGTTGGAAAGATGGATTTGACAGATGTAACTTAATAGGTGCAAAAATGT
ATGTATTTCAGTCAACCTTTCTACCTAAACTCTCTACATTCAATTATCCACGTTTTTACA
         730       740       750       760       770       780

TAAATAACAGCATTCTATCGGAAGATAGGATACCAGTTATATTATACAAAAATCACTGGT
ATTTATTGTCGTAAGATAGCCTTCTATCCTATGGTCAATATAATATGTTTTTAGTGACCA
         790       800       810       820       830       840

TGGATAAAACAGATTCTGCAATATTCGTAAAAGATGAAGATTACTGCGAATTTGTAAACT
ACCTATTTTGTCTAAGACGTTATAAGCCATTTTCTACTTCTAATGACGCTTAAACATTTGA
         850       860       870       880       890       900

ATGACAATAAAAAGCCATTTATCTCAACGACATCGTGTAATTCTTCCATGTTTTATGTAT
TACTGTTATTTTTCGGTAAATAGAGTTGCTGTAGCACATTAAGAAGGTACAAAATACATA
         910       920       930       940       950       960

GTGTTTCAGATATTATGAGATTACTATAAACTTTTTGTATACTTATATTCCGTAAACTAT
CACAAAGTCTATAATACTCTAATGATATTTGAAAAACATATGAATATAAGGCATTGATA
         970       980       990       1000      1010      1020

ATTAATCATGAAGAAAATGAAAAGTATAGAAGCTGTTCACGAGCGGTTGTTGAAAACAA
TAATTAGTACTTCTTTTACTTTTTCATATCTTCGACAAGTGCTCGCCAACAACTTTTGTT
         1030      1040      1050      1060      1070      1080

CAAAATTATACATTCAAGATGGCTTACATATACGTCTGTGAGGCTATCATGGATAATGAC
```

Figure 13 continued

```
GTTTTAATATGTAAGTTCTACCGAATGTATATGCAGACACTCCGATAGTACCTATTACTG
         1090          1100          1110          1120          1130          1140
AATGCATCTCTAAATAGGTTTTTGGACAATGGATTCGACCCTAACACGGAATATGGTACT
TTACGTAGAGATTTATCCAAAAACCTGTTACCTAAGCTGGGATTGTGCCTTATACCATGA
         1150          1160          1170          1180          1190          1200

CTACAATCTCCTCTTGAAATGGCTGTAATGTTCAAGAATACCGAGGCTATAAAAATCTTG
GATGTTAGAGGAGAACTTTACCGACATTACAAGTTCTTATGGCTCCGATATTTTAGAAC
         1210          1220          1230          1240          1250          1260

ATGAGGTATGGAGCTAAACCTGTAGTTACTGAATGCACAACTTCTTGTCTGCATGATGCG
TACTCCATACCTCGATTTGGACATCAATGACTTACGTGTTGAAGAACAGACGTACTACGC
         1270          1280          1290          1300          1310          1320

GTGTTGAGAGACGACTACAAAATAGTGAAAGATCTGTTGAAGAATAACTATGTAAACAAT
CACAACTCTCTGCTGATGTTTTATCACTTTCTAGACAACTTCTTATTGATACATTTGTTA
         1330          1340          1350          1360          1370          1380

GTTCTTTACAGCGGAGGCTTTACTCCTTTGTGTTTGGCAGCTTACCTTAACAAAGTTAAT
CAAGAAATGTCGCCTCCGAAATGAGGAAACACAAACCGTCGAATGGAATTGTTTCAATTA
         1390          1400          1410          1420          1430          1440

TTGGTTAAACTTCTATTGGCTCATTCGGCGGATGTAGATATTTCAAACACGGATCGGTTA
AACCAATTTGAAGATAACCGAGTAAGCCGCCTACATCTATAAAGTTTGTGCCTAGCCAAT
         1450          1460          1470          1480          1490          1500

ACTCCTCTACATATAGCCGTATCAAATAAAAATTTAACAATGGTTAAACTTCTATTGAAC
TGAGGAGATGTATATCGGCATAGTTTATTTTAAATTGTTACCAATTTGAAGATAACTTG
         1510          1520          1530          1540          1550          1560

AAAGGTGCTGATACTGACTTGCTGGATAACATGGACGTACTCCTTTAATGATCGCTGTA
TTTCCACGACTATGACTGAACGACCTATTGTACCCTGCATGAGGAAATTACTAGCGACAT
         1570          1580          1590          1600          1610          1620

CAATCTGGAAATATTGAAATATGTAGCACACTACTTAAAAAAATAAAATGTCCAGAACT
GTTAGACCTTTATAACTTTATACATCGTGTGATGAATTTTCTTTATTCTACAGGTCTTGA
         1630          1640          1650          1660          1670          1680
```

Figure 13 continued

```
GGGAAAAATGATCTTGCCAGCTGTAATTCATGGTAGAAAAGAAGTGCTCAGGCTACTTT
CCCTTTTTAACTAGAACGGTCGACATTAAGTACCATCTTTTCTTCACGAGTCCGATGAAA
        1690       1700       1710       1720       1730       1740

TCAACAAAGGAGCAGATGTAAACTACATCTTTGAAAGAAATGGAAAATCATATACTGTTT
AGTTGTTCCTCGTCTACATTTGATGTAGAAACTTTCTTTACCTTTTAGTATATGACAAA
        1750       1760       1770       1780       1790       1800

TGGAATTGATTAAACAAAGTTACTCTGAGACACAAAAGACGTAGCTGAAGTGGTACTCTC
ACCTTAACTAATTTCTTTCAATGAGACTCTGTGTTTTCTCCATCGACTCACCATGAGAG
        1810       1820       1830       1840       1850       1860

C5 ORF
       MET  GLN  ASN  ASP  ASP  CYS  GLU  ALA  ARG  SER  ARG  GLU  ILE  THR  LEU  TYR  ASP  PHE  LEU
AAAATGCAGAACGATGACTGCGAAGCAAGAAGTAGAGAAATAACACTTTATGACTTTCTT
TTTTACGTCTTGCTACTGACGCTTCCTTCTTCATCTCTTTATTGTGAAATACTGAAAGAA
        1870       1880       1890       1900       1910       1920
     CCATGCACTGATTAATCGA TATTTTT CCATGC GCCC     (C5B1)

SER  CYS  ARG  LYS  ASP  ARG  ASP  ILE  MET  MET  VAL  ILE  ASN  ASN  SER  ASP  ILE  ALA  SER  LYS
AGTTGTAGAAAAGATAGAGATATAATGATGGTCATAAATAACTCTGATATTGCAAGTAAA
TCAACATCTTTTCTATCTCTATATTACTACCAGTATTTATTGAGACTATAACGTTCATTT
        1930       1940       1950       1960       1970       1980

CYS  ASN  ASN  LYS  LEU  ASP  LEU  PHE  LYS  ARG  ILE  VAL  LYS  ASN  ARG  LYS  LYS  GLU  LEU  ILE
TGCAATAATAAGTTAGATTTATTTAAAAGGATAGTTAAAAATAGAAAAAAAGACTTAATT
ACGTTATTATTCAATCTAAATAAATTTTCCTATCAATTTCTATCTTTCTTTCTCAATTAA
        1990       2000       2010       2020       2030       2040

CYS  ARG  VAL  LYS  ILE  ILE  HIS  LYS  ILE  LEU  LYS  PHE  ILE  ASN  THR  HIS  ASN  ASN  LYS  ASN
TGTAGGGTTAAAAATAATACATAAGATCTTAAAAATTTATAAATACGCATAACAATAAAAT
ACATCCCAATTTTATTATGTATTCTAGAATTTTAAATATTTATGCGTATTATTATTTTA
        2050       2060       2070       2080       2090       2100

(C5C1)   GGATCC CCCG TTTTTAT GACTAGT TAATCACGCCCG
 ARG  LEU  TYR  LEU  LEU  PRO  SER  GLU  ILE  LYS  PHE  LYS  ILE  PHE  THR  TYR  LEU  THR  TYR  LYS
AGATTATACTTATTACCTTCAGAGATAAAATTTAAGATATTTACTTATTTAACTTATAAA
TCTAATATGAATAATGGAAGTCTCTATTTTAAATTCTATAAATGAATAAATGAATATTT
        2110       2120       2130       2140       2150       2160

ASP  LEU  LYS  CYS  ILE  ILE  SER  LYS  ***
GATCTAAAATGCATAATTTCTAAATAATGAAAAAAGTACATCATGAGCAACGCGTTAGT
CTACATTTACGTATTAAACATTTATTACTTTTTTTCATCTACTACTCGTTGCCCAATCA
        2170       2180       2190       2200       2210       2220
```

Figure 13 continued

```
ATATTTTACAATGGAGATTAACGCTCTATACCGTTCTATGTTATTGATTCAGATGATGT
TATAAAATGTTACCTCTAATTGCCAGATATGGCAAGATACAAATAACTAAGTCTACTACA
        2230      2240      2250      2260      2270      2280
TTTAGAAAAGAAAGTTATTGAATATGAAAACTTTAATGAAGATGAAGATGACGACGATGA
AAATCTTTTCTTTCAATAACTTATACTTTTCAAATTACTTCTACTTCTACTCCTGCTACT
        2290      2300      2310      2320      2330      2340

TTATTCTTCTAAATCTCTTTTACATCAACAACATGACCCCCTAAACTATACTATCGTTAC
AATAACAACATTTAGACAAAATCTACTTCTTCTACTGCGCGATTTCATATGATACCAATG
        2350      2360      2370      2380      2390      2400

AAAGTATAAGTCTATACTACTAATGGCGACTTGTGCAAGAAGGTATAGTATAGTGAAAAT
TTTCATATTCAGATATGATGATTACCGCTGAACACGTTCTTCCATATCATATCACTTTTA
        2410      2420      2430      2440      2450      2460

GTTGTTAGATTATGATTATGAAAAACCAAATAAATCAGATCCATATCTAAAGGTATCTCC
CAACAATCTAATACTAATACTTTTTGGTTTATTTAGTCTAGGTATAGATTTCCATAGAGG
        2470      2480      2490      2500      2510      2520

TTTGCACATAATTTCATCTATTCCTAGTTTAGAATACTTTTCATTATATTGTTTACAGC
AAACGTGTATTAAAGTAGATAAGGATCAAATCTTATGAAAAGTAATATAAACAAATGTCG
        2530      2540      2550      2560      2570      2580
                                     GACGTCGG  (C5D1)

TGAACACCAAAAAATATATCGATAATAGAAGATTATCTTAACTCTCCTAATAAGATCAA
ACTTCTGCTTTTTCTTATATAGCTATTATCTTCTAATACAATTGAGACGATTATTCTACTT
        2590      2600      2610      2620      2630      2640

ATTGAATGAGTCTGTGATAATAGCTATAATCAGAGAAGTTCTAAAAGGAAATAAAAATCT
TAACTTACTCAGACACTATTATCGATATTAGTCTCTTCAAGATTTCCTTTATTTTAGA
        2650      2660      2670      2680      2690      2700

AACTGATCAGGATATAAAAACATTCGCTCATGAAATCAACAAGCAGCAACTCAATATACC
TTGACTAGTCCTATATTTTTGTAACCGACTACTTTAGTTGTTCCTCCTTGACTTATATCG
        2710      2720      2730      2740      2750      2760

TAAACTATTGTTAGATAGAGGGGCCAAAGTAAATTACAAGGATGTTTACGGTTCTTCAGC
ATTTGATAACAATCTATCTCCCCGGTTTCATTTAATGTTCCTACAAATGCCAAGAAGTCG
        2770      2780      2790      2800      2810      2820
```

Figure 13 continued

```
TCTCCATAGAGCTGCTATTGGTACGAAACAGGATATGATAAAGCTGTTAATCGATCATGG
AGAGGTATCTCGACGATAACCATCCTTTGTCCTATACTATTTCGACAATTAGCTAGTACC
        2830        2840        2850        2860        2870        2880
AGCTCATGTAAACTCTTTAACTACTGCTAAAGATAATCTTATCAAAAAAAATAATATCA
TCGACTACATTTGAGAAATTGATAACGATTTCTATTAGAATAATTTTTTTACTATAGT
        2890        2900        2910        2920        2930        2940

CGTTTAGTAATATTAAAATATATCAATAACTCTATTACTAATAACTCCAGTGGATATGAA
GCAAATCATTATAATTTTATATAATTATTGAGATAATGATTATTCAGGTCACCTATACTT
        2950        2960        2970        2980        2990        3000

CATAATACGAAGTTTATACATTCTCATCAAAATCTTATTGACATCAAGTTAGATTGTGAA
GTATTATGCTTCAAATATGTAAGAGTAGTTTTAGAATAACTGTAGTTCAATCTAACACTT
        3010        3020        3030        3040        3050        3060

AATCAGATTATGAAATTAAGGAATACAAAAATACGATGTAAGAACTTACTAGAATGTTTT
TTACTCTAATACTTTAATTCCTTATGTTTTATCCTACATTCTTGAATGATCTACAAAA
        3070        3080        3090        3100        3110        3120

ATCAATAATGATATGAATACAGTATCTAGGGCTATAAACAATGAAACGATTAAAAATTAT
TAGTTATTACTATACTTATGTCATAGATCCCGATATTTGTTACTTTGCTAATTTTAATA
        3130        3140        3150        3160        3170        3180

AAAAATCATTTCCCTATATATAATACGCTCATAGAAAAATTCATTTCTGAAAGTATACTA
TTTTAGTAAAGGGATATATATTATGCGAGTATCTTTTTAAGTAAAGACTTTCATATGAT
        3190        3200        3210        3220        3230        3240

AGACACGAATTATTGGATGGAGTTATAAATTCTTTTCAAGGATTCAATAATAAATTGCCT
TCTGTGCTTAATAACCTACCTCAATATTTAAGAAAAGTTCCTAAGTTATTATTAACGGA
        3250        3260        3270        3280        3290        3300

TACGAGATTCAGTACATTATACTGGAGAATCTTAATAACCATGAACTAAAAAAATTTTA
ATGCTCTAAGTCATGTAATATGACCTCTTAGAATTATTGGTACTTGATTTTTCTAAAAT
        3310        3320        3330        3340        3350        3360

GATAATATACATTAAAAAGGTAAATAGATCATCTGTTATTATAAGCAAAGATGCTTGTTG
CTATTATATGTAATTTTTCCATTTATCTAGTAGACAATAATATTCGTTTCTACGAACAAC
        3370        3380        3390        3400        3410        3420
```

Figure 13 continued

```
CCAATAATATACAACAGGTATTTGTTTTTATTTTTAACTACATATTTGATGTTCATTCTC
GGTTATTATATGTTGTCCATAAACAAAAATAAAAATTGATGTATAAACTACAAGTAAGAG
      3430        3440        3450        3460        3470        3480
TTTATATAGTATACACAGAAAATCATAATCCACTTAGAATTCTAGTTATCTAGTTTTT
AAATATATCATATGTGTCTTTTAAGTATTAGGTGAATCTTAAAGATCAATAGATCAAAAA
      3490        3500        3510        3520        3530        3540

CTAGAATATTGTACTTTATTTCTAATGGAATGGCTCTCCAGCCTAGTAATTTATTAATGT
GATCTTATAACATGAAATAAAGATTACCTTACCGAGAGGTCGGATCATTAAATAATTACA
      3550        3560        3570        3580        3590        3600

TACCTGATATCTTGAAATCACGATATTCTGCTCCGTGAACAGAAAGTCCTCCAAAGTTGT
ATCGACTATAGAACTTTAGTCCTATAAGACGAGGCACTTCTCTTTCAGGAGGTTTCAACA
      3610        3620        3630        3640        3650        3660

ATATTTCCATCACTTTCATGGCTTCCTCTTTCCATAGTGTCTTCTATAAGCTGTCTATAT
TATAAAGGTAGTGAAAGTACCGAAGGAGAAAGGTATCACAGAAGATATTCGACAGATATA
      3670        3680        3690        3700        3710        3720

ATTGTAAACTTTTCTGGTTTTATGCATTTTAAACATTTAGCAATCTCATTTTCATCACAA
TAACATTTGAAAAGACCAAAATACGTAAAATTTGTAAATCGTTAGAGTAAAAGTAGTGTT
      3730        3740        3750        3760        3770        3780

TTAAGGCACAAATCTAACATGGAATGTCTACCATAACCCAATAAGGTTTTTTTCATTTCCT
AATCCGTGTTTAGATTGTACCTTACAGATGGTATTGGGTTATTCCAAAAAAGTAAAGGA
      3790        3800        3810        3820        3830        3840

CTATCTCTAATACACACTGTTCTTTCCAGACTTTCAACACGCTGCTATTTCTATTTTAT
GATAGAGATTATGTGTGACAAGAAAGGTCTGAAAGTTGTGCGACGATAAAAGATAAAATA
      3850        3860        3870        3880        3890        3900

TCAAGTCCATATTATAAGCGTCCTTGTTAGACACTTCATAATGTTTGCATTCTGGAATCA
AGTTCAGGTATAATATTCGCAGGAACAATCTGTGAAGTATTACAAACGTAAGACCTTAGT
      3910        3920        3930        3940        3950        3960
```

Figure 13 continued

```
TCATGTTAGATACTATTAATTTAGCTACTTCTATGTTGTCATCAAAAGAGTTGCTATCTG
AGTACAATCTATGATAATTAAATCGATGAAGATACAACAGTAGTTTTCTCAACGATAGAC
         3970        3980        3990        4000        4010        4020

TAATTACACTAAGAGGTGTATCACCTGATAAAGAAGTAATAGAGACATCTGCTCTGAATT
ATTAATGTGATTCTCCACATAGTGGACTATTTCTTCATTATCTCTGTAGACGAGACTTAA
         4030        4040        4050        4060        4070        4080
TAAGCAATACCTCAATAACTTCTTCTGAAGATGACTTTGCAGCTAAAAATAATGCACTTC
ATTCGTTATGGAGTTATTGAAGAAAACTTCTACTGAAACGTCGATTTTATTACCTCAAG
         4090        4100        4110        4120        4130        4140

TCTCTAAAACATCCCTTGAGTTTATATTAGCCCCCTAACTAATGACTAGTTCTGTTATAT
ACAGATTTTGTAGGGAACTCAAATATAATCGGGGCATTGATTACTCATCAAGACAATATA
         4150        4160        4170        4180        4190        4200

CTTTGGAATCTATTGATATATTATTAATTACAATTGTCATGCTGACATATATAGACATCA
GAAACCTTAGATAACTATATAATAATTAATGTTAACAGTACGACTGTATATATCTGTAGT
         4210        4220        4230        4240        4250        4260

TAATATGATGAAAATATGAAAATATAAGTGCACGTTTACTGTTACTATGATTGTGATAT
ATTATACTACTTTTTATACTTTTATATTCACGTGCAAATGACAATGATACTAACACTATA
         4270        4280        4290        4300        4310        4320

CGATATGAGTTCTTTAATAAAAGTACTGAAATAGATATAATGCAGATATGATTGATATTT
GCTATACTCAAGAAATTATTTTCATGACTTTATCTATATTACGTCTATACTAACTATAAA
         4330        4340        4350        4360        4370        4380

TAAAAGTTGAAAAAAATATGCCCTGTTTACAAATACTATTTGGAAATATTCTGTAATA
ATTTTTCAACTTTTTTTTATACGGGACAAATGTTTATGATAAACCTTTATAAGACATTAT
         4390        4400        4410        4420        4430        4440

AAGTAATAGTGATATGTCAGTCACGATGGATTTGCCAATTGATCATATGAGTATAGATAA
TTCATTATCACTATACAGTCAGTGCTACCTAAACGGTTAACTAGTATACTCATATCTATT
         4450        4460        4470        4480        4490        4500

CATAAACGAGTATAATAAAATGGATATACTAGACTTCTATATAGAGGTAGCCATGAAAAA
GTATTTGCTCATATTATTTTTACCTATGATCTGAGATATATCTCCATCGGTACTTTTT
         4510        4520        4530        4540        4550        4560
```

Figure 13 continued

```
ACGTAAAAACGTAGATAGACTTTTATATCTCGGAGCTGATCCGAATCTGGCTAGTGTAGA
TGCATTTTTGCATCTATCTGAAAATATAGAGCCTCGACTAGGCTTAGACCGATCACATCT
     4570      4580      4590      4600      4610      4620

TTCGTATTGTCCTCTTCATATTGCTGTTAGGAATGGTAGTTTAAAGATAATAAGATCATT
AAGCATAACAGGAGAAGTATAACGACAATCCTTACCATCAAATTTCTATTATTCTAGTAA
     4630      4640      4650      4660      4670      4680

GTTGAAATATGGTGCTAATATAAATCAAGAATGTCATGAAGGAGATACTGCTTTGATGAT
CAACTTTATACCACGATTATATTTAGTTCTTACAGTACTTCCTCTATGACGAAACTACTA
     4690      4700      4710      4720      4730      4740

GGCTATATCATTAGGTAATTATACAGCATGTAAAACACTTCTAGATAACAACGCCGATCC
CCGATATAGTAATCCATTAATATGTCGTACATTTTGTGAAGATCTATTGTTGCGGCTAGG
     4750      4760      4770      4780      4790      4800

TAATTATGTTAACTATTACGGTATAGTTCCGCTTATTAGAGCAATTATATGTGAAAAGCC
ATTAATACAATTGATAATGCCATATCAAGGCGAATAATCTCGTTAATATACACTTTTCGG
     4810      4820      4830      4840      4850      4860

TGACATAGTTAGACTGCTATTAGATAGAGGAGCTAATTGCAACCACTTAATTACAAAAAA
ACTGTATCAATCTGACGATAATCTATCTCCTCGATTAACGTTGGTGAATTAATGTTTTTT
     4870      4880      4890      4900      4910      4920

CGGTAGAACCTATACTGCTTTAGAGAGTCTTAGGAATTGCTTTTTTAAAGACAATTCTTC
GCCATCTTGGATATGACGAAATCTCTCAGAATCCTTAACGAAAAATTTCTGTTAAGAAG
     4930      4940      4950      4960      4970      4980

ATCATTGTCGATACTAATAT
TAGTAACAGCTATGATTATA
     4990      5000
```

Figure 14. VQH6 amplified fragment (SEQ ID NO:76)

```
                            VQ marker

BamH I           V  I  R  Q  G  E  N  E  T
AAAGGATCCGGGTTAATTAATTAGTCATCAGGCAGGGCGAGAACGAGACT
TTTCCTAGGCCCAATTAATTAATCAGTAGTCCGTCCCGCTCTTGCTCTGA

I  C  S  *  *  *        ⇒ H6p
ATCTGCTCGTTAATTAATTAGAGCTTCTTTATTCTATACTTAAAAGTGA
TAGACGAGCAATTAATTAATCTCGAAGAAATAAGATATGAATTTTTCACT

AAATAAATACAAAGGTTCTTGAGGGTTGTGTTAAATTGAAAGCGAGAAAT
TTTATTTATGTTTCCAAGAACTCCCAACACAATTTAACTTTCACTCTTTA

EcoR V
AATCATAAATTATTTCATTATCGCGATATCCGTTAAGTTTGTATCGTAGG
TTAGTATTTAATAAAGTAATAGCGCTATAGGCAATTCAAACATAGCATCC

Kpn I  Xho I  Xba I  Cla I  Sma I
TACCCTCGAGTCTAGAATCGATCCCGGGTTTT
ATGGGAGCTCAGATCTTAGCTAGGGCCCAAAA
```

Figure 15. Restriction map of pNVQH6C5LSP-18
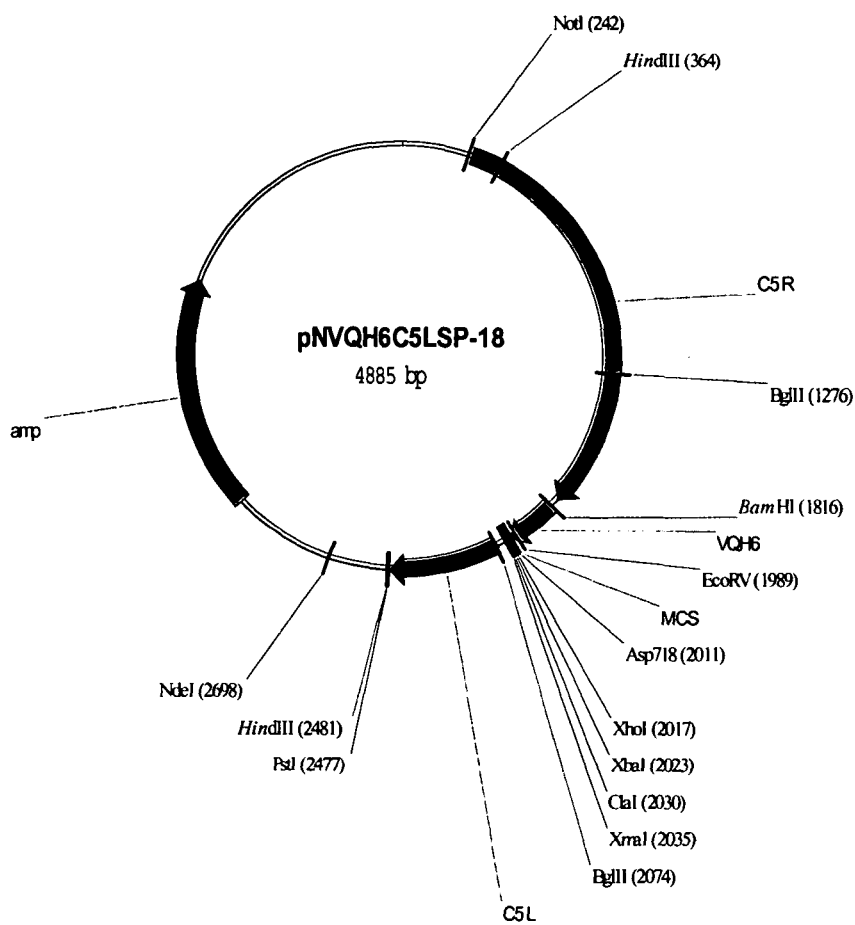

| Viremia following challenge | | | (data depict plaque-forming units per ml of serum) | | | | | | | | | | | | | |
|---|---|---|---|---|---|---|---|---|---|---|---|---|---|---|---|---|
| Study Day | Date | | DPC | AA349 | AA350 | AA351 | AA356 | AA357 | AA358 | AA359 | AA361 | AA362 | AA363 | AA364 |
| 26.0 | 2003-9-16 | AM | 0.0 | 0 | 0 | 0 | 0 | 0 | 0 | 0 | 0 | 0 | 0 | 0 |
| 26.5 | 2003-9-16 | PM | 0.5 | 0 | 0 | 0 | 0 | 0 | 0 | 0 | 0 | 0 | 0 | 0 |
| 27.0 | 2003-9-17 | AM | 1.0 | 0 | 0 | 0 | 0 | 0 | 0 | 0 | 0 | 0 | 0 | 0 |
| 27.5 | 2003-9-17 | PM | 1.5 | 0 | 0 | 0 | 0 | 0 | 0 | 0 | 0 | 0 | 10 | 0 |
| 28.0 | 2003-9-18 | AM | 2.0 | 0 | 0 | 0 | 0 | 0 | 0 | 0 | 0 | 0 | 0 | 0 |
| 28.5 | 2003-9-18 | PM | 2.5 | 0 | 0 | 0 | 0 | 0 | 5 | 5 | 0 | 0 | 0 | 0 |
| 29.0 | 2003-9-19 | AM | 3.0 | 0 | 0 | 0 | 0 | 0 | 0 | 0 | 20 | 30 | 65 | 0 |
| 29.5 | 2003-9-19 | PM | 3.5 | 0 | 0 | 0 | 0 | 10 | 15 | 10 | 65 | 0 | 40 | 0 |
| 30.0 | 2003-9-20 | AM | 4.0 | 0 | 0 | 0 | 0 | 30 | 35 | 25 | 0 | 50 | 55 | 0 |
| 30.5 | 2003-9-20 | PM | 4.5 | 0 | 0 | 0 | 0 | 55 | 145 | 50 | 0 | 0 | 75 | 0 |
| 31.0 | 2003-9-21 | AM | 5.0 | 0 | 0 | 0 | 0 | 40 | 85 | 40 | 0 | 15 | 10 | 0 |
| 31.5 | 2003-9-21 | PM | 5.5 | 0 | 0 | 0 | 0 | 30 | 10 | 35 | 0 | 0 | 0 | 0 |
| 32.0 | 2003-9-22 | AM | 6.0 | 0 | 0 | 0 | 0 | 20 | 30 | 0 | 25 | 0 | 0 | 0 |
| 32.5 | 2003-9-22 | PM | 6.5 | 0 | 0 | 0 | 0 | 0 | 0 | 0 | 0 | 0 | 0 | 0 |
| 33.0 | 2003-9-23 | AM | 7.0 | 0 | 0 | 0 | 0 | 0 | 0 | 0 | 0 | 0 | 0 | 0 |
| 33.5 | 2003-9-23 | PM | 7.5 | 0 | 0 | 0 | 0 | 0 | 0 | 0 | 0 | 0 | 0 | 0 |
| 34.0 | 2003-9-24 | AM | 8.0 | 0 | 0 | 0 | 0 | 0 | 0 | 0 | 0 | 0 | 0 | 0 |
| 34.5 | 2003-9-24 | PM | 8.5 | 0 | 0 | 0 | 0 | 0 | 0 | 0 | 0 | 0 | 0 | 0 |
| 35.0 | 2003-9-25 | AM | 9.0 | 0 | 0 | 0 | 0 | 0 | 0 | 0 | 0 | 0 | 0 | 0 |
| 35.5 | 2003-9-25 | PM | 9.5 | 0 | 0 | 0 | 0 | 0 | 0 | 0 | 0 | 0 | 0 | 0 |
| 36.0 | 2003-9-26 | AM | 10.0 | 0 | 0 | 0 | 0 | 0 | 0 | 0 | 0 | 0 | 0 | 0 |
| 36.5 | 2003-9-26 | PM | 10.5 | 0 | 0 | 0 | 0 | 0 | 0 | 0 | 0 | 0 | 0 | 0 |
| 37.0 | 2003-9-27 | AM | 11.0 | 0 | 0 | 0 | 0 | 0 | 0 | 0 | 0 | 0 | 0 | 0 |
| 37.5 | 2003-9-27 | PM | 11.5 | 0 | 0 | 0 | 0 | 0 | 0 | 0 | 0 | 0 | 0 | 0 |
| 38.0 | 2003-9-28 | AM | 12.0 | 0 | 0 | 0 | 0 | 0 | 0 | 0 | 0 | 0 | 0 | 0 |
| 38.5 | 2003-9-28 | PM | 12.5 | 0 | 0 | 0 | 0 | 0 | 0 | 0 | 0 | 0 | 0 | 0 |
| 39.0 | 2003-9-29 | AM | 13.0 | 0 | 0 | 0 | 0 | 0 | 0 | 0 | 0 | 0 | 0 | 0 |
| 39.5 | 2003-9-29 | PM | 13.5 | 0 | 0 | 0 | 0 | 0 | 0 | 0 | 0 | 0 | 0 | 0 |
| 40.0 | 2003-9-30 | AM | 14.0 | 0 | 0 | 0 | 0 | 0 | 0 | 0 | 0 | 0 | 0 | 0 |

Note: DPC = days post challenge

Figure 16

| VI Results | Day-Time | | | | | | | | | | | | | |
|---|---|---|---|---|---|---|---|---|---|---|---|---|---|---|
| Group Name | ID | 26-AM | 26-PM | 27-AM | 27-PM | 28-AM | 28-PM | 29-AM | 29-PM | 30-AM | 30-PM | 31-AM | 31-PM | 32-AM |
| Test Vaccine | AA349 | 0 | 0 | 0 | 0 | 0 | 0 | 0 | 0 | 0 | 0 | 0 | 0 | 0 |
| | AA350 | 0 | 0 | 0 | 0 | 0 | 0 | 0 | 0 | 0 | 0 | 0 | 0 | 0 |
| | AA356 | 0 | 0 | 0 | 0 | 0 | 0 | 0 | 0 | 0 | 0 | 0 | 0 | 0 |
| | AA361 | 0 | 0 | 0 | 0 | 0 | 0 | 1 | 1 | 0 | 0 | 0 | 0 | 1 |
| | AA364 | 0 | 0 | 0 | 0 | 0 | 0 | 0 | 0 | 0 | 0 | 0 | 0 | 0 |
| | AA365 | 0 | 0 | 0 | 0 | 0 | 0 | 0 | 0 | 0 | 0 | 0 | 0 | 0 |
| | AA370 | 0 | 0 | 0 | 0 | 0 | 0 | 0 | 0 | 0 | 0 | 0 | 0 | 0 |
| | AA373 | 0 | 0 | 0 | 0 | 0 | 0 | 0 | 0 | 0 | 0 | 0 | 0 | 0 |
| | AA374 | 0 | 0 | 0 | 0 | 0 | 0 | 0 | 1 | 1 | 0 | 0 | 0 | 1 |
| Test Vaccine Total | | 0 | 0 | 0 | 0 | 0 | 0 | 1 | 2 | 1 | 0 | 0 | 0 | 2 |
| Unvaccinated | AA351 | 0 | 0 | 0 | 0 | 0 | 0 | 0 | 1 | 1 | 1 | 1 | 0 | 0 |
| | AA357 | 0 | 0 | 0 | 0 | 0 | 1 | 1 | 1 | 1 | 1 | 1 | 1 | 1 |
| | AA358 | 0 | 0 | 0 | 0 | 0 | 0 | 0 | 1 | 1 | 1 | 1 | 1 | 1 |
| | AA359 | 0 | 0 | 0 | 0 | 0 | 0 | 0 | 1 | 1 | 1 | 1 | 1 | 0 |
| | AA362 | 0 | 0 | 0 | 1 | 1 | 1 | 1 | 0 | 0 | 0 | 0 | 0 | 0 |
| | AA363 | 0 | 0 | 0 | 0 | 0 | 0 | 0 | 0 | 0 | 0 | 0 | 0 | 0 |
| | AA368 | 0 | 0 | 0 | 0 | 0 | 0 | 1 | 1 | 1 | 1 | 1 | 1 | 0 |
| | AA369 | 0 | 0 | 0 | 1 | 0 | 1 | 0 | 1 | 1 | 1 | 1 | 0 | 0 |
| | AA371 | 0 | 0 | 0 | 0 | 0 | 0 | 1 | 1 | 1 | 1 | 1 | 1 | 0 |
| | AA372 | 0 | 0 | 0 | 0 | 0 | 0 | 0 | 0 | 0 | 0 | 0 | 0 | 0 |
| Unvaccinated Total | | 0 | 0 | 0 | 2 | 1 | 4 | 4 | 6 | 8 | 6 | 7 | 4 | 2 |

Figure 17a

| VI Results | | Day-Time | | | | | | | | | | | | | |
|---|---|---|---|---|---|---|---|---|---|---|---|---|---|---|---|
| Group Name | ID | 32-PM | 33-AM | 34-AM | 34-PM | 35-AM | 35-PM | 36-AM | 36-PM | 37-AM | 37-PM | 38-AM | 38-PM | 39-AM |
| Test Vaccine | AA349 | 0 | 0 | 0 | 0 | 0 | 0 | 0 | 0 | 0 | 0 | 0 | 0 | 0 |
| | AA350 | 0 | 0 | 0 | 0 | 0 | 0 | 0 | 0 | 0 | 0 | 0 | 0 | 0 |
| | AA356 | 0 | 0 | 0 | 0 | 0 | 0 | 0 | 0 | 0 | 0 | 0 | 0 | 0 |
| | AA361 | 0 | 0 | 0 | 0 | 0 | 0 | 0 | 0 | 0 | 0 | 0 | 0 | 0 |
| | AA364 | 0 | 0 | 0 | 0 | 0 | 0 | 0 | 0 | 0 | 0 | 0 | 0 | 0 |
| | AA365 | 0 | 0 | 0 | 0 | 0 | 0 | 0 | 0 | 0 | 0 | 0 | 0 | 0 |
| | AA370 | 0 | 0 | 0 | 0 | 0 | 0 | 0 | 0 | 0 | 0 | 0 | 0 | 0 |
| | AA373 | 0 | 0 | 0 | 0 | 0 | 0 | 0 | 0 | 0 | 0 | 0 | 0 | 0 |
| | AA374 | 0 | 0 | 0 | 0 | 0 | 0 | 0 | 0 | 0 | 0 | 0 | 0 | 0 |
| Test Vaccine Total | | 0 | 0 | 0 | 0 | 0 | 0 | 0 | 0 | 0 | 0 | 0 | 0 | 0 |
| Unvaccinated | AA351 | 0 | 0 | 0 | 0 | 0 | 0 | 0 | 0 | 0 | 0 | 0 | 0 | 0 |
| | AA357 | 0 | 0 | 0 | 0 | 0 | 0 | 0 | 0 | 0 | 0 | 0 | 0 | 0 |
| | AA358 | 0 | 0 | 0 | 0 | 0 | 0 | 0 | 0 | 0 | 0 | 0 | 0 | 0 |
| | AA359 | 0 | 0 | 0 | 0 | 0 | 0 | 0 | 0 | 0 | 0 | 0 | 0 | 0 |
| | AA362 | 0 | 0 | 0 | 0 | 0 | 0 | 0 | 0 | 0 | 0 | 0 | 0 | 0 |
| | AA363 | 0 | 0 | 0 | 0 | 0 | 0 | 0 | 0 | 0 | 0 | 0 | 0 | 0 |
| | AA368 | 0 | 0 | 0 | 0 | 0 | 0 | 0 | 0 | 0 | 0 | 0 | 0 | 0 |
| | AA369 | 0 | 0 | 0 | 0 | 0 | 0 | 0 | 0 | 0 | 0 | 0 | 0 | 0 |
| | AA371 | 0 | 0 | 0 | 0 | 0 | 0 | 0 | 0 | 0 | 0 | 0 | 0 | 0 |
| | AA372 | 0 | 0 | 0 | 0 | 0 | 0 | 0 | 0 | 0 | 0 | 0 | 0 | 0 |
| Unvaccinated Total | | 0 | 0 | 0 | 0 | 0 | 0 | 0 | 0 | 0 | 0 | 0 | 0 | 0 |

Figure 17b

| Average of Temp | | Study D | | | | | | | | | | | | | |
|---|---|---|---|---|---|---|---|---|---|---|---|---|---|---|---|
| Group | ID | 24-AM | 25-AM | 26-AM | 26-PM | 27-AM | 27-PM | 28-AM | 28-PM | 29-AM | 29-PM | 30-AM | 30-PM | 31-AM |
| Test Vaccine | AA349 | 99.90 | 100.10 | 100.60 | 100.50 | 101.10 | 100.00 | 100.40 | 101.00 | 100.60 | 101.00 | 100.20 | 100.40 | 99.80 |
| | AA350 | 100.40 | 100.20 | 99.80 | 100.60 | 101.20 | 99.60 | 100.60 | 99.60 | 99.80 | 99.40 | 100.00 | 99.20 | 99.00 |
| | AA356 | 100.30 | 100.10 | 100.20 | 100.80 | 100.00 | 100.20 | 100.20 | 100.00 | 99.60 | 100.40 | 100.10 | 100.20 | 100.00 |
| | AA361 | 100.00 | 99.80 | 100.10 | 99.80 | 101.00 | 100.20 | 100.20 | 100.00 | 100.60 | 100.20 | 99.20 | 100.80 | 99.60 |
| | AA364 | 100.20 | 100.00 | 99.90 | 101.10 | 101.00 | 100.40 | 100.20 | 100.00 | 99.80 | 99.80 | 100.40 | 100.20 | 100.00 |
| | AA365 | 100.00 | 99.90 | 100.00 | 100.50 | 101.10 | 101.20 | 100.00 | 100.00 | 100.40 | 100.00 | 100.20 | 100.00 | 100.00 |
| | AA370 | 100.20 | 100.30 | 100.30 | 100.60 | 101.00 | 99.80 | 100.00 | 100.60 | 100.40 | 99.60 | 99.40 | 99.00 | 98.80 |
| | AA373 | 100.20 | 100.50 | 99.80 | 100.60 | 101.20 | 99.60 | 100.00 | 100.40 | 100.00 | 99.80 | 100.20 | 99.60 | 100.60 |
| | AA374 | 100.40 | 100.30 | 100.50 | 101.20 | 101.00 | 100.40 | 99.80 | 100.20 | 100.20 | 99.60 | 100.40 | 99.80 | 99.60 |
| Test Vaccine Average | | 100.18 | 100.13 | 100.13 | 100.63 | 100.96 | 100.16 | 100.16 | 100.20 | 100.16 | 99.98 | 100.01 | 99.96 | 99.71 |
| Unvaccinated | AA351 | 99.80 | 100.50 | 100.20 | 100.60 | 100.50 | 100.60 | 99.20 | 100.00 | 100.00 | 99.80 | 100.00 | 99.80 | 99.80 |
| | AA357 | 100.50 | 99.80 | 100.20 | 100.60 | 101.00 | 100.60 | 100.20 | 100.60 | 100.00 | 101.00 | 98.80 | 100.20 | 100.40 |
| | AA358 | 100.00 | 100.20 | 100.20 | 100.80 | 101.20 | 100.00 | 100.20 | 100.80 | 100.80 | 100.40 | 100.20 | 100.20 | 99.00 |
| | AA359 | 99.90 | 99.70 | 99.60 | 100.80 | 100.80 | 100.00 | 100.00 | 100.40 | 100.40 | 100.20 | 100.20 | 100.00 | 100.00 |
| | AA362 | 100.70 | 100.30 | 100.40 | 100.80 | 100.60 | 99.80 | 100.00 | 100.40 | 100.40 | 99.60 | 99.80 | 100.00 | 98.00 |
| | AA363 | 99.70 | 99.90 | 99.90 | 99.80 | 100.20 | 100.40 | 100.40 | 100.40 | 100.40 | 100.60 | 99.80 | 99.80 | 99.80 |
| | AA368 | 100.20 | 100.40 | 100.00 | 101.00 | 101.00 | 100.60 | 100.20 | 100.40 | 100.40 | 100.00 | 99.80 | 100.00 | 99.80 |
| | AA369 | 100.50 | 100.20 | 100.80 | 101.00 | 100.40 | 100.60 | 100.20 | 100.40 | 100.40 | 100.00 | 98.60 | 100.00 | 99.80 |
| | AA371 | 100.80 | 100.00 | 100.80 | 100.60 | 101.10 | 100.40 | 100.00 | 100.40 | 100.20 | 100.20 | 100.00 | 100.20 | 99.80 |
| | AA372 | 99.80 | 100.00 | 100.10 | 100.20 | 101.20 | 100.40 | 100.60 | 100.60 | 100.60 | 100.20 | 100.20 | 100.00 | 99.20 |
| Unvaccinated Average | | 100.19 | 100.10 | 100.22 | 100.60 | 100.80 | 100.34 | 100.10 | 100.42 | 100.36 | 100.22 | 99.78 | 100.04 | 99.56 |

Figure 18a

| Average of Temp | | Study Day | | | | | | | | | | | | |
|---|---|---|---|---|---|---|---|---|---|---|---|---|---|---|
| Group | ID | 31-PM | 32-AM | 32-PM | 33-AM | 33-PM | 34-AM | 34-PM | 35-AM | 35-PM | 36-AM | 36-PM | 37-AM | 37-PM |
| Test Vaccine | AA349 | 99.00 | 99.70 | 100.20 | 100.20 | 100.00 | 100.00 | 100.60 | 100.10 | 100.60 | 99.80 | 99.80 | 100.00 | 99.60 |
| | AA350 | 99.20 | 99.80 | 100.60 | 100.20 | 100.40 | 99.70 | 100.00 | 99.90 | 99.60 | 99.90 | 98.80 | 100.20 | 99.20 |
| | AA356 | 100.20 | 100.10 | 100.00 | 99.80 | 100.00 | 100.20 | 100.00 | 100.00 | 100.30 | 99.40 | 99.80 | 99.40 | 99.80 |
| | AA361 | 100.40 | 99.80 | 100.80 | 99.40 | 99.80 | 99.90 | 99.50 | 99.80 | 100.20 | 99.40 | 100.00 | 100.10 | 100.00 |
| | AA364 | 99.80 | 99.80 | 100.00 | 100.00 | 100.00 | 99.60 | 100.20 | 99.80 | 100.80 | 99.80 | 99.60 | 99.90 | 99.80 |
| | AA365 | 100.20 | 99.90 | 100.00 | 99.90 | 99.60 | 99.90 | 99.00 | 99.60 | 99.60 | 100.00 | 99.00 | 99.80 | 99.00 |
| | AA370 | 100.00 | 99.40 | 99.20 | 99.50 | 99.80 | 99.70 | 99.50 | 99.80 | 99.60 | 99.80 | 99.00 | 99.30 | 99.50 |
| | AA373 | 100.80 | 99.50 | 99.40 | 100.00 | 99.60 | 99.60 | 100.10 | 100.00 | 99.00 | 100.30 | 99.60 | 99.80 | 99.90 |
| | AA374 | 100.80 | 99.60 | 100.00 | 100.00 | 100.60 | 100.20 | 100.00 | 99.70 | 100.00 | 99.80 | 99.70 | 100.00 | 99.80 |
| Test Vaccine Average | | 100.04 | 99.73 | 100.02 | 99.89 | 99.98 | 99.87 | 99.88 | 99.86 | 99.97 | 99.80 | 99.48 | 99.83 | 99.62 |
| Unvaccinated | AA351 | 99.60 | 100.10 | 99.00 | 99.10 | 99.00 | 99.60 | 100.60 | 99.70 | 100.40 | 99.80 | 100.00 | 99.60 | 99.00 |
| | AA357 | 99.60 | 99.70 | 99.50 | 100.00 | 99.50 | 99.80 | 100.40 | 99.90 | 100.60 | 99.60 | 99.50 | 99.80 | 99.80 |
| | AA358 | 100.40 | 99.20 | 100.40 | 100.10 | 99.60 | 100.00 | 99.80 | 99.40 | 99.60 | 99.40 | 99.40 | 99.70 | 99.40 |
| | AA359 | 100.20 | 100.20 | 99.80 | 100.10 | 100.00 | 99.80 | 100.00 | 99.70 | 99.00 | 100.00 | 99.00 | 100.00 | 100.20 |
| | AA362 | 101.00 | 99.20 | 99.60 | 99.70 | 98.50 | 100.00 | 99.90 | 99.80 | 99.60 | 99.70 | 100.00 | 99.70 | 98.50 |
| | AA363 | 100.00 | 99.90 | 99.80 | 100.30 | 99.60 | 100.00 | 99.60 | 100.10 | 100.00 | 99.80 | 99.20 | 99.70 | 99.60 |
| | AA368 | 100.40 | 100.10 | 100.00 | 99.90 | 99.00 | 99.40 | 100.60 | 99.50 | 100.00 | 99.70 | 99.80 | 100.00 | 99.00 |
| | AA369 | 99.80 | 100.10 | 100.00 | 99.80 | 100.00 | 99.90 | 100.40 | 100.00 | 100.60 | 99.60 | 100.60 | 99.50 | 102.00 |
| | AA371 | 100.80 | 99.90 | 100.60 | 99.80 | 100.00 | 100.00 | 100.50 | 99.50 | 99.80 | 100.10 | 99.80 | 99.80 | 99.60 |
| | AA372 | 99.80 | 100.00 | 100.00 | 100.30 | 99.80 | 100.10 | 99.80 | 99.90 | 99.80 | 100.10 | 100.20 | 100.10 | 99.80 |
| Unvaccinated Average | | 100.16 | 99.83 | 99.87 | 99.93 | 99.50 | 99.86 | 100.16 | 99.83 | 99.92 | 99.78 | 99.75 | 99.79 | 99.69 |

Figure 18b

| | | Plaque reduction neutralization titers | | | | | | | | | | | |
|---|---|---|---|---|---|---|---|---|---|---|---|---|---|
| Study Day | Date | DPC | Reduction | AA349 | AA350 | AA351 | AA356 | AA357 | AA358 | AA359 | AA361 | AA362 | AA363 |
| 0 | 2003-8-21 | -26 | 90% | <5 | <5 | <5 | <5 | <5 | <5 | <5 | <5 | <5 | <5 |
| 7 | 2003-8-28 | -19 | 90% | <5 | <5 | <5 | <5 | <5 | <5 | <5 | <5 | <5 | <5 |
| 14 | 2003-9-4 | -12 | 90% | <5 | <5 | <5 | <5 | <5 | <5 | <5 | 10 | <5 | <5 |
| 21 | 2003-9-11 | -5 | 90% | <5 | <5 | <5 | 5 | <5 | <5 | <5 | 10 | <5 | <5 |
| 26 | 2003-9-16 | 0 | 90% | <5 | <5 | <5 | <5 | <5 | <5 | <5 | <5 | <5 | <5 |
| 33 | 2003-9-23 | 7 | 90% | 40 | 10 | <5 | 40 | <5 | 80 | <5 | 10 | 80 | <5 |
| 40 | 2003-9-30 | 14 | 90% | >=160 | >=160 | 40 | >=160 | >=160 | >=160 | >=160 | >=160 | >=160 | >=160 |
| 0 | 2003-8-21 | -26 | 80% | <5 | <5 | <5 | <5 | <5 | <5 | <5 | <5 | <5 | <5 |
| 7 | 2003-8-28 | -19 | 80% | <5 | <5 | <5 | 5 | <5 | <5 | <5 | <5 | <5 | <5 |
| 14 | 2003-9-4 | -12 | 80% | <5 | 5 | <5 | 5 | <5 | <5 | <5 | 10 | <5 | <5 |
| 21 | 2003-9-11 | -5 | 80% | <5 | 5 | <5 | 5 | <5 | <5 | <5 | 20 | <5 | <5 |
| 26 | 2003-9-16 | 0 | 80% | <5 | <5 | <5 | 5 | <5 | <5 | <5 | 5 | <5 | <5 |
| 33 | 2003-9-23 | 7 | 80% | 80 | 20 | <5 | 40 | <5 | >=160 | <5 | 20 | >=160 | <5 |
| 40 | 2003-9-30 | 14 | 80% | >=160 | >=160 | 80 | >=160 | >=160 | >=160 | >=160 | >=160 | >=160 | >=160 |
| 0 | 2003-8-21 | -26 | 50% | <5 | <5 | <5 | <5 | <5 | <5 | <5 | <5 | <5 | <5 |
| 7 | 2003-8-28 | -19 | 50% | <5 | <5 | <5 | 10 | <5 | <5 | <5 | <5 | <5 | <5 |
| 14 | 2003-9-4 | -12 | 50% | <5 | 20 | <5 | 20 | <5 | <5 | <5 | 80 | <5 | <5 |
| 21 | 2003-9-11 | -5 | 50% | <5 | 20 | <5 | 20 | <5 | <5 | <5 | 80 | <5 | <5 |
| 26 | 2003-9-16 | 0 | 50% | <5 | 5 | <5 | 20 | <5 | <5 | <5 | 40 | <5 | <5 |
| 33 | 2003-9-23 | 7 | 50% | >=160 | 80 | 20 | >=160 | >=160 | >=160 | >=160 | >=160 | >=160 | >=160 |
| 40 | 2003-9-30 | 14 | 50% | >=160 | >=160 | >=160 | >=160 | >=160 | >=160 | >=160 | >=160 | >=160 | >=160 |

Figure 19a

| Study Day | AA364 | AA365 | AA368 | AA369 | AA370 | AA371 | AA372 | AA373 | AA374 |
|---|---|---|---|---|---|---|---|---|---|
| 0 | <5 | <5 | <5 | <5 | <5 | <5 | <5 | <5 | <5 |
| 7 | <5 | <5 | <5 | <5 | <5 | <5 | <5 | <5 | <5 |
| 14 | <5 | 5 | <5 | <5 | <5 | <5 | <5 | <5 | <5 |
| 21 | <5 | <5 | <5 | <5 | <5 | <5 | <5 | <5 | <5 |
| 26 | <5 | <5 | <5 | <5 | <5 | <5 | <5 | <5 | <5 |
| 33 | 40 | 5 | <5 | <5 | 10 | <5 | 5 | 10 | 5 |
| 40 | 80 | 80 | >=160 | >=160 | >=160 | >=160 | >=160 | >=160 | >=160 |
| 0 | <5 | <5 | <5 | <5 | <5 | <5 | <5 | <5 | <5 |
| 7 | <5 | 10 | <5 | <5 | <5 | <5 | <5 | <5 | <5 |
| 14 | <5 | <5 | <5 | <5 | <5 | <5 | <5 | <5 | <5 |
| 21 | <5 | 5 | <5 | <5 | <5 | <5 | <5 | <5 | <5 |
| 26 | 80 | 10 | <5 | <5 | 10 | <5 | 5 | 20 | 10 |
| 33 | >=160 | >=160 | >=160 | >=160 | >=160 | >=160 | >=160 | >=160 | >=160 |
| 40 | | | | | | | | | |
| 0 | <5 | <5 | <5 | <5 | <5 | <5 | <5 | <5 | <5 |
| 7 | <5 | 40 | <5 | <5 | 5 | <5 | <5 | <5 | <5 |
| 14 | 5 | 10 | <5 | <5 | 40 | 10 | 40 | 10 | 5 |
| 21 | 5 | 20 | <5 | <5 | >=160 | >=160 | >=160 | 10 | <5 |
| 26 | 10 | 20 | <5 | <5 | | | | <5 | 40 |
| 33 | >=160 | >=160 | >=160 | >=160 | | | | 80 | 40 |
| 40 | >=160 | >=160 | >=160 | >=160 | | | | >=160 | >=160 |

Figure 19b

SEQUENCE LISTING

```
<160> NUMBER OF SEQ ID NOS: 85

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 tttttttgaat tcgttaccct ctctaacttc                                    30

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 2
tttttttcta gattacctcc gactgcgtct tga                          33

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatctgcagc acgtgtctag aggatatcga attcgcggcc                   40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatccgcggc cgcgaattcg atatcctcta gacacgtgct                   40

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 tttttttgaat tctcactgac agtgcagaca                             30

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tttttttcta gattagctgt aagctggggc cac                          33

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 tttttttgaat tcttcaactg ccttggaatg                             30

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 8
tttttttcta gattaagcgt gcacgttcac gga                                      33

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 tttttttgata tcaccggaat tgcagtcatg attggc                                  36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 tttttttgata tcatgtataa tgctgatatg attgac                                  36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tttttttcta gattaacgtt tcccgaggc gaagtc                                    36

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atcatcgagc tccagctgta attcatggtc gaaaagaagt gc                            42

<210> SEQ ID NO 13
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaattcctcg agctgcagcc cgggtttta tagctaatta gtcattttt gagagtacca           60 cttcagctac ctc                                                            73

<210> SEQ ID NO 14
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14
cccgggctgc agctcgagga attctttta ttgattaact agtcattata aagatctaaa      60
atgcataatt tc                                                         72

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatgatggta ccgtaaacaa atataatgaa aagtattcta aacta                     45

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaacccgggt tctttattct atacttaaaa agtg                                 34

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaagaattc gtcgactacg atacaaactt aacggatatc gcg                       43

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttttcgcgaa ccggaattgc agtcatgatt ggc                                  33

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttttgtcgac gcggccgctt aagcgtgcac gttcacgga                            39

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 20
atcatcgagc tcgcggccgc ctatcaaaag tcttaatgag tt         42

<210> SEQ ID NO 21
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaattcctcg agctgcagcc cgggttttta tagctaatta gtcattttt cgtaagtaag    60 tatttttatt taa                                                      73

<210> SEQ ID NO 22
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cccgggctgc agctcgagga attcttttta ttgattaact agtcaaatga gtatatataa    60
ttgaaaaagt aa                                                       72

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatgatggta ccttcataaa tacaagtttg attaaactta agttg              45

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaacccgggc ggtggtttgc gattccgaaa tct                           33

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 aaagaattc ggatccgatt aaacctaaat aattgtactt tgt                 43

<210> SEQ ID NO 26
<211> LENGTH: 33
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 26
tttcacgtga tgtataatgc tgatatgatt gac                             33

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttttggatcc gcggccgctt aacgttttcc cgaggcgaag tc                   42

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 tttttttgata tcatgaccgg aattgcagtc atgattggc                      39

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttttcgcgaa tgaccggaat tgcagtcatg attggc                          36

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
atcatcgagc tcgacccttt acaagaataa aagaagaaac aa                   42

<210> SEQ ID NO 31
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctcgagctgc aggaattccc cgggttttta ttagctaatt agcaatatag attcaatatg   60
ataattactc taa                                                     73

<210> SEQ ID NO 32
<211> LENGTH: 72

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
cccggggaat tcctgcagct cgagtttta ttgactagtt aatcataaga taaataatat    60
acagcattgt aa                                                       72

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
gatgatggta ccgggtaatg gcttttgttt ataaccacgt ttgtc                   45

<210> SEQ ID NO 34
<211> LENGTH: 95
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
aaacccgggt taattaatta gtcatcaggc agggcgaaac gagactatct gctcgttaat   60
taattagagc ttctttattc tatacttaaa aagtg                              95

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
aaaactgcag gtcgactacg atacaaactt aacggatatc gcg                     43

<210> SEQ ID NO 36
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
ttttcgcgat atccgttaag tttgtatcgt aatgaccgga attgcagtca tgattggc     58

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
ttttgtcgac tctagataaa aattaagcgt gcacgttcac gga                     43

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaagtggcca tcttcgtgca cggaccaact                                      30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agttggtccg tgcacgaaga tggccacttc                                      30

<210> SEQ ID NO 40
<211> LENGTH: 30
<212> TYPE: DNA
<213> ORGANISM: West Nile virus
<220> FEATURE:
<221> NAME/KEY: CDS
<222> LOCATION: (1)..(30)

<400> SEQUENCE: 40 gaa gtg gcc att ttt gtc cat gga cca act                               30
Glu Val Ala Ile Phe Val His Gly Pro Thr
 1               5                  10

<210> SEQ ID NO 41
<211> LENGTH: 10
<212> TYPE: PRT
<213> ORGANISM: West Nile virus

<400> SEQUENCE: 41

Glu Val Ala Ile Phe Val His Gly Pro Thr
 1               5                  10

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(24)

<400> SEQUENCE: 42 aag cct acc atc gat gtg aag atg                                       24
Lys Pro Thr Ile Asp Val Lys Met
 1               5

<210> SEQ ID NO 43
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gggccctcta gataaaaatt aagcgtgcac gttcacggag aggaagagca g         51

<210> SEQ ID NO 44
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(33)

<400> SEQUENCE: 44 ctg ctc ttc ctc tcc gtg aac gtg cac gct taa tttttatcta gagggccc    51
Leu Leu Phe Leu Ser Val Asn Val His Ala
 1               5                  10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Leu Phe Leu Ser Val Asn Val His Ala
 1               5                  10

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Pro Thr Ile Asp Val Lys Met
 1               5

<210> SEQ ID NO 47
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (30)..(59)

<400> SEQUENCE: 47
atcgcgatat ccgttaagtt tgtatcgta atg acc gga att gca gtc atg att    53
                                Met Thr Gly Ile Ala Val Met Ile
                                 1               5 ggc ctg                                                            59
Gly Leu
     10

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic

```
                                            -continued
        primer

<400> SEQUENCE: 48
catcttcaca tcgatggtag gctt                                                24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(24)

<400> SEQUENCE: 49 aag cct acc atc gat gtg aag atg                                           24
Lys Pro Thr Ile Asp Val Lys Met
  1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Pro Thr Ile Asp Val Lys Met
  1               5

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Met Thr Gly Ile Ala Val Met Ile Gly Leu
  1               5                  10

<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cgatatccgt taagtttgta tcgtaatgcc cgggtcgcga a                              41

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
agctttcgcg acccgggcat tacgatacaa acttaacgga tatcg                         45
```

-continued

```
<210> SEQ ID NO 54
<211> LENGTH: 4270
<212> TYPE: DNA
<213> ORGANISM: West Nile virus
<220> FEATURE:
<221> NAME/KEY: CDS
<222> LOCATION: (1760)..(3811)

<400> SEQUENCE: 54
tgaatgttaa atgttatact ttggatgaag ctataaatat gcattggaaa aataatccat      60
ttaaagaaag gattcaaata ctacaaaacc taagcgataa tatgttaact aagcttattc     120
ttaacgacgc tttaaatata cacaaataaa cataattttt gtataaccta acaaataact     180
aaaacataaa aataataaaa ggaaatgtaa tatcgtaatt attttactca ggaatggggt     240
taaatattta tatcacgtgt atatctatac tgttatcgta tactctttac aattactatt     300
acgaatatgc aagagataat aagattacgt atttaagaga atcttgtcat gataattggg     360
tacgacatag tgataaatgc tatttcgcat cgttacataa agtcagttgg aaagatggat     420
ttgacagatg taacttaata ggtgcaaaaa tgttaaataa cagcattcta tcggaagata     480
ggataccagt tatattatac aaaaatcact ggttggataa aacagattct gcaatattcg     540
taaaagatga agattactgc gaatttgtaa actatgacaa taaaaagcca tttatctcaa     600
cgacatcgtg taattcttcc atgttttatg tatgtgtttc agatattatg agattactat     660 aaacttttg tatacttata ttccgtaaac tatattaatc atgaagaaaa tgaaaaagta     720
tagaagctgt tcacgagcgg ttgttgaaaa caacaaaatt atacattcaa gatggcttac     780
atatacgtct gtgaggctat catggataat gacaatgcat ctctaaatag gttttttggac    840 aatggattcg accctaacac ggaatatggt actctacaat ctcctcttga atggctgta      900 atgttcaaga ataccgaggc tataaaaatc ttgatgaggt atggagctaa acctgtagtt     960
actgaatgca caacttcttg tctgcatgat gcggtgttga gagacgacta caaaatagtg    1020
aaagatctgt tgaagaataa ctatgtaaac aatgttcttt acagcggagg ctttactcct    1080
ttgtgtttgg cagcttacct taacaaagtt aatttggtta aacttctatt ggctcattcg    1140
gcggatgtag atatttcaaa cacggatcgg ttaactcctc tacatatagc cgtatcaaat    1200
aaaaatttaa caatggttaa acttctattg aacaaaggtg ctgatactga cttgctggat    1260
aacatgggac gtactccttt aatgatcgct gtacaatctg gaaatattga aatatgtagc    1320
acactactta aaaaaaataa aatgtccaga actgggaaaa attgatcttg ccagctgtaa    1380
ttcatggtag aaaagaagtg ctcaggctac ttttcaacaa aggagcagat gtaaactaca    1440
tctttgaaag aaatggaaaa tcatatactg ttttggaatt gattaaagaa agttactctg    1500
agacacaaaa gaggtagctg aagtggtact ctcaaaaagg tacgtgacta attagctata    1560
aaaaggatcc gggttaatta attagtcatc aggcagggcg agaacgagac tatctgctcg    1620
ttaattaatt agagcttctt tattctatac ttaaaaagtg aaaataaata caaaggttct    1680
tgagggttgt gttaaattga agcgagaaa taatcataaa ttatttcatt atcgcgatat     1740
ccgttaagtt tgtatcgta atg acc gga att gca gtc atg att ggc ctg atc     1792
                     Met Thr Gly Ile Ala Val Met Ile Gly Leu Ile
                      1               5                  10 gcc agc gta gga gca gtt acc ctc tct aac ttc caa ggg aag gtg atg     1840
Ala Ser Val Gly Ala Val Thr Leu Ser Asn Phe Gln Gly Lys Val Met
            15                  20                  25 atg acg gta aat gct act gac gtc aca gat gtc atc acg att cca aca     1888
Met Thr Val Asn Ala Thr Asp Val Thr Asp Val Ile Thr Ile Pro Thr
        30                  35                  40
```

```
gct gct gga aag aac cta tgc att gtc aga gca atg gat gtg gga tac   1936
Ala Ala Gly Lys Asn Leu Cys Ile Val Arg Ala Met Asp Val Gly Tyr
     45                  50                  55 atg tgc gat gat act atc act tat gaa tgc cca gtg ctg tcg gct ggt   1984
Met Cys Asp Asp Thr Ile Thr Tyr Glu Cys Pro Val Leu Ser Ala Gly
 60                  65                  70                  75 aat gat cca gaa gac atc gac tgt tgg tgc aca aag tca gca gtc tac   2032
Asn Asp Pro Glu Asp Ile Asp Cys Trp Cys Thr Lys Ser Ala Val Tyr
                 80                  85                  90 gtc agg tat gga aga tgc acc aag aca cgc cac tca aga cgc agt cgg   2080
Val Arg Tyr Gly Arg Cys Thr Lys Thr Arg His Ser Arg Arg Ser Arg
             95                 100                 105 agg tca ctg aca gtg cag aca cac gga gaa agc act cta gcg aac aag   2128
Arg Ser Leu Thr Val Gln Thr His Gly Glu Ser Thr Leu Ala Asn Lys
        110                 115                 120 aag ggg gct tgg atg gac agc acc aag gcc aca agg tat ttg gta aaa   2176
Lys Gly Ala Trp Met Asp Ser Thr Lys Ala Thr Arg Tyr Leu Val Lys
    125                 130                 135 aca gaa tca tgg atc ttg agg aac cct gga tat gcc ctg gtg gca gcc   2224
Thr Glu Ser Trp Ile Leu Arg Asn Pro Gly Tyr Ala Leu Val Ala Ala
140                 145                 150                 155 gtc att ggt tgg atg ctt ggg agc aac acc atg cag aga gtt gtg ttt   2272
Val Ile Gly Trp Met Leu Gly Ser Asn Thr Met Gln Arg Val Val Phe
                160                 165                 170 gtc gtg cta ttg ctt ttg gtg gcc cca gct tac agc ttc aac tgc ctt   2320
Val Val Leu Leu Leu Leu Val Ala Pro Ala Tyr Ser Phe Asn Cys Leu
            175                 180                 185 gga atg agc aac aga gac ttc ttg gaa gga gtg tct gga gca aca tgg   2368
Gly Met Ser Asn Arg Asp Phe Leu Glu Gly Val Ser Gly Ala Thr Trp
        190                 195                 200 gtg gat ttg gtt ctc gaa ggc gac agc tgc gtg act atc atg tct aag   2416
Val Asp Leu Val Leu Glu Gly Asp Ser Cys Val Thr Ile Met Ser Lys
    205                 210                 215 gac aag cct acc atc gat gtg aag atg atg aat atg gag gcg gcc aac   2464
Asp Lys Pro Thr Ile Asp Val Lys Met Met Asn Met Glu Ala Ala Asn
220                 225                 230                 235 ctg gca gag gtc cgc agt tat tgc tat ttg gct acc gtc agc gat ctc   2512
Leu Ala Glu Val Arg Ser Tyr Cys Tyr Leu Ala Thr Val Ser Asp Leu
                240                 245                 250 tcc acc aaa gct gcg tgc ccg acc atg gga gaa gct cac aat gac aaa   2560
Ser Thr Lys Ala Ala Cys Pro Thr Met Gly Glu Ala His Asn Asp Lys
            255                 260                 265 cgt gct gac cca gct ttt gtg tgc aga caa gga gtg gtg gac agg ggc   2608
Arg Ala Asp Pro Ala Phe Val Cys Arg Gln Gly Val Val Asp Arg Gly
        270                 275                 280 tgg ggc aac ggc tgc gga cta ttt ggc aaa gga agc att gac aca tgc   2656
Trp Gly Asn Gly Cys Gly Leu Phe Gly Lys Gly Ser Ile Asp Thr Cys
    285                 290                 295 gcc aaa ttt gcc tgc tct acc aag gca ata gga aga acc atc ttg aaa   2704
Ala Lys Phe Ala Cys Ser Thr Lys Ala Ile Gly Arg Thr Ile Leu Lys
300                 305                 310                 315 gag aat atc aag tac gaa gtg gcc atc ttc gtg cac gga cca act act   2752
Glu Asn Ile Lys Tyr Glu Val Ala Ile Phe Val His Gly Pro Thr Thr
                320                 325                 330 gtg gag tcg cac gga aac tac tcc aca cag gtt gga gcc act cag gca   2800
Val Glu Ser His Gly Asn Tyr Ser Thr Gln Val Gly Ala Thr Gln Ala
            335                 340                 345 ggg aga ttc agc atc act cct gcg gcg cct tca tac aca cta aag ctt   2848
Gly Arg Phe Ser Ile Thr Pro Ala Ala Pro Ser Tyr Thr Leu Lys Leu
```

-continued

```
            350                 355                 360
gga gaa tat gga gag gtg aca gtg gac tgt gaa cca cgg tca ggg att        2896
Gly Glu Tyr Gly Glu Val Thr Val Asp Cys Glu Pro Arg Ser Gly Ile
    365                 370                 375 gac acc aat gca tac tac gtg atg act gtt gga aca aag acg ttc ttg        2944
Asp Thr Asn Ala Tyr Tyr Val Met Thr Val Gly Thr Lys Thr Phe Leu
380                 385                 390                 395 gtc cat cgt gag tgg ttc atg gac ctc aac ctc cct tgg agc agt gct        2992
Val His Arg Glu Trp Phe Met Asp Leu Asn Leu Pro Trp Ser Ser Ala
                400                 405                 410 gga agt act gtg tgg agg aac aga gag acg tta atg gag ttt gag gaa        3040
Gly Ser Thr Val Trp Arg Asn Arg Glu Thr Leu Met Glu Phe Glu Glu
            415                 420                 425 cca cac gcc acg aag cag tct gtg ata gca ttg ggc tca caa gag gga        3088
Pro His Ala Thr Lys Gln Ser Val Ile Ala Leu Gly Ser Gln Glu Gly
        430                 435                 440 gct ctg cat caa gct ttg gct gga gcc att cct gtg gaa ttt tca agc        3136
Ala Leu His Gln Ala Leu Ala Gly Ala Ile Pro Val Glu Phe Ser Ser
    445                 450                 455 aac act gtc aag ttg acg tcg ggt cat ttg aag tgt aga gtg aag atg        3184
Asn Thr Val Lys Leu Thr Ser Gly His Leu Lys Cys Arg Val Lys Met
460                 465                 470                 475 gaa aaa ttg cag ttg aag gga aca acc tat ggc gtc tgt tca aag gct        3232
Glu Lys Leu Gln Leu Lys Gly Thr Thr Tyr Gly Val Cys Ser Lys Ala
                480                 485                 490 ttc aag ttt ctt ggg act ccc gca gac aca ggt cac ggc act gtg gtg        3280
Phe Lys Phe Leu Gly Thr Pro Ala Asp Thr Gly His Gly Thr Val Val
            495                 500                 505 ttg gaa ttg cag tac act ggc acg gat gga cct tgc aaa gtt cct atc        3328
Leu Glu Leu Gln Tyr Thr Gly Thr Asp Gly Pro Cys Lys Val Pro Ile
        510                 515                 520 tcg tca gcg gct tca ttg aac gac cta acg cca gtg ggc aga ttg gtc        3376
Ser Ser Ala Ala Ser Leu Asn Asp Leu Thr Pro Val Gly Arg Leu Val
    525                 530                 535 act gtc aac cct ttt gtt tca gtg gcc acg gcc aac gct aag gtc ctg        3424
Thr Val Asn Pro Phe Val Ser Val Ala Thr Ala Asn Ala Lys Val Leu
540                 545                 550                 555 att gaa ttg gaa cca ccc ttt gga gac tca tac ata gtg gtg ggc aga        3472
Ile Glu Leu Glu Pro Pro Phe Gly Asp Ser Tyr Ile Val Val Gly Arg
                560                 565                 570 gga gaa caa cag atc aat cac cat tgg cac aag tct gga agc agc att        3520
Gly Glu Gln Gln Ile Asn His His Trp His Lys Ser Gly Ser Ser Ile
            575                 580                 585 ggc aaa gcc ttt aca acc acc ctc aaa gga gcg cag aga cta gcc gct        3568
Gly Lys Ala Phe Thr Thr Thr Leu Lys Gly Ala Gln Arg Leu Ala Ala
        590                 595                 600 cta gga gac aca gct tgg gac ttt gga tca gtt gga ggg gtg ttc acc        3616
Leu Gly Asp Thr Ala Trp Asp Phe Gly Ser Val Gly Gly Val Phe Thr
605                 610                 615 tca gtt ggg aag gct gtc cat caa gtg ttc gga gga gca ttc cgc tca        3664
Ser Val Gly Lys Ala Val His Gln Val Phe Gly Gly Ala Phe Arg Ser
620                 625                 630                 635 ctg ttc gga ggc atg tcc tgg ata acg caa gga ttg ctg ggg gct ctc        3712
Leu Phe Gly Gly Met Ser Trp Ile Thr Gln Gly Leu Leu Gly Ala Leu
                640                 645                 650 ctg ttg tgg atg ggc atc aat gct cgt gat agg tcc ata gct ctc acg        3760
Leu Leu Trp Met Gly Ile Asn Ala Arg Asp Arg Ser Ile Ala Leu Thr
            655                 660                 665 ttt ctc gca gtt gga gga gtt ctg ctc ttc ctc tcc gtg aac gtg cac        3808
```

```
              Phe Leu Ala Val Gly Gly Val Leu Phe Leu Ser Val Asn Val His
                      670                 675                 680 gct taatttttat ctagaatcga tcccgggttt ttatgactag ttaatcacgg              3861
Ala ccgccttata aagatctaaa atgcataatt tctaaataat gaaaaaaagt acatcatgag       3921
caacgcgtta gtatatttta caatggagat taacgctcta taccgttcta tgtttattga      3981
ttcagatgat gttttagaaa agaaagttat tgaatatgaa aactttaatg aagatgaaga      4041
tgacgacgat gattattgtt gtaaatctgt tttagatgaa gaagatgacg cgctaaagta      4101
tactatggtt acaaagtata agtctatact actaatggcg acttgtgcaa gaaggtatag      4161
tatagtgaaa atgttgttag attatgatta tgaaaaacca aataaatcag atccatatct      4221
aaaggtatct cctttgcaca taatttcatc tattcctagt ttagaatac                  4270

<210> SEQ ID NO 55
<211> LENGTH: 684
<212> TYPE: PRT
<213> ORGANISM: West Nile virus

<400> SEQUENCE: 55

Met Thr Gly Ile Ala Val Met Ile Gly Leu Ile Ala Ser Val Gly Ala
 1               5                  10                  15

Val Thr Leu Ser Asn Phe Gln Gly Lys Val Met Met Thr Val Asn Ala
                20                  25                  30

Thr Asp Val Thr Asp Val Ile Thr Ile Pro Thr Ala Ala Gly Lys Asn
            35                  40                  45

Leu Cys Ile Val Arg Ala Met Asp Val Gly Tyr Met Cys Asp Asp Thr
        50                  55                  60

Ile Thr Tyr Glu Cys Pro Val Leu Ser Ala Gly Asn Asp Pro Glu Asp
 65                  70                  75                  80

Ile Asp Cys Trp Cys Thr Lys Ser Ala Val Tyr Val Arg Tyr Gly Arg
                85                  90                  95

Cys Thr Lys Thr Arg His Ser Arg Arg Ser Arg Arg Ser Leu Thr Val
                100                 105                 110

Gln Thr His Gly Glu Ser Thr Leu Ala Asn Lys Lys Gly Ala Trp Met
            115                 120                 125

Asp Ser Thr Lys Ala Thr Arg Tyr Leu Val Lys Thr Glu Ser Trp Ile
        130                 135                 140

Leu Arg Asn Pro Gly Tyr Ala Leu Val Ala Ala Val Ile Gly Trp Met
145                 150                 155                 160

Leu Gly Ser Asn Thr Met Gln Arg Val Val Phe Val Val Leu Leu Leu
                165                 170                 175

Leu Val Ala Pro Ala Tyr Ser Phe Asn Cys Leu Gly Met Ser Asn Arg
            180                 185                 190

Asp Phe Leu Glu Gly Val Ser Gly Ala Thr Trp Val Asp Leu Val Leu
        195                 200                 205

Glu Gly Asp Ser Cys Val Thr Ile Met Ser Lys Asp Lys Pro Thr Ile
    210                 215                 220

Asp Val Lys Met Met Asn Met Glu Ala Ala Asn Leu Ala Glu Val Arg
225                 230                 235                 240

Ser Tyr Cys Tyr Leu Ala Thr Val Ser Asp Leu Ser Thr Lys Ala Ala
                245                 250                 255

Cys Pro Thr Met Gly Glu Ala His Asn Asp Lys Arg Ala Asp Pro Ala
            260                 265                 270
```

-continued

Phe Val Cys Arg Gln Gly Val Val Asp Arg Gly Trp Gly Asn Gly Cys
        275                 280                 285

Gly Leu Phe Gly Lys Gly Ser Ile Asp Thr Cys Ala Lys Phe Ala Cys
        290                 295                 300

Ser Thr Lys Ala Ile Gly Arg Thr Ile Leu Lys Glu Asn Ile Lys Tyr
305                 310                 315                 320

Glu Val Ala Ile Phe Val His Gly Pro Thr Thr Val Glu Ser His Gly
                325                 330                 335

Asn Tyr Ser Thr Gln Val Gly Ala Thr Gln Ala Gly Arg Phe Ser Ile
            340                 345                 350

Thr Pro Ala Ala Pro Ser Tyr Thr Leu Lys Leu Gly Glu Tyr Gly Glu
        355                 360                 365

Val Thr Val Asp Cys Glu Pro Arg Ser Gly Ile Asp Thr Asn Ala Tyr
        370                 375                 380

Tyr Val Met Thr Val Gly Thr Lys Thr Phe Leu Val His Arg Glu Trp
385                 390                 395                 400

Phe Met Asp Leu Asn Leu Pro Trp Ser Ser Ala Gly Ser Thr Val Trp
                405                 410                 415

Arg Asn Arg Glu Thr Leu Met Glu Phe Glu Pro His Ala Thr Lys
            420                 425                 430

Gln Ser Val Ile Ala Leu Gly Ser Gln Glu Gly Ala Leu His Gln Ala
        435                 440                 445

Leu Ala Gly Ala Ile Pro Val Glu Phe Ser Ser Asn Thr Val Lys Leu
        450                 455                 460

Thr Ser Gly His Leu Lys Cys Arg Val Lys Met Glu Lys Leu Gln Leu
465                 470                 475                 480

Lys Gly Thr Thr Tyr Gly Val Cys Ser Lys Ala Phe Lys Phe Leu Gly
                485                 490                 495

Thr Pro Ala Asp Thr Gly His Gly Thr Val Val Leu Glu Leu Gln Tyr
            500                 505                 510

Thr Gly Thr Asp Gly Pro Cys Lys Val Pro Ile Ser Ser Ala Ala Ser
        515                 520                 525

Leu Asn Asp Leu Thr Pro Val Gly Arg Leu Val Thr Val Asn Pro Phe
        530                 535                 540

Val Ser Val Ala Thr Ala Asn Ala Lys Val Leu Ile Glu Leu Glu Pro
545                 550                 555                 560

Pro Phe Gly Asp Ser Tyr Ile Val Val Gly Arg Gly Glu Gln Gln Ile
                565                 570                 575

Asn His His Trp His Lys Ser Gly Ser Ser Ile Gly Lys Ala Phe Thr
            580                 585                 590

Thr Thr Leu Lys Gly Ala Gln Arg Leu Ala Ala Leu Gly Asp Thr Ala
        595                 600                 605

Trp Asp Phe Gly Ser Val Gly Gly Val Phe Thr Ser Val Gly Lys Ala
610                 615                 620

Val His Gln Val Phe Gly Gly Ala Phe Arg Ser Leu Phe Gly Gly Met
625                 630                 635                 640

Ser Trp Ile Thr Gln Gly Leu Leu Gly Ala Leu Leu Leu Trp Met Gly
                645                 650                 655

Ile Asn Ala Arg Asp Arg Ser Ile Ala Leu Thr Phe Leu Ala Val Gly
            660                 665                 670

Gly Val Leu Leu Phe Leu Ser Val Asn Val His Ala
        675                 680

<210> SEQ ID NO 56
<211> LENGTH: 5109
<212> TYPE: DNA
<213> ORGANISM: West Nile virus
<220> FEATURE:
<221> NAME/KEY: CDS
<222> LOCATION: (1640)..(3691)

<400> SEQUENCE: 56

```
gacccttta  aagaataaaa  gaagaaacaa  ctgtgaaata  gtttataaat  gtaattcgta    60
tgcagaaaac  gataatatat  tttggtatga  gaaatctaaa  ggagacatag  tttgtataga   120
catgcgctct  tccgatgaga  tattcgatgc  ttttctaatg  tatcatatag  ctacaagata   180
tgcctatcat  gatgatgata  tatatctaca  aatagtgtta  tattattcta  ataatcaaaa   240
tgttatatct  tatattacga  aaaataaata  cgttaagtat  ataagaaata  aaactagaga   300
cgatattcat  aaagtaaaaa  tattagctct  agaagacttt  acaacggaag  aaatatattg   360
ttggattagt  aatatataac  agcgtagctg  cacggttttg  atcattttcc  aacaatataa   420
accaatgaag  gaggacgact  catcaaacat  aaataacatt  cacggaaaat  attcagtatc   480
agatttatca  agatgatt   atgttattga  atgtatagac  ggatcttttg  attcgatcaa   540
gtatagagat  ataaaggtta  taataatgaa  gaataacggt  tacgttaatt  gtagtaaatt   600
atgtaaaatg  cggaataaat  acttttctag  atggttgcgt  cttctactt   ctaaagcatt   660 attagacatt  tacaataata  agtcagtaga  taatgctatt  gttaaagtct  atggtaaagg   720
taagaaactt  attataacag  gattttatct  caaacaaaat  atgatacgtt  atgttattga   780
gtggataggg  gatgatttta  caaacgatat  atacaaaatg  attaatttct  ataatgcgtt   840
attcggtaac  gatgaattaa  aaatagtatc  ctgtgaaaac  actctatgcc  cgtttataga   900
acttggtaga  tgctattatg  gtaaaaaatg  taagtatata  cacggagatc  aatgtgatat   960
ctgtggtcta  tatatactac  accctaccga  tattaaccaa  cgagtttctc  acaagaaaac  1020
ttgtttagta  gatagagatt  ctttgattgt  gtttaaaaga  agtaccagta  aaaagtgtgg  1080
catatgcata  gaagaaataa  acaaaaaaca  tatttccgaa  cagtatttg   gaattctccc  1140 aagttgtaaa  catatttttt  gcctatcatg  tataagacgt  tgggcagata  ctaccagaaa  1200
tacagatact  gaaaatacgt  gtcctgaatg  tagaatagtt  tttcctttca  taatacccag  1260
taggtattgg  atagataata  aatatgataa  aaaaatatta  tataatagat  ataagaaaat  1320
gatttttaca  aaaataccta  taagaacaat  aaaaatataa  ttacatttac  ggaaaatagc  1380
tggttttagt  ttaccaactt  agagtaatta  tcatattgaa  tctatattgc  taattagcta  1440
ataaaaaccc  gggttaatta  attagtcatc  aggcagggcg  agaacgagac  tatctgctcg  1500
ttaattaatt  agagcttctt  tattctatac  ttaaaaagtg  aaaataaata  caaaggttct  1560
tgagggttgt  gttaaattga  aagcgagaaa  taatcataaa  ttatttcatt  atcgcgatat  1620
ccgttaagtt  tgtatcgta  atg acc gga att gca gtc atg att ggc ctg atc     1672
                        Met Thr Gly Ile Ala Val Met Ile Gly Leu Ile
                         1               5                  10 gcc agc gta gga gcg gtt acc ctc tct aac ttc caa ggg aag gtg atg       1720
Ala Ser Val Gly Ala Val Thr Leu Ser Asn Phe Gln Gly Lys Val Met
             15                  20                  25 atg acg gta aat gct act gac gtc aca gat gtc atc acg att cca aca       1768
Met Thr Val Asn Ala Thr Asp Val Thr Asp Val Ile Thr Ile Pro Thr
         30                  35                  40 gct gct gga aag aac cta tgc att gtc aga gca atg gat gtg gga tac       1816
Ala Ala Gly Lys Asn Leu Cys Ile Val Arg Ala Met Asp Val Gly Tyr
     45                  50                  55
```

| | |
|---|---|
| atg tgc gat gat act atc act tat gaa tgc cca gtg ctg tcg gct ggt<br>Met Cys Asp Asp Thr Ile Thr Tyr Glu Cys Pro Val Leu Ser Ala Gly<br>60                        65                      70                     75 | 1864 |
| aat gat cca gaa gac atc gac tgt tgg tgc aca aag tca gca gtc tac<br>Asn Asp Pro Glu Asp Ile Asp Cys Trp Cys Thr Lys Ser Ala Val Tyr<br>                80                     85                     90 | 1912 |
| gtc agg tat gga aga tgc acc aag aca cgc cac tca aga cgc agt cgg<br>Val Arg Tyr Gly Arg Cys Thr Lys Thr Arg His Ser Arg Arg Ser Arg<br>          95                     100                    105 | 1960 |
| agg tca ctg aca gtg cag aca cac gga gaa agc act cta gcg aac aag<br>Arg Ser Leu Thr Val Gln Thr His Gly Glu Ser Thr Leu Ala Asn Lys<br>     110                     115                    120 | 2008 |
| aag ggg gct tgg atg gac agc acc aag gcc aca agg tat ttg gta aaa<br>Lys Gly Ala Trp Met Asp Ser Thr Lys Ala Thr Arg Tyr Leu Val Lys<br>125                       130                    135 | 2056 |
| aca gaa tca tgg atc ttg agg aac cct gga tat gcc ctg gtg gca gcc<br>Thr Glu Ser Trp Ile Leu Arg Asn Pro Gly Tyr Ala Leu Val Ala Ala<br>140                       145                    150                    155 | 2104 |
| gtc att ggt tgg atg ctt ggg agc aac acc atg cag aga gtt gtg ttt<br>Val Ile Gly Trp Met Leu Gly Ser Asn Thr Met Gln Arg Val Val Phe<br>                160                    165                    170 | 2152 |
| gtc gtg cta ttg ctt ttg gtg gcc cca gct tac agc ttc aac tgc ctt<br>Val Val Leu Leu Leu Leu Val Ala Pro Ala Tyr Ser Phe Asn Cys Leu<br>     175                     180                    185 | 2200 |
| gga atg agc aac aga gac ttc ttg gaa gga gtg tct gga gca aca tgg<br>Gly Met Ser Asn Arg Asp Phe Leu Glu Gly Val Ser Gly Ala Thr Trp<br>                190                    195                    200 | 2248 |
| gtg gat ttg gtt ctc gaa ggc gac agc tgc gtg act atc atg tct aag<br>Val Asp Leu Val Leu Glu Gly Asp Ser Cys Val Thr Ile Met Ser Lys<br>205                       210                    215 | 2296 |
| gac aag cct acc atc gat gtg aag atg atg aat atg gag gcg gcc aac<br>Asp Lys Pro Thr Ile Asp Val Lys Met Met Asn Met Glu Ala Ala Asn<br>220                       225                    230                    235 | 2344 |
| ctg gca gag gtc cgc agt tat tgc tat ttg gct acc gtc agc gat ctc<br>Leu Ala Glu Val Arg Ser Tyr Cys Tyr Leu Ala Thr Val Ser Asp Leu<br>                240                    245                    250 | 2392 |
| tcc acc aaa gct gcg tgc ccg acc atg gga gaa gct cac aat gac aaa<br>Ser Thr Lys Ala Ala Cys Pro Thr Met Gly Glu Ala His Asn Asp Lys<br>     255                     260                    265 | 2440 |
| cgt gct gac cca gct ttt gtg tgc aga caa gga gtg gtg gac agg ggc<br>Arg Ala Asp Pro Ala Phe Val Cys Arg Gln Gly Val Val Asp Arg Gly<br>          270                     275                    280 | 2488 |
| tgg ggc aac ggc tgc gga cta ttt ggc aaa gga agc att gac aca tgc<br>Trp Gly Asn Gly Cys Gly Leu Phe Gly Lys Gly Ser Ile Asp Thr Cys<br>285                       290                    295 | 2536 |
| gcc aaa ttt gcc tgc tct acc aag gca ata gga aga acc atc ttg aaa<br>Ala Lys Phe Ala Cys Ser Thr Lys Ala Ile Gly Arg Thr Ile Leu Lys<br>300                       305                    310                    315 | 2584 |
| gag aat atc aag tac gaa gtg gcc atc ttc gtg cac gga cca act act<br>Glu Asn Ile Lys Tyr Glu Val Ala Ile Phe Val His Gly Pro Thr Thr<br>                320                    325                    330 | 2632 |
| gtg gag tcg cac gga aac tac tcc aca cag gtt gga gcc act cag gca<br>Val Glu Ser His Gly Asn Tyr Ser Thr Gln Val Gly Ala Thr Gln Ala<br>     335                     340                    345 | 2680 |
| ggg aga ttc agc atc act cct gcg gcg cct tca tac aca cta aag ctt<br>Gly Arg Phe Ser Ile Thr Pro Ala Ala Pro Ser Tyr Thr Leu Lys Leu<br>          350                     355                    360 | 2728 |
| gga gaa tat gga gag gtg aca gtg gac tgt gaa cca cgg tca ggg att<br>Gly Glu Tyr Gly Glu Val Thr Val Asp Cys Glu Pro Arg Ser Gly Ile | 2776 |

-continued

```
                365                 370                 375
gac acc aat gca tac tac gtg atg act gtt gga aca aag acg ttc ttg    2824
Asp Thr Asn Ala Tyr Tyr Val Met Thr Val Gly Thr Lys Thr Phe Leu
380                 385                 390                 395 gtc cat cgt gag tgg ttc atg gac ctc aac ctc cct tgg agc agt gct    2872
Val His Arg Glu Trp Phe Met Asp Leu Asn Leu Pro Trp Ser Ser Ala
                400                 405                 410 gga agt act gtg tgg agg aac aga gag acg tta atg gag ttt gag gaa    2920
Gly Ser Thr Val Trp Arg Asn Arg Glu Thr Leu Met Glu Phe Glu Glu
            415                 420                 425 cca cac gcc acg aag cag tct gtg ata gca ttg ggc tca caa gag gga    2968
Pro His Ala Thr Lys Gln Ser Val Ile Ala Leu Gly Ser Gln Glu Gly
        430                 435                 440 gct ctg cat caa gct ttg gct gga gcc att cct gtg gaa ttt tca agc    3016
Ala Leu His Gln Ala Leu Ala Gly Ala Ile Pro Val Glu Phe Ser Ser
    445                 450                 455 aac act gtc aag ttg acg tcg ggt cat ttg aag tgt aga gtg aag atg    3064
Asn Thr Val Lys Leu Thr Ser Gly His Leu Lys Cys Arg Val Lys Met
460                 465                 470                 475 gaa aaa ttg cag ttg aag gga aca acc tat ggc gtc tgt tca aag gct    3112
Glu Lys Leu Gln Leu Lys Gly Thr Thr Tyr Gly Val Cys Ser Lys Ala
                480                 485                 490 ttc aag ttt ctt ggg act ccc gca gac aca ggt cac ggc act gtg gtg    3160
Phe Lys Phe Leu Gly Thr Pro Ala Asp Thr Gly His Gly Thr Val Val
            495                 500                 505 ttg gaa ttg cag tac act ggc acg gat gga cct tgc aaa gtt cct atc    3208
Leu Glu Leu Gln Tyr Thr Gly Thr Asp Gly Pro Cys Lys Val Pro Ile
        510                 515                 520 tcg tca gcg gct tca ttg aac gac cta acg cca gtg ggc aga ttg gtc    3256
Ser Ser Ala Ala Ser Leu Asn Asp Leu Thr Pro Val Gly Arg Leu Val
    525                 530                 535 act gtc aac cct ttt gtt tca gtg gcc acg gcc aac gct aag gtc ctg    3304
Thr Val Asn Pro Phe Val Ser Val Ala Thr Ala Asn Ala Lys Val Leu
540                 545                 550                 555 att gaa ttg gaa cca ccc ttt gga gac tca tac ata gtg gtg ggc aga    3352
Ile Glu Leu Glu Pro Pro Phe Gly Asp Ser Tyr Ile Val Val Gly Arg
                560                 565                 570 gga gaa caa cag atc aat cac cat tgg cac aag tct gga agc agc att    3400
Gly Glu Gln Gln Ile Asn His His Trp His Lys Ser Gly Ser Ser Ile
            575                 580                 585 ggc aaa gcc ttt aca acc acc ctc aaa gga gcg cag aga cta gcc gct    3448
Gly Lys Ala Phe Thr Thr Thr Leu Lys Gly Ala Gln Arg Leu Ala Ala
        590                 595                 600 cta gga gac aca gct tgg gac ttt gga tca gtt gga ggg gtg ttc acc    3496
Leu Gly Asp Thr Ala Trp Asp Phe Gly Ser Val Gly Gly Val Phe Thr
    605                 610                 615 tca gtt ggg aag gct gtc cat caa gtg ttc gga gga gca ttc cgc tca    3544
Ser Val Gly Lys Ala Val His Gln Val Phe Gly Gly Ala Phe Arg Ser
620                 625                 630                 635 ctg ttc gga ggc atg tcc tgg ata acg caa gga ttg ctg ggg gct ctc    3592
Leu Phe Gly Gly Met Ser Trp Ile Thr Gln Gly Leu Leu Gly Ala Leu
                640                 645                 650 ctg ttg tgg atg ggc atc aat gct cgt gat agg tcc ata gct ctc acg    3640
Leu Leu Trp Met Gly Ile Asn Ala Arg Asp Arg Ser Ile Ala Leu Thr
            655                 660                 665 ttt ctc gca gtt gga gga gtt ctg ctc ttc ctc tcc gtg aac gtg cac    3688
Phe Leu Ala Val Gly Gly Val Leu Leu Phe Leu Ser Val Asn Val His
        670                 675                 680 gct taattttat ctagagtcga gttttattg actagttaat cataagataa            3741
Ala
```

```
ataatataca gcattgtaac catcgtcatc cgttatacgg ggaataatat taccatacag   3801
tattattaaa ttttcttacg aagaatatag atcggtattt atcgttagtt tattttacat   3861
ttattaatta aacatgtcta ctattacctg ttatggaaat gacaaattta gttatataat   3921
ttatgataaa attaagataa taataatgaa atcaaataat tatgtaaatg ctactagatt   3981
atgtgaatta cgaggaagaa agtttacgaa ctggaaaaaa ttaagtgaat ctaaaatatt   4041
agtcgataat gtaaaaaaaa taaatgataa aactaaccag ttaaaaacgg atatgattat   4101
atacgttaag gatattgatc ataaaggaag agatacttgc ggttactatg tacaccaaga   4161
tctggtatct tctatatcaa attggatatc tccgttattc gccgttaagg taaataaaat   4221
tattaactat tatatatgta atgaatatga tatacgactt agcgaaatgg aatctgatat   4281
gacagaagta atagatgtag ttgataaatt agtaggagga tacaatgatg aaatagcaga   4341
aataatatat ttgtttaata aatttataga aaaatatatt gctaacatat cgttatcaac   4401
tgaattatct agtatattaa ataatttat aaatttaat aaaaaatata ataacgacat   4461
aaaagatatt aaatctttaa ttcttgatct gaaaaacaca tctataaaac tagataaaaa   4521
gttattcgat aaagataata atgaatcgaa cgatgaaaaa ttggaaacag aagttgataa   4581 gctaatttt ttcatctaaa tagtattatt ttattgaagt acgaagtttt acgttagata   4641
aataataaag gtcgattttt actttgttaa atatcaaata tgtcattatc tgataaagat   4701
acaaaaacac acggtgatta tcaaccatct aacgaacaga tattcaaaaa atacgtcgg   4761 actatggaaa acgaagctga tagcctcaat agaagaagca ttaagaaat tgttgtagat   4821 gttatgaaga attgggatca tcctctcaac gaagaaatag ataaagttct aaactggaaa   4881
aatgatacat taaacgattt agatcatcta aatacagatg ataatattaa ggaaatcata   4941
caatgtctga ttagagaatt tgcgtttaaa aagatcaatt ctattatgta tagttatgct   5001
atggtaaaac tcaattcaga taacgaaaca ttgaaagata aaattaagga ttattttata   5061
gaaactattc ttaaagacaa acgtggttat aaacaaaagc cattaccc              5109
```

<210> SEQ ID NO 57
<211> LENGTH: 684
<212> TYPE: PRT
<213> ORGANISM: West Nile virus

<400> SEQUENCE: 57

```
Met Thr Gly Ile Ala Val Met Ile Gly Leu Ile Ala Ser Val Gly Ala
  1               5                  10                  15

Val Thr Leu Ser Asn Phe Gln Gly Lys Val Met Met Thr Val Asn Ala
             20                  25                  30

Thr Asp Val Thr Asp Val Ile Thr Ile Pro Thr Ala Ala Gly Lys Asn
         35                  40                  45

Leu Cys Ile Val Arg Ala Met Asp Val Gly Tyr Met Cys Asp Asp Thr
     50                  55                  60

Ile Thr Tyr Glu Cys Pro Val Leu Ser Ala Gly Asn Asp Pro Glu Asp
 65                  70                  75                  80

Ile Asp Cys Trp Cys Thr Lys Ser Ala Val Tyr Val Arg Tyr Gly Arg
                 85                  90                  95

Cys Thr Lys Thr Arg His Ser Arg Arg Ser Arg Arg Ser Leu Thr Val
            100                 105                 110

Gln Thr His Gly Glu Ser Thr Leu Ala Asn Lys Lys Gly Ala Trp Met
        115                 120                 125
```

-continued

```
Asp Ser Thr Lys Ala Thr Arg Tyr Leu Val Lys Thr Glu Ser Trp Ile
    130                 135                 140

Leu Arg Asn Pro Gly Tyr Ala Leu Val Ala Val Ile Gly Trp Met
145                 150                 155                 160

Leu Gly Ser Asn Thr Met Gln Arg Val Val Phe Val Val Leu Leu Leu
                    165                 170                 175

Leu Val Ala Pro Ala Tyr Ser Phe Asn Cys Leu Gly Met Ser Asn Arg
                180                 185                 190

Asp Phe Leu Glu Gly Val Ser Gly Ala Thr Trp Val Asp Leu Val Leu
            195                 200                 205

Glu Gly Asp Ser Cys Val Thr Ile Met Ser Lys Asp Lys Pro Thr Ile
    210                 215                 220

Asp Val Lys Met Met Asn Met Glu Ala Ala Asn Leu Ala Glu Val Arg
225                 230                 235                 240

Ser Tyr Cys Tyr Leu Ala Thr Val Ser Asp Leu Ser Thr Lys Ala Ala
                245                 250                 255

Cys Pro Thr Met Gly Glu Ala His Asn Asp Lys Arg Ala Asp Pro Ala
            260                 265                 270

Phe Val Cys Arg Gln Gly Val Val Asp Arg Gly Trp Gly Asn Gly Cys
        275                 280                 285

Gly Leu Phe Gly Lys Gly Ser Ile Asp Thr Cys Ala Lys Phe Ala Cys
    290                 295                 300

Ser Thr Lys Ala Ile Gly Arg Thr Ile Leu Lys Glu Asn Ile Lys Tyr
305                 310                 315                 320

Glu Val Ala Ile Phe Val His Gly Pro Thr Thr Val Glu Ser His Gly
                325                 330                 335

Asn Tyr Ser Thr Gln Val Gly Ala Thr Gln Ala Gly Arg Phe Ser Ile
            340                 345                 350

Thr Pro Ala Ala Pro Ser Tyr Thr Leu Lys Leu Gly Glu Tyr Gly Glu
        355                 360                 365

Val Thr Val Asp Cys Glu Pro Arg Ser Gly Ile Asp Thr Asn Ala Tyr
    370                 375                 380

Tyr Val Met Thr Val Gly Thr Lys Thr Phe Leu Val His Arg Glu Trp
385                 390                 395                 400

Phe Met Asp Leu Asn Leu Pro Trp Ser Ser Ala Gly Ser Thr Val Trp
                405                 410                 415

Arg Asn Arg Glu Thr Leu Met Glu Phe Glu Glu Pro His Ala Thr Lys
            420                 425                 430

Gln Ser Val Ile Ala Leu Gly Ser Gln Glu Gly Ala Leu His Gln Ala
        435                 440                 445

Leu Ala Gly Ala Ile Pro Val Glu Phe Ser Ser Asn Thr Val Lys Leu
    450                 455                 460

Thr Ser Gly His Leu Lys Cys Arg Val Lys Met Glu Lys Leu Gln Leu
465                 470                 475                 480

Lys Gly Thr Thr Tyr Gly Val Cys Ser Lys Ala Phe Lys Phe Leu Gly
                485                 490                 495

Thr Pro Ala Asp Thr Gly His Gly Thr Val Val Leu Glu Leu Gln Tyr
            500                 505                 510

Thr Gly Thr Asp Gly Pro Cys Lys Val Pro Ile Ser Ser Ala Ala Ser
        515                 520                 525

Leu Asn Asp Leu Thr Pro Val Gly Arg Leu Val Thr Val Asn Pro Phe
    530                 535                 540
```

```
Val Ser Val Ala Thr Ala Asn Ala Lys Val Leu Ile Glu Leu Glu Pro
545                 550                 555                 560

Pro Phe Gly Asp Ser Tyr Ile Val Val Gly Arg Gly Glu Gln Gln Ile
                565                 570                 575

Asn His His Trp His Lys Ser Gly Ser Ser Ile Gly Lys Ala Phe Thr
            580                 585                 590

Thr Thr Leu Lys Gly Ala Gln Arg Leu Ala Ala Leu Gly Asp Thr Ala
        595                 600                 605

Trp Asp Phe Gly Ser Val Gly Gly Val Phe Thr Ser Val Gly Lys Ala
    610                 615                 620

Val His Gln Val Phe Gly Gly Ala Phe Arg Ser Leu Phe Gly Gly Met
625                 630                 635                 640

Ser Trp Ile Thr Gln Gly Leu Leu Gly Ala Leu Leu Leu Trp Met Gly
                645                 650                 655

Ile Asn Ala Arg Asp Arg Ser Ile Ala Leu Thr Phe Leu Ala Val Gly
                660                 665                 670

Gly Val Leu Leu Phe Leu Ser Val Asn Val His Ala
                675                 680

<210> SEQ ID NO 58
<211> LENGTH: 2087
<212> TYPE: DNA
<213> ORGANISM: West Nile virus
<220> FEATURE:
<221> NAME/KEY: CDS
<222> LOCATION: (15)..(2072)

<400> SEQUENCE: 58
ctgcagccgc cacc atg gga tca acc gga att gca gtc atg att ggc ctg      50
                Met Gly Ser Thr Gly Ile Ala Val Met Ile Gly Leu
                 1               5                  10 atc gcc agc gta gga gca gtt acc ctc tct aac ttc caa ggg aag gtg      98
Ile Ala Ser Val Gly Ala Val Thr Leu Ser Asn Phe Gln Gly Lys Val
            15                  20                  25 atg atg acg gta aat gct act gac gtc aca gat gtc atc acg att cca     146
Met Met Thr Val Asn Ala Thr Asp Val Thr Asp Val Ile Thr Ile Pro
 30                  35                  40 aca gct gct gga aag aac cta tgc att gtc aga gca atg gat gtg gga     194
Thr Ala Ala Gly Lys Asn Leu Cys Ile Val Arg Ala Met Asp Val Gly
 45                  50                  55                  60 tac atg tgc gat gat act atc act tat gaa tgc cca gtg ctg tcg gct     242
Tyr Met Cys Asp Asp Thr Ile Thr Tyr Glu Cys Pro Val Leu Ser Ala
                 65                  70                  75 ggt aat gat cca gaa gac atc gac tgt tgg tgc aca aag tca gca gtc     290
Gly Asn Asp Pro Glu Asp Ile Asp Cys Trp Cys Thr Lys Ser Ala Val
             80                  85                  90 tac gtc agg tat gga aga tgc acc aag aca cgc cac tca aga cgc agt     338
Tyr Val Arg Tyr Gly Arg Cys Thr Lys Thr Arg His Ser Arg Arg Ser
             95                 100                 105 cgg agg tca ctg aca gtg cag aca cac gga gaa agc act cta gcg aac     386
Arg Arg Ser Leu Thr Val Gln Thr His Gly Glu Ser Thr Leu Ala Asn
    110                 115                 120 aag aag ggg gct tgg atg gac agc acc aag gcc aca agg tat ttg gta     434
Lys Lys Gly Ala Trp Met Asp Ser Thr Lys Ala Thr Arg Tyr Leu Val
125                 130                 135                 140 aaa aca gaa tca tgg atc ttg agg aac cct gga tat gcc ctg gtg gca     482
Lys Thr Glu Ser Trp Ile Leu Arg Asn Pro Gly Tyr Ala Leu Val Ala
                145                 150                 155 gcc gtc att ggt tgg atg ctt ggg agc aac acc atg cag aga gtt gtg     530
Ala Val Ile Gly Trp Met Leu Gly Ser Asn Thr Met Gln Arg Val Val
```

```
                Ala Val Ile Gly Trp Met Leu Gly Ser Asn Thr Met Gln Arg Val Val
                                160                 165                 170 ttt gtc gtg cta ttg ctt ttg gtg gcc cca gct tac agc ttc aac tgc              578
Phe Val Val Leu Leu Leu Leu Val Ala Pro Ala Tyr Ser Phe Asn Cys
            175                 180                 185 ctt gga atg agc aac aga gac ttc ttg gaa gga gtg tct gga gca aca              626
Leu Gly Met Ser Asn Arg Asp Phe Leu Glu Gly Val Ser Gly Ala Thr
    190                 195                 200 tgg gtg gat ttg gtt ctc gaa ggc gac agc tgc gtg act atc atg tct              674
Trp Val Asp Leu Val Leu Glu Gly Asp Ser Cys Val Thr Ile Met Ser
205                 210                 215                 220 aag gac aag cct acc atc gat gtg aag atg atg aat atg gag gcg gcc              722
Lys Asp Lys Pro Thr Ile Asp Val Lys Met Met Asn Met Glu Ala Ala
                225                 230                 235 aac ctg gca gag gtc cgc agt tat tgc tat ttg gct acc gtc agc gat              770
Asn Leu Ala Glu Val Arg Ser Tyr Cys Tyr Leu Ala Thr Val Ser Asp
    240                 245                 250 ctc tcc acc aaa gct gcg tgc ccg acc atg gga gaa gct cac aat gac              818
Leu Ser Thr Lys Ala Ala Cys Pro Thr Met Gly Glu Ala His Asn Asp
        255                 260                 265 aaa cgt gct gac cca gct ttt gtg tgc aga caa gga gtg gtg gac agg              866
Lys Arg Ala Asp Pro Ala Phe Val Cys Arg Gln Gly Val Val Asp Arg
270                 275                 280 ggc tgg ggc aac ggc tgc gga cta ttt ggc aaa gga agc att gac aca              914
Gly Trp Gly Asn Gly Cys Gly Leu Phe Gly Lys Gly Ser Ile Asp Thr
285                 290                 295                 300 tgc gcc aaa ttt gcc tgc tct acc aag gca ata gga aga acc atc ttg              962
Cys Ala Lys Phe Ala Cys Ser Thr Lys Ala Ile Gly Arg Thr Ile Leu
                305                 310                 315 aaa gag aat atc aag tac gaa gtg gcc att ttt gtc cat gga cca act             1010
Lys Glu Asn Ile Lys Tyr Glu Val Ala Ile Phe Val His Gly Pro Thr
    320                 325                 330 act gtg gag tcg cac gga aac tac tcc aca cag gtt gga gcc act cag             1058
Thr Val Glu Ser His Gly Asn Tyr Ser Thr Gln Val Gly Ala Thr Gln
        335                 340                 345 gca ggg aga ttc agc atc act cct gcg gcg cct tca tac aca cta aag             1106
Ala Gly Arg Phe Ser Ile Thr Pro Ala Ala Pro Ser Tyr Thr Leu Lys
350                 355                 360 ctt gga gaa tat gga gag gtg aca gtg gac tgt gaa cca cgg tca ggg             1154
Leu Gly Glu Tyr Gly Glu Val Thr Val Asp Cys Glu Pro Arg Ser Gly
365                 370                 375                 380 att gac acc aat gca tac tac gtg atg act gtt gga aca aag acg ttc             1202
Ile Asp Thr Asn Ala Tyr Tyr Val Met Thr Val Gly Thr Lys Thr Phe
                385                 390                 395 ttg gtc cat cgt gag tgg ttc atg gac ctc aac ctc cct tgg agc agt             1250
Leu Val His Arg Glu Trp Phe Met Asp Leu Asn Leu Pro Trp Ser Ser
    400                 405                 410 gct gga agt act gtg tgg agg aac aga gag acg tta atg gag ttt gag             1298
Ala Gly Ser Thr Val Trp Arg Asn Arg Glu Thr Leu Met Glu Phe Glu
        415                 420                 425 gaa cca cac gcc acg aag cag tct gtg ata gca ttg ggc tca caa gag             1346
Glu Pro His Ala Thr Lys Gln Ser Val Ile Ala Leu Gly Ser Gln Glu
430                 435                 440 gga gct ctg cat caa gct ttg gct gga gcc att cct gtg gaa ttt tca             1394
Gly Ala Leu His Gln Ala Leu Ala Gly Ala Ile Pro Val Glu Phe Ser
445                 450                 455                 460 agc aac act gtc aag ttg acg tcg ggt cat ttg aag tgt aga gtg aag             1442
Ser Asn Thr Val Lys Leu Thr Ser Gly His Leu Lys Cys Arg Val Lys
                465                 470                 475
```

-continued

| | | |
|---|---|---|
| atg gaa aaa ttg cag ttg aag gga aca acc tat ggc gtc tgt tca aag<br>Met Glu Lys Leu Gln Leu Lys Gly Thr Thr Tyr Gly Val Cys Ser Lys<br>480　　　　　　　　　485　　　　　　　　　490 | | 1490 |
| gct ttc aag ttt ctt ggg act ccc gca gac aca ggt cac ggc act gtg<br>Ala Phe Lys Phe Leu Gly Thr Pro Ala Asp Thr Gly His Gly Thr Val<br>　　495　　　　　　　　　500　　　　　　　　　505 | | 1538 |
| gtg ttg gaa ttg cag tac act ggc acg gat gga cct tgc aaa gtt cct<br>Val Leu Glu Leu Gln Tyr Thr Gly Thr Asp Gly Pro Cys Lys Val Pro<br>510　　　　　　　　　515　　　　　　　　　520 | | 1586 |
| atc tcg tca gcg gct tca ttg aac gac cta acg cca gtg ggc aga ttg<br>Ile Ser Ser Ala Ala Ser Leu Asn Asp Leu Thr Pro Val Gly Arg Leu<br>525　　　　　　　　　530　　　　　　　　　535　　　　　　　　　540 | | 1634 |
| gtc act gtc aac cct ttt gtt tca gtg gcc acg gcc aac gct aag gtc<br>Val Thr Val Asn Pro Phe Val Ser Val Ala Thr Ala Asn Ala Lys Val<br>　　　　　　　545　　　　　　　　　550　　　　　　　　　555 | | 1682 |
| ctg att gaa ttg gaa cca ccc ttt gga gac tca tac ata gtg gtg ggc<br>Leu Ile Glu Leu Glu Pro Pro Phe Gly Asp Ser Tyr Ile Val Val Gly<br>560　　　　　　　　　565　　　　　　　　　570 | | 1730 |
| aga gga gaa caa cag atc aat cac cat tgg cac aag tct gga agc agc<br>Arg Gly Glu Gln Gln Ile Asn His His Trp His Lys Ser Gly Ser Ser<br>575　　　　　　　　　580　　　　　　　　　585 | | 1778 |
| att ggc aaa gcc ttt aca acc acc ctc aaa gga gcg cag aga cta gcc<br>Ile Gly Lys Ala Phe Thr Thr Thr Leu Lys Gly Ala Gln Arg Leu Ala<br>590　　　　　　　　　595　　　　　　　　　600 | | 1826 |
| gct cta gga gac aca gct tgg gac ttt gga tca gtt gga ggg gtg ttc<br>Ala Leu Gly Asp Thr Ala Trp Asp Phe Gly Ser Val Gly Gly Val Phe<br>605　　　　　　　　　610　　　　　　　　　615　　　　　　　　　620 | | 1874 |
| acc tca gtt ggg aag gct gtc cat caa gtg ttc gga gga gca ttc cgc<br>Thr Ser Val Gly Lys Ala Val His Gln Val Phe Gly Gly Ala Phe Arg<br>　　　　　　　625　　　　　　　　　630　　　　　　　　　635 | | 1922 |
| tca ctg ttc gga ggc atg tcc tgg ata acg caa gga ttg ctg ggg gct<br>Ser Leu Phe Gly Gly Met Ser Trp Ile Thr Gln Gly Leu Leu Gly Ala<br>640　　　　　　　　　645　　　　　　　　　650 | | 1970 |
| ctc ctg ttg tgg atg ggc atc aat gct cgt gat agg tcc ata gct ctc<br>Leu Leu Leu Trp Met Gly Ile Asn Ala Arg Asp Arg Ser Ile Ala Leu<br>655　　　　　　　　　660　　　　　　　　　665 | | 2018 |
| acg ttt ctc gca gtt gga gga gtt ctg ctc ttc ctc tcc gtg aac gtg<br>Thr Phe Leu Ala Val Gly Gly Val Leu Leu Phe Leu Ser Val Asn Val<br>670　　　　　　　　　675　　　　　　　　　680 | | 2066 |
| cac gct taattttat ctaga<br>His Ala<br>685 | | 2087 |

<210> SEQ ID NO 59
<211> LENGTH: 686
<212> TYPE: PRT
<213> ORGANISM: West Nile virus

<400> SEQUENCE: 59

Met Gly Ser Thr Gly Ile Ala Val Met Ile Gly Leu Ile Ala Ser Val
1               5                   10                  15

Gly Ala Val Thr Leu Ser Asn Phe Gln Gly Lys Val Met Met Thr Val
            20                  25                  30

Asn Ala Thr Asp Val Thr Asp Val Ile Thr Ile Pro Thr Ala Ala Gly
        35                  40                  45

Lys Asn Leu Cys Ile Val Arg Ala Met Asp Val Gly Tyr Met Cys Asp
    50                  55                  60

Asp Thr Ile Thr Tyr Glu Cys Pro Val Leu Ser Ala Gly Asn Asp Pro
65                  70                  75                  80

-continued

```
Glu Asp Ile Asp Cys Trp Cys Thr Lys Ser Ala Val Tyr Val Arg Tyr
                85                  90                  95
Gly Arg Cys Thr Lys Thr Arg His Ser Arg Arg Ser Arg Arg Ser Leu
            100                 105                 110
Thr Val Gln Thr His Gly Glu Ser Thr Leu Ala Asn Lys Lys Gly Ala
        115                 120                 125
Trp Met Asp Ser Thr Lys Ala Thr Arg Tyr Leu Val Lys Thr Glu Ser
    130                 135                 140
Trp Ile Leu Arg Asn Pro Gly Tyr Ala Leu Val Ala Ala Val Ile Gly
145                 150                 155                 160
Trp Met Leu Gly Ser Asn Thr Met Gln Arg Val Val Phe Val Val Leu
                165                 170                 175
Leu Leu Leu Val Ala Pro Ala Tyr Ser Phe Asn Cys Leu Gly Met Ser
            180                 185                 190
Asn Arg Asp Phe Leu Glu Gly Val Ser Gly Ala Thr Trp Val Asp Leu
        195                 200                 205
Val Leu Glu Gly Asp Ser Cys Val Thr Ile Met Ser Lys Asp Lys Pro
    210                 215                 220
Thr Ile Asp Val Lys Met Met Asn Met Glu Ala Ala Asn Leu Ala Glu
225                 230                 235                 240
Val Arg Ser Tyr Cys Tyr Leu Ala Thr Val Ser Asp Leu Ser Thr Lys
                245                 250                 255
Ala Ala Cys Pro Thr Met Gly Glu Ala His Asn Asp Lys Arg Ala Asp
            260                 265                 270
Pro Ala Phe Val Cys Arg Gln Gly Val Val Asp Arg Gly Trp Gly Asn
        275                 280                 285
Gly Cys Gly Leu Phe Gly Lys Gly Ser Ile Asp Thr Cys Ala Lys Phe
    290                 295                 300
Ala Cys Ser Thr Lys Ala Ile Gly Arg Thr Ile Leu Lys Glu Asn Ile
305                 310                 315                 320
Lys Tyr Glu Val Ala Ile Phe Val His Gly Pro Thr Thr Val Glu Ser
                325                 330                 335
His Gly Asn Tyr Ser Thr Gln Val Gly Ala Thr Gln Ala Gly Arg Phe
            340                 345                 350
Ser Ile Thr Pro Ala Ala Pro Ser Tyr Thr Leu Lys Leu Gly Glu Tyr
        355                 360                 365
Gly Glu Val Thr Val Asp Cys Glu Pro Arg Ser Gly Ile Asp Thr Asn
    370                 375                 380
Ala Tyr Tyr Val Met Thr Val Gly Thr Lys Thr Phe Leu Val His Arg
385                 390                 395                 400
Glu Trp Phe Met Asp Leu Asn Leu Pro Trp Ser Ser Ala Gly Ser Thr
                405                 410                 415
Val Trp Arg Asn Arg Glu Thr Leu Met Glu Phe Glu Glu Pro His Ala
            420                 425                 430
Thr Lys Gln Ser Val Ile Ala Leu Gly Ser Gln Glu Gly Ala Leu His
        435                 440                 445
Gln Ala Leu Ala Gly Ala Ile Pro Val Glu Phe Ser Ser Asn Thr Val
    450                 455                 460
Lys Leu Thr Ser Gly His Leu Lys Cys Arg Val Lys Met Glu Lys Leu
465                 470                 475                 480
Gln Leu Lys Gly Thr Thr Tyr Gly Val Cys Ser Lys Ala Phe Lys Phe
                485                 490                 495
Leu Gly Thr Pro Ala Asp Thr Gly His Gly Thr Val Val Leu Glu Leu
```

-continued

```
                  500             505             510
  Gln Tyr Thr Gly Thr Asp Gly Pro Cys Lys Val Pro Ile Ser Ser Ala
              515                 520                 525

Ala Ser Leu Asn Asp Leu Thr Pro Val Gly Arg Leu Val Thr Val Asn
  530                 535                 540

Pro Phe Val Ser Val Ala Thr Ala Asn Ala Lys Val Leu Ile Glu Leu
  545                 550                 555                 560

Glu Pro Pro Phe Gly Asp Ser Tyr Ile Val Val Gly Arg Gly Glu Gln
                  565                 570                 575

Gln Ile Asn His His Trp His Lys Ser Gly Ser Ser Ile Gly Lys Ala
              580                 585                 590

Phe Thr Thr Thr Leu Lys Gly Ala Gln Arg Leu Ala Ala Leu Gly Asp
              595                 600                 605

Thr Ala Trp Asp Phe Gly Ser Val Gly Gly Val Phe Thr Ser Val Gly
  610                 615                 620

Lys Ala Val His Gln Val Phe Gly Gly Ala Phe Arg Ser Leu Phe Gly
  625                 630                 635                 640

Gly Met Ser Trp Ile Thr Gln Gly Leu Leu Gly Ala Leu Leu Leu Trp
                  645                 650                 655

Met Gly Ile Asn Ala Arg Asp Arg Ser Ile Ala Leu Thr Phe Leu Ala
              660                 665                 670

Val Gly Gly Val Leu Leu Phe Leu Ser Val Asn Val His Ala
  675                 680                 685

<210> SEQ ID NO 60
<211> LENGTH: 6928
<212> TYPE: DNA
<213> ORGANISM: West Nile virus
<220> FEATURE:
<221> NAME/KEY: CDS
<222> LOCATION: (2005)..(4059)

<400> SEQUENCE: 60
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg aattgcggcc     240
gcaattctga tgttaaatg ttatactttg gatgaagcta taaatatgca ttggaaaaat     300
aatccattta agaaaggat tcaaatacta caaaacctaa gcgataatat gttaactaag     360
cttattctta cgacgctttt aaatatacac aaataaacat aattttttgta taacctaaca     420 aataactaaa acataaaaat aataaaagga aatgtaatat cgtaattatt ttactcagga     480 atgggttaa atatttatat cacgtgtata tctatactgt tatcgtatac tctttacaat     540
tactattacg aatatgcaag agataataag attacgtatt taagagaatc ttgtcatgat     600
aattgggtac gacatagtga taaatgctat ttcgcatcgt tacataaagt cagttggaaa     660
gatggatttg acagatgtaa cttaataggt gcaaaaatgt taaataacag cattctatcg     720
gaagatagga taccagttat attatacaaa atcactggt tggataaaac agattctgca     780
atattcgtaa aagatgaaga ttactgcgaa tttgtaaact atgacaataa aaagccattt     840
atctcaacga catcgtgtaa ttcttccatg ttttatgtat gtgtttcaga tattatgaga     900
ttactataaa cttttttgtat acttatattc cgtaaactat attaatcatg aagaaaatga     960
aaaagtatag aagctgttca cgagcggttg ttgaaaacaa caaaattata cattcaagat    1020
```

```
                                                         -continued ggcttacata tacgtctgtg aggctatcat ggataatgac aatgcatctc taaataggtt    1080
tttggacaat ggattcgacc ctaacacgga atatggtact ctacaatctc ctcttgaaat    1140
ggctgtaatg ttcaagaata ccgaggctat aaaaatcttg atgaggtatg agctaaacc     1200 tgtagttact gaatgcacaa cttcttgtct gcatgatgcg gtgttgagag acgactacaa    1260
aatagtgaaa gatctgttga agaataacta tgtaaacaat gttctttaca gcggaggctt    1320
tactcctttg tgtttggcag cttaccttaa caaagttaat ttggttaaac ttctattggc    1380
tcattcggcg gatgtagata tttcaaacac ggatcggtta actcctctac atatagccgt    1440
atcaaataaa aatttaacaa tggttaaact tctattgaac aaaggtgctg atactgactt    1500
gctggataac atgggatgta ctccttta at gatcgctgta caatctggaa atattgaaat    1560
atgtagcaca ctacttaaaa aaaataaaat gtccagaact gggaaaaatt gatcttgcca    1620
gctgtaattc atggtagaaa agaagtgctc aggctacttt tcaacaaagg agcagatgta    1680
aactacatct ttgaaagaaa tggaaaatca tatactgttt tggaattgat taagaaagt     1740 tactctgaga cacaaaagag gtagctgaag tggtactctc aaaggtacgt gactaattag    1800
ctataaaaag gatccgggtt aattaattag tcatcaggca gggcgagaac gagactatct    1860
gctcgttaat taattagagc ttctttattc tatacttaaa aagtgaaaat aaatacaaag    1920
gttcttgagg gttgtgttaa attgaaagcg agaaataatc ataaattatt tcattatcgc    1980
gatatccgtt aagtttgtat cgta atg acc gga att gca gtc atg att ggc       2031
                                Met Thr Gly Ile Ala Val Met Ile Gly
                                 1               5 ctg atc gcc agc gta gga gcg gtt acc ctc tct aac ttc caa ggg aag     2079
Leu Ile Ala Ser Val Gly Ala Val Thr Leu Ser Asn Phe Gln Gly Lys
 10              15                  20                  25 gtg atg atg acg gta aat gct act gac gtc aca gat gtc atc acg att     2127
Val Met Met Thr Val Asn Ala Thr Asp Val Thr Asp Val Ile Thr Ile
             30                  35                  40 cca aca gct gct gga aag aac cta tgc att gtc aga gca atg gat gtg    2175
Pro Thr Ala Ala Gly Lys Asn Leu Cys Ile Val Arg Ala Met Asp Val
         45                  50                  55 gga tac atg tgc gat gat act atc act tat gaa tgc cca gtg ctg tcg    2223
Gly Tyr Met Cys Asp Asp Thr Ile Thr Tyr Glu Cys Pro Val Leu Ser
     60                  65                  70 gct ggt aat gat cca gaa gac atc gac tgt tgg tgc aca aag tca gca    2271
Ala Gly Asn Asp Pro Glu Asp Ile Asp Cys Trp Cys Thr Lys Ser Ala
 75                  80                  85 gtc tac gtc agg tat gga aga tgc acc aag aca cgc cac tca aga cgc    2319
Val Tyr Val Arg Tyr Gly Arg Cys Thr Lys Thr Arg His Ser Arg Arg
         90                  95                 100                 105 agt cgg agg tca ctg aca gtg cag aca cac gga gaa agc act cta gcg    2367
Ser Arg Arg Ser Leu Thr Val Gln Thr His Gly Glu Ser Thr Leu Ala
                110                 115                 120 aac aag aag ggg gct tgg atg gac agc acc aag gcc aca agg tat ttg    2415
Asn Lys Lys Gly Ala Trp Met Asp Ser Thr Lys Ala Thr Arg Tyr Leu
            125                 130                 135 gta aaa aca gaa tca tgg atc ttg agg aac cct gga tat gcc ctg gtg    2463
Val Lys Thr Glu Ser Trp Ile Leu Arg Asn Pro Gly Tyr Ala Leu Val
        140                 145                 150 gca gcc gtc att ggt tgg atg ctt ggg agc aac acc atg cag aga gtt    2511
Ala Ala Val Ile Gly Trp Met Leu Gly Ser Asn Thr Met Gln Arg Val
    155                 160                 165 gtg ttt gtc gtg cta ttg ctt ttg gtg gcc cca gct tac agc ttc aac    2559
Val Phe Val Val Leu Leu Leu Leu Val Ala Pro Ala Tyr Ser Phe Asn
```

-continued

| | | |
|---|---|---|
| 170 | 175 | 180 | 185 |

```
tgc ctt gga atg agc aac aga gac ttc ttg gaa gga gtg tct gga gca    2607
Cys Leu Gly Met Ser Asn Arg Asp Phe Leu Glu Gly Val Ser Gly Ala
            190                 195                 200 aca tgg gtg gat ttg gtt ctc gaa ggc gac agc tgc gtg act atc atg    2655
Thr Trp Val Asp Leu Val Leu Glu Gly Asp Ser Cys Val Thr Ile Met
        205                 210                 215 tct aag gac aag cct acc atc gat gtg aag atg atg aat atg gag gcg    2703
Ser Lys Asp Lys Pro Thr Ile Asp Val Lys Met Met Asn Met Glu Ala
        220                 225                 230 gcc aac ctg gca gag gtc cgc agt tat tgc tat ttg gct acc gtc agc    2751
Ala Asn Leu Ala Glu Val Arg Ser Tyr Cys Tyr Leu Ala Thr Val Ser
235                 240                 245 gat ctc tcc acc aaa gct gcg tgc ccg acc atg gga gaa gct cac aat    2799
Asp Leu Ser Thr Lys Ala Ala Cys Pro Thr Met Gly Glu Ala His Asn
250                 255                 260                 265 gac aaa cgt gct gac cca gct ttt gtg tgc aga caa gga gtg gtg gac    2847
Asp Lys Arg Ala Asp Pro Ala Phe Val Cys Arg Gln Gly Val Val Asp
                270                 275                 280 agg ggc tgg ggc aac ggc tgc gga cta ttt ggc aaa gga agc att gac    2895
Arg Gly Trp Gly Asn Gly Cys Gly Leu Phe Gly Lys Gly Ser Ile Asp
            285                 290                 295 aca tgc gcc aaa ttt gcc tgc tct acc aag gca ata gga aga acc atc    2943
Thr Cys Ala Lys Phe Ala Cys Ser Thr Lys Ala Ile Gly Arg Thr Ile
        300                 305                 310 ttg aaa gag aat atc aag tac gaa gtg gcc atc ttc gtg cac gga cca    2991
Leu Lys Glu Asn Ile Lys Tyr Glu Val Ala Ile Phe Val His Gly Pro
        315                 320                 325 act act gtg gag tcg cac gga aac tac tcc aca cag gtt gga gcc act    3039
Thr Thr Val Glu Ser His Gly Asn Tyr Ser Thr Gln Val Gly Ala Thr
330                 335                 340                 345 cag gca ggg aga ttc agc atc act cct gcg gcg cct tca tac aca cta    3087
Gln Ala Gly Arg Phe Ser Ile Thr Pro Ala Ala Pro Ser Tyr Thr Leu
                350                 355                 360 aag ctt gga gaa tat gga gag gtg aca gtg gac tgt gaa cca cgg tca    3135
Lys Leu Gly Glu Tyr Gly Glu Val Thr Val Asp Cys Glu Pro Arg Ser
            365                 370                 375 ggg att gac acc aat gca tac tac gtg atg act gtt gga aca aag acg    3183
Gly Ile Asp Thr Asn Ala Tyr Tyr Val Met Thr Val Gly Thr Lys Thr
        380                 385                 390 ttc ttg gtc cat cgt gag tgg ttc atg gac ctc aac ctc cct tgg agc    3231
Phe Leu Val His Arg Glu Trp Phe Met Asp Leu Asn Leu Pro Trp Ser
        395                 400                 405 agt gct gga agt act gtg tgg agg aac aga gag acg tta atg gag ttt    3279
Ser Ala Gly Ser Thr Val Trp Arg Asn Arg Glu Thr Leu Met Glu Phe
410                 415                 420                 425 gag gaa cca cac gcc acg aag cag tct gtg ata gca ttg ggc tca caa    3327
Glu Glu Pro His Ala Thr Lys Gln Ser Val Ile Ala Leu Gly Ser Gln
                430                 435                 440 gag gga gct ctg cat caa gct ttg gct gga gcc att cct gtg gaa ttt    3375
Glu Gly Ala Leu His Gln Ala Leu Ala Gly Ala Ile Pro Val Glu Phe
            445                 450                 455 tca agc aac act gtc aag ttg acg tcg ggt cat ttg aag tgt aga gtg    3423
Ser Ser Asn Thr Val Lys Leu Thr Ser Gly His Leu Lys Cys Arg Val
        460                 465                 470 aag atg gaa aaa ttg cag ttg aag gga aca acc tat ggc gtc tgt tca    3471
Lys Met Glu Lys Leu Gln Leu Lys Gly Thr Thr Tyr Gly Val Cys Ser
475                 480                 485 aag gct ttc aag ttt ctt ggg act ccc gca gac aca ggt cac ggc act    3519
```

```
Lys Ala Phe Lys Phe Leu Gly Thr Pro Ala Asp Thr Gly His Gly Thr
490             495                 500                 505 gtg gtg ttg gaa ttg cag tac act ggc acg gat gga cct tgc aaa gtt       3567
Val Val Leu Glu Leu Gln Tyr Thr Gly Thr Asp Gly Pro Cys Lys Val
                510                 515                 520 cct atc tcg tca gcg gct tca ttg aac gac cta acg cca gtg ggc aga       3615
Pro Ile Ser Ser Ala Ala Ser Leu Asn Asp Leu Thr Pro Val Gly Arg
                525                 530                 535 ttg gtc act gtc aac cct ttt gtt tca gtg gcc acg gcc aac gct aag       3663
Leu Val Thr Val Asn Pro Phe Val Ser Val Ala Thr Ala Asn Ala Lys
                540                 545                 550 gtc ctg att gaa ttg gaa cca ccc ttt gga gac tca tac ata gtg gtg       3711
Val Leu Ile Glu Leu Glu Pro Pro Phe Gly Asp Ser Tyr Ile Val Val
        555                 560                 565 ggc aga gga gaa caa cag atc aat cac cat tgg cac aag tct gga agc       3759
Gly Arg Gly Glu Gln Gln Ile Asn His His Trp His Lys Ser Gly Ser
570             575                 580                 585 agc att ggc aaa gcc ttt aca acc acc ctc aaa gga gcg cag aga cta       3807
Ser Ile Gly Lys Ala Phe Thr Thr Thr Leu Lys Gly Ala Gln Arg Leu
                590                 595                 600 gcc gct cta gga gac aca gct tgg gac ttt gga tca gtt gga ggg gtg       3855
Ala Ala Leu Gly Asp Thr Ala Trp Asp Phe Gly Ser Val Gly Gly Val
                605                 610                 615 ttc acc tca gtt ggg aag gct gtc cat caa gtg ttc gga gga gca ttc       3903
Phe Thr Ser Val Gly Lys Ala Val His Gln Val Phe Gly Gly Ala Phe
                620                 625                 630 cgc tca ctg ttc gga ggc atg tcc tgg ata acg caa gga ttg ctg ggg       3951
Arg Ser Leu Phe Gly Gly Met Ser Trp Ile Thr Gln Gly Leu Leu Gly
        635                 640                 645 gct ctc ctg ttg tgg atg ggc atc aat gct cgt gat agg tcc ata gct       3999
Ala Leu Leu Leu Trp Met Gly Ile Asn Ala Arg Asp Arg Ser Ile Ala
650             655                 660                 665 ctc acg ttt ctc gca gtt gga gga gtt ctg ctc ttc ctc tcc gtg aac       4047
Leu Thr Phe Leu Ala Val Gly Gly Val Leu Leu Phe Leu Ser Val Asn
                670                 675                 680 gtg cac gct taa tttttatcta gaatcgatcc cgggttttta tgactagtta          4099
Val His Ala
        685 atcacggccg cttataaaga tctaaaatgc ataatttcta ataatgaaa aaaagtacat     4159 catgagcaac gcgttagtat attttacaat ggagattaac gctctatacc gttctatgtt   4219 tattgattca gatgatgttt tagaaaagaa agttattgaa tatgaaaact ttaatgaaga   4279 tgaagatgac gacgatgatt attgttgtaa atctgtttta gatgaagaag atgacgcgct   4339 aaagtatact atggttacaa agtataagtc tatactacta atggcgactt gtgcaagaag   4399 gtatagtata gtgaaaatgt tgttagatta tgattatgaa aaaccaaata atcagatcc    4459 atatctaaag gtatctcctt tgcacataat ttcatctatt cctagtttag aatacctgca   4519 gccaagcttg gcactggccg tcgttttaca acgtcgtgac tgggaaaacc ctggcgttac   4579 ccaacttaat cgccttgcag cacatccccc tttcgccagc tggcgtaata gcgaagaggc   4639 ccgcaccgat cgcccttccc aacagttgcg cagcctgaat ggcgaatggc gcctgatgcg   4699 gtatttctc cttacgcatc tgtgcggtat ttcacaccgc atatggtgca ctctcagtac   4759 aatctgctct gatgccgcat agttaagcca gccccgacac ccgccaacac ccgctgacgc   4819 gccctgacgg gcttgtctgc tcccggcatc cgcttacaga caagctgtga ccgtctccgg   4879 gagctgcatg tgtcagaggt tttcaccgtc atcaccgaaa cgcgcgagac gaaagggcct   4939
```

| | | | |
|---|---|---|---|
| cgtgatacgc | ctatttttat aggttaatgt catgataata atggtttctt agacgtcagg | 4999 |
| tggcactttt | cggggaaatg tgcgcggaac ccctatttgt ttatttttct aaatacattc | 5059 |
| aaatatgtat | ccgctcatga gacaataacc ctgataaatg cttcaataat attgaaaaag | 5119 |
| gaagagtatg | agtattcaac atttccgtgt cgcccttatt ccctttttg cggcattttg | 5179 |
| ccttcctgtt | tttgctcacc cagaaacgct ggtgaaagta aaagatgctg aagatcagtt | 5239 |
| gggtgcacga | gtgggttaca tcgaactgga tctcaacagc ggtaagatcc ttgagagttt | 5299 |
| tcgccccgaa | gaacgttttc caatgatgag cactttaaa gttctgctat gtggcgcggt | 5359 |
| attatcccgt | attgacgccg ggcaagagca actcggtcgc cgcatacact attctcagaa | 5419 |
| tgacttggtt | gagtactcac cagtcacaga aaagcatctt acggatggca tgacagtaag | 5479 |
| agaattatgc | agtgctgcca taaccatgag tgataacact cggccaact tacttctgac | 5539 |
| aacgatcgga | ggaccgaagg agctaaccgc ttttttgcac aacatggggg atcatgtaac | 5599 |
| tcgccttgat | cgttgggaac cggagctgaa tgaagccata ccaaacgacg agcgtgacac | 5659 |
| cacgatgcct | gtagcaatgg caacaacgtt gcgcaaacta ttaactggcg aactacttac | 5719 |
| tctagcttcc | cggcaacaat taatagactg gatggaggcg gataaagttg caggaccact | 5779 |
| tctgcgctcg | gcccttccgg ctggctggtt tattgctgat aaatctggag ccggtgagcg | 5839 |
| tgggtctcgc | ggtatcattg cagcactggg gccagatggt aagccctccc gtatcgtagt | 5899 |
| tatctacacg | acggggagtc aggcaactat ggatgaacga atagacaga tcgctgagat | 5959 |
| aggtgcctca | ctgattaagc attggtaact gtcagaccaa gtttactcat atatacttta | 6019 |
| gattgattta | aaacttcatt tttaatttaa aaggatctag gtgaagatcc tttttgataa | 6079 |
| tctcatgacc | aaaatccctt aacgtgagtt ttcgttccac tgagcgtcag accccgtaga | 6139 |
| aaagatcaaa | ggatcttctt gagatccttt ttttctgcgc gtaatctgct gcttgcaaac | 6199 |
| aaaaaaacca | ccgctaccag cggtggtttg tttgccggat caagagctac caactctttt | 6259 |
| tccgaaggta | actggcttca gcagagcgca gataccaaat actgtccttc tagtgtagcc | 6319 |
| gtagttaggc | caccacttca agaactctgt agcaccgcct acatacctcg ctctgctaat | 6379 |
| cctgttacca | gtggctgctg ccagtggcga taagtcgtgt cttaccgggt tggactcaag | 6439 |
| acgatagtta | ccggataagg cgcagcggtc gggctgaacg gggggttcgt gcacacagcc | 6499 |
| cagcttggag | cgaacgacct acaccgaact gagatacctA cagcgtgagc tatgagaaag | 6559 |
| cgccacgctt | cccgaaggga gaaaggcgga caggtatccg gtaagcggca gggtcggaac | 6619 |
| aggagagcgc | acgagggagc ttccaggggg aaacgcctgg tatctttata gtcctgtcgg | 6679 |
| gtttcgccac | ctctgacttg agcgtcgatt tttgtgatgc tcgtcagggg ggcggagcct | 6739 |
| atggaaaaac | gccagcaacg cggccttttt acggttcctg gccttttgct ggccttttgc | 6799 |
| tcacatgttc | tttcctgcgt tatcccctga ttctgtggat aaccgtatta ccgcctttga | 6859 |
| gtgagctgat | accgctcgcc gcagccgaac gaccgagcgc agcgagtcag tgagcgagga | 6919 |
| agcggaaga | | 6928 |

<210> SEQ ID NO 61
<211> LENGTH: 684
<212> TYPE: PRT
<213> ORGANISM: West Nile virus

<400> SEQUENCE: 61

Met Thr Gly Ile Ala Val Met Ile Gly Leu Ile Ala Ser Val Gly Ala
 1               5                  10                  15

-continued

```
Val Thr Leu Ser Asn Phe Gln Gly Lys Val Met Met Thr Val Asn Ala
             20                  25                  30

Thr Asp Val Thr Asp Val Ile Thr Ile Pro Thr Ala Ala Gly Lys Asn
         35                  40                  45

Leu Cys Ile Val Arg Ala Met Asp Val Gly Tyr Met Cys Asp Asp Thr
 50                  55                  60

Ile Thr Tyr Glu Cys Pro Val Leu Ser Ala Gly Asn Asp Pro Glu Asp
 65                  70                  75                  80

Ile Asp Cys Trp Cys Thr Lys Ser Ala Val Tyr Val Arg Tyr Gly Arg
                 85                  90                  95

Cys Thr Lys Thr Arg His Ser Arg Arg Ser Arg Arg Ser Leu Thr Val
             100                 105                 110

Gln Thr His Gly Glu Ser Thr Leu Ala Asn Lys Gly Ala Trp Met
             115                 120                 125

Asp Ser Thr Lys Ala Thr Arg Tyr Leu Val Lys Thr Glu Ser Trp Ile
 130                 135                 140

Leu Arg Asn Pro Gly Tyr Ala Leu Val Ala Ala Val Ile Gly Trp Met
145                 150                 155                 160

Leu Gly Ser Asn Thr Met Gln Arg Val Val Phe Val Val Leu Leu Leu
                 165                 170                 175

Leu Val Ala Pro Ala Tyr Ser Phe Asn Cys Leu Gly Met Ser Asn Arg
             180                 185                 190

Asp Phe Leu Glu Gly Val Ser Gly Ala Thr Trp Val Asp Leu Val Leu
         195                 200                 205

Glu Gly Asp Ser Cys Val Thr Ile Met Ser Lys Asp Lys Pro Thr Ile
210                 215                 220

Asp Val Lys Met Met Asn Met Glu Ala Ala Asn Leu Ala Glu Val Arg
225                 230                 235                 240

Ser Tyr Cys Tyr Leu Ala Thr Val Ser Asp Leu Ser Thr Lys Ala Ala
                 245                 250                 255

Cys Pro Thr Met Gly Glu Ala His Asn Asp Lys Arg Ala Asp Pro Ala
             260                 265                 270

Phe Val Cys Arg Gln Gly Val Val Asp Arg Gly Trp Gly Asn Gly Cys
         275                 280                 285

Gly Leu Phe Gly Lys Gly Ser Ile Asp Thr Cys Ala Lys Phe Ala Cys
     290                 295                 300

Ser Thr Lys Ala Ile Gly Arg Thr Ile Leu Lys Glu Asn Ile Lys Tyr
305                 310                 315                 320

Glu Val Ala Ile Phe Val His Gly Pro Thr Thr Val Glu Ser His Gly
                 325                 330                 335

Asn Tyr Ser Thr Gln Val Gly Ala Thr Gln Ala Gly Arg Phe Ser Ile
             340                 345                 350

Thr Pro Ala Ala Pro Ser Tyr Thr Leu Lys Leu Gly Glu Tyr Gly Glu
         355                 360                 365

Val Thr Val Asp Cys Glu Pro Arg Ser Gly Ile Asp Thr Asn Ala Tyr
     370                 375                 380

Tyr Val Met Thr Val Gly Thr Lys Thr Phe Leu Val His Arg Glu Trp
385                 390                 395                 400

Phe Met Asp Leu Asn Leu Pro Trp Ser Ser Ala Gly Ser Thr Val Trp
                 405                 410                 415

Arg Asn Arg Glu Thr Leu Met Glu Phe Glu Pro His Ala Thr Lys
             420                 425                 430

Gln Ser Val Ile Ala Leu Gly Ser Gln Glu Gly Ala Leu His Gln Ala
```

-continued

```
                    435                 440                 445
Leu Ala Gly Ala Ile Pro Val Glu Phe Ser Ser Asn Thr Val Lys Leu
    450                 455                 460
Thr Ser Gly His Leu Lys Cys Arg Val Lys Met Glu Lys Leu Gln Leu
465                 470                 475                 480
Lys Gly Thr Thr Tyr Gly Val Cys Ser Lys Ala Phe Lys Phe Leu Gly
                485                 490                 495
Thr Pro Ala Asp Thr Gly His Gly Thr Val Val Leu Glu Leu Gln Tyr
            500                 505                 510
Thr Gly Thr Asp Gly Pro Cys Lys Val Pro Ile Ser Ser Ala Ala Ser
        515                 520                 525
Leu Asn Asp Leu Thr Pro Val Gly Arg Leu Val Thr Val Asn Pro Phe
    530                 535                 540
Val Ser Val Ala Thr Ala Asn Ala Lys Val Leu Ile Glu Leu Glu Pro
545                 550                 555                 560
Pro Phe Gly Asp Ser Tyr Ile Val Val Gly Arg Gly Glu Gln Gln Ile
                565                 570                 575
Asn His His Trp His Lys Ser Gly Ser Ser Ile Gly Lys Ala Phe Thr
            580                 585                 590
Thr Thr Leu Lys Gly Ala Gln Arg Leu Ala Ala Leu Gly Asp Thr Ala
        595                 600                 605
Trp Asp Phe Gly Ser Val Gly Gly Val Phe Thr Ser Val Gly Lys Ala
    610                 615                 620
Val His Gln Val Phe Gly Ala Phe Arg Ser Leu Phe Gly Gly Met
625                 630                 635                 640
Ser Trp Ile Thr Gln Gly Leu Leu Gly Ala Leu Leu Leu Trp Met Gly
                645                 650                 655
Ile Asn Ala Arg Asp Arg Ser Ile Ala Leu Thr Phe Leu Ala Val Gly
            660                 665                 670
Gly Val Leu Leu Phe Leu Ser Val Asn Val His Ala
        675                 680
```

```
<210> SEQ ID NO 62
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (11)..(37)

<400> SEQUENCE: 62
attatcgcga acc gga att gca gtc atg att ggc ctg                        37
          Thr Gly Ile Ala Val Met Ile Gly Leu
            1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Gly Ile Ala Val Met Ile Gly Leu
  1               5
```

-continued

```
<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (11)..(40)

<400> SEQUENCE: 64
attatcgcga atg acc gga att gca gtc atg att ggc ctg            40
           Met Thr Gly Ile Ala Val Met Ile Gly Leu
           1               5                  10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Thr Gly Ile Ala Val Met Ile Gly Leu
1               5                  10

<210> SEQ ID NO 66
<211> LENGTH: 11029
<212> TYPE: DNA
<213> ORGANISM: West Nile virus
<220> FEATURE:
<221> NAME/KEY: CDS
<222> LOCATION: (97)..(10395)

<400> SEQUENCE: 66
agtagttcgc ctgtgtgagc tgacaaactt agtagtgttt gtgaggatta acaacaatta    60
acacagtgcg agctgtttct tagcacgaag atctcg atg tct aag aaa cca gga   114
                                         Met Ser Lys Lys Pro Gly
                                         1               5 ggg ccc ggc aag agc cgg gct gtc aat atg cta aaa cgc gga atg ccc    162
Gly Pro Gly Lys Ser Arg Ala Val Asn Met Leu Lys Arg Gly Met Pro
        10                  15                  20 cgc gtg ttg tcc ttg att gga ctg aag agg gct atg ttg agc ctg atc    210
Arg Val Leu Ser Leu Ile Gly Leu Lys Arg Ala Met Leu Ser Leu Ile
    25                  30                  35 gac ggc aag ggg cca ata cga ttt gtg ttg gct ctc ttg gcg ttc ttc    258
Asp Gly Lys Gly Pro Ile Arg Phe Val Leu Ala Leu Leu Ala Phe Phe
40                  45                  50 agg ttc aca gca att gct ccg acc cga gca gtg ctg gat cga tgg aga    306
Arg Phe Thr Ala Ile Ala Pro Thr Arg Ala Val Leu Asp Arg Trp Arg
55                  60                  65                  70 ggt gtg aac aaa caa aca gcg atg aaa cac ctt ctg agt ttt aag aag    354
Gly Val Asn Lys Gln Thr Ala Met Lys His Leu Leu Ser Phe Lys Lys
            75                  80                  85 gaa cta ggg acc ttg acc agt gct atc aat cgg cgg agc tca aaa caa    402
Glu Leu Gly Thr Leu Thr Ser Ala Ile Asn Arg Arg Ser Ser Lys Gln
        90                  95                 100 aag aaa aga gga gga aag acc gga att gca gtc atg att ggc ctg atc    450
Lys Lys Arg Gly Gly Lys Thr Gly Ile Ala Val Met Ile Gly Leu Ile
    105                 110                 115 gcc agc gta gga gca gtt acc ctc tct aac ttc caa ggg aag gtg atg    498
Ala Ser Val Gly Ala Val Thr Leu Ser Asn Phe Gln Gly Lys Val Met
```

-continued

```
            120                 125                 130
atg acg gta aat gct act gac gtc aca gat gtc atc acg att cca aca    546
Met Thr Val Asn Ala Thr Asp Val Thr Asp Val Ile Thr Ile Pro Thr
135                 140                 145                 150 gct gct gga aag aac cta tgc att gtc aga gca atg gat gtg gga tac    594
Ala Ala Gly Lys Asn Leu Cys Ile Val Arg Ala Met Asp Val Gly Tyr
                155                 160                 165 atg tgc gat gat act atc act tat gaa tgc cca gtg ctg tcg gct ggt    642
Met Cys Asp Asp Thr Ile Thr Tyr Glu Cys Pro Val Leu Ser Ala Gly
                170                 175                 180 aat gat cca gaa gac atc gac tgt tgg tgc aca aag tca gca gtc tac    690
Asn Asp Pro Glu Asp Ile Asp Cys Trp Cys Thr Lys Ser Ala Val Tyr
            185                 190                 195 gtc agg tat gga aga tgc acc aag aca cgc cac tca aga cgc agt cgg    738
Val Arg Tyr Gly Arg Cys Thr Lys Thr Arg His Ser Arg Arg Ser Arg
        200                 205                 210 agg tca ctg aca gtg cag aca cac gga gaa agc act cta gcg aac aag    786
Arg Ser Leu Thr Val Gln Thr His Gly Glu Ser Thr Leu Ala Asn Lys
215                 220                 225                 230 aag ggg gct tgg atg gac agc acc aag gcc aca agg tat ttg gta aaa    834
Lys Gly Ala Trp Met Asp Ser Thr Lys Ala Thr Arg Tyr Leu Val Lys
                235                 240                 245 aca gaa tca tgg atc ttg agg aac cct gga tat gcc ctg gtg gca gcc    882
Thr Glu Ser Trp Ile Leu Arg Asn Pro Gly Tyr Ala Leu Val Ala Ala
                250                 255                 260 gtc att ggt tgg atg ctt ggg agc aac acc atg cag aga gtt gtg ttt    930
Val Ile Gly Trp Met Leu Gly Ser Asn Thr Met Gln Arg Val Val Phe
                265                 270                 275 gtc gtg cta ttg ctt ttg gtg gcc cca gct tac agc ttc aac tgc ctt    978
Val Val Leu Leu Leu Leu Val Ala Pro Ala Tyr Ser Phe Asn Cys Leu
        280                 285                 290 gga atg agc aac aga gac ttc ttg gaa gga gtg tct gga gca aca tgg    1026
Gly Met Ser Asn Arg Asp Phe Leu Glu Gly Val Ser Gly Ala Thr Trp
295                 300                 305                 310 gtg gat ttg gtt ctc gaa ggc gac agc tgc gtg act atc atg tct aag    1074
Val Asp Leu Val Leu Glu Gly Asp Ser Cys Val Thr Ile Met Ser Lys
                315                 320                 325 gac aag cct acc atc gat gtg aag atg atg aat atg gag gcg gcc aac    1122
Asp Lys Pro Thr Ile Asp Val Lys Met Met Asn Met Glu Ala Ala Asn
                330                 335                 340 ctg gca gag gtc cgc agt tat tgc tat ttg gct acc gtc agc gat ctc    1170
Leu Ala Glu Val Arg Ser Tyr Cys Tyr Leu Ala Thr Val Ser Asp Leu
                345                 350                 355 tcc acc aaa gct gcg tgc ccg acc atg gga gaa gct cac aat gac aaa    1218
Ser Thr Lys Ala Ala Cys Pro Thr Met Gly Glu Ala His Asn Asp Lys
        360                 365                 370 cgt gct gac cca gct ttt gtg tgc aga caa gga gtg gtg gac agg ggc    1266
Arg Ala Asp Pro Ala Phe Val Cys Arg Gln Gly Val Val Asp Arg Gly
375                 380                 385                 390 tgg ggc aac ggc tgc gga cta ttt ggc aaa gga agc att gac aca tgc    1314
Trp Gly Asn Gly Cys Gly Leu Phe Gly Lys Gly Ser Ile Asp Thr Cys
                395                 400                 405 gcc aaa ttt gcc tgc tct acc aag gca ata gga aga acc atc ttg aaa    1362
Ala Lys Phe Ala Cys Ser Thr Lys Ala Ile Gly Arg Thr Ile Leu Lys
            410                 415                 420 gag aat atc aag tac gaa gtg gcc att ttt gtc cat gga cca act act    1410
Glu Asn Ile Lys Tyr Glu Val Ala Ile Phe Val His Gly Pro Thr Thr
                425                 430                 435 gtg gag tcg cac gga aac tac tcc aca cag gtt gga gcc act cag gca    1458
Val Glu Ser His Gly Asn Tyr Ser Thr Gln Val Gly Ala Thr Gln Ala
```

```
            Val Glu Ser His Gly Asn Tyr Ser Thr Gln Val Gly Ala Thr Gln Ala
                440                 445                 450 ggg aga ttc agc atc act cct gcg gcg cct tca tac aca cta aag ctt          1506
Gly Arg Phe Ser Ile Thr Pro Ala Ala Pro Ser Tyr Thr Leu Lys Leu
455                 460                 465                 470 gga gaa tat gga gag gtg aca gtg gac tgt gaa cca cgg tca ggg att          1554
Gly Glu Tyr Gly Glu Val Thr Val Asp Cys Glu Pro Arg Ser Gly Ile
                475                 480                 485 gac acc aat gca tac tac gtg atg act gtt gga aca aag acg ttc ttg          1602
Asp Thr Asn Ala Tyr Tyr Val Met Thr Val Gly Thr Lys Thr Phe Leu
            490                 495                 500 gtc cat cgt gag tgg ttc atg gac ctc aac ctc cct tgg agc agt gct          1650
Val His Arg Glu Trp Phe Met Asp Leu Asn Leu Pro Trp Ser Ser Ala
        505                 510                 515 gga agt act gtg tgg agg aac aga gag acg tta atg gag ttt gag gaa          1698
Gly Ser Thr Val Trp Arg Asn Arg Glu Thr Leu Met Glu Phe Glu Glu
    520                 525                 530 cca cac gcc acg aag cag tct gtg ata gca ttg ggc tca caa gag gga          1746
Pro His Ala Thr Lys Gln Ser Val Ile Ala Leu Gly Ser Gln Glu Gly
535                 540                 545                 550 gct ctg cat caa gct ttg gct gga gcc att cct gtg gaa ttt tca agc          1794
Ala Leu His Gln Ala Leu Ala Gly Ala Ile Pro Val Glu Phe Ser Ser
                555                 560                 565 aac act gtc aag ttg acg tcg ggt cat ttg aag tgt aga gtg aag atg          1842
Asn Thr Val Lys Leu Thr Ser Gly His Leu Lys Cys Arg Val Lys Met
                570                 575                 580 gaa aaa ttg cag ttg aag gga aca acc tat ggc gtc tgt tca aag gct          1890
Glu Lys Leu Gln Leu Lys Gly Thr Thr Tyr Gly Val Cys Ser Lys Ala
            585                 590                 595 ttc aag ttt ctt ggg act ccc gca gac aca ggt cac ggc act gtg gtg          1938
Phe Lys Phe Leu Gly Thr Pro Ala Asp Thr Gly His Gly Thr Val Val
        600                 605                 610 ttg gaa ttg cag tac act ggc acg gat gga cct tgc aaa gtt cct atc          1986
Leu Glu Leu Gln Tyr Thr Gly Thr Asp Gly Pro Cys Lys Val Pro Ile
615                 620                 625                 630 tcg tca gtg gct tca ttg aac gac cta acg cca gtg ggc aga ttg gtc          2034
Ser Ser Val Ala Ser Leu Asn Asp Leu Thr Pro Val Gly Arg Leu Val
                635                 640                 645 act gtc aac cct ttt gtt tca gtg gcc acg gcc aac gct aag gtc ctg          2082
Thr Val Asn Pro Phe Val Ser Val Ala Thr Ala Asn Ala Lys Val Leu
                650                 655                 660 att gaa ttg gaa cca ccc ttt gga gac tca tac ata gtg gtg ggc aga          2130
Ile Glu Leu Glu Pro Pro Phe Gly Asp Ser Tyr Ile Val Val Gly Arg
            665                 670                 675 gga gaa caa cag atc aat cac cat tgg cac aag tct gga agc agc att          2178
Gly Glu Gln Gln Ile Asn His His Trp His Lys Ser Gly Ser Ser Ile
        680                 685                 690 ggc aaa gcc ttt aca acc acc ctc aaa gga gcg cag aga cta gcc gct          2226
Gly Lys Ala Phe Thr Thr Thr Leu Lys Gly Ala Gln Arg Leu Ala Ala
695                 700                 705                 710 cta gga gac aca gct tgg gac ttt gga tca gtt gga ggg gtg ttc acc          2274
Leu Gly Asp Thr Ala Trp Asp Phe Gly Ser Val Gly Gly Val Phe Thr
                715                 720                 725 tca gtt ggg aag gct gtc cat caa gtg ttc gga gga gca ttc cgc tca          2322
Ser Val Gly Lys Ala Val His Gln Val Phe Gly Gly Ala Phe Arg Ser
                730                 735                 740 ctg ttc gga ggc atg tcc tgg ata acg caa gga ttg ctg ggg gct ctc          2370
Leu Phe Gly Gly Met Ser Trp Ile Thr Gln Gly Leu Leu Gly Ala Leu
            745                 750                 755
```

```
ctg ttg tgg atg ggc atc aat gct cgt gat agg tcc ata gct ctc acg      2418
Leu Leu Trp Met Gly Ile Asn Ala Arg Asp Arg Ser Ile Ala Leu Thr
    760                 765                 770 ttt ctc gca gtt gga gga gtt ctg ctc ttc ctc tcc gtg aac gtg cac      2466
Phe Leu Ala Val Gly Gly Val Leu Leu Phe Leu Ser Val Asn Val His
775                 780                 785                 790 gct gac act ggg tgt gcc ata gac atc agc cgg caa gag ctg aga tgt      2514
Ala Asp Thr Gly Cys Ala Ile Asp Ile Ser Arg Gln Glu Leu Arg Cys
                795                 800                 805 gga agt gga gtg ttc ata cac aat gat gtg gag gct tgg atg gac cgg      2562
Gly Ser Gly Val Phe Ile His Asn Asp Val Glu Ala Trp Met Asp Arg
            810                 815                 820 tac aag tat tac cct gaa acg cca caa ggc cta gcc aag atc att cag      2610
Tyr Lys Tyr Tyr Pro Glu Thr Pro Gln Gly Leu Ala Lys Ile Ile Gln
        825                 830                 835 aaa gct cat aag gaa gga gtg tgc ggt cta cga tca gtt tcc aga ctg      2658
Lys Ala His Lys Glu Gly Val Cys Gly Leu Arg Ser Val Ser Arg Leu
    840                 845                 850 gag cat caa atg tgg gaa gca gtg aag gac gag ctg aac act ctt ttg      2706
Glu His Gln Met Trp Glu Ala Val Lys Asp Glu Leu Asn Thr Leu Leu
855                 860                 865                 870 aag gag aat ggt gtg gac ctt agt gtc gtg gtt gag aaa cag gag gga      2754
Lys Glu Asn Gly Val Asp Leu Ser Val Val Val Glu Lys Gln Glu Gly
                875                 880                 885 atg tac aag tca gca cct aaa cgc ctc acc gcc acc acg gaa aaa ttg      2802
Met Tyr Lys Ser Ala Pro Lys Arg Leu Thr Ala Thr Thr Glu Lys Leu
            890                 895                 900 gaa att ggc tgg aag gcc tgg gga aag agt att tta ttt gca cca gaa      2850
Glu Ile Gly Trp Lys Ala Trp Gly Lys Ser Ile Leu Phe Ala Pro Glu
        905                 910                 915 ctc gcc aac aac acc ttt gtg gtt gat ggt ccg gag acc aag gaa tgt      2898
Leu Ala Asn Asn Thr Phe Val Val Asp Gly Pro Glu Thr Lys Glu Cys
    920                 925                 930 ccg act cag aat cgc gct tgg aat agc tta gaa gtg gag gat ttt gga      2946
Pro Thr Gln Asn Arg Ala Trp Asn Ser Leu Glu Val Glu Asp Phe Gly
935                 940                 945                 950 ttt ggt ctc acc agc act cgg atg ttc ctg aag gtc aga gag agc aac      2994
Phe Gly Leu Thr Ser Thr Arg Met Phe Leu Lys Val Arg Glu Ser Asn
                955                 960                 965 aca act gaa tgt gac tcg aag atc att gga acg gct gtc aag aac aac      3042
Thr Thr Glu Cys Asp Ser Lys Ile Ile Gly Thr Ala Val Lys Asn Asn
            970                 975                 980 ttg gcg atc cac agt gac ctg tcc tat tgg att gaa agc agg ctc aat      3090
Leu Ala Ile His Ser Asp Leu Ser Tyr Trp Ile Glu Ser Arg Leu Asn
        985                 990                 995 gat acg tgg aag ctt gaa agg gca gtt ctg ggt gaa gtc aaa tca tgt      3138
Asp Thr Trp Lys Leu Glu Arg Ala Val Leu Gly Glu Val Lys Ser Cys
    1000                1005                1010 acg tgg cct gag acg cat acc ttg tgg ggc gat gga atc ctt gag agt      3186
Thr Trp Pro Glu Thr His Thr Leu Trp Gly Asp Gly Ile Leu Glu Ser
1015                1020                1025                1030 gac ttg ata ata cca gtc aca ctg gcg gga cca cga agc aat cac aat      3234
Asp Leu Ile Ile Pro Val Thr Leu Ala Gly Pro Arg Ser Asn His Asn
                1035                1040                1045 cgg aga cct ggg tac aag aca caa aac cag ggc cca tgg gac gaa ggc      3282
Arg Arg Pro Gly Tyr Lys Thr Gln Asn Gln Gly Pro Trp Asp Glu Gly
            1050                1055                1060 cgg gta gag att gac ttc gat tac tgc cca gga act acg gtc acc ctg      3330
Arg Val Glu Ile Asp Phe Asp Tyr Cys Pro Gly Thr Thr Val Thr Leu
        1065                1070                1075
```

-continued

```
agt gag agc tgc gga cac cgt gga cct gcc act cgc acc acc aca gag      3378
Ser Glu Ser Cys Gly His Arg Gly Pro Ala Thr Arg Thr Thr Thr Glu
    1080                1085                1090 agc gga aag ttg ata aca gat tgg tgc tgc agg agc tgc acc tta cca      3426
Ser Gly Lys Leu Ile Thr Asp Trp Cys Cys Arg Ser Cys Thr Leu Pro
1095                1100                1105                1110 cca ctg cgc tac caa act gac agc ggc tgt tgg tat ggt atg gag atc      3474
Pro Leu Arg Tyr Gln Thr Asp Ser Gly Cys Trp Tyr Gly Met Glu Ile
                1115                1120                1125 aga cca cag aga cat gat gaa aag acc ctc gtg cag tca caa gtg aat      3522
Arg Pro Gln Arg His Asp Glu Lys Thr Leu Val Gln Ser Gln Val Asn
            1130                1135                1140 gct tat aat gct gat atg att gac cct ttt cag ttg ggc ctt ctg gtc      3570
Ala Tyr Asn Ala Asp Met Ile Asp Pro Phe Gln Leu Gly Leu Leu Val
        1145                1150                1155 gtg ttc ttg gcc acc cag gag gtc ctt cgc aag agg tgg aca gcc aag      3618
Val Phe Leu Ala Thr Gln Glu Val Leu Arg Lys Arg Trp Thr Ala Lys
    1160                1165                1170 atc agc atg cca gct ata ctg att gct ctg cta gtc ctg gtg ttt ggg      3666
Ile Ser Met Pro Ala Ile Leu Ile Ala Leu Leu Val Leu Val Phe Gly
1175                1180                1185                1190 ggc att act tac act gat gtg tta cgc tat gtc atc ttg gtg ggg gca      3714
Gly Ile Thr Tyr Thr Asp Val Leu Arg Tyr Val Ile Leu Val Gly Ala
                1195                1200                1205 gct ttc gca gaa tct aat tcg gga gga gac gtg gta cac ttg gcg ctc      3762
Ala Phe Ala Glu Ser Asn Ser Gly Gly Asp Val Val His Leu Ala Leu
            1210                1215                1220 atg gcg acc ttc aag ata caa cca gtg ttt atg gtg gca tcg ttt ctc      3810
Met Ala Thr Phe Lys Ile Gln Pro Val Phe Met Val Ala Ser Phe Leu
        1225                1230                1235 aaa gcg aga tgg acc aac cag gag aac att ttg ttg atg ttg gcg gct      3858
Lys Ala Arg Trp Thr Asn Gln Glu Asn Ile Leu Leu Met Leu Ala Ala
    1240                1245                1250 gtt ttc ttt caa atg gct tat cac gat gcc cgc caa att ctg ctc tgg      3906
Val Phe Phe Gln Met Ala Tyr His Asp Ala Arg Gln Ile Leu Leu Trp
1255                1260                1265                1270 gag atc cct gat gtg ttg aat tca ctg gcg gta gct tgg atg ata ctg      3954
Glu Ile Pro Asp Val Leu Asn Ser Leu Ala Val Ala Trp Met Ile Leu
                1275                1280                1285 aga gcc ata aca ttc aca acg aca tca aac gtg gtt gtt ccg ctg cta      4002
Arg Ala Ile Thr Phe Thr Thr Thr Ser Asn Val Val Val Pro Leu Leu
            1290                1295                1300 gcc ctg cta aca ccc ggg ctg aga tgc ttg aat ctg gat gtg tac agg      4050
Ala Leu Leu Thr Pro Gly Leu Arg Cys Leu Asn Leu Asp Val Tyr Arg
        1305                1310                1315 ata ctg ctg ttg atg gtc gga ata ggc agc ttg atc agg gag aag agg      4098
Ile Leu Leu Leu Met Val Gly Ile Gly Ser Leu Ile Arg Glu Lys Arg
    1320                1325                1330 agt gca gct gca aaa aag aaa gga gca agt ctg cta tgc ttg gct cta      4146
Ser Ala Ala Ala Lys Lys Lys Gly Ala Ser Leu Leu Cys Leu Ala Leu
1335                1340                1345                1350 gcc tca aca gga ctt ttc aac ccc atg atc ctt gct gct gga ctg att      4194
Ala Ser Thr Gly Leu Phe Asn Pro Met Ile Leu Ala Ala Gly Leu Ile
                1355                1360                1365 gca tgt gat ccc aac cgt aaa cgc gga tgg ccc gca act gaa gtg atg      4242
Ala Cys Asp Pro Asn Arg Lys Arg Gly Trp Pro Ala Thr Glu Val Met
            1370                1375                1380 aca gct gtc ggc cta atg ttt gcc atc gtc gga ggg ctg gca gag ctt      4290
Thr Ala Val Gly Leu Met Phe Ala Ile Val Gly Gly Leu Ala Glu Leu
```

-continued

```
              1385                1390                1395
gac att gac tcc atg gcc att cca atg act atc gcg ggg ctc atg ttt       4338
Asp Ile Asp Ser Met Ala Ile Pro Met Thr Ile Ala Gly Leu Met Phe
        1400                1405                1410 gct gct ttc gtg att tct ggg aaa tca aca gat atg tgg att gag aga       4386
Ala Ala Phe Val Ile Ser Gly Lys Ser Thr Asp Met Trp Ile Glu Arg
1415                1420                1425                1430 acg gcg gac att tcc tgg gaa agt gat gca gaa att aca ggc tcg agc       4434
Thr Ala Asp Ile Ser Trp Glu Ser Asp Ala Glu Ile Thr Gly Ser Ser
            1435                1440                1445 gaa aga gtt gat gtg cgg ctt gat gat gat gga aac ttc cag ctc atg       4482
Glu Arg Val Asp Val Arg Leu Asp Asp Asp Gly Asn Phe Gln Leu Met
        1450                1455                1460 aat gat cca gga gca cct tgg aag ata tgg atg ctc aga atg gtc tgt       4530
Asn Asp Pro Gly Ala Pro Trp Lys Ile Trp Met Leu Arg Met Val Cys
        1465                1470                1475 ctc gcg att agt gcg tac acc ccc tgg gca atc ttg ccc tca gta gtt       4578
Leu Ala Ile Ser Ala Tyr Thr Pro Trp Ala Ile Leu Pro Ser Val Val
        1480                1485                1490 gga ttt tgg ata act ctc caa tac aca aag aga gga ggc gtg ttg tgg       4626
Gly Phe Trp Ile Thr Leu Gln Tyr Thr Lys Arg Gly Gly Val Leu Trp
1495                1500                1505                1510 gac act ccc tca cca aag gag tac aaa aag ggg gac acg acc acc ggc       4674
Asp Thr Pro Ser Pro Lys Glu Tyr Lys Lys Gly Asp Thr Thr Thr Gly
            1515                1520                1525 gtc tac agg atc atg act cgt ggg ctg ctc ggc agt tat caa gca gga       4722
Val Tyr Arg Ile Met Thr Arg Gly Leu Leu Gly Ser Tyr Gln Ala Gly
        1530                1535                1540 gcg ggc gtg atg gtt gaa ggt gtt ttc cac acc ctt tgg cat aca aca       4770
Ala Gly Val Met Val Glu Gly Val Phe His Thr Leu Trp His Thr Thr
        1545                1550                1555 aaa gga gcc gct ttg atg agc gga gag ggc cgc ctg gac cca tac tgg       4818
Lys Gly Ala Ala Leu Met Ser Gly Glu Gly Arg Leu Asp Pro Tyr Trp
        1560                1565                1570 ggc agt gtc aag gag gat cga ctt tgt tac gga gga ccc tgg aaa ttg       4866
Gly Ser Val Lys Glu Asp Arg Leu Cys Tyr Gly Gly Pro Trp Lys Leu
1575                1580                1585                1590 cag cac aag tgg aac ggg cag gat gag gtg cag atg att gtg gtg gaa       4914
Gln His Lys Trp Asn Gly Gln Asp Glu Val Gln Met Ile Val Val Glu
            1595                1600                1605 cct ggc aag aac gtt aag aac gtc cag acg aaa cca ggg gtg ttc aaa       4962
Pro Gly Lys Asn Val Lys Asn Val Gln Thr Lys Pro Gly Val Phe Lys
        1610                1615                1620 aca cct gaa gga gaa atc ggg gcc gtg act ttg gac ttc ccc act gga       5010
Thr Pro Glu Gly Glu Ile Gly Ala Val Thr Leu Asp Phe Pro Thr Gly
        1625                1630                1635 aca tca ggc tca cca ata gtg gac aaa aac ggt gat gtg att ggg ctt       5058
Thr Ser Gly Ser Pro Ile Val Asp Lys Asn Gly Asp Val Ile Gly Leu
        1640                1645                1650 tat ggc aat gga gtc ata atg ccc aac ggc tca tac ata agc gcg ata       5106
Tyr Gly Asn Gly Val Ile Met Pro Asn Gly Ser Tyr Ile Ser Ala Ile
1655                1660                1665                1670 gtg cag ggt gaa agg atg gat gag cca atc cca gcc gga ttc gaa cct       5154
Val Gln Gly Glu Arg Met Asp Glu Pro Ile Pro Ala Gly Phe Glu Pro
            1675                1680                1685 gag atg ctg agg aaa aaa cag atc act gta ctg gat ctc cat ccc ggc       5202
Glu Met Leu Arg Lys Lys Gln Ile Thr Val Leu Asp Leu His Pro Gly
        1690                1695                1700 gcc ggt aaa aca agg agg att ctg cca cag atc atc aaa gag gcc ata       5250
```

```
                                                  -continued

Ala Gly Lys Thr Arg Arg Ile Leu Pro Gln Ile Ile Lys Glu Ala Ile
    1705                1710                1715 aac aga aga ctg aga aca gcc gtg cta gca cca acc agg gtt gtg gct      5298
Asn Arg Arg Leu Arg Thr Ala Val Leu Ala Pro Thr Arg Val Val Ala
1720                1725                1730 gct gag atg gct gaa gca ctg aga gga ctg ccc atc cgg tac cag aca      5346
Ala Glu Met Ala Glu Ala Leu Arg Gly Leu Pro Ile Arg Tyr Gln Thr
1735                1740                1745                1750 tcc gca gtg ccc aga gaa cat aat gga aat gag att gtt gat gtc atg      5394
Ser Ala Val Pro Arg Glu His Asn Gly Asn Glu Ile Val Asp Val Met
            1755                1760                1765 tgt cat gct acc ctc acc cac agg ctg atg tct cct cac agg gtg ccg      5442
Cys His Ala Thr Leu Thr His Arg Leu Met Ser Pro His Arg Val Pro
        1770                1775                1780 aac tac aac ctg ttc gtg atg gat gag gct cat ttc acc gac cca gct      5490
Asn Tyr Asn Leu Phe Val Met Asp Glu Ala His Phe Thr Asp Pro Ala
    1785                1790                1795 agc att gca gca aga ggt tac att tcc aca aag gtc gag cta ggg gag      5538
Ser Ile Ala Ala Arg Gly Tyr Ile Ser Thr Lys Val Glu Leu Gly Glu
1800                1805                1810 gcg gcg gca ata ttc atg aca gcc acc cca cca ggc act tca gat cca      5586
Ala Ala Ala Ile Phe Met Thr Ala Thr Pro Pro Gly Thr Ser Asp Pro
1815                1820                1825                1830 ttc cca gag tcc aat tca cca att tcc gac tta cag act gag atc ccg      5634
Phe Pro Glu Ser Asn Ser Pro Ile Ser Asp Leu Gln Thr Glu Ile Pro
            1835                1840                1845 gat cga gct tgg aac tct gga tac gaa tgg atc aca gaa tac acc ggg      5682
Asp Arg Ala Trp Asn Ser Gly Tyr Glu Trp Ile Thr Glu Tyr Thr Gly
        1850                1855                1860 aag acg gtt tgg ttt gtg cct agt gtc aag atg ggg aat gag att gcc      5730
Lys Thr Val Trp Phe Val Pro Ser Val Lys Met Gly Asn Glu Ile Ala
    1865                1870                1875 ctt tgc cta caa cgt gct gga aag aaa gta gtc caa ttg aac aga aag      5778
Leu Cys Leu Gln Arg Ala Gly Lys Lys Val Val Gln Leu Asn Arg Lys
1880                1885                1890 tcg tac gag acg gag tac cca aaa tgt aag aac gat gat tgg gac ttt      5826
Ser Tyr Glu Thr Glu Tyr Pro Lys Cys Lys Asn Asp Asp Trp Asp Phe
1895                1900                1905                1910 gtt atc aca aca gac ata tct gaa atg ggg gct aac ttc aag gcg agc      5874
Val Ile Thr Thr Asp Ile Ser Glu Met Gly Ala Asn Phe Lys Ala Ser
            1915                1920                1925 agg gtg att gac agc cgg aag agt gtg aaa cca acc atc ata aca gaa      5922
Arg Val Ile Asp Ser Arg Lys Ser Val Lys Pro Thr Ile Ile Thr Glu
        1930                1935                1940 gga gaa ggg aga gtg atc ctg gga gaa cca tct gca gtg aca gca gct      5970
Gly Glu Gly Arg Val Ile Leu Gly Glu Pro Ser Ala Val Thr Ala Ala
    1945                1950                1955 agt gcc gcc cag aga cgt gga cgt atc ggt aga aat ccg tcg caa gtt      6018
Ser Ala Ala Gln Arg Arg Gly Arg Ile Gly Arg Asn Pro Ser Gln Val
1960                1965                1970 ggt gat gag tac tgt tat ggg ggg cac acg aat gaa gac gac tcg aac      6066
Gly Asp Glu Tyr Cys Tyr Gly Gly His Thr Asn Glu Asp Asp Ser Asn
1975                1980                1985                1990 ttc gcc cat tgg act gag gca cga atc atg ctg gac aac atc aac atg      6114
Phe Ala His Trp Thr Glu Ala Arg Ile Met Leu Asp Asn Ile Asn Met
            1995                2000                2005 cca aac gga ctg atc gct caa ttc tac caa cca gag cgt gag aag gta      6162
Pro Asn Gly Leu Ile Ala Gln Phe Tyr Gln Pro Glu Arg Glu Lys Val
        2010                2015                2020
```

```
tat acc atg gat ggg gaa tac cgg ctc aga gga gaa gag aga aaa aac    6210
Tyr Thr Met Asp Gly Glu Tyr Arg Leu Arg Gly Glu Glu Arg Lys Asn
            2025                2030                2035 ttt ctg gaa ctg ttg agg act gca gat ctg cca gtt tgg ctg gct tac    6258
Phe Leu Glu Leu Leu Arg Thr Ala Asp Leu Pro Val Trp Leu Ala Tyr
        2040                2045                2050 aag gtt gca gcg gct gga gtg tca tac cac gac cgg agg tgg tgc ttt    6306
Lys Val Ala Ala Ala Gly Val Ser Tyr His Asp Arg Arg Trp Cys Phe
2055                2060                2065                2070 gat ggt cct agg aca aac aca att tta gaa gac aac aac gaa gtg gaa    6354
Asp Gly Pro Arg Thr Asn Thr Ile Leu Glu Asp Asn Asn Glu Val Glu
            2075                2080                2085 gtc atc acg aag ctt ggt gaa agg aag att ctg agg ccg cgc tgg att    6402
Val Ile Thr Lys Leu Gly Glu Arg Lys Ile Leu Arg Pro Arg Trp Ile
        2090                2095                2100 gac gcc agg gtg tac tcg gat cac cag gca cta aag gcg ttc aag gac    6450
Asp Ala Arg Val Tyr Ser Asp His Gln Ala Leu Lys Ala Phe Lys Asp
    2105                2110                2115 ttc gcc tcg gga aaa cgt tct cag ata ggg ctc att gag gtt ctg gga    6498
Phe Ala Ser Gly Lys Arg Ser Gln Ile Gly Leu Ile Glu Val Leu Gly
        2120                2125                2130 aag atg cct gag cac ttc atg ggg aag aca tgg gaa gca ctt gac acc    6546
Lys Met Pro Glu His Phe Met Gly Lys Thr Trp Glu Ala Leu Asp Thr
2135                2140                2145                2150 atg tac gtt gtg gcc act gca gag aaa gga gga aga gct cac aga atg    6594
Met Tyr Val Val Ala Thr Ala Glu Lys Gly Gly Arg Ala His Arg Met
            2155                2160                2165 gcc ctg gag gaa ctg cca gat gct ctt cag aca att gcc ttg att gcc    6642
Ala Leu Glu Glu Leu Pro Asp Ala Leu Gln Thr Ile Ala Leu Ile Ala
        2170                2175                2180 tta ttg agt gtg atg acc atg gga gta ttc ttc ctc ctc atg cag cgg    6690
Leu Leu Ser Val Met Thr Met Gly Val Phe Phe Leu Leu Met Gln Arg
    2185                2190                2195 aag ggc att gga aag ata ggt ttg gga ggc gct gtc ttg gga gtc gcg    6738
Lys Gly Ile Gly Lys Ile Gly Leu Gly Gly Ala Val Leu Gly Val Ala
        2200                2205                2210 acc ttt ttc tgt tgg atg gct gaa gtt cca gga acg aag atc gcc gga    6786
Thr Phe Phe Cys Trp Met Ala Glu Val Pro Gly Thr Lys Ile Ala Gly
2215                2220                2225                2230 atg ttg ctg ctc tcc ctt ctc ttg atg att gtg cta att cct gag cca    6834
Met Leu Leu Leu Ser Leu Leu Leu Met Ile Val Leu Ile Pro Glu Pro
            2235                2240                2245 gag aag caa cgt tcg cag aca gac aac cag cta gcc gtg ttc ctg att    6882
Glu Lys Gln Arg Ser Gln Thr Asp Asn Gln Leu Ala Val Phe Leu Ile
        2250                2255                2260 tgt gtc atg acc ctt gtg agc gca gtg gca gcc aac gag atg ggt tgg    6930
Cys Val Met Thr Leu Val Ser Ala Val Ala Ala Asn Glu Met Gly Trp
2265                2270                2275 cta gat aag acc aag agt gac ata agc agt ttg ttt ggg caa aga att    6978
Leu Asp Lys Thr Lys Ser Asp Ile Ser Ser Leu Phe Gly Gln Arg Ile
            2280                2285                2290 gag gtc aag gag aat ttc agc atg gga gag ttt ctt ttg gac ttg agg    7026
Glu Val Lys Glu Asn Phe Ser Met Gly Glu Phe Leu Leu Asp Leu Arg
2295                2300                2305                2310 ccg gca aca gcc tgg tca ctg tac gct gtg aca aca gcg gtc ctc act    7074
Pro Ala Thr Ala Trp Ser Leu Tyr Ala Val Thr Thr Ala Val Leu Thr
            2315                2320                2325 cca ctg cta aag cat ttg atc acg tca gat tac atc aac acc tca ttg    7122
Pro Leu Leu Lys His Leu Ile Thr Ser Asp Tyr Ile Asn Thr Ser Leu
        2330                2335                2340
```

```
                                              -continued acc tca ata aac gtt cag gca agt gca cta ttc aca ctc gcg cga ggc      7170
Thr Ser Ile Asn Val Gln Ala Ser Ala Leu Phe Thr Leu Ala Arg Gly
    2345                2350                2355 ttc ccc ttc gtc gat gtt gga gtg tcg gct ctc ctg cta gca gcc gga      7218
Phe Pro Phe Val Asp Val Gly Val Ser Ala Leu Leu Leu Ala Ala Gly
    2360                2365                2370 tgc tgg gga caa gtc acc ctc acc gtt acg gta aca gcg gca aca ctc      7266
Cys Trp Gly Gln Val Thr Leu Thr Val Thr Val Thr Ala Ala Thr Leu
2375                2380                2385                2390 ctt ttt tgc cac tat gcc tac atg gtt ccc ggt tgg caa gct gag gca      7314
Leu Phe Cys His Tyr Ala Tyr Met Val Pro Gly Trp Gln Ala Glu Ala
            2395                2400                2405 atg cgc tca gcc cag cgg cgg aca gcg gcc gga atc atg aag aac gct      7362
Met Arg Ser Ala Gln Arg Arg Thr Ala Ala Gly Ile Met Lys Asn Ala
    2410                2415                2420 gta gtg gat ggc atc gtg gcc acg gac gtc cca gaa tta gag cgc acc      7410
Val Val Asp Gly Ile Val Ala Thr Asp Val Pro Glu Leu Glu Arg Thr
    2425                2430                2435 aca ccc atc atg cag aag aaa gtt gga cag atc atg ctg atc ttg gtg      7458
Thr Pro Ile Met Gln Lys Lys Val Gly Gln Ile Met Leu Ile Leu Val
    2440                2445                2450 tct cta gct gca gta gta gtg aac ccg tct gtg aag aca gta cga gaa      7506
Ser Leu Ala Ala Val Val Val Asn Pro Ser Val Lys Thr Val Arg Glu
2455                2460                2465                2470 gcc gga att ttg atc acg gcc gcg gtg acg ctt tgg gag aat gga      7554
Ala Gly Ile Leu Ile Thr Ala Ala Val Thr Leu Trp Glu Asn Gly
            2475                2480                2485 gca agc tct gtt tgg aac gca aca act gcc atc gga ctc tgc cac atc      7602
Ala Ser Ser Val Trp Asn Ala Thr Thr Ala Ile Gly Leu Cys His Ile
    2490                2495                2500 atg cgt ggg ggt tgg ttg tca tgt cta tcc ata aca tgg aca ctc ata      7650
Met Arg Gly Gly Trp Leu Ser Cys Leu Ser Ile Thr Trp Thr Leu Ile
    2505                2510                2515 aag aac atg gaa aaa cca gga cta aaa aga ggt ggg gca aaa gga cgc      7698
Lys Asn Met Glu Lys Pro Gly Leu Lys Arg Gly Gly Ala Lys Gly Arg
    2520                2525                2530 acc ttg gga gag gtt tgg aaa gaa aga ctc aac cag atg aca aaa gaa      7746
Thr Leu Gly Glu Val Trp Lys Glu Arg Leu Asn Gln Met Thr Lys Glu
2535                2540                2545                2550 gag ttc act agg tac cgc aaa gag gcc atc atc gaa gtc gat cgc tca      7794
Glu Phe Thr Arg Tyr Arg Lys Glu Ala Ile Ile Glu Val Asp Arg Ser
            2555                2560                2565 gcg gca aaa cac gcc agg aaa gaa ggc aat gtc act gga ggg cat cca      7842
Ala Ala Lys His Ala Arg Lys Glu Gly Asn Val Thr Gly Gly His Pro
    2570                2575                2580 gtc tct agg ggc aca gca aaa ctg aga tgg ctg gtc gaa cgg agg ttt      7890
Val Ser Arg Gly Thr Ala Lys Leu Arg Trp Leu Val Glu Arg Arg Phe
    2585                2590                2595 ctc gaa ccg gtc gga aaa gtg att gac ctt gga tgt gga aga ggc ggt      7938
Leu Glu Pro Val Gly Lys Val Ile Asp Leu Gly Cys Gly Arg Gly Gly
    2600                2605                2610 tgg tgt tac tat atg gca acc caa aaa aga gtc caa gaa gtc aga ggg      7986
Trp Cys Tyr Tyr Met Ala Thr Gln Lys Arg Val Gln Glu Val Arg Gly
2615                2620                2625                2630 tac aca aag ggc ggt ccc gga cat gaa gag ccc caa cta gtg caa agt      8034
Tyr Thr Lys Gly Gly Pro Gly His Glu Glu Pro Gln Leu Val Gln Ser
            2635                2640                2645 tat gga tgg aac att gtc acc atg aag agt gga gtg gat gtg ttc tac      8082
Tyr Gly Trp Asn Ile Val Thr Met Lys Ser Gly Val Asp Val Phe Tyr
```

```
                2650            2655            2660 aga cct tct gag tgt tgt gac acc ctc ctt tgt gac atc gga gag tcc       8130
Arg Pro Ser Glu Cys Cys Asp Thr Leu Leu Cys Asp Ile Gly Glu Ser
        2665            2670            2675 tcg tca agt gct gag gtt gaa gag cat agg acg att cgg gtc ctt gaa       8178
Ser Ser Ser Ala Glu Val Glu Glu His Arg Thr Ile Arg Val Leu Glu
    2680            2685            2690 atg gtt gag gac tgg ctg cac cga ggg cca agg gaa ttt tgc gtg aag       8226
Met Val Glu Asp Trp Leu His Arg Gly Pro Arg Glu Phe Cys Val Lys
2695            2700            2705            2710 gtg ctc tgc ccc tac atg ccg aaa gtc ata gag aag atg gag ctg ctc       8274
Val Leu Cys Pro Tyr Met Pro Lys Val Ile Glu Lys Met Glu Leu Leu
            2715            2720            2725 caa cgc cgg tat ggg ggg gga ctg gtc aga aac cca ctc tca cgg aat       8322
Gln Arg Arg Tyr Gly Gly Gly Leu Val Arg Asn Pro Leu Ser Arg Asn
        2730            2735            2740 tcc acg cac gag atg tat tgg gtg agt cga gct tca ggc aat gtg gta       8370
Ser Thr His Glu Met Tyr Trp Val Ser Arg Ala Ser Gly Asn Val Val
    2745            2750            2755 cat tca gtg aat atg acc agc cag gtg ctc cta gga aga atg gaa aaa       8418
His Ser Val Asn Met Thr Ser Gln Val Leu Leu Gly Arg Met Glu Lys
2760            2765            2770 agg acc tgg aag gga ccc caa tac gag gaa gat gta aac ttg gga agt       8466
Arg Thr Trp Lys Gly Pro Gln Tyr Glu Glu Asp Val Asn Leu Gly Ser
            2775            2780            2785            2790 gga acc agg gcg gtg gga aaa ccc ctc ctc aac tca gac acc agt aaa       8514
Gly Thr Arg Ala Val Gly Lys Pro Leu Leu Asn Ser Asp Thr Ser Lys
        2795            2800            2805 atc aag aac agg att gaa cga ctc agg cgt gag tac agt tcg acg tgg       8562
Ile Lys Asn Arg Ile Glu Arg Leu Arg Arg Glu Tyr Ser Ser Thr Trp
    2810            2815            2820 cac cac gat gag aac cac cca tat aga acc tgg aac tat cac ggc agt       8610
His His Asp Glu Asn His Pro Tyr Arg Thr Trp Asn Tyr His Gly Ser
2825            2830            2835 tat gat gtg aag ccc aca ggc tcc gcc agt tcg ctg gtc aat gga gtg       8658
Tyr Asp Val Lys Pro Thr Gly Ser Ala Ser Ser Leu Val Asn Gly Val
            2840            2845            2850 gtc agg ctc ctc tca aaa cca tgg gac acc atc acg aat gtt acc acc       8706
Val Arg Leu Leu Ser Lys Pro Trp Asp Thr Ile Thr Asn Val Thr Thr
2855            2860            2865            2870 atg gcc atg act gac act act ccc ttc ggg cag cag cga gtg ttc aaa       8754
Met Ala Met Thr Asp Thr Thr Pro Phe Gly Gln Gln Arg Val Phe Lys
        2875            2880            2885 gag aag gtg gac acg aaa gct cct gaa ccg cca gaa gga gtg aag tac       8802
Glu Lys Val Asp Thr Lys Ala Pro Glu Pro Pro Glu Gly Val Lys Tyr
    2890            2895            2900 gtg ctc aat gag acc acc aac tgg ttg tgg gcg ttt ttg gcc aga gaa       8850
Val Leu Asn Glu Thr Thr Asn Trp Leu Trp Ala Phe Leu Ala Arg Glu
2905            2910            2915 aaa cgt ccc aga atg tgc tct cga gag gaa ttc ata aga aag gtc aac       8898
Lys Arg Pro Arg Met Cys Ser Arg Glu Glu Phe Ile Arg Lys Val Asn
        2920            2925            2930 agc aat gca gct ttg ggt gcc atg ttt gaa gag cag aat caa tgg agg       8946
Ser Asn Ala Ala Leu Gly Ala Met Phe Glu Glu Gln Asn Gln Trp Arg
    2935            2940            2945            2950 agc gcc aga gaa gca gtt gaa gat cca aaa ttt tgg gag atg gtg gat       8994
Ser Ala Arg Glu Ala Val Glu Asp Pro Lys Phe Trp Glu Met Val Asp
2955            2960            2965 gag gag cgc gag gca cat ctg cgg ggg gaa tgt cac act tgc att tac       9042
```

```
Glu Glu Arg Glu Ala His Leu Arg Gly Glu Cys His Thr Cys Ile Tyr
        2970                2975                2980 aac atg atg gga aag aga gag aaa aaa ccc gga gag ttc gga aag gcc      9090
Asn Met Met Gly Lys Arg Glu Lys Lys Pro Gly Glu Phe Gly Lys Ala
        2985                2990                2995 aag gga agc aga gcc att tgg ttc atg tgg ctc gga gct cgc ttt ctg      9138
Lys Gly Ser Arg Ala Ile Trp Phe Met Trp Leu Gly Ala Arg Phe Leu
        3000                3005                3010 gag ttc gag gct ctg ggt ttt ctc aat gaa gac cac tgg ctt gga aga      9186
Glu Phe Glu Ala Leu Gly Phe Leu Asn Glu Asp His Trp Leu Gly Arg
3015                3020                3025                3030 aag aac tca gga gga ggt gtc gag ggc ttg ggc ctc caa aaa ctg ggt      9234
Lys Asn Ser Gly Gly Gly Val Glu Gly Leu Gly Leu Gln Lys Leu Gly
        3035                3040                3045 tac atc ctg cgt gaa gtt ggc acc cgg cct ggg ggc aag atc tat gct      9282
Tyr Ile Leu Arg Glu Val Gly Thr Arg Pro Gly Gly Lys Ile Tyr Ala
        3050                3055                3060 gat gac aca gct ggc tgg gac acc cgc atc acg aga gct gac ttg gaa      9330
Asp Asp Thr Ala Gly Trp Asp Thr Arg Ile Thr Arg Ala Asp Leu Glu
        3065                3070                3075 aat gaa gct aag gtg ctt gag ctg ctt gat ggg gaa cat cgg cgt ctt      9378
Asn Glu Ala Lys Val Leu Glu Leu Leu Asp Gly Glu His Arg Arg Leu
        3080                3085                3090 gcc agg gcc atc att gag ctc acc tat cgt cac aaa gtt gtg aaa gtg      9426
Ala Arg Ala Ile Ile Glu Leu Thr Tyr Arg His Lys Val Val Lys Val
        3095                3100                3105                3110 atg cgc ccg gct gct gat gga aga acc gtc atg gat gtt atc tcc aga      9474
Met Arg Pro Ala Ala Asp Gly Arg Thr Val Met Asp Val Ile Ser Arg
        3115                3120                3125 gaa gat cag agg ggg agt gga caa gtt gtc acc tac gcc cta aac act      9522
Glu Asp Gln Arg Gly Ser Gly Gln Val Val Thr Tyr Ala Leu Asn Thr
        3130                3135                3140 ttc acc aac ctg gcc gtc cag ctg gtg agg atg atg gaa ggg gaa gga      9570
Phe Thr Asn Leu Ala Val Gln Leu Val Arg Met Met Glu Gly Glu Gly
        3145                3150                3155 gtg att ggc cca gat gat gtg gag aaa ctc aca aaa ggg aaa gga ccc      9618
Val Ile Gly Pro Asp Asp Val Glu Lys Leu Thr Lys Gly Lys Gly Pro
        3160                3165                3170 aaa gtc agg acc tgg ctg ttt gag aat ggg gaa gaa aga ctc agc cgc      9666
Lys Val Arg Thr Trp Leu Phe Glu Asn Gly Glu Glu Arg Leu Ser Arg
3175                3180                3185                3190 atg gct gtc agt gga gat gac tgt gtg gta aag ccc ctg gac gat cgc      9714
Met Ala Val Ser Gly Asp Asp Cys Val Val Lys Pro Leu Asp Asp Arg
        3195                3200                3205 ttt gcc acc tcg ctc cac ttc ctc aat gct atg tca aag gtt cgc aaa      9762
Phe Ala Thr Ser Leu His Phe Leu Asn Ala Met Ser Lys Val Arg Lys
        3210                3215                3220 gac atc caa gag tgg aaa ccg tca act gga tgg tat gat tgg cag cag      9810
Asp Ile Gln Glu Trp Lys Pro Ser Thr Gly Trp Tyr Asp Trp Gln Gln
        3225                3230                3235 gtt cca ttt tgc tca aac cat ttc act gaa ttg atc atg aaa gat gga      9858
Val Pro Phe Cys Ser Asn His Phe Thr Glu Leu Ile Met Lys Asp Gly
        3240                3245                3250 aga aca ctg gtg gtt cca tgc cga gga cag gat gaa ttg gta ggc aga      9906
Arg Thr Leu Val Val Pro Cys Arg Gly Gln Asp Glu Leu Val Gly Arg
3255                3260                3265                3270 gct cgc ata tct cca ggg gcc gga tgg aac gtc cgc gac act gct tgt      9954
Ala Arg Ile Ser Pro Gly Ala Gly Trp Asn Val Arg Asp Thr Ala Cys
        3275                3280                3285
```

```
ctg gct aag tct tat gcc cag atg tgg ctg ctt ctg tac ttc cac aga    10002
Leu Ala Lys Ser Tyr Ala Gln Met Trp Leu Leu Leu Tyr Phe His Arg
        3290                3295                3300 aga gac ctg cgg ctc atg gcc aac gcc att tgc tcc gct gtc cct gtg    10050
Arg Asp Leu Arg Leu Met Ala Asn Ala Ile Cys Ser Ala Val Pro Val
    3305                3310                3315 aat tgg gtc cct acc gga aga acc acg tgg tcc atc cat gca gga gga    10098
Asn Trp Val Pro Thr Gly Arg Thr Thr Trp Ser Ile His Ala Gly Gly
  3320                3325                3330 gag tgg atg aca aca gag gac atg ttg gag gtc tgg aac cgt gtt tgg    10146
Glu Trp Met Thr Thr Glu Asp Met Leu Glu Val Trp Asn Arg Val Trp
3335                3340                3345                3350 ata gag gag aat gaa tgg atg gaa gac aaa acc cca gtg gag aaa tgg    10194
Ile Glu Glu Asn Glu Trp Met Glu Asp Lys Thr Pro Val Glu Lys Trp
            3355                3360                3365 agt gac gtc cca tat tca gga aaa cga gag gac atc tgg tgt ggc agc    10242
Ser Asp Val Pro Tyr Ser Gly Lys Arg Glu Asp Ile Trp Cys Gly Ser
        3370                3375                3380 ctg att ggc aca aga gcc cga gcc acg tgg gca gaa aac atc cag gtg    10290
Leu Ile Gly Thr Arg Ala Arg Ala Thr Trp Ala Glu Asn Ile Gln Val
    3385                3390                3395 gct atc aac caa gtc aga gca atc atc gga gat gag aag tat gtg gat    10338
Ala Ile Asn Gln Val Arg Ala Ile Ile Gly Asp Glu Lys Tyr Val Asp
  3400                3405                3410 tac atg agt tca cta aag aga tat gaa gac aca act ttg gtt gag gac    10386
Tyr Met Ser Ser Leu Lys Arg Tyr Glu Asp Thr Thr Leu Val Glu Asp
3415                3420                3425                3430 aca gta ctg tagatattta atcaattgta aatagacaat ataagtatgc            10435
Thr Val Leu ataaaagtgt agtttatag tagtatttag tggtgttagt gtaaatagtt aagaaaattt   10495
tgaggagaaa gtcaggccgg gaagttcccg ccaccggaag ttgagtagac ggtgctgcct   10555
gcgactcaac cccaggagga ctgggtgaac aaagccgcga gtgatccat gtaagccctc    10615
agaaccgtct cggaaggagg accccacatg ttgtaacttc aaagcccaat gtcagaccac   10675
gctacggcgt gctactctgc ggagagtgca gtctgcgata gtgccccagg aggactgggt   10735
taacaaaggc aaaccaacgc cccacgcggc cctagccccg gtaatggtgt taaccagggc   10795
gaaaggacta gaggttagag gagaccccgc ggtttaaagt gcacggccca gcctgactga   10855
agctgtaggt caggggaagg actagaggtt agtggagacc ccgtgccaca aaacaccaca   10915
acaaaacagc atattgacac ctgggataga ctaggagatc ttctgctctg cacaaccagc   10975
cacacggcac agtgcgccga caatggtggc tggtggtgcg agaacacagg atct         11029
```

<210> SEQ ID NO 67
<211> LENGTH: 3433
<212> TYPE: PRT
<213> ORGANISM: West Nile virus

<400> SEQUENCE: 67

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60
```

```
Val Leu Asp Arg Trp Arg Gly Val Asn Lys Gln Thr Ala Met Lys His
 65                  70                  75                  80

Leu Leu Ser Phe Lys Lys Glu Leu Gly Thr Leu Thr Ser Ala Ile Asn
                 85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220

Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
                245                 250                 255

Tyr Ala Leu Val Ala Ala Val Ile Gly Trp Met Leu Gly Ser Asn Thr
            260                 265                 270

Met Gln Arg Val Val Phe Val Val Leu Leu Leu Leu Val Ala Pro Ala
        275                 280                 285

Tyr Ser Phe Asn Cys Leu Gly Met Ser Asn Arg Asp Phe Leu Glu Gly
290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
            340                 345                 350

Ala Thr Val Ser Asp Leu Ser Thr Lys Ala Ala Cys Pro Thr Met Gly
        355                 360                 365

Glu Ala His Asn Asp Lys Arg Ala Asp Pro Ala Phe Val Cys Arg Gln
370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                405                 410                 415

Gly Arg Thr Ile Leu Lys Glu Asn Ile Lys Tyr Glu Val Ala Ile Phe
            420                 425                 430

Val His Gly Pro Thr Thr Val Glu Ser His Gly Asn Tyr Ser Thr Gln
        435                 440                 445

Val Gly Ala Thr Gln Ala Gly Arg Phe Ser Ile Thr Pro Ala Ala Pro
450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
```

-continued

```
                485                 490                 495
Gly Thr Lys Thr Phe Leu Val His Arg Glu Trp Phe Met Asp Leu Asn
            500                 505                 510
Leu Pro Trp Ser Ser Ala Gly Ser Thr Val Trp Arg Asn Arg Glu Thr
            515                 520                 525
Leu Met Glu Phe Glu Glu Pro His Ala Thr Lys Gln Ser Val Ile Ala
            530                 535                 540
Leu Gly Ser Gln Glu Gly Ala Leu His Gln Ala Leu Ala Gly Ala Ile
545                 550                 555                 560
Pro Val Glu Phe Ser Ser Asn Thr Val Lys Leu Thr Ser Gly His Leu
                565                 570                 575
Lys Cys Arg Val Lys Met Glu Lys Leu Gln Leu Lys Gly Thr Thr Tyr
            580                 585                 590
Gly Val Cys Ser Lys Ala Phe Lys Phe Leu Gly Thr Pro Ala Asp Thr
            595                 600                 605
Gly His Gly Thr Val Val Leu Glu Leu Gln Tyr Thr Gly Thr Asp Gly
            610                 615                 620
Pro Cys Lys Val Pro Ile Ser Ser Val Ala Ser Leu Asn Asp Leu Thr
625                 630                 635                 640
Pro Val Gly Arg Leu Val Thr Val Asn Pro Phe Val Ser Val Ala Thr
                645                 650                 655
Ala Asn Ala Lys Val Leu Ile Glu Leu Glu Pro Pro Phe Gly Asp Ser
                660                 665                 670
Tyr Ile Val Val Gly Arg Gly Glu Gln Gln Ile Asn His His Trp His
            675                 680                 685
Lys Ser Gly Ser Ser Ile Gly Lys Ala Phe Thr Thr Thr Leu Lys Gly
            690                 695                 700
Ala Gln Arg Leu Ala Ala Leu Gly Asp Thr Ala Trp Asp Phe Gly Ser
705                 710                 715                 720
Val Gly Gly Val Phe Thr Ser Val Gly Lys Ala Val His Gln Val Phe
                725                 730                 735
Gly Gly Ala Phe Arg Ser Leu Phe Gly Gly Met Ser Trp Ile Thr Gln
            740                 745                 750
Gly Leu Leu Gly Ala Leu Leu Leu Trp Met Gly Ile Asn Ala Arg Asp
            755                 760                 765
Arg Ser Ile Ala Leu Thr Phe Leu Ala Val Gly Gly Val Leu Leu Phe
            770                 775                 780
Leu Ser Val Asn Val His Ala Asp Thr Gly Cys Ala Ile Asp Ile Ser
785                 790                 795                 800
Arg Gln Glu Leu Arg Cys Gly Ser Gly Val Phe Ile His Asn Asp Val
                805                 810                 815
Glu Ala Trp Met Asp Arg Tyr Lys Tyr Tyr Pro Glu Thr Pro Gln Gly
            820                 825                 830
Leu Ala Lys Ile Ile Gln Lys Ala His Lys Glu Gly Val Cys Gly Leu
            835                 840                 845
Arg Ser Val Ser Arg Leu Glu His Gln Met Trp Glu Ala Val Lys Asp
            850                 855                 860
Glu Leu Asn Thr Leu Leu Lys Glu Asn Gly Val Asp Leu Ser Val Val
865                 870                 875                 880
Val Glu Lys Gln Glu Gly Met Tyr Lys Ser Ala Pro Lys Arg Leu Thr
                885                 890                 895
Ala Thr Thr Glu Lys Leu Glu Ile Gly Trp Lys Ala Trp Gly Lys Ser
            900                 905                 910
```

```
Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
        930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
            965                 970                 975

Thr Ala Val Lys Asn Asn Leu Ala Ile His Ser Asp Leu Ser Tyr Trp
                980                 985                 990

Ile Glu Ser Arg Leu Asn Asp Thr Trp Lys Leu Glu Arg Ala Val Leu
            995                 1000                1005

Gly Glu Val Lys Ser Cys Thr Trp Pro Glu Thr His Thr Leu Trp Gly
        1010                1015                1020

Asp Gly Ile Leu Glu Ser Asp Leu Ile Ile Pro Val Thr Leu Ala Gly
1025                1030                1035                1040

Pro Arg Ser Asn His Asn Arg Arg Pro Gly Tyr Lys Thr Gln Asn Gln
            1045                1050                1055

Gly Pro Trp Asp Glu Gly Arg Val Glu Ile Asp Phe Asp Tyr Cys Pro
        1060                1065                1070

Gly Thr Thr Val Thr Leu Ser Glu Ser Cys Gly His Arg Gly Pro Ala
        1075                1080                1085

Thr Arg Thr Thr Thr Glu Ser Gly Lys Leu Ile Thr Asp Trp Cys Cys
        1090                1095                1100

Arg Ser Cys Thr Leu Pro Pro Leu Arg Tyr Gln Thr Asp Ser Gly Cys
1105                1110                1115                1120

Trp Tyr Gly Met Glu Ile Arg Pro Gln Arg His Asp Glu Lys Thr Leu
            1125                1130                1135

Val Gln Ser Gln Val Asn Ala Tyr Asn Ala Asp Met Ile Asp Pro Phe
            1140                1145                1150

Gln Leu Gly Leu Leu Val Val Phe Leu Ala Thr Gln Glu Val Leu Arg
        1155                1160                1165

Lys Arg Trp Thr Ala Lys Ile Ser Met Pro Ala Ile Leu Ile Ala Leu
        1170                1175                1180

Leu Val Leu Val Phe Gly Gly Ile Thr Tyr Thr Asp Val Leu Arg Tyr
1185                1190                1195                1200

Val Ile Leu Val Gly Ala Ala Phe Ala Glu Ser Asn Ser Gly Gly Asp
            1205                1210                1215

Val Val His Leu Ala Leu Met Ala Thr Phe Lys Ile Gln Pro Val Phe
            1220                1225                1230

Met Val Ala Ser Phe Leu Lys Ala Arg Trp Thr Asn Gln Glu Asn Ile
        1235                1240                1245

Leu Leu Met Leu Ala Ala Val Phe Phe Gln Met Ala Tyr His Asp Ala
        1250                1255                1260

Arg Gln Ile Leu Leu Trp Glu Ile Pro Asp Val Leu Asn Ser Leu Ala
1265                1270                1275                1280

Val Ala Trp Met Ile Leu Arg Ala Ile Thr Phe Thr Thr Thr Ser Asn
            1285                1290                1295

Val Val Val Pro Leu Leu Ala Leu Leu Thr Pro Gly Leu Arg Cys Leu
        1300                1305                1310

Asn Leu Asp Val Tyr Arg Ile Leu Leu Leu Met Val Gly Ile Gly Ser
        1315                1320                1325
```

-continued

```
Leu Ile Arg Glu Lys Arg Ser Ala Ala Ala Lys Lys Lys Gly Ala Ser
    1330                1335                1340

Leu Leu Cys Leu Ala Leu Ala Ser Thr Gly Leu Phe Asn Pro Met Ile
1345                1350                1355                1360

Leu Ala Ala Gly Leu Ile Ala Cys Asp Pro Asn Arg Lys Arg Gly Trp
                1365                1370                1375

Pro Ala Thr Glu Val Met Thr Ala Val Gly Leu Met Phe Ala Ile Val
            1380                1385                1390

Gly Gly Leu Ala Glu Leu Asp Ile Asp Ser Met Ala Ile Pro Met Thr
        1395                1400                1405

Ile Ala Gly Leu Met Phe Ala Ala Phe Val Ile Ser Gly Lys Ser Thr
    1410                1415                1420

Asp Met Trp Ile Glu Arg Thr Ala Asp Ile Ser Trp Glu Ser Asp Ala
1425                1430                1435                1440

Glu Ile Thr Gly Ser Ser Glu Arg Val Asp Val Arg Leu Asp Asp Asp
                1445                1450                1455

Gly Asn Phe Gln Leu Met Asn Asp Pro Gly Ala Pro Trp Lys Ile Trp
            1460                1465                1470

Met Leu Arg Met Val Cys Leu Ala Ile Ser Ala Tyr Thr Pro Trp Ala
        1475                1480                1485

Ile Leu Pro Ser Val Val Gly Phe Trp Ile Thr Leu Gln Tyr Thr Lys
    1490                1495                1500

Arg Gly Gly Val Leu Trp Asp Thr Pro Ser Pro Lys Glu Tyr Lys Lys
1505                1510                1515                1520

Gly Asp Thr Thr Thr Gly Val Tyr Arg Ile Met Thr Arg Gly Leu Leu
                1525                1530                1535

Gly Ser Tyr Gln Ala Gly Ala Gly Val Met Val Glu Gly Val Phe His
            1540                1545                1550

Thr Leu Trp His Thr Thr Lys Gly Ala Ala Leu Met Ser Gly Glu Gly
        1555                1560                1565

Arg Leu Asp Pro Tyr Trp Gly Ser Val Lys Glu Asp Arg Leu Cys Tyr
    1570                1575                1580

Gly Gly Pro Trp Lys Leu Gln His Lys Trp Asn Gly Gln Asp Glu Val
1585                1590                1595                1600

Gln Met Ile Val Val Glu Pro Gly Lys Asn Val Lys Asn Val Gln Thr
                1605                1610                1615

Lys Pro Gly Val Phe Lys Thr Pro Glu Gly Glu Ile Gly Ala Val Thr
            1620                1625                1630

Leu Asp Phe Pro Thr Gly Thr Ser Gly Ser Pro Ile Val Asp Lys Asn
        1635                1640                1645

Gly Asp Val Ile Gly Leu Tyr Gly Asn Gly Val Ile Met Pro Asn Gly
    1650                1655                1660

Ser Tyr Ile Ser Ala Ile Val Gln Gly Glu Arg Met Asp Glu Pro Ile
1665                1670                1675                1680

Pro Ala Gly Phe Glu Pro Glu Met Leu Arg Lys Lys Gln Ile Thr Val
                1685                1690                1695

Leu Asp Leu His Pro Gly Ala Gly Lys Thr Arg Arg Ile Leu Pro Gln
            1700                1705                1710

Ile Ile Lys Glu Ala Ile Asn Arg Arg Leu Arg Thr Ala Val Leu Ala
        1715                1720                1725

Pro Thr Arg Val Val Ala Ala Glu Met Ala Glu Ala Leu Arg Gly Leu
    1730                1735                1740

Pro Ile Arg Tyr Gln Thr Ser Ala Val Pro Arg Glu His Asn Gly Asn
```

-continued

```
         1745                1750                1755                1760
Glu Ile Val Asp Val Met Cys His Ala Thr Leu Thr His Arg Leu Met
             1765                1770                1775
Ser Pro His Arg Val Pro Asn Tyr Asn Leu Phe Val Met Asp Glu Ala
         1780                1785                1790
His Phe Thr Asp Pro Ala Ser Ile Ala Ala Arg Gly Tyr Ile Ser Thr
         1795                1800                1805
Lys Val Glu Leu Gly Glu Ala Ala Ile Phe Met Thr Ala Thr Pro
     1810                1815                1820
Pro Gly Thr Ser Asp Pro Phe Pro Glu Ser Asn Ser Pro Ile Ser Asp
1825                1830                1835                1840
Leu Gln Thr Glu Ile Pro Asp Arg Ala Trp Asn Ser Gly Tyr Glu Trp
             1845                1850                1855
Ile Thr Glu Tyr Thr Gly Lys Thr Val Trp Phe Val Pro Ser Val Lys
         1860                1865                1870
Met Gly Asn Glu Ile Ala Leu Cys Leu Gln Arg Ala Gly Lys Lys Val
     1875                1880                1885
Val Gln Leu Asn Arg Lys Ser Tyr Glu Thr Glu Tyr Pro Lys Cys Lys
     1890                1895                1900
Asn Asp Asp Trp Asp Phe Val Ile Thr Thr Asp Ile Ser Glu Met Gly
1905                1910                1915                1920
Ala Asn Phe Lys Ala Ser Arg Val Ile Asp Ser Arg Lys Ser Val Lys
         1925                1930                1935
Pro Thr Ile Ile Thr Glu Gly Glu Gly Arg Val Ile Leu Gly Glu Pro
             1940                1945                1950
Ser Ala Val Thr Ala Ala Ser Ala Ala Gln Arg Arg Gly Arg Ile Gly
         1955                1960                1965
Arg Asn Pro Ser Gln Val Gly Asp Glu Tyr Cys Tyr Gly Gly His Thr
     1970                1975                1980
Asn Glu Asp Asp Ser Asn Phe Ala His Trp Thr Glu Ala Arg Ile Met
1985                1990                1995                2000
Leu Asp Asn Ile Asn Met Pro Asn Gly Leu Ile Ala Gln Phe Tyr Gln
             2005                2010                2015
Pro Glu Arg Glu Lys Val Tyr Thr Met Asp Gly Glu Tyr Arg Leu Arg
         2020                2025                2030
Gly Glu Glu Arg Lys Asn Phe Leu Glu Leu Leu Arg Thr Ala Asp Leu
             2035                2040                2045
Pro Val Trp Leu Ala Tyr Lys Val Ala Ala Ala Gly Val Ser Tyr His
     2050                2055                2060
Asp Arg Arg Trp Cys Phe Asp Gly Pro Arg Thr Asn Thr Ile Leu Glu
2065                2070                2075                2080
Asp Asn Asn Glu Val Glu Val Ile Thr Lys Leu Gly Glu Arg Lys Ile
             2085                2090                2095
Leu Arg Pro Arg Trp Ile Asp Ala Arg Val Tyr Ser Asp His Gln Ala
         2100                2105                2110
Leu Lys Ala Phe Lys Asp Phe Ala Ser Gly Lys Arg Ser Gln Ile Gly
     2115                2120                2125
Leu Ile Glu Val Leu Gly Lys Met Pro Glu His Phe Met Gly Lys Thr
     2130                2135                2140
Trp Glu Ala Leu Asp Thr Met Tyr Val Val Ala Thr Ala Glu Lys Gly
2145                2150                2155                2160
Gly Arg Ala His Arg Met Ala Leu Glu Glu Leu Pro Asp Ala Leu Gln
             2165                2170                2175
```

```
Thr Ile Ala Leu Ile Ala Leu Leu Ser Val Met Thr Met Gly Val Phe
        2180                2185                2190

Phe Leu Leu Met Gln Arg Lys Gly Ile Gly Lys Ile Gly Leu Gly Gly
    2195                2200                2205

Ala Val Leu Gly Val Ala Thr Phe Phe Cys Trp Met Ala Glu Val Pro
2210                2215                2220

Gly Thr Lys Ile Ala Gly Met Leu Leu Leu Ser Leu Leu Leu Met Ile
2225                2230                2235                2240

Val Leu Ile Pro Glu Pro Glu Lys Gln Arg Ser Gln Thr Asp Asn Gln
            2245                2250                2255

Leu Ala Val Phe Leu Ile Cys Val Met Thr Leu Val Ser Ala Val Ala
        2260                2265                2270

Ala Asn Glu Met Gly Trp Leu Asp Lys Thr Lys Ser Asp Ile Ser Ser
    2275                2280                2285

Leu Phe Gly Gln Arg Ile Glu Val Lys Glu Asn Phe Ser Met Gly Glu
2290                2295                2300

Phe Leu Leu Asp Leu Arg Pro Ala Thr Ala Trp Ser Leu Tyr Ala Val
2305                2310                2315                2320

Thr Thr Ala Val Leu Thr Pro Leu Leu Lys His Leu Ile Thr Ser Asp
            2325                2330                2335

Tyr Ile Asn Thr Ser Leu Thr Ser Ile Asn Val Gln Ala Ser Ala Leu
        2340                2345                2350

Phe Thr Leu Ala Arg Gly Phe Pro Phe Val Asp Val Gly Val Ser Ala
    2355                2360                2365

Leu Leu Leu Ala Ala Gly Cys Trp Gly Gln Val Thr Leu Thr Val Thr
2370                2375                2380

Val Thr Ala Ala Thr Leu Leu Phe Cys His Tyr Ala Tyr Met Val Pro
2385                2390                2395                2400

Gly Trp Gln Ala Glu Ala Met Arg Ser Ala Gln Arg Arg Thr Ala Ala
            2405                2410                2415

Gly Ile Met Lys Asn Ala Val Val Asp Gly Ile Val Ala Thr Asp Val
        2420                2425                2430

Pro Glu Leu Glu Arg Thr Thr Pro Ile Met Gln Lys Lys Val Gly Gln
    2435                2440                2445

Ile Met Leu Ile Leu Val Ser Leu Ala Ala Val Val Val Asn Pro Ser
2450                2455                2460

Val Lys Thr Val Arg Glu Ala Gly Ile Leu Ile Thr Ala Ala Ala Val
2465                2470                2475                2480

Thr Leu Trp Glu Asn Gly Ala Ser Ser Val Trp Asn Ala Thr Thr Ala
            2485                2490                2495

Ile Gly Leu Cys His Ile Met Arg Gly Gly Trp Leu Ser Cys Leu Ser
        2500                2505                2510

Ile Thr Trp Thr Leu Ile Lys Asn Met Glu Lys Pro Gly Leu Lys Arg
    2515                2520                2525

Gly Gly Ala Lys Gly Arg Thr Leu Gly Glu Val Trp Lys Glu Arg Leu
2530                2535                2540

Asn Gln Met Thr Lys Glu Glu Phe Thr Arg Tyr Arg Lys Glu Ala Ile
2545                2550                2555                2560

Ile Glu Val Asp Arg Ser Ala Ala Lys His Ala Arg Lys Glu Gly Asn
            2565                2570                2575

Val Thr Gly Gly His Pro Val Ser Arg Gly Thr Ala Lys Leu Arg Trp
        2580                2585                2590
```

-continued

```
Leu Val Glu Arg Arg Phe Leu Glu Pro Val Gly Lys Val Ile Asp Leu
    2595                2600                2605

Gly Cys Gly Arg Gly Gly Trp Cys Tyr Tyr Met Ala Thr Gln Lys Arg
2610                2615                2620

Val Gln Glu Val Arg Gly Tyr Thr Lys Gly Gly Pro Gly His Glu Glu
2625                2630                2635                2640

Pro Gln Leu Val Gln Ser Tyr Gly Trp Asn Ile Val Thr Met Lys Ser
            2645                2650                2655

Gly Val Asp Val Phe Tyr Arg Pro Ser Glu Cys Cys Asp Thr Leu Leu
        2660                2665                2670

Cys Asp Ile Gly Glu Ser Ser Ser Ala Glu Val Glu Glu His Arg
    2675                2680                2685

Thr Ile Arg Val Leu Glu Met Val Glu Asp Trp Leu His Arg Gly Pro
    2690                2695                2700

Arg Glu Phe Cys Val Lys Val Leu Cys Pro Tyr Met Pro Lys Val Ile
2705                2710                2715                2720

Glu Lys Met Glu Leu Leu Gln Arg Arg Tyr Gly Gly Leu Val Arg
            2725                2730                2735

Asn Pro Leu Ser Arg Asn Ser Thr His Glu Met Tyr Trp Val Ser Arg
            2740                2745                2750

Ala Ser Gly Asn Val Val His Ser Val Asn Met Thr Ser Gln Val Leu
        2755                2760                2765

Leu Gly Arg Met Glu Lys Arg Thr Trp Lys Gly Pro Gln Tyr Glu Glu
        2770                2775                2780

Asp Val Asn Leu Gly Ser Gly Thr Arg Ala Val Gly Lys Pro Leu Leu
2785                2790                2795                2800

Asn Ser Asp Thr Ser Lys Ile Lys Asn Arg Ile Glu Arg Leu Arg Arg
            2805                2810                2815

Glu Tyr Ser Ser Thr Trp His His Asp Glu Asn His Pro Tyr Arg Thr
            2820                2825                2830

Trp Asn Tyr His Gly Ser Tyr Asp Val Lys Pro Thr Gly Ser Ala Ser
        2835                2840                2845

Ser Leu Val Asn Gly Val Val Arg Leu Leu Ser Lys Pro Trp Asp Thr
2850                2855                2860

Ile Thr Asn Val Thr Thr Met Ala Met Thr Asp Thr Thr Pro Phe Gly
2865                2870                2875                2880

Gln Gln Arg Val Phe Lys Glu Lys Val Asp Thr Lys Ala Pro Glu Pro
            2885                2890                2895

Pro Glu Gly Val Lys Tyr Val Leu Asn Glu Thr Thr Asn Trp Leu Trp
        2900                2905                2910

Ala Phe Leu Ala Arg Glu Lys Arg Pro Arg Met Cys Ser Arg Glu Glu
        2915                2920                2925

Phe Ile Arg Lys Val Asn Ser Asn Ala Ala Leu Gly Ala Met Phe Glu
    2930                2935                2940

Glu Gln Asn Gln Trp Arg Ser Ala Arg Glu Ala Val Glu Asp Pro Lys
2945                2950                2955                2960

Phe Trp Glu Met Val Asp Glu Glu Arg Glu Ala His Leu Arg Gly Glu
            2965                2970                2975

Cys His Thr Cys Ile Tyr Asn Met Met Gly Lys Arg Glu Lys Lys Pro
            2980                2985                2990

Gly Glu Phe Gly Lys Ala Lys Gly Ser Arg Ala Ile Trp Phe Met Trp
        2995                3000                3005

Leu Gly Ala Arg Phe Leu Glu Phe Glu Ala Leu Gly Phe Leu Asn Glu
```

```
        3010            3015            3020
Asp His Trp Leu Gly Arg Lys Asn Ser Gly Gly Gly Val Glu Gly Leu
3025            3030            3035            3040

Gly Leu Gln Lys Leu Gly Tyr Ile Leu Arg Glu Val Gly Thr Arg Pro
        3045            3050            3055

Gly Gly Lys Ile Tyr Ala Asp Asp Thr Ala Gly Trp Asp Thr Arg Ile
        3060            3065            3070

Thr Arg Ala Asp Leu Glu Asn Glu Ala Lys Val Leu Glu Leu Leu Asp
3075            3080            3085

Gly Glu His Arg Arg Leu Ala Arg Ala Ile Ile Glu Leu Thr Tyr Arg
        3090            3095            3100

His Lys Val Val Lys Val Met Arg Pro Ala Ala Asp Gly Arg Thr Val
3105            3110            3115            3120

Met Asp Val Ile Ser Arg Glu Asp Gln Arg Gly Ser Gly Gln Val Val
            3125            3130            3135

Thr Tyr Ala Leu Asn Thr Phe Thr Asn Leu Ala Val Gln Leu Val Arg
        3140            3145            3150

Met Met Glu Gly Glu Gly Val Ile Gly Pro Asp Asp Val Glu Lys Leu
        3155            3160            3165

Thr Lys Gly Lys Gly Pro Lys Val Arg Thr Trp Leu Phe Glu Asn Gly
        3170            3175            3180

Glu Glu Arg Leu Ser Arg Met Ala Val Ser Gly Asp Asp Cys Val Val
3185            3190            3195            3200

Lys Pro Leu Asp Asp Arg Phe Ala Thr Ser Leu His Phe Leu Asn Ala
            3205            3210            3215

Met Ser Lys Val Arg Lys Asp Ile Gln Glu Trp Lys Pro Ser Thr Gly
        3220            3225            3230

Trp Tyr Asp Trp Gln Gln Val Pro Phe Cys Ser Asn His Phe Thr Glu
        3235            3240            3245

Leu Ile Met Lys Asp Gly Arg Thr Leu Val Val Pro Cys Arg Gly Gln
3250            3255            3260

Asp Glu Leu Val Gly Arg Ala Arg Ile Ser Pro Gly Ala Gly Trp Asn
3265            3270            3275            3280

Val Arg Asp Thr Ala Cys Leu Ala Lys Ser Tyr Ala Gln Met Trp Leu
        3285            3290            3295

Leu Leu Tyr Phe His Arg Arg Asp Leu Arg Leu Met Ala Asn Ala Ile
        3300            3305            3310

Cys Ser Ala Val Pro Val Asn Trp Val Pro Thr Gly Arg Thr Thr Trp
        3315            3320            3325

Ser Ile His Ala Gly Gly Glu Trp Met Thr Thr Glu Asp Met Leu Glu
        3330            3335            3340

Val Trp Asn Arg Val Trp Ile Glu Glu Asn Glu Trp Met Glu Asp Lys
3345            3350            3355            3360

Thr Pro Val Glu Lys Trp Ser Asp Val Pro Tyr Ser Gly Lys Arg Glu
        3365            3370            3375

Asp Ile Trp Cys Gly Ser Leu Ile Gly Thr Arg Ala Arg Ala Thr Trp
        3380            3385            3390

Ala Glu Asn Ile Gln Val Ala Ile Asn Gln Val Arg Ala Ile Ile Gly
        3395            3400            3405

Asp Glu Lys Tyr Val Asp Tyr Met Ser Ser Leu Lys Arg Tyr Glu Asp
    3410            3415            3420

Thr Thr Leu Val Glu Asp Thr Val Leu
3425            3430
```

<210> SEQ ID NO 68
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cccgggatcg atggatcctt tttatagcta attagtcacg tacctttgag agtaccactt    60
cagcta                                                                66

<210> SEQ ID NO 69
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggatccatcg atcccgggtt tttatgacta gttaatcacg gccgcttata aagatctaaa    60
atgcat                                                                66

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggctgcaggt attctaaact aggaatagat                                      30

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aattgcggcc gc                                                         12

<210> SEQ ID NO 72
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aaaggatccg ggttaattaa ttagtcatc                                       29

<210> SEQ ID NO 73
<211> LENGTH: 34
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 73
aataaagaag ctctaattaa ttaacgagca gata          34

<210> SEQ ID NO 74
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tcgttaatta attagagctt ctttattcta tacttaaaaa g          41

<210> SEQ ID NO 75
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aaaacccggg atcgattcta gactcgaggg tacctacgat acaaacttaa cggata          56

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggccgaattc tgaatgttaa atgttatact tt          32

<210> SEQ ID NO 77
<211> LENGTH: 5004
<212> TYPE: DNA
<213> ORGANISM: Canarypox virus
<220> FEATURE:
<221> NAME/KEY: CDS
<222> LOCATION: (1864)..(2187)

<400> SEQUENCE: 77
ctgaaattgt aatttctaca tgtagagaag gttttgatat tgatggtttt aacagaaacg          60
tagaaattat atcaagggat aacattttat atgatatagt tttaaagtgt aagatggaat          120
taaatttcat gtgcacaaga ggcataggag ataaaagcat tttcagactt tgtataatga          180
aggaatatga tcaaataaac aagaatctgt tagttagtta cttggataaa ttaatcgaga          240
cgcgtgataa aatgactatg taccgttatt gcatgaacga tattataaat ataggttctc          300
gtaggagaga actattgact atggcaatga atgttaaatg ttatactttg gatgaagcta          360
taaatatgca ttggaaaaat aatccattta agaaaggat tcaaatacta caaaacctaa          420
gcgataatat gttaactaag cttattctta acgacgcttt aaatatacac aaatataaca          480
aattttttgta taacctaaca aataactaaa acataaaaat aataaaagga atgtaatat          540
cgtaattatt ttactcagga atggggttaa atatttatat cacgtgtata tctatactgt          600
tatcgtatac tctttacaat tactattacg aatatgcaag agataataag attacgtatt          660
taagagaatc ttgtcatgat aattgggtac gacatagtga taaatgctat ttcgcatcgt          720
tacataaagt cagttggaaa gatggatttg acagatgtaa cttaataggt gcaaaaatgt          780

```
taaataacag cattctatcg gaagatagga taccagttat attatacaaa aatcactggt      840
tggataaaac agattctgca atattcgtaa aagatgaaga ttactgcgaa tttgtaaact      900
atgacaataa aaagccattt atctcaacga catcgtgtaa ttcttccatg ttttatgtat      960
gtgtttcaga tattatgaga ttactataaa cttttttgtat acttatattc cgtaaactat   1020
attaatcatg aagaaaatga aaagtatag aagctgttca cgagcggttg ttgaaaacaa     1080
caaaattata cattcaagat ggcttacata tacgtctgtg aggctatcat ggataatgac   1140
aatgcatctc taaataggtt tttggacaat ggattcgacc ctaacacgga atatggtact   1200
ctacaatctc ctcttgaaat ggctgtaatg ttcaagaata ccgaggctat aaaaatcttg   1260
atgaggtatg gagctaaacc tgtagttact gaatgcacaa cttcttgtct gcatgatgcg   1320
gtgttgagag acgactacaa aatagtgaaa gatctgttga agaataacta tgtaaacaat   1380
gttcttttaca gcggaggctt tactcctttg tgtttggcag cttaccttaa caaagttaat   1440
ttggttaaac ttctattggc tcattcggcg gatgtagata tttcaaacac ggatcggtta    1500
actcctctac atatagccgt atcaaataaa aatttaacaa tggttaaact tctattgaac   1560
aaaggtgctg atactgactt gctggataac atgggacgta ctccctttaat gatcgctgta   1620
caatctggaa atattgaaat atgtagcaca ctacttaaaa aaaataaaat gtccagaact   1680
gggaaaaatt gatcttgcca gctgtaattc atggtagaaa agaagtgctc aggctacttt   1740
tcaacaaagg agcagatgta aactacatct ttgaaagaaa tggaaaatca tatactgttt   1800
tggaattgat taaagaaagt tactctgaga cacaaaagag gtagctgaag tggtactctc   1860
aaa atg cag aac gat gac tgc gaa gca aga agt aga gaa ata aca ctt    1908
    Met Gln Asn Asp Asp Cys Glu Ala Arg Ser Arg Glu Ile Thr Leu
    1               5                   10                  15 tat gac ttt ctt agt tgt aga aaa gat aga gat ata atg atg gtc ata    1956
Tyr Asp Phe Leu Ser Cys Arg Lys Asp Arg Asp Ile Met Met Val Ile
                20                  25                  30 aat aac tct gat att gca agt aaa tgc aat aat aag tta gat tta ttt   2004
Asn Asn Ser Asp Ile Ala Ser Lys Cys Asn Asn Lys Leu Asp Leu Phe
            35                  40                      45 aaa agg ata gtt aaa aat aga aaa aaa gag tta att tgt agg gtt aaa   2052
Lys Arg Ile Val Lys Asn Arg Lys Lys Glu Leu Ile Cys Arg Val Lys
        50                  55                      60 ata ata cat aag atc tta aaa ttt ata aat acg cat aat aat aaa aat   2100
Ile Ile His Lys Ile Leu Lys Phe Ile Asn Thr His Asn Asn Lys Asn
65                  70                      75 aga tta tac tta tta cct tca gag ata aaa ttt aag ata ttt act tat   2148
Arg Leu Tyr Leu Leu Pro Ser Glu Ile Lys Phe Lys Ile Phe Thr Tyr
80                  85                      90                  95 tta act tat aaa gat cta aaa tgc ata att tct aaa taa tgaaaaaag     2197
Leu Thr Tyr Lys Asp Leu Lys Cys Ile Ile Ser Lys
                100                 105 tacatcatga gcaacgcgtt agtatatttt acaatggaga ttaacgctct ataccgttct   2257
atgtttattg attcagatga tgttttagaa aagaaagtta ttgaatatga aactttaat   2317
gaagatgaag atgacgacga tgattattgt tgtaaatctg ttttagatga agaagatgac   2377
gcgctaaagt atactatggt tacaaagtat aagtctatac tactaatggc gacttgtgca   2437
agaaggtata gtatagtgaa aatgttgtta gattatgatt atgaaaaacc aaataaatca   2497
gatccatatc taaaggtatc tcctttgcac ataatttcat ctattcctag tttagaatac   2557
ttttcattat atttgtttac agctgaagac gaaaaaaata tatcgataat agaagattat   2617
```

```
gttaactctg ctaataagat gaaattgaat gagtctgtga taatagctat aatcagagaa    2677
gttctaaaag gaaataaaaa tctaactgat caggatataa aaacattggc tgatgaaatc    2737
aacaaggagg aactgaatat agctaaacta ttgttagata gaggggccaa agtaaattac    2797
aaggatgttt acggttcttc agctctccat agagctgcta ttggtaggaa acaggatatg    2857
ataaagctgt taatcgatca tggagctgat gtaaactctt taactattgc taaagataat    2917
cttattaaaa aaaataata tcacgtttag taatattaaa atatattaat aactctatta    2977
ctaataactc cagtggatat gaacataata cgaagtttat acattctcat caaaatctta    3037
ttgacatcaa gttagattgt gaaaatgaga ttatgaaatt aaggaataca aaaataggat    3097
gtaagaactt actagaatgt tttatcaata atgatatgaa tacagtatct agggctataa    3157
acaatgaaac gattaaaaat tataaaaatc atttccctat atataatacg ctcatagaaa    3217
aattcatttc tgaaagtata ctaagacacg aattattgga tggagttata aattcttttc    3277
aaggattcaa taataaattg ccttacgaga ttcagtacat tatactggag aatcttaata    3337
accatgaact aaaaaaaatt ttagataata tacattaaaa aggtaaatag atcatctgtt    3397
attataagca aagatgcttg ttgccaataa tatacaacag gtatttgttt ttattttaa    3457 ctacatattt gatgttcatt ctctttatat agtatacaca gaaaattcat aatccactta    3517
gaatttctag ttatctagtt tttctagaat attgtacttt atttctaatg gaatggctct    3577
ccagcctagt aatttattaa tgttagctga tatcttgaaa tcaggatatt ctgctccgtg    3637
aagagaaagt cctccaaagt tgtatatttc catcactttc atggcttcct ctttccatag    3697
tgtcttctat aagctgtcta tatattgtaa acttttctgg ttttatgcat tttaaacatt    3757
tagcaatctc attttcatca caattaaggc acaaatctaa catggaatgt ctaccataac    3817
ccaataaggt tttttcattt cctctatctc taatacacac tgttctttcc agactttcaa    3877
cacgctgcta ttttctattt tattcaagtc catattataa gcgtccttgt tagacacttc    3937
ataatgtttg cattctggaa tcatcatgtt agatactatt aatttagcta cttctatgtt    3997
gtcatcaaaa gagttgctat ctgtaattac actaagaggt gtatcacctg ataaagaagt    4057
aatagagaca tctgctctga atttaagcaa tacctcaata acttcttttg aagatgactt    4117
tgcagctaaa aataatggag ttctctctaa aacatcccctt gagtttatat tagccccgta    4177
actaatgagt agttctgtta tatctttgga atctattgat atattattaa ttacaattgt    4237
catgctgaca tatatagaca tcataatatg atgaaaaata tgaaaatata agtgcacgtt    4297
tactgttact atgattgtga tatcgatatg agttctttaa taaaagtact gaaatagata    4357
taatgcagat atgattgata ttttaaaaag ttgaaaaaaa atatgccctg tttacaaata    4417
ctatttggaa atattctgta ataaagtaat agtgatatgt cagtcacgat ggatttgcca    4477
attgatcata tgagtataga taacataaac gagtataata aaaatggata tactagactc    4537
tatatagagg tagccatgaa aaaacgtaaa aacgtagata gacttttata tctcggagct    4597
gatccgaatc tggctagtgt agattcgtat tgtcctcttc atattgctgt taggaatggt    4657
agtttaaaga taataagatc attgttgaaa tatggtgcta atataaatca agaatgtcat    4717
gaaggagata ctgctttgat gatggctata tcattaggta attatacagc atgtaaaaca    4777
cttctagata acaacgccga tcctaggtaa ttatgttaac tattacggta tagttccgct    4837
tattagagca attatatgtg aaaagcctga catagttaga ctgctattag atagaggagc    4897
taattgcaac cacttaatta caaaaaacgg tagaacctat actgctttag agagtcttag    4957
gaattgcttt tttaaagaca attcttcatc attgtcgata ctaatat              5004
```

-continued

<210> SEQ ID NO 78
<211> LENGTH: 107
<212> TYPE: PRT
<213> ORGANISM: Canarypox virus

<400> SEQUENCE: 78

Met Gln Asn Asp Asp Cys Glu Ala Arg Ser Arg Glu Ile Thr Leu Tyr
 1               5                  10                  15

Asp Phe Leu Ser Cys Arg Lys Asp Arg Asp Ile Met Met Val Ile Asn
            20                  25                  30

Asn Ser Asp Ile Ala Ser Lys Cys Asn Asn Lys Leu Asp Leu Phe Lys
        35                  40                  45

Arg Ile Val Lys Asn Arg Lys Lys Glu Leu Ile Cys Arg Val Lys Ile
    50                  55                  60

Ile His Lys Ile Leu Lys Phe Ile Asn Thr His Asn Asn Lys Asn Arg
65                  70                  75                  80

Leu Tyr Leu Leu Pro Ser Glu Ile Lys Phe Lys Ile Phe Thr Tyr Leu
                85                  90                  95

Thr Tyr Lys Asp Leu Lys Cys Ile Ile Ser Lys
            100                 105

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggccgaattc                                                          10

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ccatgcactg attaatcgat atttttccat gggccc                             36

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggatcccggg tttttatgac tagttaatca cggccg                             36

<210> SEQ ID NO 82
<211> LENGTH: 232
<212> TYPE: DNA
<213> ORGANISM: Artificial Sequence
<220> FEATURE:
<223> OTHER INFORMATION: Description of Artificial Sequence: Synthetic
      VQH6 amplified nucleotide fragment
<220> FEATURE:
<221> NAME/KEY: CDS -continued

```
<222> LOCATION: (24)..(59)

<400> SEQUENCE: 82
aaaggatccg ggttaattaa tta gtc atc agg cag ggc gag aac gag act atc      53
                         Val Ile Arg Gln Gly Glu Asn Glu Thr Ile
                          1               5                  10 tgc tcg ttaattaatt agagcttctt tattctatac ttaaaaagtg aaaataaata        109
Cys Ser caaaggttct tgagggttgt gttaaattga aagcgagaaa taatcataaa ttatttcatt    169
atcgcgatat ccgttaagtt tgtatcgtag gtaccctcga gtctagaatc gatcccgggt   229
ttt                                                                    232

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      VQH6 amplified fragment

<400> SEQUENCE: 83

Val Ile Arg Gln Gly Glu Asn Glu Thr Ile Cys Ser
 1               5                  10

<210> SEQ ID NO 84
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gccgccacca tggg                                                          14

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cccatggtgg cggctgca                                                      18
```

RECOMBINANT VACCINE AGAINST WEST NILE VIRUS

RELATED APPLICATIONS/INCORPORATION BY REFERENCE

This application is a continuation-in-part of U.S. application Ser. No. 10/679,520 filed Oct. 6, 2003 now abandoned, which is a continuation-in-part application of U.S. application Ser. No. 10/374,953 filed Feb. 26, 2003 now abandoned, which is a continuation-in-part of U.S. application Ser. No. 10/116,298, filed Apr. 4, 2002 now abandoned, which claims priority from U.S. Provisional application Ser. No. 60/281,923, filed Apr. 6, 2001. This application is also a continuation-in-part application of U.S. application Ser. No. 10/676,502, filed Sep. 30, 2003 now abandoned, which is a continuation of U.S. application Ser. No. 10/374,953 filed Feb. 26, 2003 now abandoned, and which claims priority from U.S. Provisional Application Ser. No. 60/281,923, filed Apr. 6, 2001. This application is also related to International Application PCT/FR02/01200 filed Apr. 5, 2002, published as WO 02/081,621 on Oct. 17, 2002, which claims priority to French application 01/04737 filed Apr. 6, 2001. Each of the above applications, together with each document cited therein, and each of the documents referenced or cited in documents cited therein, are hereby incorporated herein by reference.

Indeed, more generally, each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

FIELD OF THE INVENTION

The present invention relates to vectors containing at least one polynucleotide of the West Nile fever virus (or West Nile Virus or WNV) or at least one nucleic acid molecule encoding at least one West Nile Virus antigen, immunogen or epitope, e.g., in vivo and in vitro expression vectors comprising at least one polynucleotide of the West Nile Virus or in vivo and in vitro expression vectors comprising and expressing at least one West Nile Virus antigen, immunogen or epitope, as well as immunogenic compositions and vaccines against West Nile fever; for instance, such compositions or vaccines that contain one or more of the vectors and/or one or more of the expression products of the vectors. The invention also relates to methods for using the vectors, compositions and vaccines, including for immunizing and vaccinating against this virus, expressing expression products of the polynucleotide(s), using the expression products in assays or to generate antibodies useful in assays, as well as to methods for making the, polynucleotide(s), vectors, compositions vaccines, assays, inter alia.

BACKGROUND OF THE INVENTION

The West Nile fever virus (WNV) was first identified in man in 1937 in Uganda in the West Nile Province (Zeller H. G., Med. Trop., 1999, 59, 490-494).

Widespread in Africa, it is also found in India, Pakistan and the Mediterranean basin and was identified for the first time in the USA in 1999 in New York City (Anderson J. F. et al., Science, 1999, 286, 2331-2333).

The West Nile fever virus affects birds as well as reptiles, mammals, together with man.

The disease is characterized in birds by an attack of the central nervous system and death. The lesions include encephalitis, hemorrhages in the myocardium and hemorrhages and necroses in the intestinal tract.

In chickens, experimental infections by subcutaneous inoculations of the West Nile fever virus isolated on crows led to necrosis of the myocardium, nephritis and pneumonia 5 to 10 days after inoculation and moderate to severe encephalitis 21 days after inoculation (Senne D. A. et al., Avian Disease, 2000, 44, 642-649).

The West Nile fever virus also affects horses, especially in North Africa and Europe (Cantile C. et al., Equine Vet. J., 2000, 32 (1), 31-35). These horses reveal signs of ataxia, weakness of the rear limbs, paresis evolving towards tetraplegia and death. Horses and camels are the main animals manifesting clinical signs in the form of encephalitis.

Anti-WNV antibodies were detected in certain rodents, in livestock, especially bovines and ovines, as well as in domestic animals, especially in the dog (Zeller H. G., Med. Trop., 1999, 59, 490-494; Lundstrom J. O., Journal of Vector Ecology, 1999, 24 (1), 1-39).

The West Nile fever virus also affects with a number of symptoms the human species (Sampson B. A., Human Pathology, 2000, 31 (5), 527-531; Marra C. M., Seminars in Neurology, 2000, 20 (3), 323-327).

The West Nile fever virus is transmitted to birds and mammals by the bites of certain mosquitoes (e.g. Culex, Aedes, Anopheles). Direct transmission may happen from WNV infected subject to healthy subject by oral transmission (prey and transmission through colostrum) and blood/organ vectored transmission.

Wild and domestic birds are a reservoir for the West Nile virus and a propagation vector as a result of their migrations.

The virions of the West Nile fever virus are spherical particles with a diameter of 50 nm constituted by a lipoproteic envelope surrounding an icosahedric nucleocapsid containing a positive polarity, single-strand RNA.

A single open reading frame (ORF) encodes all the viral proteins in the form of a polyprotein. The cleaving and maturation of this polyprotein leads to the production of about ten different viral proteins. The structural proteins are encoded by the 5' part of the genome and correspond to the nucleocapsid designated C (14 kDa), the envelope glycoprotein designated E (50 kDa), the pre-membrane protein designated prM (23 kDa), the membrane protein designated M (7 kDa). The non-structural proteins are encoded by the 3' part of the genome and correspond to the proteins NS1 (40 kDa), NS2A (19 kDa), NS2B (14 kDa), NS3 (74 kDa), NS4A (15 kDa), NS4B (29 kDa), NS5 (97 kDa).

Parrish C. R. et al. (J. Gen. Virol., 1991, 72, 1645-1653), Kulkarni A. B. et al. (J. Virol., 1992, 66 (6), 3583-3592) and Hill A. B. et al. (J. Gen. Virol., 1992, 73, 1115-1123), on the basis of the vaccinia virus, constructed in vivo expression vectors containing various inserts corresponding to nucleotide sequences coding for non-structural proteins of the Kunjin virus, optionally associated with structural proteins. These vectors were administered to mice to evaluate the immune cell response. The authors stress the importance of the cell response, which is essentially stimulated by non-structural proteins and especially NS3, NS4A and NS4B. These articles reveal the difficulty in providing a good vaccination strategy against West Nile fever.

Reference is also made to WO 02/081754 published Oct. 17, 2002, from PCT/US02/10764, filed Apr. 4, 2002, with a claim of priority from U.S. application Ser. No. 09/826,115, filed Apr. 4, 2001. The PCT claims a status of continuation-in-part from U.S. application Ser. No. 09/826,115. It further states that U.S. application Ser. No. 09/826,115 is a continuation-in-part of U.S. application Ser. No. 09/701,536, filed Nov. 29, 2000. It even further states that U.S. application Ser. No. 09/701,536 is the National Stage of PCT/US99/12298, filed Jun. 3, 1999, with a claim of priority to U.S. provisional application Ser. No. 60/087,908.

It would be advantageous to provide improved immunogenic and vaccine compositions against WNV, and methods for making and using such compositions, including such compositions that provide for differential diagnostic methods, assays and kits, and thus, differential diagnostic methods, assays and kits.

OBJECTS AND/OR SUMMARY OF THE INVENTION

The invention provides an immunogenic or vaccine composition to induce an immune response or protective immune response against West Nile virus (WNV) in an animal susceptible to WNV comprising or consisting essentially of a pharmaceutically or veterinarily acceptable vehicle or excipient and a vector that contains or consists essentially of heterologous nucleic acid molecule(s), and that expresses in vivo in the animal a WNV protein, antigen, immunogen or epitope thereof, such as WNV E; WNV prM and E; WNV M and E; WNV prM, WNV M and E, WNV polyprotein prM-E, WNV polyprotein M-E, or WNV polyprotein prM-M-E.

The vector can be a DNA plasmid or a recombinant virus, such as a recombinant adenovirus, herpesvirus or poxvirus, e.g., an avipox virus, such as a canarypox virus or a fowlpox virus. The animal can be selected from the group consisting of an equine, a canine, a feline, a bovine, a porcine, a chicken, a duck, a goose and a turkey.

Advantageously, the nucleic acid molecule comprises or consists essentially of nucleotides 466-741, 742-966 and 967-2469 of GenBank AF196835 encoding WNV prM, M and E, respectively, nucleotides 466-2469 of GenBank AF196835 encoding WN protein prM-M-E, or nucleotides 421-2469 of GenBank AF196835 encoding WN protein prM-M-E and the signal peptide of prM.

The immunogenic or vaccine composition can further comprise or consist essentially of an adjuvant, such as a carbomer.

The immunogenic or vaccine composition can further comprise or consist essentially of an antigen or immunogen or epitope thereof of a pathogen other than WNV of the animal, or a vector that contains and expresses in vivo in the animal a nucleic acid molecule encoding the antigen, immunogen or epitope thereof, or an inactivated or attenuated pathogen other than WNV of the animal.

The invention additionally involves a kit comprising or consisting essentially of (a) the immunogenic or vaccine composition, and (b) the antigen or immunogen or epitope thereof of a pathogen other than WNV of the animal, or the vector that contains and expresses in vivo in the animal a nucleic acid molecule encoding the antigen, immunogen or epitope thereof, or the inactivated or attenuated pathogen other than WNV of the animal, wherein (a) and (b) are in separate containers, and the kit optionally contains instructions for admixture and/or administration of (a) and (b).

The invention also comprehends a method for inducing an immunological or protective immune response against WNV in an animal comprising or consisting essentially of administering to the animal the immunogenic or vaccine composition.

The invention further comprehends a method for inducing an immunological or protective immune response against WNV in an animal comprising or consisting essentially of administering to the animal (a) the immunogenic or vaccine composition, and (b) a WNV isolated antigen, immunogen or epitope thereof, wherein (a) is administered prior to (b) in a prime-boost regimen, or (b) is administered prior to (a) in a prime-boost regimen, or (a) and (b) are administered together, either sequentially or in admixture. The invention also involves a kit for performing this comprising or consisting essentially of (a) and (b) in separate containers, optionally with instructions for admixture and/or administration.

The invention even further comprehends a prime-boost immunization or vaccination against WNV, wherein the priming is done with (a) DNA vaccine(s) or immunological or immunogenic composition(s) that contains or consists essentially of (a) nucleic acid molecule(s) encoding and express(es) in vivo a WNV immunogen, antigen or epitope and the boost is done with (a) vaccine(s) or immunological or immunogenic composition(s) that is a WNV inactivated or attenuated or subunit (antigen, immunogen and/or epitope) preparation(s) and/or (a) recombinant or modified virus vaccine or immunological or immunogenic composition(s) that contains or consists essentially of (a) nucleic acid mocule encoding and express(es) in vivo (a) WNV immunogen(s), antigen(s) or epitope(s). Thus, the invention provides a prime-boost immunization or vaccination method against WNV, such as a prime-boost immunization or vaccination which comprises or consists essentially of or consists of administering to a target species animal (a) DNA vaccine(s) or immunological or immunogenic composition(s) of the invention (that contains or consists essentially of nucleic acid molecule(s) encoding and express(es) in vivo WNV antigen(s), immunogen(s) or epitope(s)) (as the prime) and thereafter administering (as the boost) administering inactivated WNV and/or attenuated WNV or a WNV subunit (antigen, immunogen and/or epitope) preparation(s)) and/or a recombinant or modified virus vaccine or immunological or immunogenic composition that contains or consists essentially of nucleic acid molecule(s) encoding and expresse(s) in vivo WNV immunogen(s), antigen(s) or epitope(s), advantageously (a) recombinant vaccine or immunological or immunogenic composition(s) that expresses the WNV immunogen, antigen or epitope in vivo. The boost is advantageously matched to the prime, e.g., the boost contains or consists essentially of or expresses at least one antigen, epitope or immunogen that is expressed by the prime.

The prime-boost regimen according to the invention can be used in animals of any age, advantageously young animals (e.g., animals that have detectable maternal antibodies and/or are suckling or nursing or breast-feeding), pre-adult animals (animals that are older than being a young animal but have not yet reached maturity or adulthood or an age to mate or reproduce), adult animals (e.g., animals that are of an age to mate or reproduce or are beyond such a period in life), and it is advantageous to employ the prime-boost regimen in pregnant females or females prior to giving birth, laying, or insemination.

The invention also relates to such immunogenic and vaccine compositions and kits thereof suitable for use in such prime-boost regimens and prime-boost regimens. The host or target species upon which the prime-boost regimen can be practiced includes any animal (target or host) species susceptible to disease caused by WNV, including mammals, reptiles, birds, especially humans, companion mammals or animals such as canines, felines, equines, zoo mammals or animals, such as aquatic mammals e.g. seals, felines, equines, zoo reptiles such as snakes, crocodiles, aligators, and avian species, such as domesticated birds that are pets or poultry, or wild birds, e.g., canaries, parakeets, chickens, ducks, geese, turkeys, sparrows, crows, and the like.

The prime-boost regimen is especially advantageous to practice in a young animal, as it allows vaccinatation or immunization at an early age, for instance, the first administration in the prime-boost regimen when practiced on a young animal can be at an age at which the young animal has maternal antibodies. Another advantage of this regimen is that it can provide a degree of safety for pregnant females present in the same location or in close proximity to the young or to each other. Thus, the invention provides a prime-boost immunization or vaccination method against WNV, and the method may be practiced upon a young animal, such as a young foal, puppy or kitten, for instance, wherein the priming is done at a time that the young animal has maternal antibodies against WNV, with the boost advantageously at a time when maternal antibodies may be waning or decreasing or normally not present, such as a period of time post-breastfeeding.

Accordingly, the invention also involves kits for performing a prime-boost regimen comprising or consisting essentially of a priming vaccine or immunological or immunogenic composition and a boost vaccine or immunological or immunogenic compositions, in separate containers, optionally with instructions for admixture and/or administration.

Further still, the invention provides a differential diagnosis method comprising administering to animals an immunogenic or vaccine composition and/or a WNV antigen, immunogen or epitope, and testing the animals for presence or absence of a WNV protein or antibody thereto not expressed by the immunogenic or vaccine composition and/or not present in the WNV antigen, immunogen or epitope. An the invention additionally involves a kit for performing this method comprising the immunogenic or vaccine composition and/or the WNV antigen, immunogen or epitope, and an assay for testing for the presence or absence of the WNV protein, in separate containers, optionally with instructions for administration of the immunogenic or vaccine composition and/or the WNV antigen, immunogen or epitope and/or for performing the assay.

These and other embodiments are disclosed or are obvious from and encompassed by, the following Detailed Description.

BRIEF DESCRIPTION OF THE DRAWINGS

FIG. 1 is a schematic showing construction of a pC5 H6p WNV prM-M-E donor plasmid, pDS-2946-1-1.

FIG. 2 depicts the nucleic and amino acid sequence of C5H6p WNV prM-M-E C5 in pDS-2646-1-1 (SEQ ID Nos: 54 and 55).

FIG. 3 is a schematic showing construction of a pF8 H6p WNV prM-M-E donor plasmid, pSL-5513-1-1-1.

FIG. 4 depicts the nucleic and amino acid sequence of F8 H6p WNV prM-M-E F8 in pSL-5513-1-1-1 (SEQ ID Nos: 56 and 57).

FIG. 5 is two immunoblots showing the expression of WNV proteins from pox recombinants in chick embryo fibroblast cells.

FIG. 6 is an immunoblot showing the expression of WNV proteins from pox recombinants in BHK cells.

FIG. 7 is a schematic showing construction of pVR1012 WNV prM-M-E, pSL-5448-1-1.

FIG. 8 depicts the nucleic and amino acid sequences of the WNV prM-M-E region in pSL-5448-1-1, pVR1012 WNV prM-M-E (SEQ ID Nos: 58 and 59).

FIG. 9 depicts the nucleic and amino acid sequences of pDS-2946-1-1, pC5 H6p WNV prM-M-E (SEQ ID Nos: 60 and 61).

FIG. 10 is a schematic showing construction of pC5 H6p WNV prM-M-E donor plasmids with a truncated H6p and/or truncated WNV capsid leader sequence.

FIG. 11 describes primers for constructions pC5 H6p WNV prM-M-E donor plasmids with a truncated H6p and/or truncated WNV capsid leader sequence (SEQ ID NOS: 63, 62, 50, 49, 48, 65, and 64, respectively in order of appearance). Additionally, a fragment of the full length sequence of H6p 5'WNV sequence in vCP2017 is depicted (as bases 1861-2160 of SEQ ID NO: 60 and residues 1-52 of SEQ ID NO: 61.

FIG. 12 depicts the nucleic and amino acid sequences of the West Nile Virus (WNV) (SEQ ID Nos: 66 and 67).

FIG. 13 (SEQ ID NO:77) is the sequence of a 5 kb segment of canarypox DNA, encoding an ORF designated C5 initiating at position 1864 and terminating at position 2187 (SEQ ID NO: 78). The oligonucleotides shown are disclosed as SEQ ID NOS 79-81, respectively in order of appearance.

FIG. 14 depicts the sequence of a 232 bp VQ/H6p/MCS fragment. The nucleotide and amino acid sequences are disclosed as SEQ ID NOS 82 and 83, respectively.

FIG. 15 is a schematic showing the generation of plasmid pNVQH6C5LSP-18, a C5 insertion plasmid containing the H6 promoter, transcription and translation terminators functional in all reading frames, and a MCS.

FIG. 16 is a table that provides data depicting the plaque-forming units of WNV per ml of serum for each of the horses in Example 32

FIG. 17a-b is a table that provides data showing the presence or absence of virenia based on a serum titter of titer of >or <5 pfu/ml [$\log_{10}$<0.7].

FIG. 18a-b is a table providing temperature data for each of the horses in Example 32.

FIG. 19a-b is a table providing data from plaque reduction neutralization titers in all of the animals in groups I and II.

DETAILED DESCRIPTION

Figure 18C:
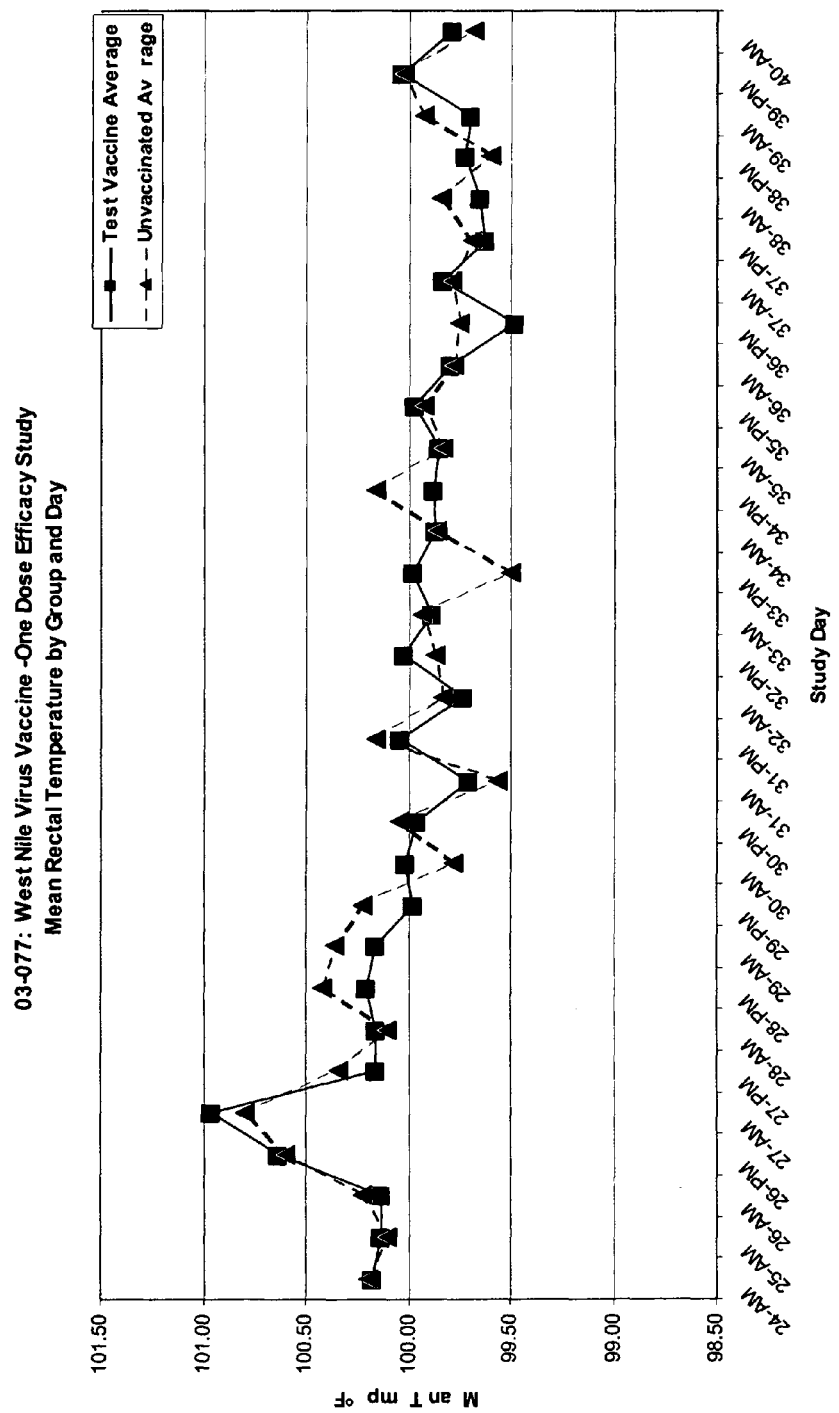
FIG. 18c is a graph depicting the temperature data as an average for each of Groups I and II.

As discussed herein, the present invention relates to vectors containing at least one polynucleotide of the West Nile fever virus (or West Nile Virus or WNV) or at least one nucleic acid molecule encoding at least one West Nile Virus antigen, immunogen or epitope, e.g., in vivo and in vitro expression vectors comprising and expressing at least one polynucleotide of the West Nile Virus or in vivo and in vitro expression vectors comprising and expressing at least one West Nile Virus antigen, immunogen or epitope, as well as immunogenic compositions and vaccines against West Nile fever; for instance, such compositions or vaccines that contain one or more of the vectors and/or one or more of the expression products of the vectors.

Advantageously, the immunogen or antigen is the envelope protein, E, or the pre-membrane protein (prM protein), or the membrane protein (M protein), or combinations thereof, e.g., E and prM; E and M; E and prM and M; prM and M. The combinations can be separate proteins or polyproteins. The compositions or vaccines can thus contain one or more vectors expressing more than one of the proteins, e.g., different proteins. The compositions or vaccines can contain, or vectors thereof express, proteins from different strains or isolates of WNV. Thus, the compositions or vaccines can contain, or the vectors thereof express, E, prM, M or combinations thereof, wherein the E, prM, and/or M are from different strains or isolates.

In this regard, it is noted that there is the NYC isolate or strain, e.g., WN-NY99 strain or GenBank AF196835 (WNV isolated from a dead Chilean flamingo at the Bronx Zoo deposited in GenBank, R. S. Lanciotti et al., *Science*, 286, pp. 2333-7 (1999); SEQ ID Nos: 66 and 67) or GenBank AAF202541 (genome of a WNV isolate from human victims of the New York outbreak of WNV-NY1999, X.-Y. Jia et al., *The Lancet*, 354, pp. 1971-2 (1999)) (see also Ebel et al., Emerg Infect Dis 7(4):650-3 (2001), Anderson et al. PNAS USA 98(23):12885-9 (2001), Shi et al., Virology 296(2):219-33 (2002), Shi et al., J Virol 76(12):5847-56 (2002)), as well as the strains of GenBank D00246 (Kunjin virus); M12294 (West Nile virus); AF130362 (West Nile virus strain R097-50); AF130363 (West Nile virus strain 96-1030)). Also, it is noted that comparative phylogenetic analysis of the NY sequences with previously reported WNV sequences indicated a high degree of homology between the NY isolates and two isolates from Romania and one from Israel (J. F. Anderson et al., supra; X.-Y. Jia et al., supra; R. S. Lanciotti et al., supra), indicating the useful of the NY sequences.

Advantageously in embodiments involving at least one epitope present in, or expressed by vector or vectors in, compositions or vaccines of the invention, the epitope or epitopes are from E, prM, M or combinations thereof, and the epitope or epitopes can be from different strains or isolates. In this regard, it is noted that one can locate or map epitopes in WNV antigens or immunogens, such as the E protein; see, e.g., Beasley et al. J Virol 76(24):13097-100 (2002), Damle et al. Acta Virol 42(6):389-95 (1998), De Groot et al., Emerg Infect Dis 7(4):706-13 (2001), Sbai et al., Curr Drug Targets Infect Disord 1(3):303-13 (2001), Kutubuddin et al., Mol Immunol 28(1-2):149-54 (1991), Becker, Virus Genes 4(3):267-82 (1990).

Also as discussed herein, the invention relates to methods for using the vectors, compositions and vaccines, including for immunizing and vaccinating against this virus, for expressing expression products of the polynucleotide(s), and methods for using the expression products in assays or to generate antibodies useful in assays, as well as to methods for making the, polynucleotide(s), vectors, compositions vaccines, assays, inter alia.

The present invention thus relates to means for preventing and/or combating diseases caused by the WNV.

The invention relates to such immunogenic and vaccine compositions suitable for use in different animal (target or host) species susceptible to disease caused by WNV, including mammals, reptiles, birds, especially humans, companion mammals or animals such as canines, felines, equines, zoo mammals or animals, such as aquatic mammals e.g. seals, felines, equines, zoo reptiles such as snakes, crocodiles, aligators, and avian species, such as domesticated birds that are pets or poultry, or wild birds, e.g., canaries, parakeets, chickens, ducks, geese, turkeys, sparrows, crows, and the like.

The invention further relates to immunization and vaccination methods involving the immunogenic and vaccine compositions, for the target or host species. And on this aspect of the invention, mention is made that as to wild or non-domesticated animals, such as wild or non-domesticated birds or mammals (e.g., raccoons, squirrels, mice, or more generally rodents, felines, canines, etc.) compositions comprising one or more vectors that express one or more WNV epitopes or antigens or immunogens can be delivered via food, e.g., a bait drop, or mammal or bird food, left for consumption by wild or non-domesticated birds or mammals, that includes or contains the one or more vectors, so there may be administration thereof orally by the mammal or bird consuming the food. This route of administration may be advantageous when the one or more vectors is one or more poxviruses, e.g., an avipox virus such as an attenuated canarypox virus, for instance ALVAC, or an attenuated fowlpox virus, for instance TROVAC, or a vaccinia virus, such as an attenuated vaccinia virus, for instance NYVAC. Accordingly, the invention envisions oral or mucosal administration, as well as edible compositions that contain one or more of the inventive vectors, akin to the MERIAL rabies product RABORAL. From this disclosure and the knowledge in the art, the skilled artisan can formulate edible animal feed for a bird or mammal that contains a suitable dose of one or more inventive vectors. Furthermore, the invention comprehends topical administration of compositions containing vectors, see, e.g., U.S. Pat. No. 6,348,450 regarding topical administration of vector compositions, and devices for topical administration of compositions to wild or non-domesticated animals, see, e.g., WO01/95715, U.S. application Ser. No. 10/374,627, filed Feb. 26, 2003, for such devices for rodents and birds; each of which, together with each document cited or referenced therein, as with each document cited herein and each document referenced or cited in each document cited herein, is hereby incorporated herein by reference.

The invention further relates to means and methods that make differential diagnosis possible, e.g., methods that make it possible to make, or allow for, a distinction between an animal infected by the West Nile (WN) pathogenic virus and an animal administered a vaccine or immunogenic composition according to the invention.

In certain embodiments, the invention provides in vitro and/or in vivo expression vectors comprising a polynucleotide encoding the envelope protein E of WNV. In addition to the sources otherwise set forth herein for nucleic acid molecules encoding WNV E, mention is made of WO 02/072036, published Sep. 19, 2002, with claims of priority to U.S. Provisional applications Ser. Nos. 60/281,947 and 60/275,025, filed Apr. 5, 2001 and Mar. 12, 2001, respectively. These vectors advantageously also comprise the elements for the expression of the polynucleotide in a host cell.

In addition to the polynucleotide encoding E, the expression vectors according to the invention can comprise one or more other polynucleotides encoding other proteins of the WN virus, preferably structural proteins of the WN virus and said sequences are preferably chosen from among those encoding the pre-membrane protein prM and the membrane protein M.

The vector preferably comprises a polynucleotide forming a single encoding frame or coding region corresponding e.g. to prM-E, M-E, or advantageously prM-M-E, or epitopes thereof; that is, expression of a polyprotein or epitopes thereof are considered advantageous. A vector comprising several separate polynucleotides encoding the different proteins (e.g. prM and/or M and E or epitopes thereof) also falls within the scope of the present invention. The vector, especially for in vivo expression, can also comprise polynucleotides corresponding to more than one WN virus strain or isolate, for instance, two or more polynucleotides encoding E or prM-M-E, or epitope(s) thereof, of different strains.

Likewise, an immunogenic or vaccine composition can comprise one or more vectors for expression of polynucleotides corresponding to more than one WN virus strain or isolate, for instance, two or more polynucleotides encoding E or prM-M-E, or epitope(s) thereof, of different strains. The vector, especially for in vivo expression, can additionally comprise one or more nucleotide sequences encoding immunogens of other pathogenic agents and/or cytokines.

According to a preferred embodiment of the invention, the expression vector comprises a polynucleotide encoding prM-M-E and preferably in a single reading frame. In this regard, and particularly in regard to the herein preference for E, prM, M and combinations thereof in view of this disclosure also acknowledging other WNV proteins, it is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. It is further noted that in combinations or polyproteins, it is advantageous that E be among the structural proteins of the combination or polyprotein.

The term polynucleotide encoding a protein of the WN virus primarily means a DNA fragment or isolated DNA molecule encoding said protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

The term protein includes peptides and polypeptides. A protein fragment is immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope relates to a protein site able to induce an immune reaction of the humoral type (B cells) and/or cellular type (T cells).

Accordingly, a minimum structure of the polynucleotide is that it comprises or consists essentially of or consists of nucleotides to encode an epitope or antigenic determinant of the WNV protein or polyprotein. A polynucleotide encoding a fragment of the total protein or polyprotein, more advantageously, comprises or consists essentially of or consists of a minimum of 21 nucleotides, advantageously at least 42 nucleotides, and preferably at least 57, 87 or 150 consecutive or contiguous nucleotides of the sequence encoding the total protein or polyprotein. As mentioned earlier, epitope determination procedures, such as, generating overlapping peptide libraries (Hemmer B. et al., Immunology Today, 1998, 19 (4), 163-168), Pepscan (Geysen H. M. et al., Proc. Nat. Acad. Sci. USA, 1984, 81 (13), 3998-4002; Geysen H. M. et al., Proc. Nat. Acad. Sci. USA, 1985, 82 (1), 178-182; Van der Zee R. et al., Eur. J. Immunol., 1989, 19 (1), 43-47; Geysen H. M., Southeast Asian J. Trop. Med. Public Health, 1990, 21 (4), 523-533; Multipin® Peptide Synthesis Kits de Chiron) and algorithms (De Groot A. et al., Nature Biotechnology, 1999, 17, 533-561), can be used in the practice of the invention, without undue experimentation. Other documents cited and incorporated herein may also be consulted for methods for determining epitopes of an immunogen or antigen and thus nucleic acid molecules that encode such epitopes.

In an advantageous embodiment, the polynucleotides according to the invention comprise or consist essentially of or consist of the nucleotide sequence encoding one or two transmembrane domains and preferably two of them, located in the terminal part C of the E protein of WNV. For the WNV NY99 strain, these domains correspond to amino acid sequences 742 to 766 and 770 to 791 of GenBank AF196835.

Elements for the expression of the polynucleotide or polynucleotides are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. prM-E, M-E, prM-M-E, advantageously, in the vector, an ATG is placed at 5' of the reading frame and a stop codon is placed at 3'. Other elements for controlling expression may be present, such as enhancer sequences, stabilizing sequences and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 6,130,066, 5,494,807, 5,514,375, 5,744,140, 5,744, 141, 5,756,103, 5,762,938, 5,766,599, 5,990,091, 6,004,777, 6,130,066, 6,497,883, 6,464,984, 6,451,770, 6,391,314, 6,387,376, 6,376,473, 6,368,603, 6,348,196, 6,306,400, 6,228,846, 6,221,362, 6,217,883, 6,207,166, 6,207,165, 6,159,477, 6,153,199, 6,090,393, 6,074,649, 6,045,803, 6,033,670, 6,485,729, 6,103,526, 6,224,882, 6,312,682, 6,312,683, 6,348,450, 4,603,112; 4,769,330; 5,174,993; 5,505,941; 5,338,683; 5,494,807; 4,394,448; 4,722,848; 4,745,051; 4,769,331; 5,591,639; 5,589,466; 4,945,050; 5,677,178; 5,591,439; 5,552,143; and 5,580,859; U.S. patent application Ser. No. 920,197, filed Oct. 16, 1986; WO 94/16716; WO 96/39491; W091/11525; WO 98/33510; WO 90/01543; EP 0 370 573; EP 265785; Paoletti (1996) Proc. Natl. Acad. Sci. USA 93:11349-11353; Moss (1996) Proc. Natl. Acad. Sci. USA 93:11341-11348; Richardson (Ed) (1995) Methods in Molecular Biology 39, "Baculovirus Expression Protocols," Humana Press Inc.; Smith et al. (1983) Mol. Cell. Biol. 3:2156-2165; Pennock et al. (1984) Mol. Cell. Biol. 4:399-406; Roizman Proc. Natl. Acad. Sci. USA 93:11307-11312; Andreansky et al. Proc. Natl. Acad. Sci. USA 93:11313-11318; Robertson et al. Proc. Natl. Acad. Sci. USA 93:11334-11340; Frolov et al. Proc. Natl. Acad. Sci. USA 93:11371-11377; Kitson et al. (1991) J. Virol. 65:3068-3075; Grunhaus et al. (1992) Sem. Virol. 3:237-52; Ballay et al. (1993) EMBO J. 4:3861-65; Graham (1990) Tibtech 8:85-87; Prevec et al. J. Gen. Virol. 70.429-434; Felgner et al. (1994) J. Biol. Chem. 269:2550-2561; (1993) Science 259: 174549; McClements et al. (1996) Proc. Natl. Acad. Sci. USA 93:11414-11420; Ju et al. (1998) Diabetologia 41:736-739; and Robinson et al. (1997) Sem. Immunol. 9:271. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-WNV proteins or epitopes thereof, e.g., non-WNV immunogens or epitopes thereof, cytokines, etc. to be expressed by vector or vectors in, or included in, multivalent or cocktail immunogenic compositions or vaccines of the invention.

The present invention also relates to preparations comprising vectors, such as expression vectors, e.g., vaccines or immunogenic compositions. The preparations can comprise, consist essentially of, or consist of one or more vectors, e.g., expression vectors, such as in vivo expression vectors, comprising, consisting essentially or consisting of (and advantageously expressing) one or more of the WNV polynucleotides encoding E, prM, M or combinations or polyproteins thereof, especially as above-mentioned (e.g., E, or E and prM, or E and M, or E and prM and M, or polyprotein E-prM-M, or polyprotein prM-E, or polyprotein M-E, or at least an epitope thereof); and, advantageously, the vector contains and expresses a polynucleotide that includes, consists essentially of, or consists of a coding region encoding WNV E, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of the WN virus, e.g. prM, M, prM-M, or an epitope thereof.

According to another embodiment, the vector or vectors in the preparation comprise, or consist essentially of, or consist of polynucleotide(s) encoding one or more proteins or epitope(s) thereof of WNV, e.g., of one or more WN virus strains or isolates; and, advantageously, in a suitable host cell or under appropriate conditions, the vector or vectors have express of the polynucleotide(s). The inventive preparation advantageously comprises, consists essentially of, or consists of, at least two vectors comprising, consisting essentially of, or consisting of, and advantageously also expressing, preferably in vivo under appropriate conditions or suitable conditions or in a suitable host cell, polynucleotides from different WN strains or isolates encoding the same proteins and/or for different proteins, but preferably for the same proteins. As to preparations containing one or more vectors containing, consisting essentially of or consisting of polynucleotides encoding, and preferably expressing, advantageously in vivo, WNV E, or prM-M-E, or an epitope thereof, it is preferred that the expression products be from two, three or more different WN strains or isolates, advantageously strains. The invention is also directed at mixtures of vectors that contain, consist essentially of, or consist of coding for, and express, prM, M, E, prM-M, prM-E or M-E of different strains. It is preferred that in such mixtures, at least one vector contain, consist essentially of, or consist of, coding for, and express, E.

According to yet another embodiment and as will be shown in greater detail hereinafter, the other vector or vectors in the preparation comprise and express one or more cytokines and/or one or more immunogens of one or more other pathogenic agents. Sources for cytokines, immunogens for other pathogenic agents or epitope(s) thereof, and nucleic acid molecules encoding the same, may be found in herein cited documents, as well as in, WO02096349, WO0208162, WO0020025, WO00152888, WO0145735, WO00127097, WO01/16330, WO0077210, WO0077188, WO0077043, WO9842743, WO9833928, WO9749826, WO9749825, U.S. Pat. Nos. 6,387,376, 6,306,400, 6,159,477, 6,156,567, 6,153,199, 6,090,393, 6,074,649, 6,033,670.

The invention also relates to various combinations of different embodiments herein disclosed, e.g., compositions or vaccines containing various vectors, compositions or vaccines containing a vector and a protein (WNV and/or non-WNV) and/or cytokine, etc.

The preparations comprising an in vitro or in vivo expression vector comprising and expressing a polynucleotide encoding prM-M-E constitute a preferred embodiment of the invention. According to another advantageous embodiment of the invention, the in vivo or in vitro expression vectors comprise as the sole polynucleotide or polynucleotides of the WN virus, a polynucleotide encoding the protein E, optionally associated with prM and/or M, preferably encoding prM-M-E and optionally a signal sequence of the WN virus. Thus, in advantageous embodiments the polynucleotide can additionally encode a signal sequence of WNV.

According to a further advantageous embodiment, one or more of the non-structural proteins NS2A, NS2B and NS3 are expressed jointly with the structural proteins according to the invention, either via the same expression vector, or via their own expression vector. They are preferably expressed together on the basis of a single polynucleotide, e.g., as a polyprotein. That is, in certain embodiments, the vector further contains, consists essentially of or consists of, one or more nucleotides encoding NS2A, NS2B and/or NS3, or a composition or vaccine further contains, consists essentially of or consists of one or more additional vectors that contains, consists essentially of or consists of, one or more nucleotides encoding NS2A, NS2B and/or NS3; this vector or these vectors advantageously express(es) the non-structural protein(s); and, NS2A, NS2B and NS3 are advantageously expressed jointly, and more advantageously, as a polyprotein.

Thus, the invention also relates to vector such as an in vivo or in vitro expression vector comprising, consisting essentially of or consisting of the polynucleotide(s) encoding NS2A, NS2B, NS3, combinations thereof, including polyproteins thereof, such as NS2A-NS2B-NS3. The vector can be one of the above-described vectors comprising, consisting essentially of or consisting of a polynucleotide encoding one or more structural proteins, e.g., E, prM, M, combinations and polyproteins thereof such as prM-E, M-E, or prM-M-E, e.g., such a vector that contains or consists essentially of polynucleotides encoding structural protein or proteins or epitopes thereof can also contain or consist essentially thereof polynucleotides encoding one or more non-structural proteins, combination thereof, polyproteins thereof, or epitopes thereof. As an alternative, the invention relates to a preparation as described hereinbefore, also incorporating at least one of the vectors that contain polynucleotide(s) encoding and advantageously expressing a non-structural protein and optionally a pharmaceutically or veterinarily acceptable carrier, vehicle or excipient.

For preparing vectors, e.g., expression vectors, according to the invention, the skilled artisan has available various strains of the WN virus and the description of the nucleotide sequence of their genome, see, e.g., discussion herein and Savage H. M. et al. (Am. J. Trop. Med. Hyg. 1999, 61 (4), 600-611), table 2, which refers to 24 WN virus strains and gives access references to polynucleotide sequences in GenBank, as well as other herein cited and incorporated by reference documents.

Reference is, for example, made to strain NY99 (GenBank AF196835). In GenBank, for each protein the corresponding DNA sequence is given (nucleotides 466-741 for prM, 742-966 for M, 967-2469 for E, or 466-2469 for prM-M-E, 3526-4218 for NS2A, 4219-4611 for NS2B and 4612-6468 for NS3, or 3526-6468 for NS2A-NS2B-NS3). By comparison and alignment of the sequences, the determination of a polynucleotide encoding such a protein in another WNV strain is readily determined.

As discussed herein, the term polynucleotide is understood to mean a nucleic acid sequence encoding a protein or a fragment thereof or an epitope thereof specific to a particular WN virus; and, by equivalence, the term polynucleotide is understood to include the corresponding nucleotide sequences of the different WN virus strains and nucleotide sequences differing by due to codon degeneracy. Thus, a polynucleotide encoding WNV E is understood as comprising, consisting essentially of or consisting of (a) nt 466-2469 of NY99 (GenBank AF196835), (b) corresponding sequences of different WNV strains, and (c) nucleotide sequences that encode WNV E but differ from (a) and (b) due to codon degeneracy.

Within the family of WN viruses, identity between amino acid sequences ("sequence identity") prM-M-E relative to that of NY99 is equal to or greater than 90%. Thus, the invention covers polynucleotides encoding proteins having amino acid sequences, whose sequence identity or homology with the native WNV amino acid sequence for the protein is equal to or greater than 90%, advantageously 92%, preferably 95% and more specifically 98%. For instance, an expressed E protein can have greater than 90% identity with the sequence of the polypeptide expressed from (a) nt 466-2469 of NY99 (GenBank AF196835), (b) corresponding sequences of different WNV strains, and/or (c) nucleotide sequences that encode WNV E but differ from (a) and (b) due to codon degeneracy; advantageously at least 92%, more advantageously at least 95%, and even more advantageously at least 98%.

Therefore, the invention comprehends polynucleotides that express such homologous polypeptides; and the corresponding degrees of homology or identity of those polynucleotides to polynucleotides encoding polypeptides to which homologous polypeptides have homology or identity. Homologous polypeptides advantageously contain one or more epitopes of the polypeptide to which there is identity or homology, such that homologous polypeptides exhibit immunological similarity or identity to the polypeptide to which there is identity or homology, e.g., the homologous polyptide elicits similar or better immune response (to the skilled immunologist) than polypeptide to which there is identity or homology and/or the homologous polypeptide binds to antibodies elicited by and/or to which the polypeptide to which there is identity or homology binds, advantageously and not to other antibodies.

Accordingly, fragments of homologous polypeptides and of polypeptides to which there is identity or homology, advantageously those fragments which exhibit immunological similarity or identity to homologous polypeptides or polypeptides to which there is identity or homology, are envisoned as being expressed, and therefore, polynucleotides therefor which may represent fragments of polynucleotides of homologous polypeptides and of polypeptides to which there is identity or homology, are also envisioned by and useful in the instant invention.

The term "sequence identity" indicates a quantitative measure of the degree of homology between two amino acid sequences of equal length or between two nucleotide sequences of equal length. If the two sequences to be compared are not of equal length, they must be aligned to best possible fit possible with the insertion of gaps or alternatively, truncation at the ends of the protein sequences. The sequence identity can be calculated as $((N_{ref}-N_{dif})/N_{ref}) \times 100$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (Pearson W. R and D. J. Lipman (1988) PNAS USA 85:2444-2448) (www.ncbi.nlm.nih.gov/cgi-bin/BLAST). In one aspect of the invention, alignment is performed with the sequence alignment method ClustalW with default parameters as described by Thompson J., et al 1994, available at http://www2.ebi.ac.uk/clustalw/. Thus, a polynucleotide can be any nucleic acid molecule including DNA, RNA, LNA (locked nucleic acids), PNA, RNA, dsRNA, RNA-DNA-hybrid, and non-naturally occurring nucleosides.

And from the herein disclosure, advantageously, proteins or polypeptides expressed by vectors of the invention are immunologically active peptides and polypeptides, e.g., with respect to polypeptides or proteins of NY99, proteins or polypeptides expressed by vectors of the invention can be:

a) corresponding proteins or polypeptides of one or more different WN virus strains or isolates, b) proteins differing therefrom (from NY99 and/or a)), but maintaining with a native WN protein an identity equal to or greater than 90%, advantageously greater than or equal to 92%, more advantageously greater than or equal to 95% and even more advantageously greater than or equal to 98%.

Thus, a reference to a WNV protein may involve additional proteins as herein discussed.

Different WN virus strains are accessible in collections, especially in the American Type Culture Collection (ATCC), e.g. under access numbers VR-82 or VR-1267, and as otherwise herein discussed, with it noted that the Kunjin virus is considered to be a WN virus.

In the invention, preferably the polynucleotide also comprises a nucleotide sequence encoding a signal peptide, located upstream of the coding for the expressed protein to facilitate the secretion thereof; and accordingly, the invention comprehends the expression of a WNV polypeptide, such as a WNV antigen, immunogen, or fragment thereof, e.g., epitope, with a leader or signal sequence. The leader or signal sequence can be an endogenous sequence, e.g. the natural signal sequence of a WNV polypeptide, which can be from the same WN virus strain or isolate or another strain or isolate. For example, for the NY99 WN virus, the endogenous signal sequence for E is encoded at nucleotides 922 to 966 of the GenBank sequence and for prM it is encoded at nucleotides 421 to 465. The leader or signal sequence can also be a heterologous sequence, and thus encoded by a nucleotide sequence that is heterologous to WNV. For example, the leader or signal sequence can be endogenous to the vector, or a leader or signal sequence that is heterologous to both the vector and WNV, such as a signal peptide of tissue plasminogen activator (tPA), e.g., human tPA, and thus, the vector or the polynucleotide therein can include a sequence encoding the leader or signal peptide, e.g., the leader or signal peptide of human tissue plasminogen activator (tPA) (Hartikka J. et al., Human Gene Therapy, 1996, 7, 1205-1217). The nucleotide sequence encoding the signal peptide is advantageiously inserted in frame and upstream of the sequence encoding the WNV polypeptide, e.g., E or its combinations, e.g. prM-M-E, M-E, prM-E.

According to an embodiment of the invention, the vectors, e.g., in vivo expression vectors, are viral vectors.

Viral vectors, e.g., viral expression vectors are advantageously: poxviruses, e.g. vaccinia virus or an attenuated vaccinia virus, (for instance, MVA, a modified Ankara strain obtained after more than 570 passages of the Ankara vaccine strain on chicken embryo fibroblasts; see Stickl H. and Hochstein-Mintzel V., Munch. Med. Wschr., 1971, 113, 1149-1153; Sutter G. et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), avipox virus or an attenuated avipox virus (e.g., canarypox, fowlpox, dovepox, pigeonpox, quailpox, ALVAC or TRO-VAC; see, e.g. U.S. Pat. No. 5,505,941, 5,494,807), swinepox, raccoonpox, camelpox, or myxomatosis virus; adenoviruses, such as avian, canine, porcine, bovine, human adenoviruses; or herpes viruses, such as equine herpes virus (EHV serotypes 1 and 4), canine herpes virus (CHV), feline herpes virus (FHV), bovine herpes viruses (BHV serotypes 1 and 4), porcine herpes virus (PRV), Marek's disease virus (MDV serotypes 1 and 2), turkey herpes virus (HVT or MDV serotype 3), or duck herpes virus. When a herpes virus is used, the vector HVT is preferred for the vaccination of the avian species and the vector EHV for the vaccination of horses.

More generally in certain embodiments, it may be advantageous to match a vector to a host, such as an equine virus, e.g., EHV to use in equines, or a vector that is an avian pathogen, such as fowlpox HVT, MDV or duck herpes to use in avians such as poultry or chickens, or a vector that is a bovine pathogen such as BHV to use in bovines such as cows, or a vector that is a porcine pathogen such a porcine herpes virus to use in porcines, or a vector that is a canine pathogen such as canine adenovirus or canine herpes virus to use in canines such as dogs, a vector that is a feline pathogen such as FHV to use in felines, as this may allow for an immune response against the vector and thus provide an immune response against a pathogen of the host or target species in addition to an immune response against WNV.

However, it is also noted that it can be advantageous that the vector not be a natural pathogen of the host; for instance, so that the vector can have expression of the exogenous, e.g., WNV coding sequences, but with limited or no replication; for example, the use of an avipox vector in a mammalian host, as in U.S. Pat. No. 5,174,993. It is also noted that the invention comprehends vaccines, immunological and immunogenic compositions, with those terms being used in the sense attributed to them in the art; see, e.g., documents cited herein, such as U.S. Pat. No. 6,497,883.

According to another embodiment of the invention, the poxvirus vector, e.g., expression vector, is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by Intervet; and, reference is also made to U.S. Pat. No. 5,766,599 which pertains to the attenuated fowlpox strain TROVAC.

For information on poxviruses and how to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and 5,766,599 inter alia; as to canarypox mention is made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Preferably, when the expression vector is a poxvirus, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

Preferably, for the vaccination of mammals the expression vector is a canarypox or a fowlpox. In this way, there can be expression of the heterologous proteins, e.g., WNV proteins, with limited or no productive replication. Preferably, for the vaccination of avians, e.g., chickens, ducks, turkeys and geese, the expression vector is a canarypox or a fowlpox.

When the expression vector is a herpes virus of turkeys or HVT, advantageous insertion site or sites are located in the BamHI I fragment or in the BamHI M fragment of HVT. The HVT Bam-HI I restriction fragment comprises several open reading frames (ORFs) and three intergene regions and comprises several preferred insertion zones, such as the three intergene regions 1, 2 and 3, which are preferred regions, and ORF UL55 (see, e.g., FR-A-2 728 795, U.S. Pat. No. 5,980,906). The HVT BamHI M restriction fragment comprises ORF UL43, which is also a preferred insertion site (see, e.g., FR-A-2 728 794, U.S. Pat. No. 5,733,554).

When the expression vector is an EHV-1 or EHV-4 herpes virus, advantageous insertion site or sites include TK, UL43 and UL45 (see, e.g., EP-A-668355).

Preferably, when the expression vector is a herpes virus, the polynucleotide to be expressed is inserted under the control of a eukaryotic promoter, such as a strong eukaryote promoter, preferably a CMV-IE (murine or human) promoter; that is, in embodiments herein, the polynucleotide to be expressed is operably linked to a promoter, and in herpes virus embodiments, advantageously the polynucleotide to be expressed is operably linked to a strong eukatyotic promoter such as a mCMV-IE or hCMV-IE promoter. Strong promoters are also discussed herein in relation to plasmids as vectors.

According to a yet further embodiment of the invention, the vector, e.g., in vivo expression vector, is a plasmidic vectors, also known as a plasmid vector or a DNA plasmid vector, e.g., the type of plasmid vector employed in that which is known as a DNA vaccine (in contrast with a transfection plasmid used in homologous recombination to generate a recombinant virus, which is not used in a DNA vaccine).

The term plasmid covers any DNA transcription unit in the form of a polynucleotide sequence comprising a polynucleotide according to the invention and the elements necessary for its in vivo expression of that which is encoded by the polynucleotide in a cell or cells of the desired host or target; and, in this regard, it is noted that there is a supercoiled or non-supercoiled, circular plasmid, as well as linear forms, all of which are intended to be within the scope of the invention.

Each plasmid comprises or contains or consists essentially of, in addition to the polynucleotide encoding the antigen or epitope of the pathogen or pathogens, e.g., WNV (or WNV and another pathogen), a promoter for expression, in the host cells cor cells, of the polynucleotide; and, the polynucleotide may be said to be operably linked to the promoter or under the control of the promoter or dependent upon the promoter. In general, it is advantageous to employ a eukaryotic promoter, e.g., a strong eukaryotic promoter. The preferred strong eukaryote promoter is the early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT WO87/03905. The CMV-IE promoter is preferably a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18 (22), 2337-2344), or the actin promoter (Miyazaki J. et al., Gene, 1989, 79 (2), 269-277).

Functional subfragments of these promoters, i.e., portions of these promoters that maintain an adequate promoting activity, are included within the present invention, e.g. truncated CMV-IE promoters according to WO98/00166 or U.S. Pat. No. 6,156,567 can be used in the practice of the invention. A promoter in the practice of the invention consequently includes derivatives and subfragments of a full-length promoter that maintain an adequate promoting activity and hence function as a promoter, preferably promoting activity substantially similar to that of the actual or full-length promoter from which the derivative or subfragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and subfragments.

Preferably, the plasmids comprise or consist essentially of other expression control elements. It is particularly advantageous to incorporate stabilizing sequence(s), e.g., intron sequence(s), preferably intron II of the rabbit β-globin gene (van Ooyen et al., Science, 1979, 206: 337-344).

As to the polyadenylation signal (polyA) for the plasmids and viral vectors other than poxviruses, use can more be made of the polyA signal of the bovine growth hormone (bGH) gene (see U.S. Pat. No. 5,122,458), or the poly(A) signal of the rabbit β-globin gene or the poly(A) signal of the SV40 virus.

As to other expression control elements usable in plasmids, attention is directed to expression control elements that are useful in herpes virus expression vectors.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

Protein production can take place by the transfection of mammalian cells by plasmids, by replication or expression without productive replication of viral vectors on mammal cells or avian cells, or by Baculovirus replication (see, e.g., U.S. Pat. No. 4,745,051; Vialard J. et al., J. Virol., 1990 64 (1), 37-50; Verne A., Virology, 1988, 167, 56-71), e.g. *Autographa californica* Nuclear Polyhedrosis Virus AcNPV, on insect cells (e.g. Sf9 Spodoptera frugiperda cells, ATCC CRL 1711; see also U.S. Pat. Nos. 6,228,846, 6,103,526). Mammalian cells which can be used are advantageously hamster cells (e.g. CHO or BHK-21) or monkey cells (e.g. COS or VERO). Thus, the invention accordingly comprehends expression vectors incorporating a polynucleotide according to the invention, as well as the thus produced or expressed WNV proteins or fragments thereof from in vitro expression, and the preparations containing the same.

Accordingly, the present invention also relates to WNV protein-concentrated and/or purified preparations. When the polynucleotide encodes several proteins, they are cleaved, and the aforementioned preparations then contain cleaved proteins.

The present invention also relates to immunogenic compositions and vaccines against the WN virus comprising at least one in vivo expression vector according to the invention and a pharmaceutically or veterinarily acceptable excipient or carrier or vehicle, and optionally an adjuvant.

An immunogenic composition covers any composition which, once administered to the target species, induces an immune response against the WN virus. The term vaccine is understood to mean a composition able to induce an effective protection. The target species include mammals, e.g., equines, canines, felines, bovines, porcines and humans; reptiles, and birds or avians; preferably horse, dog, cat, pig, alligator; and, in the case of birds or avians, geese, turkeys, chickens and ducks. This list is meant to include reproducing animals, egg-laying animals, meat-producing animals or production animals (animals whose flesh is commonly consumed by some humans), and companion animals (animals who are kept as pets by humans).

The pharmaceutically or veterinarily acceptable carriers or vehicles or excipients are well known to the one skilled in the art. For example, a pharmaceutically or veterinarily acceptable carrier or vehicle or excipient can be a 0.9% NaCl saline solution or a phosphate buffer. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description of immunization and vaccination methods, and can also be determined by the skilled artisan from this disclosure read in conjunction with the knowledge in the art, without any undue experimentation.

The immunogenic compositions and vaccines according to the invention preferably comprise or consist essentially of one or more adjuvants. Particularly suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman D. M. et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) other adjuvants discussed in any document cited and incorporated by reference into the instant application, or (8) any combinations or mixtures thereof.

The oil in water emulsion (3), which is especially appropriate for viral vectors, can be based on:

light liquid paraffin oil (European pharmacopoeia type), isoprenoid oil such as squalane, squalene,
oil resulting from the oligomerization of alkenes, e.g. isobutene or decene,
esters of acids or alcohols having a straight-chain alkyl group, such as vegetable oils, ethyl oleate, propylene glycol, di(caprylate/caprate), glycerol tri(caprylate/caprate) and propylene glycol dioleate, or
esters of branched, fatty alcohols or acids, especially isostearic acid esters.

The oil is used in combination with emulsifiers to form an emulsion. The emulsifiers may be nonionic surfactants, such as:

esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated,
polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, Jun. 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., Nature 186: 778-780, Jun. 4, 1960.

With regard to structure, the acrylic or methacrylic acid polymers and EMA are preferably formed by basic units having the following formula:

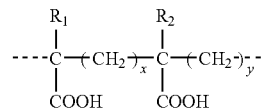

in which:
$R_1$ and $R_2$, which can be the same or different, represent H or $CH_3$
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

The cationic lipids (4) containing a quaternary ammonium salt which are advantageously but not exclusively suitable for plasmids, are preferably those having the following formula:

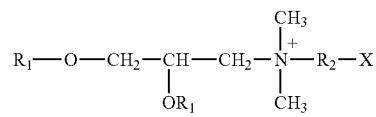

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group.

Among these cationic lipids, preference is given to DMRIE (N-(2-hydroxyethyl)-N,N-dimethyl-2,3-bis(tetradecyloxy)-1-propane ammonium; WO96/34109), preferably associated with a neutral lipid, preferably DOPE (dioleoyl-phosphatidyl-ethanol amine; Behr J. P., 1994, Bioconjugate Chemistry, 5, 382-389), to form DMRIE-DOPE.

Preferably, the plasmid mixture with the adjuvant is formed extemporaneously and preferably contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is preferably about 95: about 5 to about 5:about 95, more preferably about 1: about 1, e.g., 1:1.

The DMRIE or DMRIE-DOPE adjuvant:plasmid weight ratio can be between about 50: about 1 and about 1: about 10, such as about 10: about 1 and about 1:about 5, and preferably about 1: about 1 and about 1: about 2, e.g., 1:1 and 1:2.

The cytokine or cytokines (5) can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The cytokine(s) can be chosen from: interleukin 18 (IL-18), interleukin 12 (IL-12), interleukin 15 (IL-15), MIP-1α (macrophage inflammatory protein 1α; Marshall E. et al., Br., J. Cancer, 1997, 75 (12), 1715-1720), GM-CSF (Granulocyte-Macrophage Colony-Stimulating Factor). Particular reference is made to avian cytokines, for instance, those of the chicken, such as cIL-18 (Schneider K. et al., J. Interferon Cytokine Res., 2000, 20 (10), 879-883), cIL-15 (Xin K. -Q. et al., Vaccine, 1999, 17, 858-866), and equine cytokines, for instance equine GM-CSF (WO00/77210). Preferably, use is made of cytokines of the species to be vaccinated; that is, advantageously, the cytokine is matched to the target or host species, and, note for example, canine GM-CSF (example 8 of WO00/77043), feline GM-CSF (example 9 of WO00/77043).

WO00/77210 provides the nucleotide sequence and the amino acid sequence corresponding to equine GM-CSF, the in vitro GM-CSF production and the construction of vectors (e.g., plasmids and viral vectors) permitting in vivo equine GM-CSF expression. These proteins, plasmids and viral vectors can be used in immunogenic compositions and equine vaccines according to the invention. For example, use can be made of the plasmid pJP097 described in example 3 of WO00/77210 or use can be made of the teaching of the latter in order to produce other vectors or for the in vitro production of equine GM-CSF and the incorporation of the vectors or the equine GM-CSF into immunogenic compositions or equine vaccines according to the invention.

The present invention also relates to immunogenic compositions and so-called subunit vaccines, incorporating or comprising or consisting essentially of the protein E and optionally one or more other herein mentioned proteins of the WN virus, e.g., prM or M and advantageously produced by in vitro expression in the manner described herein, as well as a pharmaceutically or veterinarily acceptable carrier or vehicle or excipient.

The pharmaceutically or veterinarily acceptable carrier or vehicle or excipient can be determined by the skilled artisan without undue experimentation from the disclosure herein and the knowledge in the art, e.g., by reference to documents cited and incorporated herein or documents referenced in herein cited documents and incorporated herein by reference; and, can for example, be 0.9% NaCl saline solution or phosphate buffer.

The immunogenic compositions and subunit vaccines according to the invention preferably comprise or consist essentially of one or more adjuvants. Especially suitable for use in the present invention are (1) an acrylic or methacrylic acid polymer, or a maleic anhydride and alkenyl derivative polymer, (2) an immunostimulating sequence (ISS), such as an oligodeoxyribonucleotide sequence having one or more non-methylated CpG units (Klinman D. M. et al., Proc. Natl. Acad. Sci. USA, 1996, 93, 2879-2883; WO98/16247), (3) an oil in water emulsion, such as the emulsion SPT described on p 147 of "Vaccine Design, The Subunit and Adjuvant Approach", published by M. Powell, M. Newmann, Plenum Press 1995, and the emulsion MF59 described on p 183 of the same work, (4) a water in oil emulsion (EP-A-639 071), (5) saponin, such as Quil-A, or (6) alumina hydroxide or an equivalent. The different types of adjuvants defined under 1), 2) and 3) have been described in greater detail herein in connection with the expression vector-based vaccines and immunogenic compositions.

The doses and dose volumes are discussed herein in connection with the general description of immunization and vaccination methods.

Animals immunized with immunogenic compositions or vaccines according to the invention develop a specific immunity against WNV, which during a WNV infection involves a decrease of the viremia, and indeed can totally block the virus, as compared with unvaccinated control animals. This advantageous aspect of the invention may be used to stop the transmission of the WN virus, to limit the existence of viral reservoirs and to prevent outbreaks of West Nile disease, notably in human.

Another advantageous aspect of the invention is that protective immunity can be transmitted from vaccinated subjects to the offspring.

According to the invention, the vaccination against the WN virus can be combined with other vaccinations within the framework of vaccination programs, in the form of immunization or vaccination kits or methods, or in the form of multivalent immunogenic compositions and multivalent vaccines, i.e. comprising or consisting essentially of at least one vaccine component against the WN virus and at least one vaccine component against at least one other pathogenic agent. This also includes the expression by the same expression vector of genes of at least two pathogenic agents, including the WN virus.

The invention thus also relates to a multivalent or "cocktail" immunogenic composition or a multivalent or "cocktail" vaccine against the WN virus and against at least one other pathogen of the target species, using the same in vivo expression vector containing and expressing at least one polynucleotide of the WN virus according to the invention and at least one polynucleotide expressing an immunogen of another pathogen. As to combination or multivalent or "cocktail" immunogenic compositions or vaccines, as well as to immunogens or antigens or epitopes thereof to be in or expressed by such compositions or vaccines, attention is directed to herein cited and incorporated by reference documents, as well as to U.S. Pat. Nos. 5,843,456 and 6,368,603.

The "immunogen" expressed by a vector of the invention or used in multivalent or "cocktail" compositions or vaccines is understood to mean a protein, glycoprotein, polypeptide, peptide, epitope or derivative, e.g. fusion protein, inducing an immune response, preferably of a protective nature.

As discussed herein, these multivalent compositions or vaccines can also comprise or consist essentially of a pharmaceutically or veterinarily acceptable carrier or vehicle or excipient, and optionally an adjuvant.

The invention also relates to a multivalent immunogenic composition or a multivalent vaccine comprising at least one in vivo expression vector in which at least one polynucleotide of the WN virus is inserted (and expressed in vivo) and at least a second expression vector in which a polynucleotide encoding an immunogen of another pathogenic agent is inserted (and expressed in vivo). Such multivalent compositions or vaccines also comprise or consist essentially of a pharmaceutically or veterinarily acceptable carrier or vehicle or excipient, and optionally an adjuvant.

For antigen(s) or immunogen(s) or epitope(s) to be included in or expressed by a multivalent immunogenic composition or vaccine (in addition to WNV antigen(s), immunogen(s) or epitope(s)), including as to determining or ascertaining epitope(s), the skilled artisan may consult herein cited documents and documents cited in herein cited documents, all of which are incorporated by reference into the instant application.

For equine multivalent immunogenic compositions and multivalent vaccines, the additional equine pathogen(s), as to which additional equine antigen(s) or immunogen(s) or epitope(s) thereof are included in and/or expressed by the multivalent immunogenic compositions and multivalent vaccines, are advantageously chosen from among the group including viruses of equine rhinopneumonia, EHV-1 and/or EHV-4 (and preferably there is a combination of immunogens of EHV-1 and EHV-4), equine influenza virus, EIV, eastern encephalitis virus, EEV, western encephalitis virus, WEV, Venezuelan encephalitis virus, VEV (preference being given to a combination of the three, i.e., EEV, WEV and VEV), *Clostridium tetani* (tetanus), and mixtures thereof. Preferably, for EHV the immunogen is gB and/or gD see also U.S. Pat. Nos. 6,395,283, 6,248,333, 5,338,683, 6,183,750; for herpesvirus immunogens and constructs expressing the same); for EIV the immunogen is advantageously HA, NP and/or N; for viruses of encephalitis, the immunogen is advantageously C and/or E2; and for *Clostridium tetani* the immunogen is all or part of the subunit C of the tetanic toxin. Thus, the invention comprehends the use of polynucleotide(s) encoding (an) immunologically active fragment(s) or (an) epitope(s) of such immunogen(s).

For canine multivalent immunogenic compositions and multivalent vaccines, the additional canine pathogen(s), as to which additional canine antigen(s) or immunogen(s) or epitope(s) thereof are included in and/or expressed by the multivalent immunogenic compositions and multivalent vaccines, are advantageously chosen from among the group including viruses of measles disease virus, canine distemper virus (CDV), canine parainfluenza type 2 virus (CPI-2), canine herpesvirus type 1 (CHV-1), rabies virus (rhabdovirus), canine parvovirus (CPV), canine coronavirus (CCV), canine adenovirus, *Borrelia burgdorferi*, *Leptospira* and mixtures thereof. Preferably, for CDV the immunogen is advantageously F and/or HA (see also U.S. Pat. Nos. 6,309,647, 5,756,102 regarding CDV immunogens and constructs); for CPV the immunogen is advantageously VP2; for CCV the immunogen is advantageously S and/or M; for CHV-1 the immunogen is advantageously gB and/or gC and/or gD (see also U.S. Pat. No. 5,688,920, 5,529,780, regarding CHV immunogens and constructs); for rabies virus the immunogen is advantageously G (see also U.S. Pat. No. 5,843,456 regarding rabies combination compositions); for *Borrelia burgdorferi* the immunogen is advantageously OspA (see also U.S. Pat. No. 6,368,603 regarding OspA combination compositions). The invention thus comprehends the use of polynucleotide(s) encoding (an) immunologically active fragment(s) or an epitope(s) of such immunogen(s).

For feline multivalent immunogenic compositions and multivalent vaccines, the additional feline pathogen(s), as to which additional feline antigen(s) or immunogen(s) or epitope(s) thereof are included in and/or expressed by the multivalent immunogenic compositions and multivalent vaccines, are advantageously chosen from among the group including viruses of the feline herpesvirus type 1 (FHV-1), feline calicivirus (FCV), rabies virus (rhabdovirus), feline parvovirus (FPV), feline infectious peritonitis virus (FIPV), feline leukaemia virus (FeLV), feline immunodeficiency virus (FIV), *Chlamydia* and mixtures thereof. Preferably, for FeLV the immunogen is advantageously A and/or B and/or gag and/or pol, e.g., gag/pol; for FPV the immunogen is advantageously VP2; for FIPV the immunogen is advantageously S and/or M and/or N, e.g., S and M and/or N (see also U.S. Pat. Nos. 6,348,196 and 5,858,373 and immunogens and constructs thereof); for FHV the immunogen is advantageously gB and/or gC and/or gD, e.g., gB and gC and/or gD (see also U.S. Pat. Nos. 5,338,683, 6,183,750; for herpesvirus immunogens and constructs expressing the same); for FCV the immunogen is advantageously C; for FIV the immunogen is advantageously env and/or gag and/or pro, e.g., gag/pro, env, or env and gag/pro (see also immunogens and constructs discussed in Tartaglia et al., U.S. application Ser. No. 08/746, 668, filed Nov. 14, 1996); for rabies virus the immunogen is advantageously G. The invention thus comprehends the use of polynucleotide(s) encoding (an) immunologically active fragment(s) or (an) epitope(s) of said immunogen(s).

For avian multivalent immunogenic compositions and multivalent vaccines, the additional avian pathogen(s), as to which additional avian antigen(s) or immunogen(s) or epitope(s) thereof are included in and/or expressed by the multivalent immunogenic compositions and multivalent vaccines, are advantageously chosen from among the group including viruses of the Marek's disease virus (MDV) (e.g., serotypes 1 and 2, preferably 1), Newcastle disease virus (NDV), Gumboro disease virus or infectious bursal disease virus (IBDV), infectious bronchitis virus (IBV), infectious anaemia virus or chicken anemia virus (CAV), infectious laryngotracheitis virus (ILTV), encephalomyelitis virus or avian encephalomyelitis virus (AEV or avian leukosis virus ALV), virus of hemorragic enteritis of turkeys (HEV), pneumovirosis virus (TRTV), fowl plague virus (avian influenza), chicken hydropericarditis virus, avian reoviruses, *Escherichia coli, Mycoplasma gallinarum, Mycoplasma gallisepticum, Haemophilus avium, Pasteurella gallinarum, Pasteurella multocida gallicida*, and mixtures thereof. Preferably, for MDV the immunogen is advantageously gB and/or gD, e.g., gB and gD, for NDV the immunogen is advantageously HN and/or F, e.g., HN and F; for IBDV the immunogen advantageously is VP2; for IBV the immunogen is advantageously S (more advantageously S1) and/or M and/or N, e.g., S (or S1) and M and/or N; for CAV the immunogen is advantageously VP1 and/or VP2; for ILTV the immunogen is advantageously gB and/or gD; for AEV the immunogen advantageously is env and/or gag/pro, e.g., env and gag/pro or gag/pro; for HEV the immunogen is advantageously the 100K protein and/or hexon; for TRTV the immunogen is advantageously F and/or G, and for fowl plague the immunogen is advantageously HA and/or N and/or NP, e.g., HA and N and/or NP. The invention thus comprehends the use of polynucleotide(s) encoding (an) immunologically active fragment(s) or (an) epitope(s) of said immunogen(s).

By way of example, in a multivalent immunogenic composition or a multivalent vaccine according to the invention, to which one or more adjuvants has optionally been added (and hence the composition contains or consists essentially of or consists of one or more adjuvants) as discussed herein, and which is intended for equine species, it is possible to incorporate (and hence for the composition or vaccine to comprise, consist essentially of or consist of) one or more of the plasmids described in WO98/03198, advantageously as discussed in examples 8 to 25 thereof, and/or those described in WO/0077043 and which relate to the equine species, advantageously those described in examples 6 and 7 thereof. For the canine species, a multivalent composition or vaccine may contain or consist essentially of or consist of one or more of the plasmids described in WO98/03199, advantageously as discussed in examples 8 to 16 thereof, and/or those described in WO00/77043 and which relate to the canine species, advantageously those described in examples 2, 3 and 4 thereof; and, such compositions or vaccines can contain, consist essentially of or consist of one or more adjuvants. For the feline species, a multivalent composition or vaccine may contain or consist essentially of or consist of one or more of the plasmids described in WO98/03660, advantageously in examples 8 to 19 thereof, and/or those described in WO00/77043 and which relate to the feline species, advantageously those described in example 5 thereof; and, such compositions or vaccines can contain, consist essentially of or consist of one or more adjuvants. And for the avian species, a multivalent composition or vaccine may contain or consist essentially of or consist of one or more of the plasmids described in WO98/03659, advantageously in examples 7 to 27 thereof; and, such compositions or vaccines can contain, consist essentially of or consist of one or more adjuvants.

The immunogenic compositions or vaccines as discussed herein can also be combined with at least one conventional vaccine (e.g., inactivated, live attenuated, or subunit) directed against the same pathogen or at least one other pathogen of the species to which the composition or vaccine is directed. The immunogenic compositions or vaccines discussed herein can be administered prior to or after the conventional vaccine, e.g., in a "prime-boost" regimen.

The invention further comprehends combined vaccination employing immunogenic composition(s) and subunit vaccine(s) according to the invention. Thus, the invention also relates to multivalent immunogenic compositions and multivalent vaccines comprising one or more proteins according to the invention and one or more immunogens (as the term immunogen is discussed herein) of at least one other pathogenic agent (advantageously from among those herein and in documents cited and incorporated herein by reference) and/or another pathogenic agent in inactivated or attenuated form or as a subunit. In the manner described, these multivalent vaccines or compositions also contain, consist essentially of or consist of a pharmaceutically or veterinarily acceptable vehicle or excipient and optionally one or more adjuvants.

The present invention also relates to methods for the immunization and vaccination of a target species, e.g., as discussed herein.

The present invention also relates to methods for the immunization and/or vaccination of a target species, using a prime-boost regimen. The term of "prime-boost" refers to the successive administrations of two different vaccine types or immunogenic or immunological composition types having at least one immunogen in common. The priming administration (priming) is the administration of a first vaccine or immunogenic or immunological composition type and may comprise one, two or more administrations. The boost administration is the administration of a second vaccine or immunogenic or immunological composition type and may comprise one, two or more administrations, and, for instance, may comprise or consist essentially of annual administrations.

An embodiment of a prime-boost immunization or vaccination against WNV according to the invention is a prime-boost immunization or vaccination wherein the animal is first administered a (priming) DNA vaccine or immunological or immunogenic composition comprising or consisting essentially of and expressing in vivo at least one immunogen, antigen or epitope of WNV, and thereafter is administered (boosted with) a second type of vaccine or immunogenic or immunological composition containing or consisting essentially of or expressing at least one immunogen, antigen or epitope that is common to the priming vaccine or immunogenic or immunological composition. This second type of vaccine can be a an inactivated, or attenuated or subunit vaccine or immunogenic or immunological composition or a vector, e.g., recombinant or modified virus vaccine or immunogenic or immunological composition that has in vivo expression (e.g. poxvirus, herpesvirus, adenovirus). Poxviruses may be advantageously employed, e.g., attenuated vaccinia viruses, like MVA or NYVAC, and avipox viruses, like canarypox viruses and fowlpox viruses.

Advantageously, the DNA vaccine is intended to induce a priming immune response specific for the expressed immunogen, antigen or epitope or "DNA induced immune response" (such as a gamma-interferon+($IFN_\gamma$+) T cell memory response specific for the expressed immunogen, antigen or epitope) which is boostable (can be boosted) by a subsequent administration (boost) of an inactivated vaccine or immunological composition or a live recombinant vaccine comprising or consisting essentially of a viral vector, such as a live recombinant poxvirus, containing or consisting essentially of and expressing in vivo at least the same immunogen(s) or antigen(s) or epitope(s) expressed by the DNA vaccine. The $IFN_\gamma$+ T cell memory response specific for the expressed WNV immunogen can be shown in a quantitative enzyme-linked immune spot (ELISPOT) assay using peripheral blood mononuclear cells (PBMCs) (Laval F. et al., Vet. Immunol. Immunopathol., 2002, 90(3-4), 191-201).

The "boost" may be administered from about 2 weeks to about 6 months after the "priming", such as from about 3 to about 8 weeks after the priming, and advantageously from about 3 to about 6 weeks after the priming, and more advantageously, about 4 weeks after the priming.

For equines, the priming can be done with a DNA vaccine or immunogenic or immunological composition comprising or consisting essentially of and expressing in vivo nucleic acid molecule(s) encoding a WNV immunogen, antigen or epitope according to the invention and the boost is advantageously done with a vaccine or immunogenic or immunological composition comprising a recombinant live viral vector (e.g. poxvirus, herpesvirus, adenovirus), such as a recombinant fowlpox virus or recombinant canarypox virus, recombinant EHV-1 or EHV-4, comprising or consisting essentially of nucleic acid molecule(s) encoding and expressing in vivo at least one of the same WNV immunogen(s), antigen(s) or epitope(s) as the DNA vaccine or immunogenic or immunological composition expresses. In another embodiment these priming and boost vaccines or immunological or immunogenic compositions can be adjuvanted, for instance, by DMRIE-DOPE for the priming DNA vaccine or immunological or immunogenic composition and by Carbopol® for the boost recombinant vaccine or immunological or immunogenic composition.

The priming may be performed on a young foal that can have maternal antibodies against WNV (against which immunization or vaccination is directed). Advantageously, the DNA vaccine or immunological or immunogenic composition is administered to the young foal from foaling up to and including about 16 weeks of age, such as from foaling up to and including about 8 weeks of age, for instance, from foaling up to and including about 6 weeks of age, e.g., from foaling up to and including about 4 weeks of age.

For felines, the priming can be done with a DNA vaccine or immunogenic or immunological composition according to the invention comprising or consisting essentially of and expressing in vivo nucleic acid molecule(s) encoding a WNV immunogen, antigen or epitope and the boost is advantageously done with a vaccine or immunogenic or immunological composition comprising or consisting essentially a recombinant live viral vector (e.g. poxvirus, herpesvirus, adenovirus, advantageously recombinant fowlpox virus or recombinant canarypox virus, recombinant FHV, recombinant canine adenovirus), comprising or consisting essentially of nucleic acid molecule(s) encoding and expressing in vivo at least one WNV immunogen, antigen or epitope that is the same as that expressed by the DNA vaccine do. In another embodiment these priming and boost vaccines or immunological or immunogenic compositions can be adjuvanted, for instance, by DMRIE-DOPE for the priming DNA vaccine or immunological or immunogenic composition and by Carbopol® for the boost recombinant vaccine or immunological or immunogenic composition.

The priming may be performed on a young kitten that can have maternal antibodies against WNV (against which immunization or vaccination is directed). The DNA vaccine or immunological or immunogenic composition can be administered to the young kitten from birth up to and including about 12 weeks of age, for instance, from birth up to and including about 8 weeks of age, advantageously from birth up to and including about 6 weeks of age, e.g., from birth up to and including about 4 weeks of age.

For canines, the priming can be done with a DNA vaccine or immunogenic or immunological composition according to the invention comprising or consisting essentially of and expressing in vivo nucleic acid molecule(s) encoding a WNV immunogen, antigen or epitope and the boost is advantageously done with a vaccine or immunogenic or immunological composition comprising or consisting essentially a recombinant live viral vector (e.g. poxvirus, herpesvirus, adenovirus, advantageously recombinant fowlpox virus or recombinant canarypox virus, recombinant CHV, recombinant canine adenovirus), comprising or consisting essentially of nucleic acid molecule(s) encoding and expressing in vivo at least one WNV immunogen, antigen or epitope that is the same as that expressed by the DNA vaccine do. In another embodiment these priming and boost vaccines or immunological or immunogenic compositions can be adjuvanted, for instance, by DMRIE-DOPE for the priming DNA vaccine or immunological or immunogenic composition and by Carbopol® for the boost recombinant vaccine or immunological or immunogenic composition.

The priming may be performed on a young puppy that can have maternal antibodies against WNV (against which immunization or vaccination is directed).The DNA vaccine or immunological or immunogenic composition can be administered to the young puppy from birth up to and including about 12 weeks of age, for instance, from birth up to and including about 8 weeks of age, advantageously from birth up to and including about 6 weeks of age, e.g., from birth up to and including about 4 weeks of age.

For avians, the priming can be done with a DNA vaccine or immunogenic or immunological composition according to the invention comprising or consisting essentially of and expressing in vivo nucleic acid molecule(s) encoding a WNV immunogen, antigen or epitope and the boost is advantageously done with a vaccine or immunogenic or immunological composition comprising or consisting essentially a recombinant live viral vector (e.g. poxvirus, herpesvirus, adenovirus, advantageously recombinant fowlpox virus or recombinant canarypox virus, recombinant HVT, recombinant MDV, recombinant avian adenovirus), comprising or consisting essentially of nucleic acid molecule(s) encoding and expressing in vivo at least one WNV immunogen, antigen or epitope that is the same as that expressed by the DNA vaccine do. In another embodiment these priming and boost vaccines or immunological or immunogenic compositions can be adjuvanted, for instance, by DMRIE-DOPE for the priming DNA vaccine or immunological or immunogenic composition and by Carbopol® for the boost recombinant vaccine or immunological or immunogenic composition.

The priming may be performed on a young avian (bird, e.g., chicken) that can have maternal antibodies against WNV (against which immunization or vaccination is directed).The DNA vaccine or immunological or immunogenic composition can be administered to the young avian (bird, such as chicken) from about one day up to and including about 4 weeks of age, for instance, from one day up to and including about 3 weeks of age; and, the boost is administered from about 2 to about 8 weeks after the priming, advantageously from about 2 weeks to about 4 weeks after priming. For the layers, the boost vaccine or immunological or immunogenic composition may alternatively be administered to about 17 weeks of age for hens, to about 25 weeks of age for ducks and to about 30 weeks of age for turkey hens. Another administration of the boost vaccine or immunological or immunogenic composition can be done before each laying period.

In an embodiment, the priming DNA vaccine or immunological or immunogenic composition comprises or consists essentially of a plasmid encoding and expressing prM-M-E polyprotein, such as the plasmid pFC115 (example 17), that so encodes and expresses the prM-M-E polyprotein, and the boost recombinant vaccine or immunological or immunogenic composition comprises or consists essentially of a poxvirus such as a canarypox virus, for instance, the recombinant canarypox virus vCP2017 (example 18.1). In another embodiment these priming and boost vaccines or immunological or immunogenic compositions can be adjuvanted: the DNA vaccine or immunological or immunogenic composition containing the plasmid pFC115 can be adjuvanted by DMRIE-DOPE, such as described in example 20; and the recombinant vaccine or immunological or immunogenic composition containing vCP2017 can be adjuvanted by Carbopol®, such as described in example 19.

In a further embodiment, the priming DNA vaccine or immunological or immunogenic composition comprises or consists essentially of a plasmid encoding and expressing prM-M-E polyprotein, such as the plasmid pFC115 (example 17) and the boost recombinant vaccine or immunological or immunogenic composition comprises a poxvirus such as a fowlpox virus, e.g., the recombinant fowlpox virus vFP2000 (example 28). In another embodiment these priming and boost vaccines or immunological or immunogenic compositions can be adjuvanted: the DNA vaccine or immunological or immunogenic composition containing the plasmid pFC115 can be adjuvanted by DMRIE-DOPE, as described in example 20; and the recombinant vaccine or immunological or immunogenic composition containing vFP2000 can be adjuvanted by Carbopol®, as described in example 29.

The invention also relates to kits for performing prime-boost methods comprising or consisting essentially of a priming vaccine or immunological or immunogenic composition and a boost vaccine or immunological or immunogenic compositions in separate containers, optionally with instructions for admixture and/or administration.

The amounts (doses) administered in the priming and the boost and the route of administration for the priming and boost can be as herein discussed, such that from this disclosure and the knowledge in the art, the prime-boost regimen can be practiced without undue experimentation. Furthermore, from the disclosure herein and the knowledge in the art, the skilled artisan can practice the methods, kits, etc. herein with respect to any of the herein-mentioned target species.

These methods can comprise, consist essentially of or consist of the administration of an effective quantity of an immunogenic composition or vaccine according to the invention.

This administration can be by the parenteral route, e.g. by subcutaneous, intradermic or intramuscular administration, and/or by oral and/or nasal routes. Advantageously, this administration is intramuscularly or subcutaneously. One or more administrations can take place, such as two administrations.

Vaccines or immunogenic compositions can be injected by a needleless, liquid jet injector or powder jet injector. For plasmids it is also possible to use gold particles coated with plasmid and ejected in such a way as to penetrate the cells of the skin of the subject to be immunized (Tang et al., Nature 1992, 356, 152-154). Other documents cited and incorporated herein may be consulted for administration methods and apparatus of vaccines or immunogenic compositions of the invention. The needleless injector can also be for example Biojector 2000 (Bioject Inc., Portland Oreg., USA).

Advantageously, the immunogenic compositions and vaccines according to the invention comprise or consist essentially of or consist of an effective quantity to elicit an immunological response and/or a protective immunological response of one or more expression vectors and/or polypeptides as discussed herein; and, an effective quantity can be determined from this disclosure, including the documents incorporated herein, and the knowledge in the art, without undue experimentation.

In the case of immunogenic compositions or vaccines based on a plasmid vector, a dose can comprise, consist essentially of or consist of, in general terms, about in 10 µg to about 2000 µg, advantageously about 50 µg to about 1000 µg. The dose volumes can be between about 0.1 and about 2 ml, preferably between about 0.2 and about 1 ml.

These doses and dose volumes are suitable for the vaccination of equines and other target species that are mammals such as canines, felines.

For the vaccination or immunization of an avian, a dose is advantageously between about 10 µg and about 500 µg and preferably between about 50 µg and about 200 µg. The dose volumes can be between about 0.1 and about 1 ml, preferably between about 0.2 and about 0.5 ml.

One skilled in the art can determine the effective plasmid dose to be used for each immunization or vaccination protocol and species from this disclosure and the knowledge in the art.

In the case of immunogenic compositions or vaccines based on a poxvirus, a dose can be between about $10^2$ pfu and about $10^9$ pfu.

For equines and other target species that are mammals such as felines and canines, when the vector is a vaccinia virus, the dose is more advantageously between about $10^4$ pfu and about $10^9$ pfu, preferably between about $10^6$ pfu and about $10^8$ pfu and when the vector is a canarypox virus, the dose is more advantageously between about $10^5$ pfu and about $10^9$ pfu and preferably between about $10^{5.5}$ pfu or about $10^6$ pfu and about $10^8$ pfu.

For an avian, when the vector is a poxvirus such as a canarypox virus, the dose is more advantageously between about $10^3$ pfu and about $10^7$ pfu, preferably between about $10^4$ pfu and about $10^6$ pfu; and, when the vector is a poxvirus such as a fowlpox virus, the dose is more advantageously between about $10^2$ pfu and about $10^5$ pfu, preferably between about $10^3$ pfu and about $10^5$ pfu. From this disclosure and the knowledge in the art, the skilled artisan can determine the suitable dose when the vector is another avipox virus, such as a dovepox, pigeonpox, etc.

In the case of immunogenic compositions or vaccines for a mammalian target species, based on a viral vector other than a poxvirus, such as a herpes viruses or adenovirus, a dose is generally between about $10^3$ pfu and about $10^8$ pfu; and, in the case of such non-poxvirus-viral-vector-based immunogenic compositions for avian species or avian vaccines, a dose is generally between about $10^3$ pfu and about $10^6$ pfu. For such non-poxvirus-viral-vector-based immunogenic or vaccine compositions for larger target mammal species, e.g., larger cats (e.g., kept in a zoo) or equines, e.g., in the case of equine immunogenic or vaccine compositions, a dose is advantageously between about $10^6$ pfu and about $10^8$ pfu.

The dose volume of immunogenic and vaccine compositions for target species that are mammals, e.g., the dose volume of equine immunogenic or vaccine compositions, based on viral vectors, e.g., non-poxvirus-viral-vector-based immunogenic or vaccine compositions, is generally between about 0.5 and about 2.5 ml, such as between about 0.5 and about 2.0 ml, preferably between about 1.0 and about 2.0 ml, preferably about 1.0 ml. The dose volume of immunogenic or vaccine compositions for avians based on viral vectors, e.g., the dose volume of non-poxvirus-viral-vector-based avian immunogenic or vaccine compositions, is generally between about 0.1 and about 1.0 ml, preferably between about 0.1 and about 0.5 ml and more advantageously between about 0.2 and about 0.3 ml. Also in connection with such a vaccine or immunogenic composition, from the disclosure herein and the knowledge in the art, the skilled artisan can determine the number of administrations, the administration route, and the doses to be used for each immunization or vaccination protocol, without any undue experimentation. For instance, there can be two administrations to a horse, e.g. at 35 day intervals.

In the case of subunit immunogenic compositions or subunit vaccines, with reference to the amount of active ingredient, e.g., subunit (antigen, immunogen, epitope) a dose comprises or consists essentially of or consists of, in general terms, about 10 µg to about 2000 µg, advantageously about 50 µg to approximately 1000 µg. The dose volume of such immunogenic or vaccine compositions for target species that are mammals, e.g., for equines, is generally between about 1.0 and about 2.0 ml, preferably between about 0.5 and about 2.0 ml and more advantageously about 1.0 ml. The dose volumes of such immunogenic or vaccine compositions avians is generally between about 0.1 and about 1.0 ml, preferably between about 0.1 and about 0.5 ml, and more advantageously between 0.2 and 0.3 ml. Also for such a vaccine or immunogenic composition, the skilled artisan, from this disclosure and the knowledge in the art, can, without any undue experimentation, determine the number of administrations, the administration route and the doses to be used for each immunization or vaccination protocol.

The invention also relates to the use of an in vivo expression vector or a preparation of vectors and/or polypeptides according to the invention, for the formulation of an immunogenic composition or a vaccine intended to protect a target species, or elicit in the target species an immunological response, against the WN virus, and in certain embodiments, against at least one other pathogenic agent.

A vaccine based on plasmid or a viral vaccine expressing one or more proteins of the WN virus or a WN subunit vaccine according to the present invention will not induce in the immunized or vaccinated animal antibodies against other proteins of the virus, which are not presented in or by the immunogenic composition or vaccine (e.g., not present in the immunogenic composition or vaccine and/or not expressed by the immunogenic composition or vaccine). By this feature, the instant invention provides differential diagnostic methods. The present invention makes it possible to make a distinction between animals infected by the WN pathogenic virus and animals vaccinated or immunized with vaccines or compositions according to the invention. In the former, proteins and/or antibodies directed against them are present and can be detected by an antigen-antibody reaction. In the latter (the animals vaccinated or immunized according to the invention), this is not the case, as such animals remain negative in such an antigen-antibody reaction as to proteins not presented in or by the immunogenic or vaccine composition or antibodies thereto. In order to bring about this discrimination, the diagnostic method employs a protein which is not represented in or by the vaccine or immunogenic composition (not present and/or not expressed), e.g. protein C or protein NS1, NS2A, NS2B or NS3 when it is not represented in the vaccine or immunogenic composition.

Accordingly, the instant invention comprehends diagnostic assays or kits that employ a protein or antibody thereto that is not presented in or by a vaccine or immunogenic composition of the invention; and, kits that contain such a diagnostic assay or kit and such a vaccine or immunogenic composition, whereby the user can innoculate and/or vaccinate animals and thereafter test the animals, to determine those animals that have been exposed to WNV vs. those animals that have only been immunuzed and/or vaccinated against WNV.

Thus, the present invention relates to the use of vectors, preparations and polypeptides according to the invention for the preparation of immunogenic compositions and vaccines making it possible to discriminate between vaccinated or immunized animals and infected animals.

The instant invention also relates to an immunization and vaccination method associated with a diagnostic method permitting such a discrimination.

The protein selected for the diagnosis or one of its fragments or epitopes is used as the antigen in the diagnostic test and/or is used for producing polyclonal or monoclonal antibodies.

The one skilled in the art has sufficient practical knowledge to produce these antibodies and to implement antigens and/or antibodies in conventional diagnostic methods, e.g. ELISA tests, and thereby perform differential diagnostic tests according to the instant invention.

The invention will now be further described and illustrated by way of the following, non-limiting examples.

EXAMPLES

All the constructions are implemented using standard molecular biology methods (cloning, digestion by restriction enzymes, synthesis of a complementary single-strand DNA, polymerase chain reaction, elongation of an oligonucleotide by DNA polymerase, etc.) described by Sambrook J. et al. (Molecular Cloning: A Laboratory Manual, 2nd edition, Cold Spring Harbor Laboratory, Cold Spring Harbor. New York, 1989). All the restriction fragments used for these examples of the present invention, as well as the various polymerase chain reaction (PCR) products are isolated and purified using the Qiagen gel extraction or PCR purification kits Example 1

Culture of the West Nile Fever Virus

For amplification, West Nile fever virus NY99 (Lanciotti R. S. et al., Science, 1999, 286, 2333-7)) are cultured on VERO cells (monkey renal cells), obtainable from the American Type Culture Collection (ATCC) under no. CCL-81.

The VERO cells were cultured in 25 cm² Falcon with eagle-MEM medium supplemented by 1% yeast extracts and 10% calf serum containing approximately 100,000 cells/ml. The cells were cultured at +37° C. under a 5% $CO_2$ atmosphere.

After three days the cellular layer reaches to confluence. The culture medium was then replaced by the eagle-MEM medium supplemented by 1% yeast extract and 0.1% cattle serum albumin and the West Nile fever virus was added at a rate of 5 pfu/cell.

When the cytopathogenic effect (CPE) was complete (generally 48 to 72 hours after the start of culturing), the viral suspensions were harvested and then clarified by centrifugation and frozen at −70° C. In general, three to four successive passages were necessary for producing a viral batch, which is stored at −70° C.

Example 1.1

Construction of an Insertion Plasmid for the Canarypox C5 Locus

FIG. 13 (SEQ ID NO: 77) is the sequence of a 5 kb segment of canarypox DNA, encoding an ORE designated CS initiating at position 1864 and terminating at position 2187. The following describes a C5 insertion plasmid constructed by deleting the majority of the C5 ORF and replacing it with the Virogenetics VQ marker, the H6 promoter, a multiple cloning site (MCS) and transcriptional and translational termination sequences in all reading rames. A 1590 bp PCR fragment, containing the upstream C5R arm is amplified from genomic canarypox DNA using primers C5A1 (SEQ ID NO:76) and C5B1(SEQ ID NO:68). This fragment includes an EcoR I site at the 5'-end, termination sequences and an MCS containing BamH I, Cla I and Xma I sites at the 3'-end. A 458 bp PCR fragment, containing the downstream C5L arm is amplified from genomic canarypox DNA using primers C5C1 (SEQ ID NO:69) and C5D1 (SEQ ID NO:70). The fragment includes 5' BamH I, Cla I and Xma I sites, termination sequences and a Pst I site at the 3'-end. The PCR fragments were fused together by re-amplifying with primers C5A and C5D, generating a 2030 bp EcoR I-Pst I fragment, which is cloned into pUC 8, generating pUC/C5L/B Cla Xm/C5R. Oligonucleotides (SEQ ID NO:71) were used to introduce a unique Not I sequence at the 5'-end of the C5R arm, by inserting into the EcoR I site, generating pUC/Not I/C5R/MCS/C5L.

The Virogenetics VQ marker is contained on plasmid pRW823 and the vaccinia H6 promoter is contained on plasmid pBSH6-1. An 82 bp fragment containing the VQ marker and a 5' BamH I site, was PCR amplified from pRW823 using primers VQA1 (SEQ ID NO:72) and VQB1 (SEQ ID NO:73). A 176 bp fragment containing the H6 promoter and recognition sequences for a multiple cloning site containing Asp718 I, Xho I, Xba I, Cla I and Sma I, was amplified using primers H6A1 (SEQ ID NO:74) and H6B1 (SEQ ID NO:75). The VQ and H6 fragments were pooled and re-amplified using primers VQA1 and H6B1 to generate a 232 bp VQ/H6p/MCS fragment (FIG. 14, SEQ ID NO 82) that was inserted into pUC/C5L/B Cla Xm/C5R between the BamH I and Xma I sites. FIG. 15 shows the resultant plasmid, pNVQH6C5LSP-18, a C5 insertion plasmid containing the H6 promoter, transcription and translation terminators functional in all reading frames, and a MCS.

```
Primer C5A1
                                        (SEQ ID NO:76)
5' GGCCGAATTCTGAATGTTAAATGTTATACTTT 3'
```

-continued

Primer C5B1
(SEQ ID NO:68)
5' CCCGGGATCGATGGATCCTTTTTATAGCTAATTAGTCACGTACCTTT
GAGAGTACCACTTCAGCTA 3'

Primer C5C1
(SEQ ID NO:69)
5' GGATCCATCGATCCCGGGTTTTTATGACTAGTTAATCACGGCCGCTT
ATAAAGATCTAAAATGCAT 3'

Primer C5D1
(SEQ ID NO:70)
5' GGCTGCAGGTATTCTAAACTAGGAATAGAT 3'

Oligonucleotide for Not I
(SEQ ID NO:71)
5' AATTGCGGCCGC 3'

Primer VQA1
(SEQ ID NO:72)
5' AAAGGATCCGGGTTAATTAATTAGTCATC 3'

Primer VQB1
(SEQ ID NO:73)
5' AATAAAGAAGCTCTAATTAATTAACGAGCAGATA 3'

Primer H6A1
(SEQ ID NO:74)
5' TCGTTAATTAATTAGAGCTTCTTTATTCTATACTTAAAAAG 3'

Primer H6B1
(SEQ ID NO:75)
5' AAAACCCGGGATCGATTCTAGACTCGAGGGTACCTACGATACAAACT
TAACGGATA 3'

Example 2

Extraction of Viral RNA From the West Nile Fever Virus

The viral RNA contained in 100 ml of viral suspension of the West Nile fever virus strain NY99 was extracted after thawing with solutions of the High Pure Viral RNA Kit Cat # 1 858 882, Roche Molecular Biochemicals, whilst following the instructions of the supplier for the extraction stages. The RNA sediment obtained at the end of extraction was resuspended with 1 to 2 ml of RNase-free, sterile distilled water.

Example 3

Construction of Plasmid pFC101

The complementary DNA (cDNA) of the West Nile fever virus NY99 was synthesized with the Gene Amp RNA PCR Kit (Cat # N 808 0017, Perkin-Elmer, Norwalk, Conn. 06859, USA) using the conditions supplied by the manufacture.

A reverse transcriptase polymerase chain reaction (RT-PCR reaction) was carried out with 50 µl of viral RNA suspension of the West Nile fever virus NY99 (Example 2) and with the following oligonucleotides:

FC101 (30 mer)
(SEQ ID NO:1)
5'TTTTTTGAATTCGTTACCCTCTCTAACTTC 3'
and

FC102 (33 mer)
(SEQ ID NO:2)
5'TTTTTTTCTAGATTACCTCCGACTGCGTCTTGA 3'

This pair of oligonucleotides allows the incorporation of an EcoRI restriction site, a XbaI restriction site and a stop codon at 3' of the insert.

The synthesis of the first cDNA strand takes place by elongation of oligonucleotide FC102, following the hybridization of the latter with the RNA matrix.

The synthesis conditions of the first cDNA strand were a temperature of 42° C. for 15 min, then 99° C. for 5 min and finally 4° C. for 5 min. The conditions of the PCR reaction in the presence of the pair of oligonucleotides FC101 and FC102 were a temperature of 95° C. for 2 min, then 35 cycles (95° C. for 1 min, then 62° C. for 1 min and 72° C. for 2 min) and finally 72° C. for 7 min to produce a 302 bp fragment.

This fragment was digested by EcoRI and then by XbaI in order to isolate, following agarose gel electrophoresis, the approximately 290 bp EcoRI-XbaI fragment, which was called fragment A.

The pVR1020 eukaryotic expression plasmid (C. J. Luke et al. of Infectious Diseases, 1997, 175, 95-97) derived from the plasmid pVR1012 (FIG. 1 and example 7 of WO98/03199—Hartikka J. et al., 1997, Human Gene Therapy, 7, 1205-1217), contains the frame encoding the signal sequence of the human tissue plasminogen activator (tPA).

A pVR1020 plasmid was modified by BamHI-BglII digestion and insertion of a sequence containing several cloning sites (BamHI, NotI, EcoRI, XbaI, PmlI, PstI, BglII) resulting from hybridization of the following oligonucleotides.

BP326 (40 mer)
(SEQ ID NO: 3)
5'GATCTGCAGCACGTGTCTAGAGGATATCGAATTCGCGGCC 3'
and

BP329 (40 mer)
(SEQ ID NO: 4)
5'GATCCGCGGCCGCGAATTCGATATCCTCTAGACACGTGCT 3'

The thus obtained vector with a size of approximately 5105 base pairs (or bp) was called pAB110.

Fragment A was ligated with the pAB110 expression plasmid previously digested by XbaI and EcoRI, in order to give the plasmid pFC101 (5376 bp). Under the control of the early promoter of human cytomegalovirus or hCMV-IE (human Cytomegalovirus Immediate Early), the plasmid contains an insert encoding the signal sequence of the activator of tPA followed by the sequence encoding the protein prM.

Example 3.1

Construction of a DNA Immunization Vector, pVR1012 WNVprM-M-E, pSL-5448-1-1.

Figure 7:
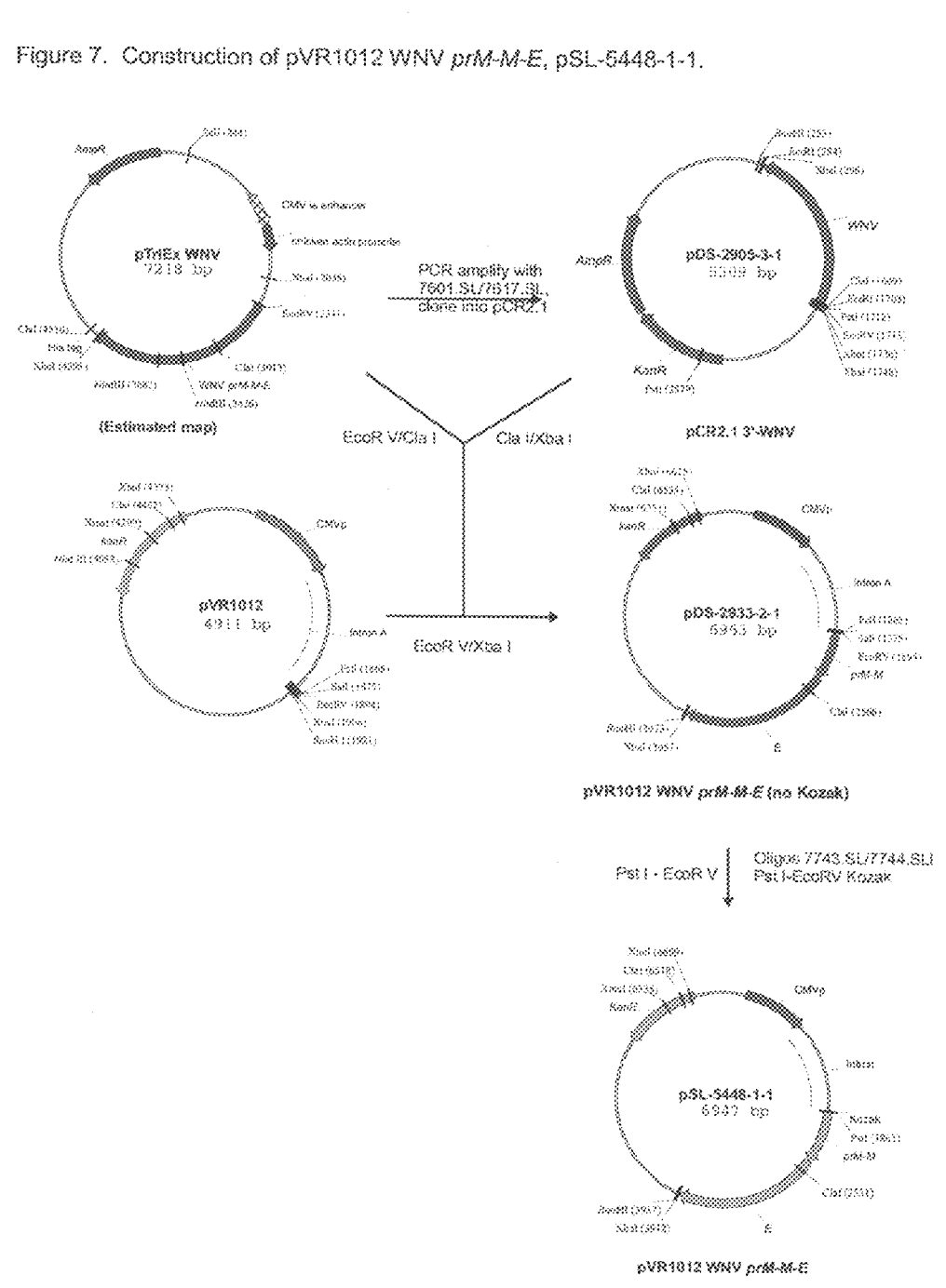

The construction scheme is shown in FIG. 7.

Plasmid pTriEx-WNV containing the NY99 WNV prM-M-E genes, was received from Cornell University. There is a poly-His tag at the 3' end of the E gene. A 1.2 kb Cla I-Xba I 3'-WNV fragment was PCR amplified using primers 7601.SL and 7617.SL, to remove the poly-His tag and introduce a stop codon and Xba I site for cloning. The resultant fragment was cloned into pCR 2.1, generating pDS-2905-3-1.

Plasmid pVR1012 is a DNA immunization vector containing the human CMV promoter, intronA, a multiple cloning site, and a kanamycin resistance gene and has been described by Hartikka et al (Human Gene Therapy 7:1205-1217, 1997). The pVR1012 vector was digested with EcoR V and Xba I and ligated with the 1.2 kb Cla I-Xba I 3'-insert from pDS-2905-3-1 and a 0.7 kb EcoR V-Cla I 5'-fragment from pTri-Ex-WNV, to generate pDS-2933-2-2.

In order to introduce a 5' Kozak sequence, the Pst I-EcoR V fragment of pDS-2933-2-2 was replaced by annealed oligonucleotides 7743.SL and 7744.SL, generating clone pSL-5448-1-1, pVR1012prM-M-E. The sequence of the WNV prM-M-E region is shown in FIG. 8.

```
            K  P  T  I  D  V  K  M    (SEQ ID NO: 46)
7617.SL  5' AAGCCTACCATCGATGTGAAGATG  (SEQ ID NO: 42)
                    Cla I

L  L  F  L  S  V  N  V  H  A  *       Xba I
            CTGCTCTTCCTCTCCGTGAACGTGCACGCTTAATTTTTATCTAGAGGGCCC
7601.SL  3' GACGAGAAGGAGAGGCACTTGCACGTGCGAATTAAAAATACATCTCCCGGG
            (SEQ ID NOS 45, 44 AND 43, respectively, in order of
            appearance Pst I       Kozak
                            M
7743.SL  5'    GCCGCCACCATGGG  (SEQ ID NO: 84)
7744.SL  3'    ACGTCGCAGGTGGTACCC (SEQ ID NO: 85)
```

Example 3.2

Analysis of the Immunogenicity of pSL-5448-1-1, pVR1012 WNVprM-M-E in Mice

Six to eight week old BALB/c mice were immunized intramuscularly with 100 μg of plasmid DNA in PBS, on days 0, 14, 28, and 42. Bleeds were taken on days 0, 28, 42 and 56, processed and analysed by immunoblot.

Samples for immunoblot analysis were prepared by transient transfection of Chinese Hamster Ovary (CHO) cells with pTriEx-WNV DNA. CHO cells were transfected with 10 μg of pTriEx-WNV DNA using electroporation at settings 1.5 kV, 25 uF and infinite resistance. Mock samples were prepared by the electroporation of CHO cells at the same settings, without DNA. After approximately 65 hours, supernatants were harvested and clarified by spinning at 3000 rpm for 5 min. The plates were washed twice with PBS, then 500 μl of PBS was added and the cells were scraped off. After spinning at 3000 rpm for 5 min, the supernatant was removed and the cells resuspended in 100 μl of SDS-PAGE lysis buffer.

Immunoblots were performed using the CHO/pTriEx-WNV and CHO/mock pellets to assess antigenicity and specificity of the mouse antisera. Samples were suspended in SDS-PAGE loading buffer minus β-mercaptoethanol and separated on a 12% SDS-PAGE gel before electrotransfer to immobilon P nylon membrane. The membranes were processed and probed with 1:1000 dilution of mouse anti-WNV antisera. Peroxidase-conjugated goat anti-mouse antisera was used as secondary antibody and bands were visualized using luminol reagents (NEN). All five mouse anti-WNV antisera reacted specifically with a single protein band in the pTriEx-WNV samples, of the expected size for the WNV E protein. None of the five antisera reacted with anything in the mock samples.

The serum samples were also assayed for virus neutralizing antibodies and titres were found to range between 1:8 and 1:128.

Example 4

Construction of Plasmid pFC102

The complementary DNA (cDNA) of the West Nile fever virus NY99 was synthesized with the Gene Amp RNA PCR Kit (Cat # N 808 0017, Perkin-Elmer, Norwalk, Conn. 06859, USA) using the conditions provided by the supplier.

A reverse transcriptase polymerase chain reaction (RT-PCR reaction) was carried out with 50 μl of viral RNA suspension of the West Nile fever virus NY99 (Example 2) and with the following oligonucleotides:

```
FC103 (30 mer)
                                         (SEQ ID NO: 5)
5'TTTTTTGAATTCTCACTGACAGTGCAGACA 3'
and FC104 (33 mer)
                                         (SEQ ID NO: 6)
5'TTTTTTTCTAGATTAGCTGTAAGCTGGGGCCAC 3'
```

This pair of oligonucleotides allows the incorporation of an EcoRI restriction site and a XbaI restriction site and a stop codon at 3' of the insert.

The first cDNA strand was synthesized by elongation of oligonucleotide FC104, following the hybridization of the latter on the RNA matrix.

The synthesis conditions of the first cDNA strand were a temperature of 42° C. for 15 min, then 99° C. for 5 min and finally 4° C. for 5 min. The conditions of the PCR reaction in the presence of the pair of oligonucleotides FC103 and FC104 were a temperature of 95° C. for 2 min, then 35 cycles (95° C. for 1 min, then 62° C. for 1 min and 72° C. for 2 min) and finally 72° C. for 7 min to produce a 252 bp fragment.

This fragment was digested by EcoRI and then XbaI in order to isolate, following agarose gel electrophoresis, the approximately 240 bp EcoRI-XbaI fragment. This fragment was ligated with the pAB110 expression plasmid (Example 3) previously digested by XbaI and EcoRI in order to give the plasmid pFC102 (5326 bp). Under the control of the early human cytomegalovirus or hCMV-IE (human Cytomegalovirus Immediate Early) promoter, this plasmid contains an insert encoding the signal sequence of the activator of tPA, followed by the sequence encoding the protein M.

Example 5

Construction of Plasmid pFC103

The complementary DNA (cDNA) of the West Nile fever virus NY99 was synthesized with the Gene Amp RNA PCR Kit (Cat # N 808 0017, Perkin-Elmer, Norwalk, Conn. 06859, USA) using the conditions provided by the supplier.

A reverse transcriptase polymerase chain reaction (RT-PCR reaction) was carried out with 50 μl of viral RNA suspension of the West Nile fever virus NY99 (Example 2) and with the following oligonucleotides:

```
FC105 (30 mer)
                                          (SEQ ID NO: 7)
5'TTTTTTGAATTCTTCAACTGCCTTGGAATG 3'
and FC106 (33 mer)
                                          (SEQ ID NO: 8)
5'TTTTTTTCTAGATTAAGCGTGCACGTTCACGGA 3'.
```

This pair of oligonucleotides allows the incorporation of an EcoRI restriction site and a XbaI restriction site, together with a stop codon at 3' of the insert.

The synthesis of the first cDNA strand takes place by elongation of oligonucleotide FC106, following its hybridization with the RNA matrix.

The synthesis conditions of the first cDNA strand were a temperature of 42° C. for 15 min, then 99° C. for 5 min and finally 4° C. for 5 min. The PCR reaction conditions in the presence of the pair of oligonucleotides FC105 and FC106 were a temperature of 95° C. for 2 min, then 35 cycles (95° C. for 1 min, then 62° C. for 1 min and 72° C. for 2 min), and finally 72° C. for 7 min for producing a 1530 bp fragment.

This fragment was digested by EcoRI and then by XbaI in order to isolate, following agarose gel electrophoresis, the approximately 1518 bp EcoRI-XbaI fragment. This fragment was ligated with the pAB 110 expression plasmid (Example 3) previously digested by XbaI and EcoRI in order to give the plasmid pFC103 (6604 bp). Under the control of the early promoter of human cytomegalovirus or hCMV-IE (human Cytomegalovirus Immediate Early), the plasmid contains an insert encoding the signal sequence of the activator of tPA, followed by the sequence encoding the protein E.

Example 6

Construction of Plasmid pFC104

The complementary DNA (cDNA) of the West Nile fever virus NY99 was synthesized with the Gene Amp RNA PCR Kit (Cat # N 808 0017, Perkin-Elmer, Norwalk, Conn. 06859, USA) using the conditions provided by the supplier.

A reverse transcriptase polymerase chain reaction (RT-PCR reaction) was carried out with 50 µl of viral RNA suspension of the West Nile fever virus NY99 (Example 2) and with the following oligonucleotides:
FC101 (30 mer) (SEQ ID NO: 1)
and FC106 (33 mer) (SEQ ID NO: 8)

This pair of oligonucleotides allows the incorporation of an EcoRI restriction site, a XbaI restriction site and a stop codon at 3' of the insert.

Synthesis of the first cDNA strand takes place by elongation of oligonucleotide FC106, following its hybridization with the RNA matrix.

The synthesis conditions of the first cDNA strand were a temperature of 42° C. for 15 min, then 99° C. for 5 min and finally 4° C. for 5 min. The PCR reaction conditions in the presence of the pair of oligonucleotides FC101 and FC106 are a temperature of 95° C. for 2 min, then 35 cycles (95° C. for 1 min, then 62° C. for 1 min and 72° C. for 2 min) and finally 72° C. for 7 min in order to produce a 2031 bp fragment.

This fragment was digested by EcoRI and then XbaI in order to isolate, following agarose gel electrophoresis, the approximately 2019 bp EcoRI-XbaI fragment. This fragment was ligated with the pAB110 expression plasmid (Example 3), previously digested by XbaI and EcoRI in order to give the pFC104 plasmid (7105 bp). Under the control of the early human cytomegalovirus promoter or hCMV-IE (human Cytomegalovirus Immediate Early), the plasmid contains an insert encoding the signal sequence of the activator of tPA, followed by the sequence encoding the protein prM-M-E.

Example 7

Construction of Plasmid pFC105

The complementary DNA (cDNA) of the West Nile fever virus NY99 was synthesized with the Gene Amp RNA PCR Kit (Cat # N 808 0017, Perkin-Elmer, Norwalk, Conn. 06859, USA) using the conditions provided by the supplier.

A reverse transcriptase polymerase chain reaction (RT-PCR reaction) was carried out with 50 µl of viral RNA suspension of the West Nile fever virus NY99 (Example 2) and with the following oligonucleotides:

```
FC107 (36 mer)
                                          (SEQ ID NO: 9)
5'TTTTTTGATATCACCGGAATTGCAGTCATGATTGGC 3'
and FC106 (33 mer).
                                          (SEQ ID NO: 8)
```

This pair of oligonucleotides allows the incorporation of an EcoRV restriction site, a XbaI restriction site and a stop codon at 3' of the insert.

Synthesis of the first cDNA strand takes place by elongation of the FC106 oligonucleotide, following its hybridization with the RNA matrix.

The synthesis conditions of the first cDNA strand were a temperature of 42° C. for 15 min, then 99° C. for 5 min and finally 4° C. for 5 min. The PCR reaction conditions in the presence of the pair of oligonucleotides FC106 and FC107 are a temperature of 95° C. for 2 min, then 35 cycles (95° C. for 1 min, then 62° C. for 1 min and 72° C. for 2 min) and finally 72° C. for 7 min in order to produce a 2076 bp fragment.

This fragment was digested by EcoRV and then XbaI in order to isolate, following agarose gel electrophoresis, the approximately 2058 bp EcoRV-XbaI fragment.

This fragment was ligated with the pVR1012 expression plasmid, previously digested by XbaI and EcoRV, in order to give the plasmid pFC105 (6953 bp). Under the control of the early human cytomegalovirus promoter or hCMV-IE (human Cytomegalovirus Immediate Early), this plasmid contains an insert encoding the polyprotein prM-M-E.

Example 8

Construction of Plasmid pFC106

The complementary DNA (cDNA) of the West Nile fever virus NY99 was synthesized with the Gene Amp RNA PCR Kit (Cat # N 808 0017, Perkin-Elmer, Norwalk, Conn. 06859, USA) using the conditions provided by the supplier.

A reverse transcriptase polymerase chain reaction (RT-PCR reaction) was carried out with 50 µl of viral RNA suspension of the West Nile fever virus NY99 (example 2) and with the following oligonucleotides:

```
FC108 (36 mer)
                                      (SEQ ID NO: 10)
5'TTTTTTGATATCATGTATAATGCTGATATGATTGAC 3'
and FC109 (36 mer)
                                      (SEQ ID NO: 11)
5'TTTTTTTCTAGATTAACGTTTTCCCGAGGCGAAGTC 3'
```

This pair of oligonucleotides allows the incorporation of an EcoRV restriction site, a XbaI restriction site, an initiating ATG codon in 5' and a stop codon at 3' of the insert.

Synthesis of the first cDNA strand takes place by elongation of the oligonucleotide FC109, following its hybridization with the RNA matrix.

The synthesis conditions of the first cDNA strand were a temperature of 42° C. for 15 min, then 99° C. for 5 min and finally 4° C. for 5 min. The PCR reaction conditions in the presence of the pair of nucleotides FC108 and FC109 are a temperature of 95° C. for 2 min, then 35 cycles (95° C. for 1 min, 62° C. for 1 min and then 72° C. for 2 min) and finally 72° C. for 7 min to produce a 2973 bp fragment.

This fragment was digested by EcoRV and then XbaI in order to isolate, following agarose gel electrophoresis, the approximately 2955 bp EcoRV-XbaI fragment.

This fragment was ligated with the pVR 1012 expression plasmid previously digested by XbaI and EcoRV in order to give the plasmid pFC106 (7850 bp). Under the control of the early human cytomegalovirus promoter or hCMV-IE (human Cytomegalovirus Immediate Early), this plasmid contains an insert encoding the polyprotein NS2A-NS2B-NS3.

Example 9

Construction of Donor Plasmid for Insertion into C5 Site of Canarypox Virus (ALVAC)

FIG. 16 of U.S. Pat. No. 5,756,103 shows the sequence of a genomic DNA 3199 bp fragment of the canarypox virus. Analysis of this sequence has revealed an open reading frame (ORF) called C5.H, which starts at position 1538 and ends at position 1859. The construction of an insertion plasmid leading to the deletion of the ORF C5.H and its replacement by a multiple cloning site flanked by transcription and translation stop signals was implemented in the following way.

A PCR reaction was performed on the basis of the matrix constituted by genomic DNA of the canarypox virus and with the following oligonucleotides:

```
C5A1 (42 mer)
                                      (SEQ ID NO: 12)
5'ATCATCGAGCTCCAGCTGTAATTCATGGTCGAAAAGAAGTGC 3':
and C5B1 (73 mer)
                                      (SEQ ID NO: 13)
5'GAATTCCTCGAGCTGCAGCCCGGGTTTTTATAGCTAATTAGTCATTTT
TTGAGAGTACCACTTCAGCTACCTC 3':
``` in order to isolate a 223 bp PCR fragment (fragment B).

A PCR reaction was carried out on the basis of the matrix constituted by genomic DNA of the canarypox virus and with the following oligonucleotides:

```
C5C1 (72 mer)
                                      (SEQ ID NO: 14)
5'CCCGGGCTGCAGCTCGAGGAATTCTTTTTATTGATTAACTAGTCATTA
TAAAGATCTAAAATGCATAATTTC 3':
and C5D1 (45 mer)
                                      (SEQ ID NO: 15)
5'GATGATGGTACCGTAAACAAATATAATGAAAAGTATTCTAAACTA 3':
``` in order to isolate a 482 bp PCR fragment (fragment C).

Fragments B and C were hybridized together in order to serve as a matrix for a PCR reaction performed with the oligonucleotides C5A1 (SEQ ID NO: 12) and C5D1 (SEQ ID NO: 15) in order to generate a 681 bp PCR fragment. This fragment was digested by the restriction enzymes SacI and KpnI in order to isolate, following agarose gel electrophoresis, a 664 bp SacI-KpnI fragment. This fragment was ligated with the pBlueScript® II SK+ vector (Stratagene, La Jolla, USA, Cat # 212205), previously digested by the restriction enzymes SacI and KpnI, in order to give the plasmid pC5.H. The sequence of this plasmid was verified by sequencing. This plasmid contains 166 bp of sequences upstream of ORF C5.H (left flanking arm C5L.H), an early transcription stop signal, stop codons in 6 reading frames, a multiple cloning site containing restriction sites SmaI, PstI, XhoI and EcoRI and finally 425 bp of sequences located downstream of ORF C5.H (right flanking arm C5R.H).

The plasmid pMP528HRH (Perkus M. et al. J. Virol. 1989, 63, 3829-3836) was used as the matrix for amplifying the complete sequence of the vaccinia promoter H6 (GenBank access no. M28351) with the following oligonucleotides:

```
JCA291 (34 mer)
                                      (SEQ ID NO: 16)
5'AAACCCGGGTTCTTTATTCTATACTTAAAAAGTG 3'
and JCA292 (43 mer)
                                      (SEQ ID NO: 17)
5'AAAAGAATTCGTCGACTACGATACAAACTTAACGGATATCGCG 3'
``` in order to amplify a 149 bp PCR fragment. This fragment was digested by restriction enzymes SmaI and EcoRi in order to isolate, following agarose gel electrophoresis, a 138 bp SmaI-EcoRI restriction fragment. This fragment was then ligated with the plasmid pC5, previously digested by SmaI and EcoRI, in order to give the plasmid pFC107.

Example 10

Construction of the Recombinant Virus vCP1712

A PCR reaction was performed using the plasmid pFC105 (example 7) as the matrix and the following oligonucleotides:

```
FC110 (33 mer):
                                      (SEQ ID NO: 18)
5'TTTTCGCGAACCGGAATTGCAGTCATGATTGGC 3'
and FC111 (39mer):
                                      (SEQ ID NO: 19)
5'TTTTGTCGACGCGGCCGCTTAAGCGTGCACGTTCACGGA 3'
``` in order to amplify an approximately 2079 bp PCR fragment. This fragment was digested by restriction enzymes NruI and SalI in order to isolate, following agarose gel electrophoresis, an approximately 2068 bp NruI-SalI restriction fragment.

This fragment was then ligated with plasmid pFC107 (example 9) previously digested by restriction enzymes NruI and SalI in order to give the plasmid pFC108, which contains C5L-H6p-WNV prM-M-E-C5R.

Plasmid pFC108 was linearized by NotI, then transfected in primary chicken embryo cells. The cells were then infected with the canarypox virus (ALVAC strain) according to the previously described calcium phosphate precipitation method (Panicali and Paoletti, Proc. Nat. Acad. Sci. 1982, 79, 4927-4931; Piccini et al. In Methods in Enzymology, 1987, 153, 545-563, publishers Wu R. and Grossman L. Academic Press). Positive plaques were selected on the basis of a hybridization with a radioactively labelled probe specific to the nucleotide sequence of the envelope glycoprotein E. These plaques underwent 2-4 successive selection/purification cycles until a pure population was isolated. A representative plaque corresponding to in vitro recombination between the donor plasmid pFC108 and the genome of the ALVAC canarypox virus was then amplified and the recombinant virus stock obtained was designated vCP1712. (The actual vCP2017, which contains the full-length promoter and signal sequence, was derived after two rounds of screening).

Example 11

Construction of the Recombinant Virus vCP1713

Plasmid pFC104 (Example 6) was digested by the restriction enzyme SalI and PmlI in order to isolate, following agarose gel electrophoresis, an approximately 2213 bp PmlI-SalI restriction fragment. This fragment was ligated with plasmid pFC107 (Example 9) previously digested by the NruI and SalI restriction enzymes in order to give the plasmid pFC109.

Plasmid pFC109 was linearized by NotI, then transfected in primary chicken embryo cells infected with the canarypox virus (ALVAC strain) according to the method of Example 10. A representative plaque corresponding to in vitro recombination between the donor plasmid pFC109 and the genome of the ALVAC canarypox virus was selected on the basis of a hybridization of a radioactively labelled probe specific to the nucleotide sequence of the envelope glycoprotein E and was then amplified. The recombinant virus stock obtained was designated vCP1713, ALVAC WNV prM-M-E.

Example 12

Construction of the Recombinant Virus vCP1714

Plasmid pFC103 (Example 5) was digested by the SalI and PmlI restriction enzymes in order to isolate, following agarose gel electrophoresis, an approximately 1712 bp PmlI-SalI restriction fragment. This fragment was ligated with the plasmid pFC107 (Example 9) previously digested by the NruI and SalI restriction enzymes in order to give the plasmid pFC110.

Plasmid pFC110 was linearized by NotI, then transfected in primary chicken embryo cells infected with the canarypox virus (ALVAC strain) according to the method of example 10. A representative plaque corresponding to in vitro recombination between the donor plasmid pFC110 and the genome of the ALVAC canarypox virus was selected on the basis of a hybridization with a radioactively labelled probe specific to the nucleotide sequence of the envelope glycoprotein E and was then amplified. The recombinant virus stock obtained was then designated vCP1714, ALVAC WNV E.

Example 13

Construction of the Recombinant Virus vCP1715

Plasmid pFC102 (Example 4) was digested by the SalI and PmlI restriction enzymes in order to isolate, following agarose gel electrophoresis, an approximately 434 bp PmlI-SalI restriction fragment. This fragment was ligated with the plasmid pFC107 (Example 9) previously digested by the NruI and SalI restriction enzymes to give the plasmid pFC111.

Plasmid pFC111 was linearized by NotI, then transfected in primary chicken embryo cells infected with the canarypox virus (ALVAC strain) according to the method of Example 10. A representative plaque corresponding to in vitro recombination between the donor plasmid pFC111 and the genome of the ALVAC canarypox virus was selected on the basis of hybridization with a radioactively labelled probe specific to the nucleotide sequence of the membrane M glycoprotein and was then amplified. The recombinant virus stock obtained was designated vCP1715, ALVAC WNV M.

Example 14

Construction of the Recombinant Virus vCP1716

Plasmid pFC101 (Example 3) is digested by the SalI and PmlI restriction enzymes in order to isolate, following agarose gel electrophoresis, an approximately 484 bp PmlI-SalI restriction fragment. This fragment is ligated with the plasmid pFC107 (Example 9) previously digested by the NruI and SalI restriction enzymes to give the plasmid pFC112.

Plasmid pFC112 was linearized by NotI and then transfected in primary chicken embryo cells infected with the canarypox virus (ALVAC strain) according to the method of Example 10. A representative plaque corresponding to in vitro recombination between the donor plasmid pFC112 and the genome of the ALVAC canarypox virus was selected on the basis of a hybridization with a radioactively labelled probe specific to the nucleotide sequence of the pre-membrane prM glycoprotein and was then amplified. The recombinant virus stock obtained was designated vCP1716, ALVAC WNV prM.

Example 15

Construction of Donor Plasmid for Insertion into C6 Site of Canarypox Virus (ALVAC)

FIG. 4 of WO01/05934 (see also Audonnet et al., allowed U.S. application Ser. No. 09/617,594, filed Jul. 14, 2000, now U.S. Pat. No. 6,541,458 issued Apr. 1, 2003) shows the sequence of a 3700 bp genomic DNA fragment of the canarypox virus. Analysis of this sequence revealed an open reading frame (ORF) called C6, which starts at position 377 and ends at position 2254. The construction of an insertion plasmid leading to the deletion of the ORF C6 and its replacement by a multiple cloning site flanked by transcription and translation stop signals was implemented in the following way.

A PCR reaction was performed on the basis of the matrix constituted by the genomic DNA of the canarypox virus and with the following oligonucleotides:

```
C6A1 (42 mer):
                                              (SEQ ID NO: 20)
5'ATCATCGAGCTCGCGGCCGCCTATCAAAAGTCTTAATGAGTT 3'
and C6B1 (73 mer):
                                              (SEQ ID NO: 21)
5'GAATTCCTCGAGCTGCAGCCCGGGTTTTTATAGCTAATTAGTCATTTT
TTCGTAAGTAAGTATTTTTATTTAA 3'
``` to isolate a 432 bp PCR fragment (fragment D).

A PCR reaction was performed on the basis of the matrix constituted by the genomic DNA of the canarypox virus and with the following oligonucleotides:

```
C6C1 (72 mer):
                                              (SEQ ID NO: 22)
5'CCCGGGCTGCAGCTCGAGGAATTCTTTTTATTGATTAACTAGTCAAAT
GAGTATATATAATTGAAAAGTAA 3'
and C6D1 (45 mer):
                                              (SEQ ID NO: 23)
5'GATGATGGTACCTTCATAAATACAAGTTTGATTAAACTTAAGTTG 3'
``` to isolate a 1210 bp PCR fragment (fragment E).

Fragments D and E were hybridized together to serve as a matrix for a PCR reaction performed with the oligonucleotides C6A1 (SEQ ID NO: 20) and C6D1 (SEQ ID NO: 23) to generate a 1630 bp PCR fragment. This fragment was digested by the SacI and KpnI restriction enzymes to isolate, after agarose gel electrophoresis, a 1613 bp SacI-KpnI fragment. This fragment was ligated with the pBlueScript® II SK+vector (Stratagene, La Jolla, Calif., USA, Cat # 212205) previously digested by the SacI and KpnI restriction enzymes to give the plasmid pC6L. The sequence of this plasmid was verified by sequencing. The plasmid contains 370 bp of sequences upstream of ORF C6L (C6 left flanking arm), an early transcription stop vaccinia signal, stop codons in the six reading frames, a multiple cloning site containing the SmaI, PstI, XhoI and EcoRI restriction sites and finally 1156 bp of sequences downstream of the ORF C6L (C6 right flanking arm).

Plasmid pMPIVC (Schmitt J. F. C. et al., J. Virol., 1988, 62, 1889-1897, Saiki R. K. et al., Science, 1988, 239, 487-491) was used as the matrix for amplifying the complete sequence of the I3L vaccine promoter with the following oligonucleotides:

```
FC112 (33 mer):
                                              (SEQ ID NO: 24)
5'AAACCCGGGCGGTGGTTTGCGATTCCGAAATCT 3'
and FC113 (43 mer):
                                              (SEQ ID NO: 25)
5'AAAAGAATTCGGATCCGATTAAACCTAAATAATTGTACTTTGT 3'
``` to amplify a 151 bp PCR fragment. This fragment was digested by the SmaI and EcoRI restriction enzymes in order to isolate, following agarose gel electrophoresis, an approximately 136 bp SmaI-EcoRI restriction fragment. This fragment was then ligated with plasmid pC6L previously digested by SmaI and EcoRI to give the plasmid pFC113.

Example 16

Construction of Recombinant Viruses vCP1717 and vCP1718

A PCR reaction was performed using the plasmid pFC106 (Example 8) as the matrix and the following oligonucleotides:

```
FC114 (33 mer):
                                              (SEQ ID NO: 26)
5'TTTCACGTGATGTATAATGCTGATATGATTGAC 3'
and FC115 (42 mer):
                                              (SEQ ID NO: 27)
5'TTTTGGATCCGCGGCCGCTTAACGTTTTCCCGAGGCGAAGTC 3'
``` to amplify an approximately 2973 bp PCR fragment. This fragment was digested with the PmlI and BamHI restriction enzymes to isolate, following agarose gel electrophoresis, the approximately 2958 bp PmlI-BamHI restriction fragment (fragment F). Plasmid pFC113 (example 15) was digested by the PmlI and BamHI restriction enzymes to isolate, following agarose gel electrophoresis, the approximately 4500 bp PmlI-BamHI restriction fragment (fragment G). Fragments F and G were then ligated together to give the plasmid pFC114.

Plasmid pFC114 was linearized by NotI, then transfected in primary chicken embryo cells infected with canarypox virus vCP1713 (Example 11) according to the previously described calcium phosphate precipitation method (Panicali et Paoletti Proc. Nat. Acad. Sci. 1982, 79, 4927-4931; Piccini et al. In Methods in Enzymology, 1987, 153, 545-563, publishers Wu R. and Grossman L. Academic Press). Positive plaques were selected on the basis of hybridization with a radioactively labelled probe specific to the nucleotide sequence of envelope glycoprotein E NS2A-NS2B. Four successive selection/purification cycles were performed until a pure population was isolated. A representative plaque corresponding to in vitro recombination between the donor plasmid pFC114 and the genome of the ALVAC canarypox virus was then amplified and the recombinant virus stock obtained was designated vCP1717, ALVAC C5 H6p WNV prM-M-E/C6 I3Lp WNV NS2A-NS2B-NS3.

The NotI-linearized pFC114 plasmid was also used for transfecting primary chicken embryo cells infected with the vCP1712 canarypox virus (Example 10) using the procedure described herein. The thus obtained recombinant virus stock was designated vCP1718, ALVAC C5 H6p WNV prM-M-E/C6 I3Lp WNV NS2A-NS2B-NS3.

Example 17

Construction of Plasmid pFC115

The complementary DNA (cDNA) of the West Nile fever virus NY99 was synthesized with Gene Amp RNA PCR Kit (Cat # N 808 0017, Perkin-Elmer, Norwalk, Conn. 06859, USA) using the conditions provided by the supplier.

A reverse transcriptase polymerase chain reaction (RT-PCR reaction) was carried out with 50 µl of viral RNA suspension of the West Nile fever virus NY99 (Example 2) and with the following oligonucleotides:

```
FC116 (39 mer)
                                        (SEQ ID NO: 28)
5'TTTTTTGATATCATGACCGGAATTGCAGTCATGATTGGC 3'
and FC106 (33 mer)
                                        (SEQ ID NO: 8).
```

This pair of oligonucleotides makes it possible to incorporate an EcoRV restriction site, a XbaI restriction site, an initiator code at 5' and a stop code at 3' of the insert.

Synthesis of the first cDNA strand takes place by elongation of the oligonucleotide FC106, following its hybridization with the RNA matrix.

The synthesis conditions of the first cDNA strand were a temperature of 42° C. for 15 min, then 99° C. for 5 min and finally 4° C. for 5 min. The conditions of the PCR reaction in the presence of the pair of oligonucleotides FC106 and FC116 were a temperature of 95° C. for 2 min, then 35 cycles (95° C. for 1 min, 62° C. for 1 min and then 72° C. for 2 min) and finally 72° C. for 7 min to produce a 2079 bp fragment.

This fragment was digested by EcoRV and then XbaI to isolate, following agarose gel electrophoresis, the approximately 2061 bp EcoRV-XbaI fragment.

This fragment was ligated with the pVR1012 expression plasmid previously digested by XbaI and EcoRV to give the plasmid pFC115 (6956 bp). Under the control of the early human cytomegalovirus promoter or hCMV-IE (human Cytomegalovirus Immediate Early), this plasmid contains an insert encoding the polyprotein prM-M-E.

Example 18

Construction of the Recombinant Viruses vCP2017-H

A PCR reaction was carried out using the plasmid pFC115 (Example 17) as the matrix and the following oligonucleotides:

```
FC117 (36 mer):
                                        (SEQ ID NO: 29)
5'TTTTCGCGAATGACCGGAATTGCAGTCATGATTGGC 3'
and FC111 (39mer)
                                        (SEQ ID NO: 19)
``` to amplify an approximately 2082 bp PCR fragment. This fragment was digested by NruI and SalI restriction enzymes to isolate, after agarose gel electrophoresis, an approximately 2071 bp NrI-SalI restriction fragment. This fragment was then ligated with plasmid pFC107 (Example 9) previously digested by the NruI and SalII restriction enzymes to give the plasmid pFC116.

Plasmid pFC116 was linearized by NotI and then transfected in primary chicken embryo cells infected with canarypox virus (ALVAC strain) using the procedure of Example 10. A representative plaque corresponding to in vitro recombination between the donor plasmid pFC116 and the genome of the ALVAC canarypox virus was selected on the basis of a hybridization with a radioactively labelled probe specific to the nucleotide sequence of the envelope glycoprotein E and was then amplified. The recombinant virus stock obtained was designed vCP2017-H.

Example 18.1

Construction of a C5 H6p WNVprM-M-E Donor Plasmid (PDS-2946-1-1) for the Generation of ALVAC WNV (vCP2017) or ALVAC-2 WNV (vCP2018).

The construction scheme is illustrated in FIG. 1.

A pTriEx-WNV vector containing the 3'-end of the West Nile Virus capsid gene, and the prM/M and E genes with a poly-His tag at the end of the E protein from a NY99-related isolate, was obtained from Cornell University, and ALVAC (containing WNV prM-M-E in C5 locus) is illustrated in FIG. 1. The WNV E gene contains an internal T5NT sequence, which is known to result in premature transcriptional termination in pox-based recombinants (Yuen and Moss, Proc. Natl. Acad. Sci. USA 84:6417-6421, 1987). In order to mutate the T5NT sequence, the 1.4 kb Cla I-Xho I 3'-WNV fragment from pTriEx-WNV was inserted into pUC-4K, generating clone pDS-2889-1, pUC 3' WNV. Site-directed mutagenesis was performed using the Amersham QuikChange kit and primers 7598.SL (SEQ ID NO: 38) and 7599.SL (SEQ ID NO: 39).

```
                K V A I F V H G P T              SEQ ID NO:41
                GAAGTGGCCATTTTTGTCCATGGACCAACT    SEQ ID NO:40
                                ↓
      7598.SL 5' GAAGTGGCCATCTTCGTGCACGGACCAACT 5' SEQ ID NO:38
      7599.SL 3' CTTCACCGGTAGAAGCACGTGCCTGGTTGA 3' SEQ ID NO:39
                                ApaL I
```

An ApaL I site was introduced for screening purposes. Clone pDS-2897-5-1 (pUC 3'-WNV'T5NT) was confirmed as correct by sequence analysis.

In order to remove the poly-His tag and introduce a translation stop and terminal T5NT, the 1.4 kb 3' fragment from pDS-2897-5-1 was PCR amplified using primers 7617.SL (SEQ ID NO: 42) and 7601.SL (SEQ ID NO: 43).

```
                        Cla I
              K  P  T  I  D  V  K  M                   SEQ ID NO:46
7617.SL  5'   AAGCCTACCATCGATGTGAAGATG        3'       SEQ ID NO:41

SEQ ID Nos:45, 44 and 43)
              L  L  F  L  S  V  N  V  H  A  *     Xba I
              CTGCTCTTCCTCTCCGTGAACGTGCACGCTTAATTTTTATCTAGAGGGCCC
7601.SL  3'   GACGAGAAGGAGAGGCACTTGCACGTGCGAATTAAAAATAGATCTCCCGGG 5'
```

Primer 7601.SL introduces a stop codon, T5NT transcription termination signal, and an Xba I site for cloning. The resultant fragment was inserted into pCR2.1 and clone pDS-2918-1 (pCR2.1 3'-WNV-T5NT+stop) was confirmed as correct by sequence analysis.

The 0.7 kb EcoR V-Cla I 5'-end of the WNV gene cassette was PCR amplified using primers 7600.SL (SEQ ID NO: 47) and 7616.SL (SEQ ID NO: 48) and the fragment inserted into pCR2.1 to generate plasmid pDS-2905-2-1 described in U.S. Pat. No. 5,756,103. To generate ALVAC-or ALVAC-2-based WNV recombinants, primary chick embryo firbroblast cells (CEFs) were transfected with Not I-linearized pDS-2946-1-1 plasmid DNA (pC5 H6p WNV prM-M-E) mixed with FuGENE-6 transfection reagent (Roche), then infected with ALVAC or ALVAC-2 as rescue virus at an MOI of 10. After 24-48 hours, recombinant plaques were lifted onto nylon membrane and hybridized with a WNV-specific DNA probe which was labelled with horseradish peroxidase according to the manufacturer's protocol (Amersham Cat# RPM3001). Following 2-4 sequential rounds of plaque purification, single plaques were amplified to produce stocks of vCP2017 and vCP2018. Recombinant viruses were characterized by restriction enzyme and Southern blot analyses. The C5-H6p WNV-C5 locus was PCR-amplified and the complete sequence confirmed. Expression of the WNV proteins

```
SEQ ID NOS 51 and 47, respectively in order of appearance)
              EcoR V           H6p          M  T  G  I  A  V  M  I  G  L
7600.SL  5'   ATCGCGATATCCGTTAAGTTTGTATCGTAATGACCGGAATTGCAGTCATGATTGGCCTG Cla I
              K  P  T  I  D  V  K  M                   SEQ ID NO:50
              AAGCCTACCATCGATGTGAAGATG                 SEQ ID NO:49
7616.SL  3'   TTCGGATGGTAGCTACACTTCTAC       5'        SEQ ID NO:48
```

The sequence of the insert was confirmed.

Primer 7600.SL contains the 3'-end of the H6 promoter from the NruI site and primer 7616.SL spans a Cla I site in the WNV E gene. The EcoR V-Cla I 5'-fragment from pDS-2905-2-1 and the Cla I-Xba I 3' fragment from pDS-2918-1 were inserted into the ALVAC C5 donor plasmid pNVQH6C5LSP-18 (pC5 H6p donor plasmid) that had been digested with EcoR V and Xba I. Clone pDS-2946-1-1 was confirmed by restriction enzyme analysis and the H6p WNV prM-M-E insert was confirmed by sequence analysis. The sequence of the C5-H6p WNV prM-M-E -C5 gene cassette is illustrated in FIG. 2, and the full sequence is illustrated in FIG. 9. From the sequences depicted in FIG. 2 and FIG. 9, one of skill in the art may clone these sequences and easily generate the plasmids herein without following this exact procedure.

Alternatively, plasmids with a truncated H6p and/or truncated WNV capsid leader sequence may be useful (see FIG. 10 and FIG. 11).

Example 18.2

Generation and Characterization of ALVAC WNV, (vCP2017) and ALVAC-2 WNV (vCP2018)

ALVAC-2 is a canarypox virus containing an E3LK3L gene cassette inserted at the unique C6 locus of ALVAC and is was confirmed by immunoplaque and immunoblot analyses. Both of these recombinants contain two copies of the H6p WNVprM-M-E genes.

Example 19

Production of Recombinant Vaccines

For the preparation of equine vaccines, the recombinant canarypox vCP1712 virus (Example 10) is adjuvanted with carbomer solutions, namely Carbopol™974P manufactured by BF Goodrich, Ohio, USA (molecular weight about 3,000,000).

A 1.5% Carbopol™974P stock solution was initially prepared in distilled water containing 1 g/l of sodium chloride. This stock solution was then used for the preparation of a 4 mg/ml Carbopol™974P solution in physiological salt solution. The stock solution was mixed with the adequate volume of the physiological salt solution, either in a single stage or in several successive stages, the pH value being adjusted in each stage with a 1N sodium hydroxide solution (or even more concentrated) in order to obtain a final pH value of 7.3 to 7.4.

The ready-to-use Carbopol™974P solution obtained in this way was used for taking up recombinant, lyophilized viruses or for diluting concentrated, recombinant virus stock solutions. For example, to obtain a viral suspension containing $10^8$ pfU/1 ml dose, a viral stock solution was diluted so as to obtain a titer of $10^{8.3}$ pfu/ml, followed by dilution in equal parts with said ready-to-use 4 mg/ml Carbopol™974P solution.

Recombinant vaccines can also be produced with recombinant canarypox viruses vCP1713 (Example 11) or vCP1717 (Example 16) or vCP1718 (Example 16) or vCP2017 (Example 18.1) or a mixture of three canarypox viruses vCP1714 (Example 12), vCP1715 (Example 13) and vCP1716 (Example 14) according to the procedure described herein.

Example 20

Production of DNA Vaccines for Equines

A DNA solution containing the plasmid pFC104 (Example 6) was concentrated by ethanol precipitation in the manner described by Sambrook et al (1989). The DNA sediment was taken up by a 0.9% NaCl solution so as to obtain a concentration of 1 mg/ml. A 0.75 mM DMRIE-DOPE solution is prepared by taking up a DMRIE-DOPE lyophilizate by a suitable sterile $H_2O$ volume.

The formation of plasmid-lipid DNA complexes was brought about by diluting in equal parts the 0.75 mM DMRIE-DOPE solution (1:1) with the 1 mg/ml DNA solution in 0.9% NaCl. The DNA solution was progressively introduced with the aid of a 26G crimped needle along the wall of the flask containing the cationic lipid solution so as to prevent the formation of foam. Gentle stirring takes place as soon as the two solutions mixed. Finally a composition comprising 0.375 mM of DMRIE-DOPE and 500 μg/ml plasmid was obtained.

It is desirable for all the solutions used to be at ambient temperature for all the operations described herein. DNA/DMRIE-DOPE complexing takes place at ambient temperature for 30 minutes before immunizing the animals.

DNA vaccines can also be produced with DNA solutions containing plasmids pFC104 (Example 6) and pFC106 (Example 8) or containing plasmids pFC105 (Example 7) and pFC106, plasmids pFC115 (Example 17) and pFC106, or containing plasmid pFC101, pFC102 and pFC103 (Examples 3 to 5), or containing plasmid pFC105 or pFC115 according to the procedure described in the present Example.

Example 21

In Vitro Expression Tests

The expression of WN proteins was tested for each construction by conventional indirect immunofluorescence and Western Blot methods.

These tests were carried out on 96 well plates containing CHO cells cultured in monolayers and transfected by plasmids or containing CEF cells cultured in monolayers and infected by recombinant viruses.

The WN proteins were detected by the use of infected chicken or horse sera and of labelled anti-sera.

The size of the fragments obtained after migration on agarose gel was compared with those expected.

Example 22

Effectiveness on Animals

The recombinant vaccines and plasmid vaccines were injected twice at approximately two week intervals into approximately seven day old, unvaccinated SPF chickens by the intramuscular route and in a volume of approximately 0.1 ml. An unvaccinated control group was included in the study.

The chickens were challenged by subcutaneous administration into the neck of $10^{3.5}TCID_{50}$ of pathogenic WN virus.

Viremia, antibody response and mortality were observed. Autopsies were carried out to observe lesions.

Example 23

Titrating Anti-WNV Neutralizing Antibodies

Dilution series were produced for each serum at a rate of 3 in DMEM medium to which was added 10% fetal calf serum in 96 well plates of the cellular culture type. To 0.05 ml of diluted serum was added 0.05 ml of culture medium containing approximately 100 $CCIP_{50}$/ml of WNV. This mixture was incubated for 2 hours at 37° C. in an oven in an atmosphere containing 5% CO2.

0.15 ml of a suspension of VERO cells containing approximately 100,000 cells/ml was then added to each mixture. The cytopathic effect (CPE) was observed by phase contrast microscopy after 4 to 5 days culturing at 37° C. in an atmosphere containing 5% $CO_2$. The neutralizing titers of each serum were calculated using the Kärber method. The titers were given in the form of the largest dilution inhibiting the cytopathic effect for 50% of the wells. The titers were expressed in log10 VN50. Each serum was titrated at least twice and preferably four times.

Example 24

Test on Horses of vCP2017

Recombinant vaccines containing vCP2017 (Example 18.1) formulated extemporaneously with 1 ml of Carbopol©974P adjuvant (4 mg/ml) were injected twice at 35 day intervals into horses aged more than three months and which had not been previously vaccinated, using the intramuscular route and a volume of approximately 1 ml. Three groups of animals were vaccinated, with doses of $10^{5.8}CCID_{50}$ (i.e. $10^{5.64}$ pfu) for group 1, $10^{6.8}CCID_{50}$ (i.e. $10^{6.64}$ pfu) for group 2 and $10^{7.8}CCID_{50}$ (i.e. $10^{7.64}$ pfu) for group 3. An unvaccinated control group was included in the study.

The neutralizing antibody titers were determined as indicated in Example 23 The titers were expressed in log10 VN50.

| Group | Titers at day 0 | Titers at day 35 | Titers at day 49 |
|---|---|---|---|
| 1 | <0.6 | <0.78 | 2.66 |
| 2 | <0.6 | 1.14 | 2.58 |
| 3 | <0.6 | 1.16 | 2.26 |
| Control | <0.6 | <0.6 | <0.6 |

Example 25

Protection after Challenge in Horses

Twenty horses (mares), 3-11 years old, were randomly allocated into two groups of 10 horses each. 1 ml of vaccine containing the recombinant vCP2017 $10^{6.3}$ $CCID_{50}$ (example 18.1) was formulated extemporaneously with 1 ml of Carbopol© 974P adjuvant at 4 mg/ml. Horses of group 1 were injected twice at 35 day intervals using the intramuscular route and a volume of approximately 1 ml containing $10^{6.0}CCID_{50}$ (i.e. $10^{5.84}$ pfu). One of the vaccinated horses had to be removed from the study prior to challenge due to recurrent colic.

Horses of group 2 remained unvaccinated and served as controls.

Horses from both groups were challenged on day 49 with WNV via the bites from WNV-infected *Aedes albopictus* mosquitoes. The *Aedes albopictus* mosquitoes were infected intrathoracically with WNV NY99 eight days prior to the challenge. Each mosquito received approximately 150 pfu. At challenge, a round carton capped with a fine nylon mesh (containing approximately 20 WNV-infected *Aedes albopictus* mosquitoes) was held (mesh side down) over a clipped area of the horse skin for 5 to 8 minutes.

The neutralizing antibody titers were determined as indicated in example 23. The titers were expressed in log10 VN50.

| Group | D0 | D35 | D42 | D49 | D63 |
|---|---|---|---|---|---|
| Vaccinated | <0.84 | <0.93 | 2.42 | 2.78 | 3.36 |
| Control | <0.72 | <0.75 | <0.78 | <0.78 | 3.43 |

None of the 9 vaccinated horses developed detectable WNV viremia while 8 of 10 control horses developed detectable WNV viremia.

Example 26

Test on Cats of vCP2017

41 cats, 14-20 weeks old, were randomly allocated into four groups.

Vaccines containing the recombinant vCP2017 (example 18.1) in 1 ml of sterile water per dose were injected twice at 28 day intervals via the subcutaneous route. Three groups of animals were vaccinated, with doses of $10^{7.9}CCID_{50}$ (i.e. $10^{7.74}$ pfu) for group 1 (8 cats), $10^{6.4}CCID_{50}$ (i.e. $10^{6.24}$ pfu) for group 2 (14 cats) and $10^{5.9}CCID_{50}$ (i.e. $10^{5.74}$ pfu) for group 3 (8 cats).

An unvaccinated control group was included in the study. The 11 cats of this group received placebo injections (1.0 ml of Phosphate Buffered saline (PBS) subcutaneously, twice 4 weeks apart).

The neutralizing antibody titers in serum were determined according to example 23. The titers were expressed in log10 VN50.

| Group | D0 | D28 | D42 |
|---|---|---|---|
| Control | <1.01 | <1.01 | <1.03 |
| 1 | <0.9 | <1.08 | 2.26 |
| 2 | <1.08 | <0.99 | 2.16 |
| 3 | <0.95 | <0.97 | 1.36 |

The neutralizing antibody titers in serum were determined with PRNT method (plaque reduction neutralization test; see Bunning M. L. et al., Emerging infectious diseases, 8(4), 380-386, 2002). The titers were expressed as a dilution starting from 1:5. The mean PRNT results at day 42 at 90%, 80% and 50% reduction by group:

| Group | Titers at day 42 (reduction of 90%) | Titers at day 42 (reduction of 80%) | Titers at day 42 (reduction of 50%) |
|---|---|---|---|
| Control | 5.00 | 5.00 | 5.00 |
| 1 | 16.88 | 29.38 | 55.63 |
| 2 | 15.36 | 11.92 | 45.36 |
| 3 | 5.00 | 5.00 | 6.25 |

Example 27

Protection after Challenge in Cats

The cats of the groups 2, 3 and control of the example 26 were challenged, 4 months after the second injection (example 26), with WNV via the bites of WNV-infected *Aedes albopictus* mosquitoes. The *Aedes albopictus* mosquitoes were infected intrathoracically with WNV NY99 8-10 days prior to the challenge. Each mosquito received approximately 150 pfu. At challenge, a round carton capped with a fine nylon mesh (containing approximately 5-15 WNV-infected *Aedes albopictus* mosquitoes) was held (mesh side down) over a clipped area of the cat skin for 5 to 10 minutes. The feeding of mosquitoes was confirmed by visualization of engorgement.

A representative sample of engorged, infected mosquitoes was titrated for WNV in order to determine the infection rate of mosquitoes. About 3 representative engorged mosquitoes from each cat were titrated for WNV. The results are 8.4 log pfu/mosquito for control group cats, 8.4 log pfu/mosquito for group 2 cats and 8.3 log pfu/mosquito for group 3 cats.

The neutralizing antibody titers and post-challenge WNV viremia were determined. The titers were calculated with PRNT method (plaque reduction neutralization test) and expressed in dilution starting at 1:5.

The mean PRNT results at 90% reduction by group and by post-challenge day:

| Group | D0 | D7 | D14 |
|---|---|---|---|
| Control | 5.00 | 5.00 | 20 |
| 2 | 7.14 | 89.64 | 148.57 |
| 3 | 5.00 | 47.50 | 47.50 |

The mean PRNT results at 80% reduction by group and by post-challenge day:

| Group | D0 | D7 | D14 |
|---|---|---|---|
| Control | 5.00 | 5.45 | 21.82 |
| 2 | 9.29 | 101.43 | 214.29 |
| 3 | 5.63 | 53.75 | 125.00 |

Incidence of WN virus isolation (number of cats having a positive WN virus isolation) by group and by post-challenge day:

| Group | Day 0 | day 1 | day 2 | day 3 | day 4 | day 5 | day 6 | days 7-10 | day 14 |
|---|---|---|---|---|---|---|---|---|---|
| Control | 0 | 0 | 3 | 5 | 7 | 7 | 5 | 0 | 0 |
| 2 | 0 | 0 | 0 | 0 | 0 | 0 | 0 | 0 | 0 |
| 3 | 0 | 0 | 1 | 0 | 0 | 0 | 0 | 0 | 0 |

None of the 14 vaccinated cats of group 2 developed a detectable WNV viremia, only one of the 8 vaccinated cats of group 3 developed a detectable WNV viremia while 9 of 11 control cats developed a detectable WNV viremia.

Example 28

Construction of the Recombinant Viruses vFP2000

As illustrative of one embodiment of the invention a specific fowlpox recombinant construct is described in this Example.

A PCR reaction was performed on the basis of the matrix constituted by genomic DNA of a fowlpox virus (DIFTOSEC CT©) strain marketed by MERIAL) and with the following oligonucleotides:

F8FCA1 (42 mer):
(SEQ ID NO: 30)
5'ATCATCGAGCTCGACCCTTTACAAGAATAAAAGAAGAAACAA 3'
and F8FCB1 (73 mer):
(SEQ ID NO: 31)
5'CTCGAGCTGCAGGAATTCCCCGGGTTTTTATTAGCTAATTAGCAATAT AGATTCAATATGATAATTACTCTAA 3' in order to isolate a 1483 bp PCR fragment (fragment H).

A PCR reaction was carried out on the basis of the matrix constituted by genomic DNA of the fowlpox virus and with the following oligonucleotides:

F8FCC1 (72 mer):
(SEQ ID NO: 32)
5'CCCGGGGAATTCCTGCAGCTCGAGTTTTTATTGACTAGTTAATCATAA GATAAATAATATACAGCATTGTAA 3'
and F8FCD1 (45 mer):
(SEQ ID NO: 33)
5'GATGATGGTACCGGGTAATGGCTTTTGTTTATAACCACGTTTGTC 3' in order to isolate a 1433 bp PCR fragment (fragment I).

Fragments H and I were hybridized together in order to serve as a matrix for a PCR reaction performed with the oligonucleotides F8FCA1 (SEQ ID NO: 30) and F8FCD1 (SEQ ID NO: 33) in order to generate a 2892 bp PCR fragment. This fragment was digested by the restriction enzymes SacI and KpnI in order to isolate, following agarose gel electrophoresis, a 2875 bp SacI-KpnI fragment. This fragment was ligated with the pBlueScript® II SK+ vector (Stratagene, La Jolla, USA, Cat # 212205), previously digested by the restriction enzymes SacI and KpnI, in order to give the plasmid pF8L. The sequence of this plasmid was verified by sequencing. This plasmid contains 1424 bp of sequences upstream of ORF F8 (left flanking arm F8), an early transcription stop vaccine signal, stop codons in 6 reading frames, a multiple cloning site containing restriction sites SmaI, PstI, XhoI and EcoRI and finally 1376 bp of sequences located downstream of ORF F8 (right flanking arm F8).

The plasmid pMP528HRH (Perkus M. et al. J. Virol. 1989, 63, 3829-3836) was used as the matrix for amplifying the complete sequence of the vaccine promoter H6 (GenBank accession no. M28351) with the following oligonucleotides:

FC125 (95 mer)
(SEQ ID NO: 34)
5'AAACCCGGGTTAATTAATTAGTCATCAGGCAGGGCGAAACGAGACTAT CTGCTCGTTAATTAATTAGAGCTTCTTTATTCTATACTTAAAAAGTG 3'
and FC126 (43 mer)
(SEQ ID NO: 35)
5'AAAACTGCAGGTCGACTACGATACAAACTTAACGGATATCGCG 3' in order to amplify a 211 bp PCR fragment. This fragment was digested by restriction enzymes SmaI and PstI in order to isolate, following agarose gel electrophoresis, a 200 bp SmaI-PstI restriction fragment. This fragment was then ligated with the plasmid pF8L, previously digested by SmaI and PstI, in order to give the plasmid pFC121.

A PCR reaction was performed using the plasmid pFC115 (example 17) as the matrix and the following oligonucleotides:

FC127 (58 mer)
(SEQ ID NO: 36)
5' TTTTCGCGATATCCGTTAAGTTTGTATCGTAATGACCGGAATTGCAG TCATGATTGGC 3'
and FC128 (43 mer)
(SEQ ID NO: 37)
5' TTTTGTCGACTCTAGATAAAAATTAAGCGTGCACGTTCACGGA 3' in order to amplify an approximately 2111 bp PCR fragment. This fragment was digested by restriction enzymes NruI and SalI in order to isolate, following agarose gel electrophoresis, an approximately 2096 bp NruI-SalI restriction fragment. This fragment was then ligated with plasmid pFC121 previously digested by restriction enzymes NruI and XhoI in order to give the plasmid pFC122.

Plasmid pFC122 was linearized by PvuI, then transfected in primary chicken embryo cells infected with the fowlpox virus according to the previously described calcium phosphate precipitation method (Panicali et Paoletti Proc. Nat. Acad. Sci. 1982, 79, 4927-4931; Piccini et al. In Methods in Enzymology, 1987, 153, 545-563, publishers Wu R. and Grossman L. Academic Press). Positive plaques were selected on the basis of a hybridization with a radioactively labelled probe specific to the nucleotide sequence of the envelope glycoprotein E. These plaques underwent 4 successive selection/purification cycles until a pure population was isolated. A representative plaque corresponding to in vitro recombination between the donor plasmid pFC122 and the genome of the fowlpox virus was then amplified and the recombinant virus stock obtained was designated vFP2000, fowlpox WNV prM-M-E.

Example 28.1

Construction of a pF8 H6p WNVprM-M-E Donor Plasmid (pSL-5513-1-1-1) for the Generation of Fowlpox WNV (vFP2000)

The construction scheme is illustrated in FIG. 3.

There is one commonly used recombination site in the Fowlpox genome, designated as F8. Plasmid pMAW112-2/F8 AIV HA has been described in patent application xxx and was used as the source of the Fowlpox F8 arms. The 1.7 kb AIV HA insert in pMAW112-2/F8 AIV HA was deleted by digestion with Nru I and Hind III, to be replaced by oligonucleotides 7737.SL (SEQ ID NO: 52) and 7738.SL (SEQ ID NO: 53) encoding the 3'-end of the H6 promoter and a Sma I/Xma I site. The correct insertion of the oligos was confirmed in plasmid pF8 H6p MCS, pSL-5440-5-1. This plasmid contains ~1.4 kb of the upstream F8 flanking sequence, designated as F8R and ~1.4 kb of the downstream flanking sequence of F8, designated as F8L, as well as the H6 promoter and a multiple cloning site of Xma I, Hind III, BamH I and Xho I.

```
SEQ ID NOS 52 and 53
                         H6p                    Xma I
7737.SL  5'  CGATATCCGTTAAGTTTGTATCGTAATGCCCGGGTCGCGAA      3'
7738.SL  3'  GCTATAGGCAATTCAAACATAGCATTACGGGCCCAGCGCTTTCGA  5'
```

Plasmid pDS-2946-1-1 is an ALVAC donor plasmid that contains the H6 promoter and West Nile Virus prM-M-E genes, between the C5 arms and is described in Example 18.1 and FIG. 1. pDS-2946-1-1 was digested with Bgl II and Xba I and the 2.8 kb C5R-H6p WNV fragment was inserted into pT7-7, between Bgl II and Xba I, generating plasmid pT7C5R-WNV, pSL-5501-2. Plasmid pSL-5501-2 was digested with Nru I and SalI and the 2.1 kb fragment inserted into pSL-5440-5-1 that had been digested with Nru I and Xho I. The resultant pF8 H6p WNV prM-M-E plasmid, pSL-5513-1-1-1, was confirmed by restriction enzyme digestion and nucleotide sequence analysis. The sequence of the F8-H6p WNV prM-M-E-F8 gene cassette from pSL-5513-1-1-1 is shown in FIG. 4.

Example 28.2

Generation and Characterization of a Fowlpox Recombinant Expressing West Nile Virus prM-M-E, vFP2000

Primary CEFs were transfected with Not I-linearized pSL-5513-1-1-1 plasmid DNA (15 ug) using Fugene reagent (Roche) by the method suggested by the supplier. The transfected cells were subsequently infected with fowlpox as rescue virus at MOI of 10 and after ~24 h, the transfected-infected cells were harvested, sonicated and used for recombinant virus screening. Recombinant plaques were screened based on the plaque lift hybridization method using a WNV-specific probe, which was directly labelled with horseradish peroxidase according to the manufacturer's protocol (Amersham). After five sequential rounds of plaque purification, the recombinants designated as vFP2000.2.1.1.1.1 and vFP2000.3.2.1.2.1 were generated and confirmed by hybridization as 100% positive for the WNV insert and 100% negative for the F8 ORF. Agarose punches were selected from the fifth round of plaque purification, and expanded to obtain stocks of vFP2000. Recombinant viruses were characterized by restriction enzyme and Southern blot analyses. The F8-H6p WNV-F8 locus was PCR-amplified and the complete sequence confirmed. Expression of the WNV proteins was confirmed by immuno-plaque and immunoblot analyses. The fowlpox recombinants contain one copy of the H6p WNVprM-M-E gene cassette.

Example 29

Test on Geese of vFP2000

20 Chinese geese, one-weeks old, were randomly allocated into four groups.

Vaccine was prepared by mixing extemporaneously 1 ml of the recombinant vFP2000 (Example 28) at $10^{6.3}$ CCID$_{50}$ with 1 ml of Carbopol©974P adjuvant at 4 mg/ml. One group of 5 birds was vaccinated with 0.2 ml by the intramuscular route twice at 13 day interval (called vFP2000 group).

Two unvaccinated control groups were included in the study. One control group of 7 geese was not vaccinated and was not challenged (called sham control group). One control group of 8 geese was not vaccinated but was challenged (called challenged control group). The geese of these groups received by intramuscular route placebo injections (0.2 ml of a Carbopol© 974P solution at 2 mg/ml) twice 13 days apart.

Geese from the vFP2000 group and from the control group were challenged on day 26 with 0.2 ml containing about $10^{3.5}$ CCID$_{50}$ of WNV by subcutaneous route.

The morbidity and post-challenge WNV viremia were observed. The virus titer was calculated and expressed as TCID$_{50}$/0.1 ml virus titers.

| Group | D0 | D1 | D2 | D3 | D4 | D5 | D7 | D10 |
|---|---|---|---|---|---|---|---|---|
| Challenged control | <0.3 | 4.2 | 4.5 | 3.3 | 3.9 | 0.7 | <0.3 | <0.3 |
| vFP2000 | <0.3 | 0.5 | 0.6 | 0.5 | 0.8 | <0.3 | <0.3 | <0.3 |
| Sham control | <0.3 | <0.3 | <0.3 | <0.3 | <0.3 | <0.3 | <0.3 | <0.3 |

The viremia was expressed as the percentage of WNv-excreting animals for each group.

| Group | D0 | D1 | D2 | D3 | D4 | D5 | D7 | D10 |
|---|---|---|---|---|---|---|---|---|
| Challenged control | 0% | 87.5% | 100% | 100% | 100% | 62.5% | 0% | 0% |
| vFP2000 | 0% | 20% | 40% | 20% | 40% | 0% | 0% | 0% |
| Sham control | 0% | 0% | 0% | 0% | 0% | 0% | 0% | 0% |

None of the five vFP2000 vaccinated geese developed detectable morbidity while 4 of 8 challenged control geese developed detectable morbidity. None of the sham control geese developed detectable morbidity.

Example 30

Immunoblot Analysis of the Expression of WNV Proteins from ALVAC WNV (vCP2017), ALVAC-2 WNV (vCP2018) and Fowlpox WNV (vFP2000) Recombinants ALVAC recombinants vCP2017 and vCP2018 each contain two copies of the H6p WNV prM-M-E gene cassette located at the C5 loci, while vFP2000 contains a single copy of H6p WNvprM-M-E at the F8 locus. CEFs were infected with vCP2017, vCP2018 or vFP2000 at an MOI of 10 and grown in serum-free DMEM medium for 24 and 48 hours at 37° C., 5% $CO_2$. The culture medium was collected and the cells were resuspended in PBS, then centrifuged and the PBS discarded. Cell lysate samples were prepared by resuspending the pellets in water, adding 5xSDS-PAGE sample buffer (without β-mercaptoethanol), and boiling for 5 minutes. Supernatant samples were prepared by adding 5xSDS-PAGE sample buffer (without β-mercaptoethanol), and boiling for 5 minutes. Samples were run on a 12% SDS-PAGE gel and the separated proteins were transferred to nylon membrane (Millipore Immobilon P). The immunoblot was probed with chicken anti-WNV antisera (Merial Ltd.), then horseradish peroxidase conjugated donkey-anti-chicken antibody (Jackson Labs) was used as secondary antibody. The reactive bands were visualized with Chemiluminescence Reagent (Perkin Elner). As illustrated in FIG. 5, the expression of both the WNV E and M proteins was higher in the cell fraction from the fowlpox recombinant than from the ALVAC recombinants. The production of the WNV E protein was also higher in the supernatant fraction from the fowlpox recombinant than the ALVAC recombinants, but there was no M protein secreted.

In order to determine whether this finding was reproducible in non-avian cells, baby hamster kidney (BHK) cells were infected with vCP2017, vCP2018 or vFP2000 at an MOI of 10. After ~24 h, culture supernatants and cells were collected, as described above. For SDS-PAGE analysis, 5x sample buffer (without β-mercaptoethanol) was added to the culture supernatants and the samples boiled for 5 min. The infected cells were resuspended in PBS, then spun to concentrate them and for SDS-PAGE analysis, lysis buffer was added, samples boiled for 5 min, then 5x sample buffer was added and the samples re-boiled for 5 min. Samples were separated on a 12% SDS-PAGE gel and proteins transferred to Millipore Immobilon P nylon membrane. Chicken anti-WNV antibody (Merial Ltd.) was used as primary antibody and horseradish peroxidase-conjugated donkey-anti-chicken antibody (Jackson Labs) was used as secondary antibody. Reactive protein bands were visualized with Chemiluminescence Reagent (Perkin Elmer). As illustrated in FIG. 6, the expression of the WNV E protein in the supernatant fraction from the fowlpox recombinant was higher than the ALVAC recombinants, in mammalian cells. There was no obvious difference in expression levels for the various recombinants in the cell fraction, however the fowlpox recombinant has only one gene copy compared to two gene copies in the ALVAC vectors.

Example 31

Generation and Characterization of Specific Antisera to West Nile Virus Proteins Expressed by ALVAC WNV (vCP2017), ALVAC-2 WNV (vCP2018) and Fowlpox WNV (vFP2000) Recombinants The in vitro expression of West Nile Virus M and E proteins from ALVAC or fowlpox recombinants in primary CEFs and BHK cells was demonstrated in Example 30. In order to determine whether the recombinants were immunogenic and if there was a demonstrable difference in the quality of the antisera, mice were immunized with vCP2017, vCP2018 and vFP2000. Balb/c mice (Charles River, Quebec) were immunized IM with $4\times10^7$ pfu of recombinant virus in 1 mM PBS, at days 0 and 21. Blood from day 35 was processed and used to probe immunoblots. Samples for immunoblot analysis of antisera from ALVAC WNV immunizations were prepared by transient transfection of Chinese hamster ovary (CHO) cells with pTriEx-WNV DNA, which had been shown to express the WNV M and E genes. CHO cells were transfected with 10 ug of pTriEx-WNV DNA, using electroporation at settings 1.5 kV, 25 uF and infinite resistance. Mock samples were prepared by the electroporation of CHO cells at the same settings, without DNA. After approximately 65 hours, supernatants were harvested and clarified by spinning at 3000 rpm for 5 min. The plates were washed twice with PBS, then 500 μl of PBS was added and the cells were scraped off. After spinning at 3000 rpm for 5 min, the supernatant was removed and the cells resuspended in 100 μl of SDS-PAGE lysis buffer. Samples were suspended in SDS-PAGE loading buffer (minus β-mercaptoethanol) and separated on a 12% SDS-PAGE gel before electrotransfer to Immobilon P nylon membrane. The membranes were processed and probed with 1:1000 dilution of the mouse anti-WNV antisera. Peroxidase-conjugated goat anti-mouse antisera (Jackson Labs) were used as secondary antibody at a dilution of 1:500 and bands were visualized using Chemiluminescence Reagent (Perkin Elmer). Five of five mouse anti-WNV antisera generated by vCP2017 immunization, reacted specifically with a protein band in the pTriEx-WNV samples, of the expected size for the WNV E protein. All of these antisera also reacted with media components in both the pTriEx-WNV and mock samples. Four of five mouse anti-WNV antisera generated by vCP2018 immunization, reacted specifically with a protein band in the pTriEx-WNV samples, of the expected size for the WNV E protein. All of the five antisera also reacted with media components in both the pTriEx-WNV and mock samples.

For analysis of anti-WNV antibodies following vFP2000 immunization, vFP2000 pellet and supernatant samples were run on 12% SDS-PAGE gels and transferred to Immobilon P nylon membrane (Millipore). The membranes were processed and probed with 1:1000 dilution of the mouse anti-WNV antisera. Peroxidase-conjugated goat anti-mouse antibody (Jackson Labs) was used as secondary antibody at a dilution of 1:500 and bands were visualized using Chemiluminescence Reagent (Perkin Elmer). Five of five mouse anti-WNV antisera generated by vFP2000 immunization, recognized specific bands in the vFP2000 samples, corresponding to WNV E and M proteins. Anti-vFP2000 antisera also recognized specific WNV bands expressed in vCP2017 and vCP2018.

Example 32

One Dose Efficacy of a Canarypox Vectored West Nile Virus (WNV) Vaccine (vCP2017) Against a WNV-infected Mosquito Challenge in Horses The efficacy of a single dose of a canarypox vectored West Nile Virus vaccine comprising vCP2017 (described in Example 18.1, above) was tested in horses. After acclimation, the animals were randomly assigned to each of two treatment groups: 19 horses were divided into Group I (9 horses, vaccinated) and Group II (10 horses, control). The clinician performing laboratory analyses and clinical observations was blind to the group assignment.

Each of the 9 horses in Group I was intramuscularly vaccinated in the lateral cervical area on Day 0 with a 1 ml dose of vaccine containing 10E06 TCID50 of the recombinant canarypox VCP 2017 (described in Example 18.1, above) and 4 mg of Carbopol 974P. The 10 horses of the control group (Group II) remained unvaccinated. Blood samples were collected on Days 0, 7, 14, 21, and 26 before challenge and on Days 33 and 40 post-challenge to test the presence of neutralizing antibodies.

*Aedes albopictus* mosquitoes were infected intrathoracically with WNV NY99, 7-14 days prior to the challenge. A representative sample of the pool of infected mosquitoes was titrated for WNV in order to determine the infection rate of the mosquitoes and the variability of virus load per mosquito. Each horse was challenged on Day 26 by the bite of 10-20 of the infected *Aedes*. Mosquitoes were allowed to feed on the horses for 5-10 minutes.

After challenge, the mosquitoes were chilled in a refrigerator, sorted and classified as engorged or not. The number of engorged mosquitoes was recorded and the engorged mosquitoes were frozen at $-75°$ C. and held until the virus assay was performed (WNV post-challenge titration). The mosquitoes were homogenized in 1 ml BA1 and titrated by plaque assay on Vero cells. The quantity of West Nile virus present in the engorged mosquitoes after feeding on the horses ranged between 10E07 to 10E09 pfu per mosquito.

All 19 animals were observed for depression, neurological signs and hyperthermia. Blood samples were collected twice daily on Days 26 to 40 for detection of West Nile virus viremia.

Animals were observed for depression and neurological signs (ataxia, head shaking, muscle fasciculation, reluctance to move, anxiety and lip twitching) were recorded as present or absent. Examination also included recording of rectal temperatures ($°$ F.). Data collected prior to challenge were used to establish the baseline for clinical signs.

All sera was tested for the presence of SN antibodies against West Nile Virus using the Plaque Endpoints determined at 50%, 80%, and 90% plaque-reduction levels. Titrations started at 1:5 dilution. Titers $\leq 1:5$ at 50% plaque reduction were considered negative. In this assay, 100 to 150 plaque-forming units per well were used.

Blood samples were tested by plaque titration for detection of WNV viremia. Viremia was reported as negative (titer of $<5$ pfu/ml [$\log_{10}<0.7$]) or positive (titer of $\geq 5$ pfu/ml [$\log_{10}\geq 0.7$]).

One out of nine vaccinated horses of Group I developed detectable West Nile virus viremia (11.1%), whereas eight out ten control horses (Group II) developed detectable viremia (80%) post challenge (see FIGS. 16, 17*a-b*).

One unvaccinated horse had a single episode of fever (102° F.) post challenge (see FIG. 18*a-c*). There was no incidence of any clinical signs after challenge. None of the challenged horses died from exposure to West Nile virus infection. Additionally, there were no inicdences of any clinical signs that were observed for this study in any of the challenged horses.

Prior to vaccination all horses were seronegative (titer<1:5). On Days 14, 21, 26 three vaccinated horses had positive West Nile neutralizing antibody titers (titer >or =1:5 at 80% plaque reduction according to the Plaque reduction neutralization test [PRNT]). All control animals remained negative. The data is shown in FIGS. 19*a-b*.

Having thus described in detail preferred embodiments of the present invention, it is to be understood that the invention defined by the appended claims is not to be limited to particular details set forth in the above description as many apparent variations thereof are possible without departing from the spirit or scope of the present invention.

---

What is claimed is:

1. A vaccine composition to induce a protective immune response against West Nile virus (WNV) in an animal susceptible to WNV comprising a vector comprising a recombinant canarypox virus that encodes and expresses in vivo in the animal WNV polyprotein prM-M-E.

2. The vaccine composition of claim 1 wherein the canarypox virus is ALVAC.

3. The vaccine composition of claim 1 wherein the nucleic acid molecule comprises nucleotides 466-741, 742-966 and 967-2469 of GenBank AF196835 (SEQ ID NO: 66) encoding WNV prM, M and E, respectively.

4. The vaccine composition of claim 1 wherein the nucleic acid molecule comprises nucleotides 466-2469 of GenBank AF196835 (SEQ ID NO: 66) encoding WN protein prM-M-E.

5. The vaccine composition of claim 1 wherein the nucleic acid molecule comprises nucleotides 421-2469 of GenBank AF196835 (SEQ ID NO: 66) encoding WN protein prM-M-E and the signal peptide of prM.

6. The vaccine composition of claim 1, further comprising an adjuvant.

7. The vaccine composition according to claim 3, wherein the adjuvant is a carbomer.

8. The vaccine composition of claim 1 further comprising an antigen or immunogen or epitope thereof of a pathogen other than WNV of the animal, or a vector that contains and expresses in vivo in the animal a nucleic acid molecule encoding the antigen, immunogen or epitope thereof, or an inactivated or attenuated pathogen other than WNV of the animal.

9. The vaccine composition of claim 1, wherein the animal is a cat or a horse.

10. A method for inducing a protective immune response against WNV in an animal comprising administering to the animal the vaccine composition according to claim 1.

11. A method for inducing a protective response against WNV in an animal comprising administering to the animal the vaccine composition according to claim 1, wherein the composition additionally comprises an adjuvant.

12. The method according to claim 11 wherein the adjuvant comprises a carbomer adjuvant.

13. A method for inducing a protective immune response against WNV and a second pathogen in an animal comprising administering to the animal the vaccine composition according to claim 8.

14. A method for inducing a protective immune response against WNV in an animal comprising administering to the animal (a) the vaccine composition according to claim 1, and (b) a WNV isolated antigen, immunogen or epitope thereof, wherein (a) is administered prior to (b) in a prime-boost regimen, or (b) is administered prior to (a) in a prime-boost regimen, or (a) and (b) are administered together, either sequentially or in admixture.

15. The method of any of claims 10, 13 or 14, wherein the animal is a cat or a horse.

16. The vaccine composition of claim 2, wherein the recombinant ALVAC virus is vCP2017.

* * * * *